(12) United States Patent
Breitbart et al.

(10) Patent No.: US 11,311,583 B2
(45) Date of Patent: Apr. 26, 2022

(54) TREATMENT METHODS USING ADENOVIRUS

(71) Applicant: Vascular Biogenics Ltd., Modiin (IL)

(72) Inventors: Eyal Breitbart, Hashmonaim (IL); Andrea Leubitz, Efrat (IL); Erez Feige, Hemed (IL); Richard Penson, Braintree, MA (US)

(73) Assignee: Vascular Biogenetics Ltd., Modiin (IL)

( * ) Notice: Subject to any disclaimer, the term of this patent is extended or adjusted under 35 U.S.C. 154(b) by 0 days.

(21) Appl. No.: 16/042,596

(22) Filed: Jul. 23, 2018

(65) Prior Publication Data

US 2019/0054130 A1 Feb. 21, 2019

Related U.S. Application Data

(60) Division of application No. 14/949,779, filed on Nov. 23, 2015, now abandoned, which is a continuation of application No. 14/527,667, filed on Oct. 29, 2014, now Pat. No. 9,200,056, which is a continuation of application No. PCT/IB2013/003015, filed on Oct. 17, 2013.

(60) Provisional application No. 61/785,287, filed on Mar. 14, 2013, provisional application No. 61/715,206, filed on Oct. 17, 2012.

(51) Int. Cl.

| | |
|---|---|
| A61K 48/00 | (2006.01) |
| C12N 15/79 | (2006.01) |
| C07H 21/04 | (2006.01) |
| A61K 35/761 | (2015.01) |
| C12N 15/86 | (2006.01) |
| C07K 14/705 | (2006.01) |
| A61K 31/337 | (2006.01) |
| A61K 31/713 | (2006.01) |
| A61K 45/06 | (2006.01) |
| C12N 7/00 | (2006.01) |
| A61K 9/00 | (2006.01) |

(52) U.S. Cl.
CPC .......... *A61K 35/761* (2013.01); *A61K 9/0019* (2013.01); *A61K 31/337* (2013.01); *A61K 31/713* (2013.01); *A61K 45/06* (2013.01); *A61K 48/00* (2013.01); *A61K 48/0058* (2013.01); *C07K 14/70503* (2013.01); *C07K 14/70578* (2013.01); *C12N 7/00* (2013.01); *C12N 15/86* (2013.01); *C12N 2710/10043* (2013.01); *C12N 2710/10332* (2013.01); *C12N 2800/24* (2013.01); *C12N 2830/008* (2013.01)

(58) Field of Classification Search
CPC .... A61K 48/005; A61K 35/761; C12N 15/86; C12N 2710/10043; C07H 21/04
See application file for complete search history.

(56) References Cited

U.S. PATENT DOCUMENTS

| | | |
|---|---|---|
| 3,773,919 A | 11/1973 | Boswell et al. |
| 7,067,649 B2 | 6/2006 | Harats |
| 7,579,327 B2 | 8/2009 | Harats et al. |
| 7,585,666 B2 | 9/2009 | Harats et al. |
| 7,989,427 B2 | 8/2011 | Harats et al. |
| 8,039,261 B2 | 10/2011 | Harats et al. |
| 8,071,740 B2 | 12/2011 | Harats et al. |
| 8,206,743 B2 | 6/2012 | Harats et al. |
| 8,415,318 B2 | 4/2013 | Harats et al. |
| 8,835,398 B2 | 9/2014 | Harats et al. |
| 8,846,401 B2 | 9/2014 | Harats et al. |
| 8,859,745 B2 | 10/2014 | Harats et al. |
| 8,859,747 B2 | 10/2014 | Harats et al. |
| 9,682,154 B2 | 6/2017 | Leubitz et al. |
| 2007/0286845 A1 | 12/2007 | Harats et al. |
| 2010/0034775 A1 | 2/2010 | Xie |
| 2010/0067129 A1 | 10/2010 | Kipps et al. |
| 2010/0282634 A1 | 11/2010 | Harats et al. |
| 2010/0298226 A1 | 11/2010 | Breitbart et al. |
| 2011/0201677 A1 | 8/2011 | Harats et al. |
| 2011/0207985 A1 | 8/2011 | Harats et al. |
| 2011/0251122 A1 | 10/2011 | Harats et al. |
| 2011/0319479 A1 | 12/2011 | Breitbart et al. |
| 2013/0052165 A1 | 2/2013 | Bangio et al. |
| 2013/0101557 A1 | 4/2013 | Yun |
| 2013/0209450 A1 | 8/2013 | Cohen et al. |
| 2013/0272998 A1 | 10/2013 | Harats et al. |

(Continued)

FOREIGN PATENT DOCUMENTS

| | | |
|---|---|---|
| CN | 1335398 A | 2/2002 |
| CN | 101348512 A | 1/2009 |

(Continued)

OTHER PUBLICATIONS

Appajahgagi (Expert Opin. Biol. Ther. (2015) 15(3):337-351 (Year: 2015).*

(Continued)

*Primary Examiner* — Shin Lin Chen

(74) *Attorney, Agent, or Firm* — Sterne, Kessler, Goldstein & Fox P.L.L.C.

(57) ABSTRACT

The invention provides methods of reducing or decreasing a size of a tumor or eliminating a tumor by inhibiting, decreasing, or reducing neo-vascularization or angiogenesis in a tumor in a patient by administering an adenovirus comprising a nucleic acid construct comprising a FAS-chimera gene operably linked to an endothelial cell-specific promoter. Also provided is a homogeneous population of an adenovirus comprising a FAS-chimera gene operably linked to an endothelial cell-specific promoter and its uses thereof.

11 Claims, 3 Drawing Sheets

Figure 1:
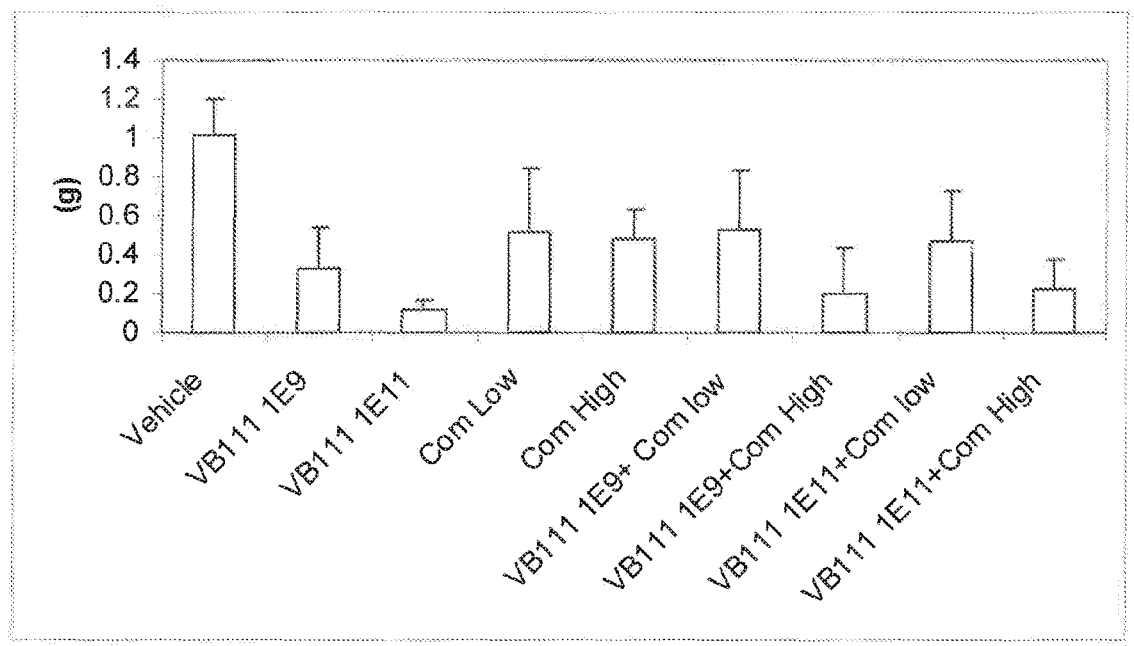

Specification includes a Sequence Listing.

(56) References Cited

U.S. PATENT DOCUMENTS

| | | |
|---|---|---|
| 2013/0280216 A1 | 10/2013 | Cohen et al. |
| 2013/0280217 A1 | 10/2013 | Cohen et al. |
| 2013/0295053 A1 | 11/2013 | Bangio et al. |
| 2013/0303595 A1 | 11/2013 | Cohen et al. |
| 2014/0010785 A1 | 1/2014 | Cohen et al. |
| 2015/0044280 A1 | 2/2015 | Breitbart et al. |
| 2015/0111957 A1 | 4/2015 | Breitbart et al. |
| 2017/0354746 A1 | 12/2017 | Leubitz et al. |

FOREIGN PATENT DOCUMENTS

| | | |
|---|---|---|
| EP | 0058481 A1 | 8/1982 |
| EP | 0133988 A2 | 3/1985 |
| EP | 2128261 A1 | 12/2009 |
| KR | 20120010697 A | 2/2012 |
| UA | 00043917 C2 | 1/2002 |
| UA | 70909 C2 | 11/2004 |
| WO | WO 9511984 A2 | 5/1995 |
| WO | WO 9528948 A1 | 11/1995 |
| WO | WO-03033514 A1 | 4/2003 |
| WO | WO-03093409 A2 | 11/2003 |
| WO | WO-2006051545 A2 | 5/2006 |
| WO | WO 2007049924 A1 | 5/2007 |
| WO | WO-2007096882 A2 | 8/2007 |
| WO | WO-2008015675 A2 | 2/2008 |
| WO | WO 2011081294 A2 | 7/2011 |
| WO | WO-2011083464 A2 | 7/2011 |
| WO | WO-2011083466 A1 | 7/2011 |
| WO | WO-2011086509 A1 | 7/2011 |
| WO | WO-2012046943 A2 | 4/2012 |
| WO | WO-2012052878 A1 | 4/2012 |
| WO | WO 2014060848 A2 | 4/2014 |
| WO | WO-2014118643 A2 | 8/2014 |

OTHER PUBLICATIONS

Lee (Genes & Diseases, 4: 43-63, 2017) (Year: 2017).*
Khare (Current Gene Therapy, 11: 241-258, 2011 (Year: 2011).*
Lentz et al. (Neurobiol Dis, 48(2): 179-88, 2012) (Year: 2012).*
Chen (J Neurosurg, 103(2): 311-9, 2005) (Year: 2005).*
Goswami (Frontiers in Oncology, 9: 1-25, 2019) (Year: 2019).*
Bouard (Br J Pharmacol, 57(2):153-65, 2009) (Year: 2009).*
Kuroda (J Gene Med, 10(11): 1163-75, 2008) (Year: 2008).*
Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Abboud, C.N. and Lichtman, M.A., "Structure of the Marrow and the Hematopoietic Microenvironment," in *Williams' Hematology*, vol. 6, pp. 29-58, Beutler, E., eds, McGraw-Hill, New York (2001).
Boldin, M.P., et al., "A novel protein that interacts with the death domain of Fas/APO1 contains a sequence motif related to the death domain," The Journal of Biological Chemistry 270(14):7795-7798, The American Society for Biochemistry and Molecular Biology, USA (1995).
Boldin, M.P., et al., "Self-association of the "death domains" of the p55 tumor necrosis factor (TNF) receptor and Fas/APO1 prompts signaling for TNF and Fas/APO1 effects," The Journal of Biological Chemistry 270(1):387-391, The American Society for Biochemistry and Molecular Biology, USA (1995).
Chen, Y-H., et al., "Upstream Stimulatory Factors Regulate Aortic Preferentially Expressed Gene-1 Expression in Vascular Smooth Muscle Cells," The Journal of Biological Chemistry 276(50):47658-47663, The American Society for Biochemistry and Molecular Biology, Inc., USA (2001).
Collins, C.J., et al., "Molecular Cloning of the Human Gene for Von Willebrand Factor and Identification of the Transcription Initiation Site," Proceedings of the National Academy of Sciences USA 84(13):4393-4397, National Academy of Sciences, USA (1987).
Collins, T., et al., "Structure and chromosomal location of the gene for endothelial-leukocyte adhesion molecule 1.," The Journal of Biological Chemistry 266(4):2466-2473, The American Society for Biochemistry and Molecular Biology, Inc., USA (1991).
Dennis, M.S., et al., "Albumin Binding as a General Strategy for Improving the Pharmacokinetics of Proteins," The Journal of Biological Chemistry 277(38):35035-35043, The American Society for Biochemistry and Molecular Biology, Inc., USA (2002).
English language Abstract of European Patent Publication No. 0 133 988 A2, European Patent Office, espacenet database—Worldwide, (2014) (listed as document EP0133988A2 on the accompanying form PTO/SB/08A).
Goodman and Gilman's, "The Pharmacological Basis of Therapeutics," Eighth Edition: 1202-1263, Pergamon Press, USA (1990).
Harats, D., et al., "Targeting Gene Expression to the Vascular Wall in Transgenic Mice Using the Murine Preproendothelin-1 Promoter," Journal of Clinical Investigation 95(3):1335-1344, The American Society for Clinical Investigation, Inc., USA (1995).
Hoffman, R., et al., "Hematology Basic Principals and Practice," Third Edition:3, Churchill Livingstone, New York (2000).
Horley, K.J., et al., "Molecular Cloning Of Murine Intercellular Adhesion Molecule (ICAM-1)," The EMBO Journal 8(10):2889-2896, IRL Press, England (1989).
Horowitz, N.S., et al., "Safety, Efficacy, and Biomarker Exploration in a Phase II Study of Bevacizumab, Oxaliplatin and Gemcitabine in Recurrent Mullerian Carcinoma," Clinical ovarian cancer and other gynecologic malignancies 4(1):26-33, Elsevier Inc., USA (2011).
Iademarco, M.F., et al., "Characterization of the Promoter for Vascular Cell Adhesion Molecule-1 (VCAM-1)," The Journal of Biological Chemistry 267(23): 16323-16329, The American Society for Biochemistry and Molecular Biology, Inc., USA (1992).
Jain, R.K., et al., "Biomarkers of Response and Resistance to Antiangiogenic Therapy," Nature Reviews Clinical Oncology 6(6):327-338, Macmillan Publishers Limited, England (2009).
Wold, F., "Posttranslational Protein Modifications: Perspectives and Prospectives," in *Posttranslational Covalent Modification of Proteins*, pp. 1-21, Academic Press, New York, USA (1983).
Joussen, A.M., et al., "Retinal Vascular Disease," Documenta Ophthalmologica 117(3):263-265, Springer-Verlag, UK (2008).
Langer, R., "Controlled release of macromolecules," Chem. Tech 12(2):98-105, American Chemical Society, USA (1982).
Langer, R., et al., "Biocompatibility of Polymeric Delivery Systems for Macromolecules," Journal of Biomedical Materials Research 15(2):267-277, John Wiley & Sons, Inc., USA (1981).
Layne, M.D., et al., "Characterization of the Mouse Aortic Carboxypeptidase-Like Protein Promoter Reveals Activity in Differentiated and Dedifferentiated Vascular Smooth Muscle Cells," Circulation Research 90(6):728-736, American Heart Association, Inc., USA (2002).
Schalm, O.W., "The Hematopoietic System," in *Schalm's Veterinary Hematology*, 4th edition, pp. 350-387, Lea & Febiger, Philadelphia, USA (1990).
Morishita, K., et al., "A Novel Promoter for Vascular Endothelial Growth Factor Receptor (flt-1) That Confers Endothelial-Specific Gene Expression," The Journal of Biological Chemistry 270(46):27948-27953, The American Society for Biochemistry and Molecular Biology, Inc., USA, (1995).
Newman, P.J., et al., "PECAM-1 (CD31) Cloning and Relation to Adhesion Molecules of the Immunoglobulin Gene Superfamily," Science 247(4947):1219-1222, American Association for the Advancement of Science, USA (1990).
Oken, M.M., et al., "Toxicity and Response Criteria of the Eastern Cooperative Oncology Group," American Journal of Clinical Oncology 5(6):649-655, Lippincott Williams & Wilkins, USA, (1982).
Picker, L.J. and Siegelman, M.H., "Lymphoid Tissues and Organs," in *Fundamental Immunology*, 4th Edition, pp. 479-531, Paul,W.E. ,ed, Lippincott-Raven, Philadelphia, PA, USA (1999).
Rattan, S.I.S., et al., "Protein Synthesis, Posttranslational Modifications, and Aging," Annals of the New York Academy of Sciences 663:48-62, John Wiley & Sons, Inc., USA, (1992).

(56) References Cited

OTHER PUBLICATIONS

Rius, C., et al., "Cloning of the Promoter Region of Human Endoglin, the Target Gene for Hereditary Hemorrhagic Telangiectasia Type 1," Blood 92(12):4677-4690, The American Society of Hematology, USA (1998).
Ronicke, V., et al., "Characterization of the Endothelium-Specific Murine Vascular Endothelial Growth Factor Receptor-2 (Flk-1) Promoter," Circulation Research 79(2):277-285, American Heart Association, Inc., USA, (1996).
Sato, T.N., et al., "Tie-1 and Tie-2 Define Another Class of Putative Receptor Tyrosine Kinase Genes Expressed in Early Embryonic Vascular System," Proceedings of the National Academy of Sciences USA 90(20):9355-9358, National Academy of Sciences, USA, (1993).
Seifter, S. and Englard, S., "Analysis for Protein Modifications and Nonprotein Cofactors," Methods in Enzymology 182:626-646, Academic Press, USA, (1990).
Sidman, K.R., et al., "Controlled Release of Macromolecules and Pharmaceuticals from Synthetic Polypeptides Based on Glutamic Acid," Biopolymers 22:547-556, John Wiley & Sons, Inc., USA, (1983).
Sukhatme, V.P., et al., "A Novel Early Growth Response Gene Rapidly Induced By Fibroblast, Epithelial Cell and Lymphocyte Mitogens," Oncogene Research 1(4):343-355, Harwood Academic Publishers GmbH, USA (1987).
UniProtKB Database, "Recommended name: Tumor necrosis factor receptor superfamily member 1A", Accession No. O19131, Entry Date Jun. 11, 2014.
UniProtKB Database, "Recommended name: Tumor necrosis factor receptor superfamily member 1A", Accession No. P19438-1, Entry Date Jul. 9, 2014.
UniProtKB Database, "Recommended name: Tumor necrosis factor receptor superfamily member 1A", Accession No. P19438-2, Entry Date Jul. 9, 2014.
UniProtKB Database, "Recommended name: Tumor necrosis factor receptor superfamily member 1A", Accession No. P19438-3, Entry Date Jul. 9, 2014.
UniProtKB Database, "Recommended name: Tumor necrosis factor receptor superfamily member 1A", Accession No. P22934, Entry Date Jun. 11, 2014.
UniProtKB Database, "Recommended name: Tumor necrosis factor receptor superfamily member 1A", Accession No. P25118, Entry Date Jul. 9, 2014.
UniProtKB Database, "Recommended name: Tumor necrosis factor receptor superfamily member 1A", Accession No. P50555, Entry Date Apr. 16, 2014.
UniProtKB Database, "Recommended name: Tumor necrosis factor receptor superfamily member 6", Accession No. P25445, Entry Date Jul. 9, 2014.
UniProtKB Database, "Recommended name: Tumor necrosis factor receptor superfamily member 6", Accession No. P25446, Entry Date Jul. 9, 2014.
UniProtKB Database, "Recommended name: Tumor necrosis factor receptor superfamily member 6", Accession No. P51867, Entry Date May 14, 2014.
UniProtKB Database, "Recommended name: Tumor necrosis factor receptor superfamily member 6", Accession No. Q63199, Entry Date Jun. 11, 2014.
UniProtKB Database, "Recommended name: Tumor necrosis factor receptor superfamily member 6", Accession No. Q9BDN4, Entry Date Feb. 19, 2014.
UniProtKB Database, "Recommended name: Tumor necrosis factor receptor superfamily member 6", Accession No. Q9BDP2, Entry Date Feb. 19, 2014.
UniProtKB Database, "Submitted name: Tumor necrosis factor receptor 1", Accession No. D1MH71, Entry Date Apr. 16, 2014.
Varda-Bloom, N., et al., "Tissue-Specific Gene Therapy Directed to Tumor Angiogenesis," Gene Therapy 8:819-827, Nature Publishing Group, England (2001).
Weiss, L. and Geduldig, U., "Barrier Cells: Stromal Regulation Of Hematopoiesis And Blood Cell Release In Normal And Stressed Murine Bone Marrow," Blood 78(4):975-990, The American Society of Hematology, USA (1991).
Wickramasinghe, S. N., "Bone marrow," in *Histology for Pathologists*, Chapter 1, pp. 1-31, Sternberg, S.S., ed, Raven Press, New York, USA (1992).
Greenberger, S., et al., "Transcription-controlled gene therapy against tumor angiogenesis," *J. Clin. Invest.* 113:1017-1034, American Society for Clinical Investigation, United States (2004).
International Search Report for International Application No. PCT/IB2013/003015, Patent Cooperation Treaty, dated Sep. 3, 2014.
Extended European Search Report for European Application No. i 3 84 77! L2, European Patent Office, Germany, dated Apr. 21, 2016, 13 pages.
Reddi, RV., et al., "Antitumor Activity of VB-HI, a Novel Antiangiogenic Virotherapeutic, in Thyroid Cancer Xenograft .Mouse Models," Genes & Cancer 2(10):993-995, Impact Journals LLC, United States (2011).
Triozzi, P.L. and Borden, E.C., "VB-111 for cancer," Expert Opinion on Biological Therapy J 1 (12):1669-1676, Infonna UK Ltd., United Kingdom (2011).
Brenner, A.J ., et al., "Phase I Dose-Escalation Study of VB-111, an Anti-Angiogenic Virotherapy, in Patients with Advanced Solid Tumors," Clinical Cancer Research 1 9(14):3996-4007, American Association for Cancer Research, United States (2013).
Fonsato, V., et al., "Vascular Biology, Atherosclerosis and Endothelium Biology Expression of Pax2 in Human Renal Tumor-Derived Endothelial Cells Sustains Apoptosis Resistance and Angiogenesis," American Journal of Pathology 1 68(2):706-713, American Society for Investigative Pathology, United States (2006).
Hu, J., et al., "Hypoxia Regulates Expression of the Endothelin-1 Gene through a Proximal Hypoxia-Inducible Factor-! Binding Site on the Antisense Strand," Biochemical And Biophysical Research Communications 245(3):894-899, Academic Press, United States ( 1998).
Kaluz, S., et al., "Regulation of gene expression by hypoxia: integration of the HIF-transduced hypoxic signal at the hypoxia-responsive element," Clinica Chimica Acta 395(1-2):6-13, Elsevier B.V., Netherlands (2008).
Penson, R.T., et al., "A phase I/II trial of multiple dose VB-111 and weekly paclitaxel in recurrent platinum-resistant MUllerian cancer," J Clin Oneal 33:Abstract 5542, 2015 ASCO Annual Meeting, Poster Session, Gynecologic Cancer, American Society of Clinical Oncology, United States (2015).
Tang, J., et al., "P-Adrenergic system, a backstage manipulator regulating tumour progression and drug target in cancer therapy," Seminars in Cancer Biology 23(6 Part B):533-542, Elsevier Ltd., England (2013).
Communication pursuant to Article 94(3) EPC in EP Application No. 13847711.2, dated Mar. 9, 2017, European Patent Office, Rijswijk, Netherlands, 10 pages.
Breitbart, E. et al., "VB-111 novel anti-angiogenic vector and a promising treatment for metastatic cancer in combination with other anticancer drugs," Proceedings of AACR, 102nd Annual Meeting (Apr. 2-6, 2011), Cancer Res 71(8suppl) Abstract 3283.
Tsunoda, T. and Takagi, T., "Estimating transcription factor bindability on DNA," *Bioinformatics*, 15(7/8): 622-630, Oxford University Press, England (Jul.-Aug. 1999).
Arany, Z., et al., "An essential role for p300/CBP in the cellular response to hypoxia," *Proc Natl Acad Sci USA* 93(23):12969-12973, National Academy of Sciences, United States (1996).
VBL Therapeutics, "Company Presentation," accessed at https://vblrx.gcs-web.com/jstatic-files/8e6ca5af-3400-4be6-b333-3856915a8454 on Jan. 28, 2019, 47 pages (Jun. 2017).
Brenner, A. J., et al., "A Phase I Trial of VB-111, a Tissue- and Condition-Specific Dual Action Vascular Disruptive and Antiangiogenic Agent, for Treatment of Patients With Advanced Metastatic Cancer," presented at the 2011 American Society of Clinical Oncology (ASCO) Annual Meeting, United States, Poster 3038, 1 page (Jun. 2011).
Triozzi, P., et al., "A Phase I Trial of VB-111, a Tissue and Condition Specific Vascular Disruptive Anti-Angiogenic Agent, Based on

(56) References Cited

OTHER PUBLICATIONS

Novel Vascular Targeting System™, VTS™, for Treatment of Patients With Advanced Metastatic Cancer," presented at the 101st Annual Meeting of the American Association for Cancer Research, United States, Poster 1361, 1 page (Apr. 2010).

Gruslova, A., et al., "VB-111: A novel anti-vascular therapeutic for glioblastoma multiforme," *J Neurooncol* 124(3):365-372, Kluwer Academic Publishers, Netherlands (Sep. 2015).

\* cited by examiner

SEQUENCE LISTING

```
<160> NUMBER OF SEQ ID NOS: 27

<210> SEQ ID NO 1
<211> LENGTH: 1365
<212> TYPE: DNA
<213> ORGANISM: Homo sapiens
<220> FEATURE:
<223> OTHER INFORMATION: TNFRSF1A

<400> SEQUENCE: 1
atgggcctct ccaccgtgcc tgacctgctg ctgccgctgg tgctcctgga gctgttggtg      60
ggaatatacc cctcagggt tattggactg gtccctcacc taggggacag ggagaagaga     120
gatagtgtgt gtccccaagg aaaatatatc cacccctcaaa ataattcgat ttgctgtacc    180
aagtgccaca aaggaaccta cttgtacaat gactgtccag gcccggggca ggatacggac    240
tgcagggagt gtgagagcgg ctccttcacc gcttcagaaa accacctcag acactgcctc    300
agctgctcca aatgccgaaa ggaaatgggt caggtggaga tctcttcttg cacagtggac    360
cgggacaccg tgtgtggctg caggaagaac cagtaccggc attattggag tgaaaacctt    420
ttccagtgct tcaattgcag cctctgcctc aatgggaccg tgcacctctc ctgccaggag    480
aaacagaaca ccgtgtgcac ctgccatgca ggtttctttc taagagaaaa cgagtgtgtc    540
```

```
tcctgtagta actgtaagaa aagcctggag tgcacgaagt tgtgcctacc ccagattgag    600
aatgttaagg gcactgagga ctcaggcacc acagtgctgt tgcccctggt cattttcttt    660
ggtctttgcc ttttatccct cctcttcatt ggtttaatgt atcgctacca acggtggaag    720
tccaagctct actccattgt ttgtgggaaa tcgacacctg aaaaagaggg ggagcttgaa    780
ggaactacta ctaagcccct ggccccaaac ccaagcttca gtcccactcc aggcttcacc    840
cccaccctgg gcttcagtcc cgtgcccagt tccaccttca cctccagctc acctataccc    900
cccggtgact gtcccaactt gcggctcccc gcagagagg tggcaccacc ctatcagggg    960
gctgacccca tccttgcgac agccctcgcc tccgacccca tccccaaccc ccttcagaag    1020
tgggaggaca gcgcccacaa gccacagagc ctagacactg atgaccccgc gacgctgtac    1080
gccgtggtgg agaacgtgcc cccgttcgcc tggaaggaat cgtgcgcgcg cctagggctg    1140
agcgaccacg agatcgatcg gctggagctg cagaacgggc gctgcctgcg cgaggcgcaa    1200
tacagcatgc tggcgacctg gaggcggcgc acgccgcggc gcgaggccac gctggagctg    1260
ctgggacgcg tgctccgcga catggacctg ctgggctgcc tggaggacat cgaggaggcg    1320
ctttgcggcc ccgccgccct cccgcccgcg cccagtcttc tcaga                   1365
```

<210> SEQ ID NO 2
<211> LENGTH: 455
<212> TYPE: PRT
<213> ORGANISM: Homo sapiens
<220> FEATURE:
<223> OTHER INFORMATION: Wild Type TNF Receptor 1

<400> SEQUENCE: 2

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
```

| | | | | | | | | | | | |
|---|---|---|---|---|---|---|---|---|---|---|---|
| | | | | 210 | | | | 215 | | | 220 |

Leu Ser Leu Leu Phe Ile Gly Leu Met Tyr Arg Tyr Gln Arg Trp Lys
225                                230                            235                      240

Ser Lys Leu Tyr Ser Ile Val Cys Gly Lys Ser Thr Pro Glu Lys Glu
                      245                            250                            255

Gly Glu Leu Glu Gly Thr Thr Thr Lys Pro Leu Ala Pro Asn Pro Ser
                260                            265                            270

Phe Ser Pro Thr Pro Gly Phe Thr Pro Thr Leu Gly Phe Ser Pro Val
           275                            280                            285

Pro Ser Ser Thr Phe Thr Ser Ser Ser Thr Tyr Thr Pro Gly Asp Cys
290                              295                            300

Pro Asn Phe Ala Ala Pro Arg Arg Glu Val Ala Pro Pro Tyr Gln Gly
305                              310                            315                      320

Ala Asp Pro Ile Leu Ala Thr Ala Leu Ala Ser Asp Pro Ile Pro Asn
                325                            330                            335

Pro Leu Gln Lys Trp Glu Asp Ser Ala His Lys Pro Gln Ser Leu Asp
           340                            345                            350

Thr Asp Asp Pro Ala Thr Leu Tyr Ala Val Val Glu Asn Val Pro Pro
                355                            360                            365

Leu Arg Trp Lys Glu Phe Val Arg Arg Leu Gly Leu Ser Asp His Glu
370                              375                            380

Ile Asp Arg Leu Glu Leu Gln Asn Gly Arg Cys Leu Arg Glu Ala Gln
385                              390                            395                      400

Tyr Ser Met Leu Ala Thr Trp Arg Arg Arg Thr Pro Arg Arg Glu Ala
                405                            410                            415

Thr Leu Glu Leu Leu Gly Arg Val Leu Arg Asp Met Asp Leu Leu Gly
           420                          425                            430

Cys Leu Glu Asp Ile Glu Glu Ala Leu Cys Gly Pro Ala Ala Leu Pro
                435                            440                            445

Pro Ala Pro Ser Leu Leu Arg
    450                            455

<210> SEQ ID NO 3
<211> LENGTH: 591
<212> TYPE: DNA
<213> ORGANISM: Homo sapiens
<220> FEATURE:
<223> OTHER INFORMATION: Ligand Binding Domain of TNFR1

<400> SEQUENCE: 3

```
atgggcctct ccaccgtgcc tgacctgctg ctgccgctgg tgctcctgga gctgttggtg      60
ggaatatacc cctcaggggt tattggactg gtccctcacc taggggacag ggagaagaga     120
gatagtgtgt gtcccccaagg aaatatatc caccctcaaa ataattcgat ttgctgtacc     180
aagtgccaca aggaaccta cttgtacaat gactgtccag gcccggggca ggatacggac     240
tgcagggagt gtgagagcgg ctccttcacc gcttcagaaa accacctcag acactgcctc     300
agctgctcca atgccgaaa ggaaatgggt caggtggaga tctcttcttg cacagtggac     360
cgggacaccg tgtgtggctg caggaagaac cagtaccggc attattggag tgaaaacctt     420
ttccagtgct tcaattgcag cctctgcctc aatgggaccg tgcacctctc ctgccaggag     480
aaacagaaca ccgtgtgcac ctgccatgca ggtttcttc taagagaaaa cgagtgtgtc     540
tcctgtagta actgtaagaa aagcctggag tgcacgaagt tgtgcctacc a               591
```

<210> SEQ ID NO 4

<211> LENGTH: 197
<212> TYPE: PRT
<213> ORGANISM: Homo sapiens
<220> FEATURE:
<223> OTHER INFORMATION: Ligand Binding Domain of TNFR1

<400> SEQUENCE: 4

Met Gly Leu Ser Thr Val Pro Asp Leu Leu Leu Pro Leu Val Leu Leu
1               5                   10                  15
Glu Leu Leu Val Gly Ile Tyr Pro Ser Gly Val Ile Gly Leu Val Pro
            20                  25                  30
His Leu Gly Asp Arg Glu Lys Arg Asp Ser Val Cys Pro Gln Gly Lys
        35                  40                  45
Tyr Ile His Pro Gln Asn Asn Ser Ile Cys Cys Thr Lys Cys His Lys
    50                  55                  60
Gly Thr Tyr Leu Tyr Asn Asp Cys Pro Gly Pro Gly Gln Asp Thr Asp
65                  70                  75                  80
Cys Arg Glu Cys Glu Ser Gly Ser Phe Thr Ala Ser Glu Asn His Leu
                85                  90                  95
Arg His Cys Leu Ser Cys Ser Lys Cys Arg Lys Glu Met Gly Gln Val
            100                 105                 110
Glu Ile Ser Ser Cys Thr Val Asp Arg Asp Thr Val Cys Gly Cys Arg
        115                 120                 125
Lys Asn Gln Tyr Arg His Tyr Trp Ser Glu Asn Leu Phe Gln Cys Phe
    130                 135                 140
Asn Cys Ser Leu Cys Leu Asn Gly Thr Val His Leu Ser Cys Gln Glu
145                 150                 155                 160
Lys Gln Asn Thr Val Cys Thr Cys His Ala Gly Phe Phe Leu Arg Glu
                165                 170                 175
Asn Glu Cys Val Ser Cys Ser Asn Cys Lys Lys Ser Leu Glu Cys Thr
            180                 185                 190
Lys Leu Cys Leu Pro
        195

<210> SEQ ID NO 5
<211> LENGTH: 1008
<212> TYPE: DNA
<213> ORGANISM: Homo sapiens
<220> FEATURE:
<223> OTHER INFORMATION: full-length FAS

<400> SEQUENCE: 5
atgctgggca tctggaccct cctacctctg gttcttacgt ctgttgctag attatcgtcc      60
aaaagtgtta atgcccaagt gactgacatc aactccaagg gattggaatt gaggaagact     120
gttactacag ttgagactca gaacttggaa ggcctgcatc atgatggcca attctgccat     180
aagccctgtc ctccaggtga aggaaagct agggactgca cagtcaatgg ggatgaacca     240
gactgcgtgc cctgccaaga agggaaggag tacacagaca agcccatttt tcttccaaa     300 tgcagaagat gtagattgtg tgatgaagga catggcttag aagtggaaat aaactgcacc     360
cggacccaga taccaagtg cagatgtaaa ccaaactttt tttgtaactc tactgtatgt     420
gaacactgtg acccttgcac caaatgtgaa catggaatca tcaaggaatg cacactcacc     480
agcaacacca gtgcaaaga ggaaggatcc agatctaact gggggtggct ttgtcttctt     540
cttttgccaa ttccactaat tgtttgggtg aagagaaagg aagtacagaa acatgcaga     600 aagcacagaa aggaaaacca aggttctcat gaatctccaa ctttaaatcc tgaaacagtg     660

-continued

```
gcaataaatt tatctgatgt tgacttgagt aaatatatca ccactattgc tggagtcatg   720
acactaagtc aagttaaagg ctttgttcga agaatggtg tcaatgaagc caaaatagat    780
gagatcaaga atgacaatgt ccaagacaca gcagaacaga aagttcaact gcttcgtaat   840
tggcatcaac ttcatggaaa gaaagaagcg tatgacacat tgattaaaga tctcaaaaaa   900
gccaatcttt gtactcttgc agagaaaatt cagactatca tcctcaagga cattactagt   960
gactcagaaa attcaaactt cagaaatgaa atccaaagct tggtctag              1008
```

<210> SEQ ID NO 6
<211> LENGTH: 335
<212> TYPE: PRT
<213> ORGANISM: Homo sapiens
<220> FEATURE:
<223> OTHER INFORMATION: full-length FAS

<400> SEQUENCE: 6

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300
```

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
            325                 330                 335

<210> SEQ ID NO 7
<211> LENGTH: 505
<212> TYPE: DNA
<213> ORGANISM: Homo sapiens
<220> FEATURE:
<223> OTHER INFORMATION: Effector Domain of FAS

<400> SEQUENCE: 7
aggatccaga tctaacttgg ggtggctttg tcttcttctt ttgccaattc cactaattgt      60
ttgggtgaag agaaaggaag tacagaaaac atgcagaaag cacagaaagg aaaaccaagg    120
ttctcatgaa tctccaacct aaatcctga aacagtggca ataaatttat ctgatgttga     180
cttgagtaaa tatatcacca ctattgctgg agtcatgaca ctaagtcaag ttaaaggctt    240
tgttcgaaag aatggtgtca atgaagccaa atagatgag atcaagaatg acaatgtcca     300
agacacagca gaacagaaag ttcaactgct tcgtaattgg catcaacttc atggaaagaa    360
agaagcgtat gacacattga ttaaagatct caaaaaagcc aatctttgta ctcttgcaga    420
gaaaattcag actatcatcc tcaaggacat tactagtgac tcagaaaatt caaacttcag    480
aaatgaaatc caaagcttgg tctag                                          505

<210> SEQ ID NO 8
<211> LENGTH: 167
<212> TYPE: PRT
<213> ORGANISM: Homo sapiens
<220> FEATURE:
<223> OTHER INFORMATION: Effector Domain of FAS

<400> SEQUENCE: 8

Gly Ser Arg Ser Asn Leu Gly Trp Leu Cys Leu Leu Leu Pro Ile
1               5                   10                  15

Pro Leu Ile Val Trp Val Lys Arg Lys Glu Val Gln Lys Thr Cys Arg
                20                  25                  30

Lys His Arg Lys Glu Asn Gln Gly Ser His Glu Ser Pro Thr Leu Asn
            35                  40                  45

Pro Glu Thr Val Ala Ile Asn Leu Ser Asp Val Asp Leu Ser Lys Tyr
        50                  55                  60

Ile Thr Thr Ile Ala Gly Val Met Thr Leu Ser Gln Val Lys Gly Phe
65                  70                  75                  80

Val Arg Lys Asn Gly Val Asn Glu Ala Lys Ile Asp Glu Ile Lys Asn
                85                  90                  95

Asp Asn Val Gln Asp Thr Ala Glu Gln Lys Val Gln Leu Leu Arg Asn
            100                 105                 110

Trp His Gln Leu His Gly Lys Lys Glu Ala Tyr Asp Thr Leu Ile Lys
        115                 120                 125

Asp Leu Lys Lys Ala Asn Leu Cys Thr Leu Ala Glu Lys Ile Gln Thr
    130                 135                 140

Ile Ile Leu Lys Asp Ile Thr Ser Asp Ser Glu Asn Ser Asn Phe Arg
145                 150                 155                 160

Asn Glu Ile Gln Ser Leu Val
                165

<210> SEQ ID NO 9

<211> LENGTH: 1101
<212> TYPE: DNA
<213> ORGANISM: Homo sapiens
<220> FEATURE:
<223> OTHER INFORMATION: FAS-chimera

<400> SEQUENCE: 9

```
atgggcctct ccaccgtgcc tgacctgctg ctgccgctgg tgctcctgga gctgttggtg      60
ggaatatacc cctcaggggt tattggactg gtccctcacc taggggacag ggagaagaga     120
gatagtgtgt gtccccaagg aaaatatatc caccctcaaa ataattcgat ttgctgtacc     180
aagtgccaca aggaaccta cttgtacaat gactgtccag gccgggggca ggatacggac      240
tgcagggagt gtgagagcgg ctccttcacc gcttcagaaa accacctcag acactgcctc     300
agctgctcca aatgccgaaa ggaaatgggt caggtggaga tctcttcttg cacagtggac     360
cgggacaccg tgtgtggctg caggaagaac cagtaccggc attattggag tgaaaacctt     420
ttccagtgct tcaattgcag cctctgcctc aatgggaccg tgcacctctc ctgccaggag     480
aaacagaaca ccgtgtgcac ctgccatgca ggtttctttc taagagaaaa cgagtgtgtc     540
tcctgtagta actgtaagaa agcctggag tgcacgaagt tgtgcctacc aagcttagga      600
tccagatcta acttggggtg gctttgtctt cttcttttgc caattccact aattgtttgg     660
gtgaagagaa aggaagtaca gaaaacatgc agaaagcaca gaaaggaaaa ccaaggttct     720
catgaatctc caaccttaaa tcctgaaaca gtggcaataa atttatctga tgttgacttg     780
agtaaatata tcaccactat tgctggagtc atgacactaa gtcaagttaa aggctttgtt     840
cgaaagaatg tgtcaatga agccaaaata tgatgagatca agaatgacaa tgtccaagac     900
acagcagaac agaaagttca actgcttcgt aattggcatc aacttcatgg aaagaaagaa     960
gcgtatgaca cattgattaa agatctcaaa aaagccaatc tttgtactct tgcagagaaa    1020
attcagacta tcatcctcaa ggacattact agtgactcag aaaattcaaa cttcagaaat    1080
gaaatccaaa gcttggtcta g                                              1101
```

<210> SEQ ID NO 10
<211> LENGTH: 366
<212> TYPE: PRT
<213> ORGANISM: Homo sapiens
<220> FEATURE:
<223> OTHER INFORMATION: FAS-chimera

<400> SEQUENCE: 10

```
Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125
```

```
Lys Asn Gln Tyr Arg His Tyr Trp Ser Glu Asn Leu Phe Gln Cys Phe
    130                 135                 140
Asn Cys Ser Leu Cys Leu Asn Gly Thr Val His Leu Ser Cys Gln Glu
145                 150                 155                 160
Lys Gln Asn Thr Val Cys Thr Cys His Ala Gly Phe Phe Leu Arg Glu
                165                 170                 175
Asn Glu Cys Val Ser Cys Ser Asn Cys Lys Lys Ser Leu Glu Cys Thr
            180                 185                 190
Lys Leu Cys Leu Pro Ser Leu Gly Ser Arg Ser Asn Leu Gly Trp Leu
        195                 200                 205
Cys Leu Leu Leu Leu Pro Ile Pro Leu Ile Val Trp Val Lys Arg Lys
    210                 215                 220
Glu Val Gln Lys Thr Cys Arg Lys His Arg Lys Glu Asn Gln Gly Ser
225                 230                 235                 240
His Glu Ser Pro Thr Leu Asn Pro Glu Thr Val Ala Ile Asn Leu Ser
                245                 250                 255
Asp Val Asp Leu Ser Lys Tyr Ile Thr Thr Ile Ala Gly Val Met Thr
            260                 265                 270
Leu Ser Gln Val Lys Gly Phe Val Arg Lys Asn Gly Val Asn Glu Ala
        275                 280                 285
Lys Ile Asp Glu Ile Lys Asn Asp Asn Val Gln Asp Thr Ala Glu Gln
    290                 295                 300
Lys Val Gln Leu Leu Arg Asn Trp His Gln Leu His Gly Lys Lys Glu
305                 310                 315                 320
Ala Tyr Asp Thr Leu Ile Lys Asp Leu Lys Lys Ala Asn Leu Cys Thr
                325                 330                 335
Leu Ala Glu Lys Ile Gln Thr Ile Ile Leu Lys Asp Ile Thr Ser Asp
            340                 345                 350
Ser Glu Asn Ser Asn Phe Arg Asn Glu Ile Gln Ser Leu Val
        355                 360                 365

<210> SEQ ID NO 11
<211> LENGTH: 47
<212> TYPE: DNA
<213> ORGANISM: Artificial Sequence
<220> FEATURE:
<223> OTHER INFORMATION: Endothelial Cell-Specific Enhancer Elements

<400> SEQUENCE: 11
ctggagggtg actttgcttc tggagccagt acttcatact tttcatt            47

<210> SEQ ID NO 12
<211> LENGTH: 47
<212> TYPE: DNA
<213> ORGANISM: Artificial Sequence
<220> FEATURE:
<223> OTHER INFORMATION: Endothelial Cell-Specific Enhancer

<400> SEQUENCE: 12
aatgaaaagt atgaagtact ggctccagaa gcaaagtcac cctccag             47

<210> SEQ ID NO 13
<211> LENGTH: 44
<212> TYPE: DNA
<213> ORGANISM: Artificial Sequence
<220> FEATURE:
<223> OTHER INFORMATION: Endothelial Cell-Specific Enhancer

<400> SEQUENCE: 13
```
gtacttcata cttttcattc caatggggtg actttgcttc tgga                    44

<210> SEQ ID NO 14
<211> LENGTH: 44
<212> TYPE: DNA
<213> ORGANISM: Artificial Sequence
<220> FEATURE:
<223> OTHER INFORMATION: Endothelial Cell-Specific Enhancer Element

<400> SEQUENCE: 14
tccagaagca aagtcacccc attggaatga aaagtatgaa gtac                    44

<210> SEQ ID NO 15
<211> LENGTH: 131
<212> TYPE: DNA
<213> ORGANISM: Artificial Sequence
<220> FEATURE:
<223> OTHER INFORMATION: Endothelial Cell-Specific 3X Enhancer Element

<400> SEQUENCE: 15
ctccagaagc aaagtcaccc cattggaatg aaaagtatga agtacaatga aaagtatgaa   60
gtactggctc cagaagcaaa gtcaccctcc agaagcaaag tcaccccatt ggaatgaaaa  120
gtatgaagta c                                                       131

<210> SEQ ID NO 16
<211> LENGTH: 131
<212> TYPE: DNA
<213> ORGANISM: Artificial Sequence
<220> FEATURE:
<223> OTHER INFORMATION: Endothelial Cell-Specific 3X Enhancer Element

<400> SEQUENCE: 16
gtacttcata cttttcattc caatggggtg actttgcttc tggagggtga ctttgcttct   60
ggagccagta cttcatactt ttcattgtac ttcatacttt tcattccaat ggggtgactt  120
tgcttctgga g                                                       131

<210> SEQ ID NO 17
<211> LENGTH: 850
<212> TYPE: DNA
<213> ORGANISM: Artificial Sequence
<220> FEATURE:
<223> OTHER INFORMATION: Endothelial Cell-Specific PPE-1 Promoter

<400> SEQUENCE: 17
gtacgtgtac ttctgatcgg cgatactagg gagataagga tgtgcctgac aaaaccacat   60
tgttgttgtt atcattatta tttagttttc cttccttgct aactcctgac ggaatctttc  120
tcacctcaaa tgcgaagtac tttagtttag aaaagacttg gtggaagggg tggtggtgga  180
aaagtagggt gatcttccaa actaatctgg ttccccgccc gccccagtag ctgggattca  240
agagcgaaga gtggggatcg tccccttgtt tgatcagaaa gacataaaag gaaaatcaag  300
tgaacaatga tcagccccac ctccacccca cccccctgcg cgcgcacaat acaatctatt  360
taattgtact tcatactttt cattccaatg gggtgacttt gcttctggag aaactcttga  420
ttcttgaact ctggggctgg cagctagcaa aaggggaagc gggctgctgc tctctgcagg  480
ttctgcagcg gtctctgtct agtgggtgtt ttcttttttct tagccctgcc cctggattgt  540
cagacggcgg gcgtctgcct ctgaagttag ccgtgatttc ctctagagcc gggtcttatc  600
tctggctgca cgttgcctgt gggtgactaa tcacacaata acattgttta gggctggaat  660

```
gaagtcagag ctgtttaccc ccactctata ggggttcaat ataaaaaggc ggcggagaac    720
tgtccgagtc agaagcgttc ctgcaccggc gctgagagcc tgacccggtc tgctccgctg    780
tccttgcgcg ctgcctcccg gctgcccgcg acgctttcgc cccagtggaa gggccacttg    840
ctgcggccgc                                                           850
```

<210> SEQ ID NO 18
<211> LENGTH: 987
<212> TYPE: DNA
<213> ORGANISM: Artificial Sequence
<220> FEATURE:
<223> OTHER INFORMATION: Endothelial Cell-Specific PPE-1 3X Promoter

<400> SEQUENCE: 18

```
gtacgtgtac ttctgatcgg cgatactagg gagataagga tgtgcctgac aaaaccacat     60
tgttgttgtt atcattatta tttagttttc cttccttgct aactcctgac ggaatctttc    120
tcacctcaaa tgcgaagtac tttagtttag aaaagacttg gtggaagggg tggtggtgga    180
aaagtagggt gatcttccaa actaatctgg ttccccgccc gccccagtag ctgggattca    240
agagcgaaga gtggggatcg tccccttgtt tgatcagaaa gacataaaag gaaaatcaag    300
tgaacaatga tcagccccac ctccacccca cccccctgcg cgcgcacaat acaatctatt    360
taattgtact tcatactttt cattccaatg gggtgacttt gcttctggag aaactcttga    420
ttcttgaact ctggggctgg cagctagcct ccagaagcaa agtcaccccca ttggaatgaa    480 aagtatgaag tacaatgaaa agtatgaagt actggctcca gaagcaaagt caccctccag    540
aagcaaagtc accccattgg aatgaaaagt atgaagtacg ctagcaaaag gggaagcggg    600
ctgctgctct ctgcaggttc tgcagcggtc tctgtctagt gggtgttttc ttttcttag     660 ccctgccct ggattgtcag acggcgggcg tctgcctctg aagttagccg tgatttcctc     720
tagagccggg tcttatctct ggctgcacgt tgcctgtggg tgactaatca cacaataaca    780
ttgtttaggg ctggaatgaa gtcagagctg tttacccca ctctataggg gttcaatata     840
aaaaggcggc ggagaactgt ccgagtcaga agcgttcctg caccggcgct gagagcctga    900
cccggtctgc tccgctgtcc ttgcgcgctg cctcccggct gcccgcgacg ctttcgcccc    960
agtggaaggg ccacttgctg cggccgc                                        987
```

<210> SEQ ID NO 19
<211> LENGTH: 35207
<212> TYPE: DNA
<213> ORGANISM: Artificial Sequence
<220> FEATURE:
<223> OTHER INFORMATION: VB-111 entire construct

<400> SEQUENCE: 19

```
catcatcaat aatataccttt attttggatt gaagccaata tgataatgag ggggtggagt    60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagtacgta cgtgtacttc tgatcggcga    480
tactagggag ataaggatgt gcctgacaaa accacattgt tgttgttatc attattattt    540
```

```
agttttcctt ccttgctaac tcctgacgga atctttctca cctcaaatgc gaagtacttt    600
agtttagaaa agacttggtg gaaggggtgg tggtggaaaa gtagggtgat cttccaaact    660
aatctggttc cccgcccgcc ccagtagctg ggattcaaga gcgaagagtg gggatcgtcc    720
ccttgtttga tcagaaagac ataaaaggaa atcaagtga acaatgatca gccccacctc    780 cacccccacccccctgcgcgc gcacaataca atctatttaa ttgtacttca tacttttcat    840
tccaatgggg tgactttgct tctggagaaa ctcttgattc ttgaactctg gggctggcag    900
ctagcctcca gaagcaaagt caccccattg gaatgaaaag tatgaagtac aatgaaaagt    960
atgaagtact ggctccagaa gcaaagtcac cctccagaag caaagtcacc ccattggaat   1020
gaaaagtatg aagtacgcta gcaaagggg aagcgggctg ctgctctctg caggttctgc    1080
agcggtctct gtctagtggg tgttttcttt ttcttagccc tgcccctgga ttgtcagacg   1140
gcgggcgtct gcctctgaag ttagccgtga tttcctctag agccgggtct tatctctggc   1200
tgcacgttgc ctgtgggtga ctaatcacac aataacattg tttagggctg gaatgaagtc   1260
agagctgttt accccccactc tatagggtt caatataaaa aggcggcgga gaactgtccg    1320
agtcagaagc gttcctgcac cggcgctgag agcctgaccc ggtctgctcc gctgtccttg   1380
cgcgctgcct cccggctgcc cgcgacgctt tcgccccagt ggaagggcca cttgctgcgg   1440
ccgctaattc tgcagatcgg gatccggcat gggcctctcc accgtgcctg acctgctgct   1500
gccgctggtg ctcctggagc tgttggtggg aatataccccc tcagggtta ttggactggt    1560 ccctcaccta ggggacaggg agaagagaga tagtgtgtgt ccccaaggaa aatatatcca   1620
ccctcaaaat aattcgattt gctgtaccaa gtgccacaaa ggaacctact tgtacaatga   1680
ctgtccaggc ccggggcagg atacggactg cagggagtgt gagagcggct ccttcaccgc   1740
ttcagaaaac cacctcagac actgcctcag ctgctccaaa tgccgaaagg aaatgggtca   1800
ggtggagatc tcttcttgca cagtggaccg ggacaccgtg tgtggctgca ggaagaacca   1860
gtaccggcat tattggagtg aaaaccttt ccagtgcttc aattgcagcc tctgcctcaa    1920
tgggaccgtg cacctctcct gccaggagaa acagaacacc gtgtgcacct gccatgcagg   1980
tttctttcta agagaaaacg agtgtgtctc ctgtagtaac tgtaagaaaa gcctggagtg   2040
cacgaagttg tgcctaccaa gcttaggatc cagatctaac ttggggtggc tttgtcttct   2100
tcttttgcca attccactaa ttgtttgggt gaagagaaag gaagtacaga aaacatgcag   2160
aaagcacaga aaggaaaacc aaggttctca tgaatctcca accttaaatc ctgaaacagt   2220
ggcaataaat ttatctgatg ttgacttgag taaatatatc accactattg ctggagtcat   2280
gacactaagt caagttaaag gctttgttcg aaagaatggt gtcaatgaag ccaaaataga   2340
tgagatcaag aatgacaatg tccaagacac agcagaacag aaagttcaac tgcttcgtaa   2400
ttggcatcaa cttcatggaa agaaagaagc gtatgacaca ttgattaaag atctcaaaaa   2460
agccaatctt tgtactcttg cagagaaaat tcagactatc atcctcaagg acattactag   2520
tgactcagaa aattcaaact tcagaaatga atccaaagc ttggtctagc tcgagcatgc    2580
atctaggcgg ccgcatggca gaaattcgcg aattcgctag cgttaacgga tcctctagac   2640
gagatccgaa cttgtttatt gcagcttata atggttacaa ataaagcaat agcatcacaa   2700
atttcacaaa taaagcattt ttttcactgc attctagttg tggtttgtcc aaactcatca   2760
atgtatctta tcatgtctag atctgtactg aaatgtgtgg gcgtggctta agggtgggaa   2820
agaatatata aggtgggggt cttatgtagt tttgtatctg ttttgcagca gccgccgccg   2880
```

```
ccatgagcac caactcgttt gatggaagca ttgtgagctc atatttgaca acgcgcatgc   2940
ccccatgggc cggggtgcgt cagaatgtga tgggctccag cattgatggt cgccccgtcc   3000
tgcccgcaaa ctctactacc ttgacctacg agaccgtgtc tggaacgccg ttggagactg   3060
cagcctccgc cgccgcttca gccgctgcag ccaccgcccg cgggattgtg actgactttg   3120
ctttcctgag cccgcttgca agcagtgcag cttcccgttc atccgcccgc gatgacaagt   3180
tgacggctct tttggcacaa ttggattctt tgacccggga acttaatgtc gtttctcagc   3240
agctgttgga tctgcgccag caggtttctg ccctgaaggc ttcctcccct cccaatgcgg   3300
tttaaaacat aaataaaaaa ccagactctg tttggatttg gatcaagcaa gtgtcttgct   3360
gtctttattt aggggttttg cgcgcgcggt aggcccggga ccagcggtct cggtcgttga   3420
gggtcctgtg tattttttcc aggacgtggt aaaggtgact ctggatgttc agatacatgg   3480
gcataagccc gtctctgggg tggaggtagc accactgcag agcttcatgc tgcggggtgg   3540
tgttgtagat gatccagtcg tagcaggagc gctgggcgtg gtgcctaaaa atgtctttca   3600
gtagcaagct gattgccagg ggcaggccct tggtgtaagt gtttacaaag cggttaagct   3660
gggatgggtg catacgtggg gatatgagat gcatcttgga ctgtattttt aggttggcta   3720
tgttcccagc catatccctc cggggattca tgttgtgcag aaccaccagc acagtgtatc   3780
cggtgcactt gggaaatttg tcatgtagct tagaaggaaa tgcgtggaag aacttggaga   3840
cgcccttgtg acctccaaga ttttccatgc attcgtccat aatgatggca atgggcccac   3900
gggcggcggc ctgggcgaag atatttctgg gatcactaac gtcatagttg tgttccagga   3960
tgagatcgtc ataggccatt tttacaaagc gcggcggag ggtgccagac tgcggtataa   4020
tggttccatc cggcccaggg gcgtagttac cctcacagat ttgcatttcc cacgctttga   4080
gttcagatgg ggggatcatg tctacctgcg ggcgatgaa gaaaacggtt ccggggtag   4140 gggagatcag ctgggaagaa agcaggttcc tgagcagctg cgacttaccg cagccggtgg   4200
gcccgtaaat cacacctatt accggctgca actggtagtt aagagagctg cagctgccgt   4260
catccctgag caggggggcc acttcgttaa gcatgtccct gactcgcatg ttttccctga   4320
ccaaatccgc cagaaggcgc tcgccgccca gcgatagcag ttcttgcaag gaagcaaagt   4380
ttttcaacgg tttgagaccg tccgccgtag gcatgctttt gagcgtttga ccaagcagtt   4440
ccaggcggtc ccacagctcg gtcacctgct ctacggcatc tcgatccagc atatctcctc   4500
gtttcgcggg ttggggcggc tttcgctgta cggcagtagt cggtgctcgt ccagacgggc   4560
cagggtcatg tctttccacg ggcgcagggt cctcgtcagc gtagtctggg tcacggtgaa   4620
ggggtgcgct ccgggctgcg cgctggccag ggtgcgcttg aggctggtcc tgctggtgct   4680
gaagcgctgc cggtcttcgc cctgcgcgtc ggccaggtag catttgacca tggtgtcata   4740
gtccagcccc tccgcggcgt ggcccttggc gcgcagcttg cccttggagg aggcgccgca   4800
cgaggggcag tgcagacttt tgagggcgta gagcttgggc gcgagaaata ccgattccgg   4860
ggagtaggca tccgcgccgc aggccccgca gacggtctcg cattccacga gccaggtgag   4920
ctctggccgt tcggggtcaa aaaccaggtt tcccccatgc tttttgatgc gtttcttacc   4980
tctggtttcc atgagccggt gtccacgctc ggtgacgaaa aggctgtccg tgtcccgta   5040 tacagacttg agaggcctgt cctcgagcgg tgttccgcgg tcctcctcgt atagaaactc   5100
ggaccactct gagacaaagg ctcgcgtcca ggccagcacg aaggaggcta agtgggaggg   5160
gtagcggtcg ttgtccacta gggggtccac tcgctccagg gtgtgaagac acatgtcgcc   5220
ctcttcggca tcaaggaagg tgattggttt gtaggtgtag gccacgtgac cgggtgttcc   5280
```

```
tgaaggggg ctataaaagg gggtgggggc gcgttcgtcc tcactctctt ccgcatcgct    5340
gtctgcgagg gccagctgtt ggggtgagta ctccctctga aaagcgggca tgacttctgc    5400
gctaagattg tcagtttcca aaacgagga ggatttgata ttcacctggc ccgcggtgat    5460
gcctttgagg gtggccgcat ccatctggtc agaaaagaca atcttttgt tgtcaagctt     5520 ggtggcaaac gacccgtaga gggcgttgga cagcaacttg gcgatggagc gcagggtttg    5580 gttttgtcg cgatcggcgc gctccttggc cgcgatgttt agctgcacgt attcgcgcgc     5640
aacgcaccgc cattcgggaa agacggtggt gcgctcgtcg ggcaccaggt gcacgcgcca    5700
accgcggttg tgcagggtga caaggtcaac gctggtggct acctctccgc gtaggcgctc    5760
gttggtccag cagaggcggc cgcccttgcg cgagcagaat ggcggtaggg ggtctagctg    5820
cgtctcgtcc gggggtctg cgtccacggt aaagaccccg ggcagcaggc gcgcgtcgaa      5880
gtagtctatc ttgcatcctt gcaagtctag cgcctgctgc catgcgcggg cggcaagcgc    5940
gcgctcgtat gggttgagtg ggggacccca tggcatgggg tgggtgagcg cggaggcgta    6000
catgccgcaa atgtcgtaaa cgtagagggg ctctctgagt attccaagat atgtagggta    6060
gcatcttcca ccgcggatgc tggcgcgcac gtaatcgtat agttcgtgcg agggagcgag    6120
gaggtcggga ccgaggttgc tacgggcggg ctgctctgct cggaagacta tctgcctgaa    6180
gatggcatgt gagttggatg atatggttgg acgctgaaag acgttgaagc tggcgtctgt    6240
gagacctacc gcgtcacgca cgaaggaggc gtaggagtcg cgcagcttgt tgaccagctc    6300
ggcggtgacc tgcacgtcta gggcgcagta gtccagggtt tccttgatga tgtcatactt    6360
atcctgtccc tttttttcc acagctcgcg gttgaggaca aactcttcgc ggtctttcca     6420
gtactcttgg atcggaaacc cgtcggcctc cgaacggtaa gagcctagca tgtagaactg    6480
gttgacggcc tggtaggcgc agcatccctt ttctacgggt agcgcgtatg cctgcgcggc    6540
cttccggagc gaggtgtggg tgagcgcaaa ggtgtccctg accatgactt tgaggtactg    6600
gtatttgaag tcagtgtcgt cgcatccgcc ctgctcccag agcaaaaagt ccgtgcgctt    6660
tttggaacgc ggatttggca gggcgaaggt gacatcgttg aagagtatct ttcccgcgcg    6720
aggcataaag ttgcgtgtga tgcggaaggg tcccggcacc tcggaacggt tgttaattac    6780
ctgggcggcg agcacgatct cgtcaaagcc gttgatgttg tggcccacaa tgtaaagttc    6840
caagaagcgc gggatgccct tgatggaagg caatttttta agttcctcgt aggtgagctc    6900
ttcaggggag ctgagcccgt gctctgaaag ggcccagtct gcaagatgag ggttggaagc    6960
gacgaatgag ctccacaggt cacgggccat tagcatttgc aggtggtcgc gaaaggtcct    7020
aaactggcga cctatggcca tttttctgg ggtgatgcag tagaaggtaa gcgggtcttg     7080
ttcccagcgg tcccatccaa ggttcgcggc taggtctcgc gcggcagtca ctagaggctc    7140
atctccgccg aacttcatga ccagcatgaa gggcacgagc tgcttcccaa aggcccccat    7200
ccaagtatag gtctctacat cgtaggtgac aaagagacgc tcggtgcgag gatgcgagcc    7260
gatcgggaag aactggatct cccgccacca attggaggag tggctattga tgtggtgaaa    7320
gtagaagtcc ctgcgacggg ccgaacactc gtgctggctt ttgtaaaaac gtgcgcagta    7380
ctggcagcgg tgcacgggct gtacatcctg cacgaggtta acctgacgac cgcgcacaag    7440
gaagcagagt gggaatttga gcccctcgcc tggcgggttt ggctggtggt cttctacttc    7500
ggctgcttgt ccttgaccgt ctggctgctc gaggggagtt acggtggatc ggaccaccac    7560
gccgcgcgag cccaaagtcc agatgtccgc gcgcggcggt cggagcttga tgacaacatc    7620
```

```
gcgcagatgg gagctgtcca tggtctggag ctcccgcggc gtcaggtcag gcgggagctc   7680
ctgcaggttt acctcgcata gacgggtcag ggcgcgggct agatccaggt gatacctaat   7740
ttccagggcc tggttggtgg cggcgtcgat ggcttgcaag aggccgcatc cccgcggcgc   7800
gactacggta ccgcgcggcg ggcggtgggc gcgggggtg tccttggatg atgcatctaa    7860
aagcggtgac gcgggcgagc ccccggaggt aggggggggct ccggaccggc cgggagaggg  7920
ggcaggggca cgtcggcgcc gcgcgcgggc aggagctggt gctgcgcgcg taggttgctg   7980
gcgaacgcga cgacgcggcg gttgatctcc tgaatctggc gcctctgcgt gaagacgacg   8040
ggcccggtga gcttgaacct gaaagagagt tcgacagaat caatttcggt gtcgttgacg   8100
gcggcctggc gcaaaatctc ctgcacgtct cctgagttgt cttgataggc gatctcggcc   8160
atgaactgct cgatctcttc ctcctggaga tctccgcgtc cggctcgctc acggtggcg    8220 gcgaggtcgt tggaaatgcg ggccatgagc tgcgagaagg cgttgaggcc tccctcgttc   8280
cagacgcggc tgtagaccac gccccttcg gcatcgcggg cgcgcatgac cacctgcgcg    8340
agattgagct ccacgtgccg ggcgaagacg gcgtagtttc gcaggcgctg aaagaggtag   8400
ttgagggtgg tggcggtgtg ttctgccacg aagaagtaca taaccccagcg tcgcaacgtg  8460 gattcgttga tatcccccaa ggcctcaagg cgctccatgg cctcgtagaa gtccacggcc   8520
aagttgaaaa actgggagtt gcgcgccgac acggttaact cctcctccag aagacggatg   8580
agctcggcga cagtgtcgcg cacctcgcgc tcaaaggcta caggggcctc ttcttcttct   8640
tcaatctcct cttccataag ggcctccccct tcttcttctt ctggcggcgg tgggggaggg  8700
gggacacggc ggcgacgacg gcgcaccggg aggcggtcga caaagcgctc gatcatctcc   8760
ccgcggcgac ggcgcatggt ctcggtgacg gcgcggccgt tctcgcgggg gcgcagttgg   8820
aagacgccgc ccgtcatgtc ccggttatgg gttggcgggg ggctgccatg cggcagggat   8880
acggcgctaa cgatgcatct caacaattgt tgtgtaggta ctccgccgcc gagggacctg   8940
agcgagtccg catcgaccgg atcggaaaac ctctcgagaa aggcgtctaa ccagtcacag   9000
tcgcaaggta ggctgagcac cgtggcgggc ggcagcgggc ggcggtcggg gttgtttctg   9060
gcggaggtgc tgctgatgat gtaattaaag taggcggtct tgagacgcg gatggtcgac    9120 agaagcacca tgtccttggg tccggcctgc tgaatgcgca ggcggtcggc catgcccag    9180 gcttcgtttt gacatcggcg caggtctttg tagtagtctt gcatgagcct ttctaccggc   9240
acttcttctt ctccttcctc ttgtcctgca tctcttgcat ctatcgctgc ggcggcggcg   9300
gagtttggcc gtaggtggcg ccctcttcct cccatgcgtg tgaccccgaa gcccctcatc   9360
ggctgaagca gggctaggtc ggcgacaacg cgctcggcta atatggcctg ctgcacctgc   9420
gtgagggtag actggaagtc atccatgtcc acaaagcggt ggtatgcgcc cgtgttgatg   9480
gtgtaagtgc agttggccat aacggaccag ttaacggtct ggtgacccgg ctgcgagagc   9540
tcggtgtacc tgagacgcga gtaagccctc gagtcaaata cgtagtcgtt gcaagtccgc   9600
accaggtact ggtatcccac caaaaagtgc ggcggcggct ggcggtagag gggccagcgt   9660
agggtggccg gggctccggg ggcgagatct tccaacataa ggcgatgata tccgtagatg   9720
tacctggaca tccaggtgat gccgcggcg gtggtgagg cgcgcggaaa gtcgcggacg     9780
cggttccaga tgttgcgcag cggcaaaaag tgctccatgg tcgggacgct ctggccggtc   9840
aggcgcgcgc aatcgttgac gctctagacc gtgcaaaagg agagcctgta agcgggcact   9900
cttccgtggt ctggtggata aattcgcaag ggtatcatgg cggacgaccg gggttcgagc   9960
cccgtatccg gccgtccgcc gtgatccatg cggttaccgc ccgcgtgtcg aacccaggtg  10020
```

```
tgcgacgtca gacaacgggg gagtgctcct tttggcttcc ttccaggcgc ggcggctgct    10080
gcgctagctt ttttggccac tggccgcgcg cagcgtaagc ggttaggctg aaagcgaaa     10140 gcattaagtg gctcgctccc tgtagccgga gggttatttt ccaagggttg agtcgcggga    10200
cccccggttc gagtctcgga ccggccggac tgcggcgaac gggggtttgc ctccccgtca    10260
tgcaagaccc cgcttgcaaa ttcctccgga aacagggacg agccccttt ttgcttttcc     10320 cagatgcatc cggtgctgcg gcagatgcgc ccccctcctc agcagcggca agagcaagag    10380
cagcggcaga catgcagggc accctcccct cctcctaccg cgtcaggagg ggcgacatcc    10440
gcggttgacg cggcagcaga tggtgattac gaaccccgc ggcgccgggc ccggcactac     10500
ctggacttgg aggagggcga gggcctggcg cggctaggag cgccctctcc tgagcggcac    10560
ccaagggtgc agctgaagcg tgatacgcgt gaggcgtacg tgccgcggca gaacctgttt    10620
cgcgaccgcg agggagagga gcccgaggag atgcgggatc gaaagttcca cgcagggcgc    10680
gagctgcggc atggcctgaa tcgcgagcgg ttgctgcgcg aggaggactt tgagcccgac    10740
gcgcgaaccg ggattagtcc cgcgcgcgca cacgtggcgg ccgccgacct ggtaaccgca    10800
tacgagcaga cggtgaacca ggagattaac tttcaaaaaa gctttaacaa ccacgtgcgt    10860
acgcttgtgg cgcgcgagga ggtggctata ggactgatgc atctgtggga ctttgtaagc    10920
gcgctggagc aaaacccaaa tagcaagccg ctcatggcgc agctgttcct tatagtgcag    10980
cacagcaggg acaacgaggc attcagggat gcgctgctaa acatagtaga gcccgagggc    11040
cgctggctgc tcgatttgat aaacatcctg cagagcatag tggtgcagga gcgcagcttg    11100
agcctggctg acaaggtggc cgccatcaac tattccatgc ttagcctggg caagttttac    11160
gcccgcaaga tataccatac cccttacgtt cccatagaca aggaggtaaa gatcgagggg    11220
ttctacatgc gcatggcgct gaaggtgctt accttgagcg acgacctggg cgtttatcgc    11280
aacgagcgca tccacaaggc cgtgagcgtg agccggcggc gcgagctcag cgaccgcgag    11340
ctgatgcaca gcctgcaaag ggccctggct ggcacgggca gcggcgatag agaggccgag    11400
tcctactttg acgcgggcgc tgacctgcgc tgggccccaa gccgacgcgc cctggaggca    11460
gctggggccg gacctgggct ggcggtggca cccgcgcgcg ctggcaacgt cggcggcgtg    11520
gaggaatatg acgaggacga tgagtacgag ccagaggacg gcgagtacta agcggtgatg    11580
tttctgatca gatgatgcaa gacgcaacgg acccggcggt gcgggcggcg ctgcagagcc    11640
agccgtccgg ccttaactcc acggacgact ggcgccaggt catggaccgc atcatgtcgc    11700
tgactgcgcg caatcctgac gcgttccggc agcagccgac ggccaaccgg ctctccgcaa    11760
ttctggaagc ggtggtcccg gcgcgcgcaa accccacgca cgagaaggtg ctggcgatcg    11820
taaacgcgct ggccgaaaac agggccatcc ggcccgacga ggccggcctg gtctacgacg    11880
cgctgcttca gcgcgtggct cgttacaaca gcggcaacgt gcagaccaac ctggaccggc    11940
tggtggggga tgtgcgcgag gccgtggcgc agcgtgagcg cgcgcagcag cagggcaacc    12000
tgggctccat ggttgcacta aacgccttcc tgagtacaca gcccgccaac gtgccgcggg    12060
gacaggagga ctacaccaac tttgtgagcg cactgcggct aatggtgact gagacaccgc    12120
aaagtgaggt gtaccagtct gggccagact atttttccca gaccagtaga caaggcctgc    12180
agaccgtaaa cctgagccag gctttcaaaa acttgcaggg gctgtggggg gtgcgggctc    12240
ccacaggcga ccgcgcgacc gtgtctagct tgctgacgcc caactcgcgc ctgttgctgc    12300
tgctaatagc gcccttcacg gacagtggca gcgtgtcccg ggacacatac ctaggtcact    12360
```

```
tgctgacact gtaccgcgag gccataggtc aggcgcatgt ggacgagcat actttccagg   12420
agattacaag tgtcagccgc gcgctggggc aggaggacac gggcagcctg gaggcaaccc   12480
taaactacct gctgaccaac cggcggcaga agatcccctc gttgcacagt ttaaacagcg   12540
aggaggagcg cattttgcgc tacgtgcagc agagcgtgag ccttaacctg atgcgcgacg   12600
gggtaacgcc cagcgtggcg ctggacatga ccgcgcgcaa catggaaccg ggcatgtatg   12660
cctcaaaccg gccgtttatc aaccgcctaa tggactactt gcatcgcgcg gccgccgtga   12720
accccgagta tttcaccaat gccatcttga acccgcactg gctaccgccc cctggtttct   12780
acaccggggg attcgaggtg cccgagggta acgatggatt cctctgggac gacatagacg   12840
acagcgtgtt ttccccgcaa ccgcagaccc tgctagagtt gcaacagcgc gagcaggcag   12900
aggcggcgct gcgaaaggaa agcttccgca ggccaagcag cttgtccgat ctaggcgctg   12960
cggccccgcg gtcagatgct agtagcccat ttccaagctt gatagggtct cttaccagca   13020
ctcgcaccac ccgcccgcgc ctgctgggcg aggaggagta cctaaacaac tcgctgctgc   13080
agccgcagcg cgaaaaaaac ctgcctccgg catttcccaa caacgggata gagagcctag   13140
tggacaagat gagtagatgg aagacgtacg cgcaggagca cagggacgtg ccaggcccgc   13200
gcccgcccac ccgtcgtcaa aggcacgacc gtcagcgggg tctggtgtgg gaggacgatg   13260
actcggcaga cgacagcagc gtcctggatt tgggagggag tggcaacccg tttgcgcacc   13320
ttcgccccag gctggggaga atgttttaaa aaaaaaaaaa gcatgatgca aataaaaaa    13380 ctcaccaagg ccatggcacc gagcgttggt tttcttgtat tccccttagt atgcggcgcg   13440
cggcgatgta tgaggaaggt cctcctccct cctacgagag tgtggtgagc gcggcgccag   13500
tggcggcggc gctgggttct cccttcgatg ctcccctgga cccgccgttt gtgcctccgc   13560
ggtacctgcg gcctaccggg gggagaaaca gcatccgtta ctctgagttg caccccctat   13620
tcgacaccac ccgtgtgtac ctggtggaca acaagtcaac ggatgtggca tccctgaact   13680
accagaacga ccacagcaac tttctgacca cggtcattca aaacaatgac tacagcccgg   13740
gggaggcaag cacacagacc atcaatcttg cgaccggtc gcactggggc ggcgacctga   13800
aaaccatcct gcataccaac atgccaaatg tgaacgagtt catgtttacc aataagttta   13860
aggcgcgggt gatggtgtcg cgcttgccta ctaaggacaa tcaggtggag ctgaaatacg   13920
agtgggtgga gttcacgctg cccgagggca actactccga gaccatgacc atagaccttc   13980
tgaacaacgc gatcgtggag cactacttga aagtgggcag acagaacggg ttctggaaa    14040 gcgacatcgg ggtaaagttt gacacccgca acttcagact ggggtttgac cccgtcactg   14100
gtcttgtcat gcctgggta tatacaaacg aagccttcca tccagacatc attttgctgc    14160
caggatgcgg ggtggacttc acccacagcc gcctgagcaa cttgttgggc atccgcaagc   14220
ggcaaccctt ccaggagggc tttaggatca cctacgatga tctggagggt ggtaacattc   14280
ccgcactgtt ggatgtggac gcctaccagg cgagcttgaa agatgacacc gaacagggcg   14340
ggggtggcgc aggcggcagc aacagcagtg gcagcggcgc ggaagagaac tccaacgcgg   14400
cagccgcggc aatgcagccg gtggaggaca tgaacgatca tgccattcgc ggcgacacct   14460
ttgccacacg ggctgaggag aagcgcgctg aggccgaagc agcggccgaa gctgccgccc   14520
ccgctgcgca acccgaggtc gagaagcctc agaagaaacc ggtgatcaaa ccctgacag    14580 aggacagcaa gaaacgcagt tacaacctaa taagcaatga cagcaccttc acccagtacc   14640
gcagctggta ccttgcatac aactacgcg accctcagac cggaatccgc tcatggaccc    14700
tgctttgcac tcctgacgta acctgcggct cggagcaggt ctactggtcg ttgccagaca   14760
```

```
tgatgcaaga ccccgtgacc ttccgctcca cgcgccagat cagcaacttt ccggtggtgg   14820
gcgccgagct gttgcccgtg cactccaaga gcttctacaa cgaccaggcc gtctactccc   14880
aactcatccg ccagtttacc tctctgaccc acgtgttcaa tcgctttccc gagaaccaga   14940
ttttggcgcg cccgccagcc cccaccatca ccaccgtcag tgaaaacgtt cctgctctca   15000
cagatcacgg gacgctaccg ctgcgcaaca gcatcggagg agtccagcga gtgaccatta   15060
ctgacgccag acgccgcacc tgccctacg tttacaaggc cctgggcata gtctcgccgc   15120
gcgtcctatc gagccgcact ttttgagcaa gcatgtccat ccttatatcg cccagcaata   15180
acacaggctg gggcctgcgc ttcccaagca agatgtttgg cggggccaag aagcgctccg   15240
accaacaccc agtgcgcgtg cgcgggcact accgcgcgcc ctgggcgcg cacaaacgcg   15300 gccgcactgg gcgcaccacc gtcgatgacg ccatcgacgc ggtggtggag gaggcgcgca   15360
actacacgcc cacgccgcca ccagtgtcca cagtggacgc ggccattcag accgtggtgc   15420
gcggagcccg gcgctatgct aaaatgaaga cacggcggag gcgcgtagca cgtcgccacc   15480
gccgccgacc cggcactgcc gcccaacgcg cggcggcggc cctgcttaac cgcgcacgtc   15540
gcaccggccg acgggcggcc atgcgggccg ctcgaaggct ggccgcgggt attgtcactg   15600 tgcccccag gtccaggcga cgagcggccg ccgcagcagc cgcggccatt agtgctatga   15660
ctcagggtcg caggggcaac gtgtattggg tgcgcgactc ggttagcggc ctgcgcgtgc   15720
ccgtgcgcac ccgccccccg cgcaactaga ttgcaagaaa aaactactta gactcgtact   15780
gttgtatgta tccagcggcg gcggcgcgca acgaagctat gtccaagcgc aaaatcaaag   15840
aagagatgct ccaggtcatc gcgccggaga tctatggccc cccgaagaag gaagagcagg   15900
attacaagcc ccgaaagcta aagcgggtca aaaagaaaaa gaaagatgat gatgatgaac   15960 tgacgacga ggtggaactg ctgcacgcta ccgcgcccag gcgacgggta cagtggaaag   16020
gtcgacgcgt aaaacgtgtt ttgcgacccg gcaccaccgt agtctttacg cccggtgagc   16080
gctccacccg cacctacaag cgcgtgtatg atgaggtgta cggcgacgag gacctgcttg   16140
agcaggccaa cgagcgcctc ggggagtttg cctacgaaaa gcggcataag gacatgctgg   16200
cgttgccgct ggacgagggc aacccaacac ctagcctaaa gcccgtaaca ctgcagcagg   16260
tgctgcccgc gcttgcaccg tccgaagaaa agcgcggcct aaagcgcgag tctggtgact   16320
tggcacccac cgtgcagctg atggtaccca agcgccagcg actggaagat gtcttggaaa   16380
aaatgaccgt ggaacctggg ctggagcccg aggtccgcgt gcggccaatc aagcaggtgg   16440
cgccgggact gggcgtgcag accgtggacg ttcagatacc cactaccagt agcaccagta   16500
ttgccaccgc cacagagggc atggagacac aaacgtcccc ggttgcctca gcggtggcgg   16560
atgccgcggt gcaggcggtc gctgcggccg cgtccaagac ctctacggag gtgcaaacgg   16620
acccgtggat gtttcgcgtt tcagcccccc ggcgcccgcg ccgttcgagg aagtacggcg   16680
ccgccagcgc gctactgccc gaatatgccc tacatccttc cattgcgcct accccggct   16740 atcgtggcta cacctaccgc cccagaagac gagcaactac ccgacgccga accaccactg   16800
gaacccgccg ccgccgtcgc cgtcgccagc ccgtgctggc cccgatttcc gtgcgcaggg   16860
tggctcgcga aggaggcagg accctggtgc tgccaacagc gcgctaccac cccagcatcg   16920
tttaaaagcc ggtctttgtg gttcttgcag atatggccct cacctgccgc ctccgtttcc   16980
cggtgccgga attccgagga agaatgcacc gtaggagggg catggccggc cacggcctga   17040
cgggcggcat gcgtcgtgcg caccaccggc ggcggcgcgc gtcgcaccgt cgcatgcgcg   17100
```

```
gcggtatcct gccctccctt attccactga tcgccgcggc gattggcgcc gtgcccggaa   17160
ttgcatccgt ggccttgcag gcgcagagac actgattaaa aacaagttgc atgtggaaaa   17220
atcaaaataa aaagtctgga ctctcacgct cgcttggtcc tgtaactatt ttgtagaatg   17280
gaagacatca actttgcgtc tctggccccg cgacacggct cgcgcccgtt catgggaaac   17340
tggcaagata tcggcaccag caatatgagc ggtggcgcct tcagctgggg ctcgctgtgg   17400
agcggcatta aaaatttcgg ttccaccgtt aagaactatg cagcaaggc  ctggaacagc    17460 agcacaggcc agatgctgag ggataagttg aaagagcaaa atttccaaca aaggtggta    17520 gatggcctgg cctctggcat tagcggggtg gtggacctgg ccaaccaggc agtgcaaaat   17580
aagattaaca gtaagcttga tccccgccct cccgtagagg agcctccacc ggccgtggag   17640
acagtgtctc cagaggggcg tggcgaaaag cgtccgcgcc ccgacaggga agaaactctg   17700
gtgacgcaaa tagacgagcc tccctcgtac gaggaggcac taaagcaagg cctgcccacc   17760
acccgtccca tcgcgcccat ggctaccgga gtgctgggcc agcacacacc cgtaacgctg   17820
gacctgcctc ccccgccga cacccagcag aaacctgtgc tgccaggccc gaccgccgtt    17880
gttgtaaccc gtcctagccg cgcgtccctg cgccgcgccg ccagcggtcc gcgatcgttg   17940
cggcccgtag ccagtggcaa ctggcaaagc acactgaaca gcatcgtggg tctggggtg   18000 caatccctga agcgccgacg atgcttctga tagctaacgt gtcgtatgtg tgtcatgtat   18060
gcgtccatgt cgccgccaga ggagctgctg agccgccgcg cgcccgcttt ccaagatggc   18120
taccccttcg atgatgccgc agtggtctta catgcacatc tcgggccagg acgcctcgga   18180
gtacctgagc cccgggctgg tgcagtttgc ccgcgccacc gagacgtact tcagcctgaa   18240
taacaagttt agaaaccccca cggtggcgcc tacgcacgac gtgaccacag accggtccca   18300
gcgtttgacg ctgcggttca tccctgtgga ccgtgaggat actgcgtact cgtacaaggc   18360
gcggttcacc ctagctgtgg gtgataaccg tgtgctggac atggcttcca cgtactttga   18420
catccgcggc gtgctggaca ggggccctac ttttaagccc tactctggca ctgcctacaa   18480
cgccctggct cccaagggtg ccccaaatcc ttgcgaatgg gatgaagctg ctactgctct   18540
tgaaataaac ctagaagaag aggacgatga caacgaagac gaagtagacg agcaagctga   18600
gcagcaaaaa actcacgtat ttgggcaggc gccttattct ggtataaata ttacaaagga   18660
gggtattcaa ataggtgtcg aaggtcaaac acctaaatat gccgataaaa catttcaacc   18720
tgaacctcaa ataggagaat ctcagtggta cgaaacagaa attaatcatg cagctgggag   18780
agtcctaaaa aagactaccc caatgaaacc atgttacggt tcatatgcaa acccacaaa   18840 tgaaaatgga gggcaaggca ttcttgtaaa gcaacaaaat ggaaagctag aaagtcaagt   18900
ggaaatgcaa ttttttctcaa ctactgaggc agccgcaggc aatggtgata acttgactcc   18960
taaagtggta ttgtacagtg aagatgtaga tatagaaacc ccagacactc atatttctta   19020
catgcccact attaaggaag gtaactcacg agaactaatg ggccaacaat ctatgcccaa   19080
caggcctaat tacattgctt ttagggacaa ttttattggt ctaatgtatt acaacagcac   19140
gggtaatatg ggtgttctgg cgggccaagc atcgcagttg aatgctgttg tagatttgca   19200
agacagaaac acagagcttt cataccagct tttgcttgat tccattggtg atagaaccag   19260
gtacttttct atgtggaatc aggctgttga cagctatgat ccagatgtta gaattattga   19320
aaatcatgga actgaagatg aacttccaaa ttactgcttt ccactgggag gtgtgattaa   19380
tacagagact cttaccaagg taaacctaa aacaggtcag gaaaatggat gggaaaaga    19440 tgctacagaa ttttcagata aaaatgaaat aagagttgga aataatttg ccatggaaat    19500
```

```
caatctaaat gccaacctgt ggagaaattt cctgtactcc aacatagcgc tgtatttgcc    19560
cgacaagcta aagtacagtc cttccaacgt aaaaatttct gataacccaa acacctacga    19620
ctacatgaac aagcgagtgg tggctcccgg gctagtggac tgctacatta accttggagc    19680
acgctggtcc cttgactata tggacaacgt caacccattt aaccaccacc gcaatgctgg    19740
cctgcgctac cgctcaatgt tgctgggcaa tggtcgctat gtgcccttcc acatccaggt    19800
gcctcagaag ttctttgcca ttaaaaacct ccttctcctg ccgggctcat acacctacga    19860
gtggaacttc aggaaggatg ttaacatggt tctgcagagc tccctaggaa atgacctaag    19920
ggttgacgga gccagcatta agtttgatag catttgcctt tacgccacct tcttccccat    19980
ggcccacaac accgcctcca cgcttgaggc catgcttaga aacgacacca acgaccagtc    20040
ctttaacgac tatctctccg ccgccaacat gctctaccct atacccgcca acgctaccaa    20100
cgtgcccata tccatcccct cccgcaactg ggcggctttc cgcggctggg ccttcacgcg    20160
ccttaagact aaggaaaccc catcactggg ctcgggctac gacccttatt acacctactc    20220
tggctctata ccctacctag atggaacctt ttacctcaac cacacccttta agaaggtggc    20280 cattaccttt gactcttctg tcagctggcc tggcaatgac cgcctgctta ccccaacga    20340 gtttgaaatt aagcgctcag ttgacgggga gggttacaac gttgcccagt gtaacatgac    20400
caaagactgg ttcctggtac aaatgctagc taactataac attggctacc agggcttcta    20460
tatcccagag agctacaagg accgcatgta ctccttcttt agaaacttcc agcccatgag    20520
ccgtcaggtg gtggatgata ctaaatacaa ggactaccaa caggtgggca tcctacacca    20580
acacaacaac tctggatttg ttggctacct tgcccccacc atgcgcgaag acaggccta    20640 ccctgctaac ttcccctatc cgcttatagg caagaccgca gttgacagca ttacccagaa    20700
aaagtttctt tgcgatcgca cccttttggcg catcccattc tccagtaact ttatgtccat    20760
gggcgcactc acagacctgg gccaaaacct tctctacgcc aactccgccc acgcgctaga    20820
catgactttt gaggtggatc ccatggacga gcccacccct ctttatgttt tgtttgaagt    20880
ctttgacgtg gtccgtgtgc accagccgca ccgcggcgtc atcgaaaccg tgtacctgcg    20940
cacgcccttc tcggccggca cgccacaac ataaagaagc aagcaacatc aacaacagct    21000
gccgccatgg gctccagtga gcaggaactg aaagccattg tcaaagatct tggttgtggg    21060 ccatatttt tgggcaccta tgacaagcgc tttccaggct ttgttctcc acacaagctc    21120 gcctgcgcca tagtcaatac ggccggtcgc gagactgggg gcgtacactg gatggccttt    21180
gcctggaacc cgcactcaaa acatgctac ctctttgagc cctttggctt ttctgaccag    21240
cgactcaagc aggtttacca gtttgagtac gagtcactcc tgcgccgtag cgccattgct    21300
tcttcccccg accgctgtat aacgctgaa agtccaccc aaagcgtaca ggggcccaac    21360
tcggccgcct gtggactatt ctgctgcatg tttctccacg cctttgccaa ctggccccaa    21420
actcccatga tcacaacccc caccatgaac cttattaccg gggtacccaa ctccatgctc    21480
aacagtcccc aggtacagcc caccctgcgt cgcaaccagg aacagctcta cagcttcctg    21540
gagcgccact cgccctactt ccgcagccac agtgcgcaga ttaggagcgc cacttctttt    21600
tgtcacttga aaaacatgta aaaataatgt actagagaca ctttcaataa aggcaaatgc    21660
ttttatttgt acactctcgg gtgattattt accccacccc ttgccgtctg cgccgtttaa    21720
aaatcaaagg ggttctgccg cgcatcgcta tgcgccactg gcagggacac gttgcgatac    21780
tggtgtttag tgctccactt aaactcaggc acaaccatcc gcggcagctc ggtgaagttt    21840
```

```
tcactccaca ggctgcgcac catcaccaac gcgtttagca ggtcgggcgc cgatatcttg   21900
aagtcgcagt tggggcctcc gccctgcgcg cgcgagttgc gatacacagg gttgcagcac   21960
tggaacacta tcagcgccgg gtggtgcacg ctggccagca cgctcttgtc ggagatcaga   22020
tccgcgtcca ggtcctccgc gttgctcagg gcgaacggag tcaactttgg tagctgcctt   22080
cccaaaaagg gcgcgtgccc aggctttgag ttgcactcgc accgtagtgg catcaaaagg   22140
tgaccgtgcc cggtctgggc gttaggatac agcgcctgca taaaagcctt gatctgctta   22200
aaagccacct gagcctttgc gccttcagag aagaacatgc cgcaagactt gccggaaaac   22260
tgattggccg gacaggccgc gtcgtgcacg cagcaccttg cgtcggtgtt ggagatctgc   22320
accacatttc ggccccaccg gttcttcacg atcttggcct tgctagactg ctccttcagc   22380
gcgcgctgcc cgttttcgct cgtcacatcc atttcaatca cgtgctcctt atttatcata   22440
atgcttccgt gtagacactt aagctcgcct tcgatctcag cgcagcggtg cagccacaac   22500
gcgcagcccg tgggctcgtg atgcttgtag gtcacctctg caaacgactg caggtacgcc   22560
tgcaggaatc gccccatcat cgtcacaaag gtcttgttgc tggtgaaggt cagctgcaac   22620
ccgcggtgct cctcgttcag ccaggtcttg catacggccg ccagagcttc cacttggtca   22680
ggcagtagtt tgaagttcgc cttagatcg ttatccacgt ggtacttgtc catcagcgcg   22740
cgcgcagcct ccatgccctt ctcccacgca gacacgatcg gcacactcag cgggttcatc   22800
accgtaattt cactttccgc ttcgctgggc tcttcctctt cctcttgcgt ccgcatacca   22860
cgcgccactg ggtcgtcttc attcagccgc cgcactgtgc gcttacctcc tttgccatgc   22920
ttgattagca ccggtgggtt gctgaaaccc accatttgta cgccacatc ttctctttct   22980
tcctcgctgt ccacgattac ctctggtgat ggcgggcgct cgggcttggg agaagggcgc   23040
ttcttttct tcttgggcgc aatggccaaa tccgccgccg aggtcgatgg ccgcgggctg   23100
ggtgtgcgcg gcaccagcgc gtcttgtgat gagtcttcct cgtcctcgga ctcgatacgc   23160
cgcctcatcc gcttttttgg gggcgcccgg ggaggcggcg cgacgggga cggggacgac   23220
acgtcctcca tggttggggg acgtcgcgcc gcaccgcgtc cgcgctcggg ggtggtttcg   23280
cgctgctcct cttcccgact ggccatttcc ttctcctata ggcagaaaaa gatcatggag   23340
tcagtcgaga agaaggacag cctaaccgcc ccctctgagt tcgccaccac cgcctccacc   23400
gatgccgcca acgcgcctac caccttcccc gtcgaggcac ccccgcttga ggaggaggaa   23460
gtgattatcg agcaggaccc aggttttgta agcgaagacg acgaggaccg ctcagtacca   23520
acagaggata aaaagcaaga ccaggacaac gcagaggcaa acgaggaaca agtcgggcgg   23580
ggggacgaaa ggcatggcga ctacctagat gtgggagacg acgtgctgtt gaagcatctg   23640
cagcgccagt gcgccattat ctgcgacgcg ttgcaagagc gcagcgatgt gcccctcgcc   23700
atagcggatg tcagccttgc ctacgaacgc caccattct caccgcgcgt accccccaaa   23760
cgccaagaaa acggcacatg cgagcccaac ccgcgcctca acttctaccc cgtatttgcc   23820
gtgccagagg tgcttgccac ctatcacatc ttttttccaaa actgcaagat accctatcc   23880
tgccgtgcca accgcagccg agcggacaag cagctggcct gcggcagggg cgctgtcata   23940
cctgatatcg cctcgctcaa cgaagtgcca aaaatctttg agggtcttgg acgcgacgag   24000
aagcgcgcgg caaacgctct gcaacaggaa aacagcgaaa atgaaagtca ctctggagtg   24060
ttggtggaac tcgaggggtga caacgcgcgc ctagccgtac taaaacgcag catcgaggtc   24120
acccactttg cctacccggc acttaaccta ccccccaagg tcatgagcac agtcatgagt   24180
gagctgatcg tgcgccgtgc gcagcccctg gagagggatg caaatttgca agaacaaaca   24240
```

```
gaggagggcc tacccgcagt tggcgacgag cagctagcgc gctggcttca aacgcgcgag   24300
cctgccgact tggaggagcg acgcaaacta atgatggccg cagtgctcgt taccgtggag   24360
cttgagtgca tgcagcggtt ctttgctgac ccggagatgc agcgcaagct agaggaaaca   24420
ttgcactaca cctttcgaca gggctacgta cgccaggcct gcaagatctc caacgtggag   24480
ctctgcaacc tggtctccta ccttggaatt ttgcacgaaa accgccttgg caaaacgtg    24540 cttcattcca cgctcaaggg cgaggcgcgc cgcgactacg tccgcgactg cgtttactta   24600
tttctatgct acacctggca gacggccatg ggcgtttggc agcagtgctt ggaggagtgc   24660
aacctcaagg agctgcagaa actgctaaag caaaacttga aggacctatg acggccttc    24720 aacgagcgct ccgtggccgc gcacctggcg gacatcattt tccccgaacg cctgcttaaa   24780
accctgcaac agggtctgcc agacttcacc agtcaaagca tgttgcagaa ctttaggaac   24840
tttatcctag agcgctcagg aatcttgccc gccacctgct gtgcacttcc tagcgacttt   24900
gtgcccatta gtaccgcga atgccctccg ccgctttggg gccactgcta ccttctgcag   24960
ctagccaact accttgccta ccactctgac ataatggaag acgtgagcgg tgacggtcta   25020
ctggagtgtc actgtcgctg caacctatgc accccgcacc gctccctggt ttgcaattcg   25080
cagctgctta acgaaagtca aattatcggt acctttgagc tgcagggtcc ctcgcctgac   25140
gaaaagtccg cggctccggg gttgaaactc actccggggc tgtggacgtc ggcttacctt   25200
cgcaaatttg tacctgagga ctaccacgcc cacgagatta ggttctacga agaccaatcc   25260
cgcccgccta atgcggagct taccgcctgc gtcattaccc agggccacat tcttggccaa   25320
ttgcaagcca tcaacaaagc ccgccaagag tttctgctac gaaagggacg ggggtttac    25380 ttggaccccc agtccggcga ggagctcaac ccaatccccc cgccgccgca gccctatcag   25440
cagcagccgc gggcccttgc ttcccaggat ggcacccaaa agaagctgc agctgccgcc    25500 gccacccacg gacgaggagg aatactggga cagtcaggca gaggaggttt tggacgagga   25560
ggaggaggac atgatggaag actgggagag cctagacgag gaagcttccg aggtcgaaga   25620
ggtgtcagac gaaacaccgt caccctcggt cgcattcccc tcgccggcgc cccagaaatc   25680
ggcaaccggt tccagcatgg ctacaacctc cgctcctcag gcgccgccgg cactgcccgt   25740
tcgccgaccc aaccgtagat gggacaccac tggaaccagg gccggtaagt ccaagcagcc   25800
gccgccgtta gcccaagagc aacaacgcg ccaaggctac cgctcatggc gcgggcacaa    25860
gaacgccata gttgcttgct tgcaagactg tgggggcaac atctccttcg cccgccgctt   25920
tcttctctac catcacggcg tggccttccc ccgtaacatc ctgcattact accgtcatct   25980
ctacagccca tactgcaccg gcggcagcgg cagcaacagc agcggccaca cagaagcaaa   26040
ggcgaccgga tagcaagact ctgacaaagc ccaagaaatc cacagcggcg gcagcagcag   26100
gaggaggagc gctgcgtctg gcgcccaacg aacccgtatc gacccgcgag cttagaaaca   26160
ggatttttcc cactctgtat gctatatttc aacagagcag gggccaagaa caagagctga   26220
aaataaaaaa caggtctctg cgatccctca cccgcagctg cctgtatcac aaaagcgaag   26280
atcagcttcg gcgcacgctg gaagacgcgg aggctctctt cagtaaatac tgcgcgctga   26340
ctcttaagga ctagtttcgc gcccttctc aaatttaagc gcgaaaacta cgtcatctcc    26400
agcggccaca cccggcgcca gcacctgttg tcagcgccat tatgagcaag gaaattccca   26460
cgccctacat gtggagttac cagccacaaa tgggacttgc ggctgagct gcccaagact    26520 actcaacccg aataaactac atgagcgcgg gaccccacat gatatcccgg gtcaacggaa   26580
```

-continued

```
tacgcgccca ccgaaaccga attctcctgg aacaggcggc tattaccacc acacctcgta   26640
ataaccttaa tccccgtagt tggcccgctg ccctggtgta ccaggaaagt cccgctccca   26700
ccactgtggt acttcccaga gacgcccagg ccgaagttca gatgactaac tcagggcgc    26760 agcttgcggg cggctttcgt cacagggtgc ggtcgcccgg gcagggtata actcacctga   26820
caatcagagg gcgaggtatt cagctcaacg acgagtcggt gagctcctcg cttggtctcc   26880
gtccggacgg gacatttcag atcggcggcg ccggccgctc ttcattcacg cctcgtcagg   26940
caatcctaac tctgcagacc tcgtcctctg agccgcgctc tggaggcatt ggaactctgc   27000
aatttattga ggagtttgtg ccatcggtct actttaaccc cttctcggga cctcccggcc   27060
actatccgga tcaatttatt cctaactttg acgcggtaaa ggactcggcg gacggctacg   27120
actgaatgtt aagtggagag gcagagcaac tgcgcctgaa acacctggtc cactgtcgcc   27180
gccacaagtg ctttgcccgc gactccggtg agttttgcta ctttgaattg cccgaggatc   27240
atatcgaggg cccggcgcac ggcgtccggc ttaccgccca gggagagctt gcccgtagcc   27300
tgattcggga gtttacccag cgcccctgc tagttgagcg ggacagggga ccctgtgttc    27360
tcactgtgat ttgcaactgt cctaaccctg gattacatca agatctttgt tgccatctct   27420
gtgctgagta taataaatac agaaattaaa atatactggg gctcctatcg ccatcctgta   27480
aacgccaccg tcttcacccg cccaagcaaa ccaaggcgaa ccttacctgg tacttttaac   27540
atctctccct ctgtgattta caacagtttc aacccagacg gagtgagtct acgagagaac   27600
ctctccgagc tcagctactc catcagaaaa aacaccaccc tccttacctg ccgggaacgt   27660
acgagtgcgt caccggccgc tgcaccacac ctaccgcctg accgtaaacc agactttttc   27720
cggacagacc tcaataactc tgtttaccag aacaggaggt gagcttagaa aacccttagg   27780
gtattaggcc aaaggcgcag ctactgtggg gtttatgaac aattcaagca actctacggg   27840
ctattctaat tcaggtttct ctagaatcgg ggttggggtt attctctgtc ttgtgattct   27900
ctttattctt atactaacgc ttctctgcct aaggctcgcc gcctgctgtg tgcacatttg   27960
catttattgt cagctttta aacgctgggg tcgccaccca agatgattag gtacataatc   28020
ctaggtttac tcacccttgc gtcagcccac ggtaccaccc aaaaggtgga ttttaaggag   28080
ccagcctgta atgttacatt cgcagctgaa gctaatgagt gcaccactct tataaaatgc   28140
accacagaac atgaaaagct gcttattcgc cacaaaaaca aaattggcaa gtatgctgtt   28200 tatgctatt ggcagccagg tgacactaca gagtataatg ttacagtttt ccagggtaaa   28260
agtcataaaa cttttatgta tactttccca ttttatgaaa tgtgcgacat taccatgtac   28320
atgagcaaac agtataagtt gtggccccca caaaattgtg tggaaaacac tggcactttc   28380
tgctgcactg ctatgctaat tacagtgctc gctttggtct gtaccctact ctatattaaa   28440
tacaaaagca gacgcagctt tattgaggaa aagaaaatgc cttaatttac taagttacaa   28500
agctaatgtc accactaact gctttactcg ctgcttgcaa aacaaattca aaagttagc    28560 attataatta gaataggatt taaacccccc ggtcatttcc tgctcaatac cattcccctg   28620
aacaattgac tctatgtggg atatgctcca gcgctacaac cttgaagtca ggcttcctgg   28680
atgtcagcat ctgactttgg ccagcacctg tcccgcggat ttgttccagt ccaactacag   28740
cgacccaccc taacagagat gaccaacaca accaacgcgg ccgccgctac cggacttaca   28800
tctaccacaa atacacccca agtttctgcc tttgtcaata actgggataa cttgggcatg   28860
tggtggttct ccatagcgct tatgtttgta tgccttatta ttatgtggct catctgctgc   28920
ctaaagcgca aacgcgcccg accacccatc tatagtccca tcattgtgct acacccaaac   28980
```

```
aatgatggaa tccatagatt ggacggactg aaacacatgt tcttttctct tacagtatga    29040
ttaaatgaga catgattcct cgagttttta tattactgac ccttgttgcg cttttttgt     29100
gcgtgctcca cattggctgc ggtttctcac atcgaagtag actgcattcc agccttcaca    29160
gtctatttgc tttacggatt tgtcaccctc acgctcatct gcagcctcat cactgtggtc    29220
atcgccttta tccagtgcat tgactgggtc tgtgtgcgct ttgcatatct cagacaccat    29280
ccccagtaca gggacaggac tatagctgag cttcttagaa ttctttaatt atgaaattta    29340
ctgtgacttt tctgctgatt atttgcaccc tatctgcgtt ttgttccccg acctccaagc    29400
ctcaaagaca tatatcatgc agattcactc gtatatggaa tattccaagt tgctacaatg    29460
aaaaaagcga tctttccgaa gcctggttat atgcaatcat ctctgttatg gtgttctgca    29520
gtaccatctt agccctagct atatatccct accttgacat tggctggaac gcaatagatg    29580
ccatgaacca cccaactttc cccgcgcccg ctatgcttcc actgcaacaa gttgttgccg    29640
gcggctttgt cccagccaat cagcctcgcc caccttctcc cacccccact gaaatcagct    29700
actttaatct aacaggagga gatgactgac accctagatc tagaaatgga cggaattatt    29760
acagagcagc gcctgctaga aagacgcagg gcagcggccg agcaacagcg catgaatcaa    29820
gagctccaag acatggttaa cttgcaccag tgcaaaaggg gtatcttttg tctggtaaag    29880
caggccaaag tcacctacga cagtaatacc accggacacc gccttagcta caagttgcca    29940
accaagcgtc agaaattggt ggtcatggtg ggagaaaagc ccattaccat aactcagcac    30000
tcggtagaaa ccgaaggctg cattcactca ccttgtcaag gacctgagga tctctgcacc    30060
cttattaaga ccctgtgcgg tctcaaagat cttattccct ttaactaata aaaaaaaata    30120
ataaagcatc acttacttaa aatcagttag caaatttctg tccagtttat tcagcagcac    30180
ctccttgccc tcctcccagc tctggtattg cagcttcctc ctggctgcaa actttctcca    30240
caatctaaat ggaatgtcag tttcctcctg ttcctgtcca tccgcaccca ctatcttcat    30300
gttgttgcag atgaagcgcg caagaccgtc tgaagatacc ttcaaccccg tgtatccata    30360
tgacacggaa accggtcctc caactgtgcc ttttcttact cctcccttg tatcccccaa     30420
tgggtttcaa gagagtcccc ctggggtact ctctttgcgc ctatccgaac ctctagttac    30480
ctccaatggc atgcttgcgc tcaaaatggg caacggcctc tctctggacg aggccggcaa    30540
ccttacctcc caaaatgtaa ccactgtgag cccacctctc aaaaaaacca agtcaaacat    30600
aaacctggaa atatctgcac ccctcacagt tacctcagaa gccctaactg tggctgccgc    30660
cgcacctcta atggtcgcgg gcaacacact caccatgcaa tcacaggccc cgctaaccgt    30720
gcacgactcc aaacttagca ttgccaccca aggaccoctc acagtgtcag aaggaaagct    30780
agccctgcaa acatcaggcc ccctcaccac caccgatagc agtaccctta ctatcactgc    30840
ctcacccccct ctaactactg ccactggtag cttgggcatt gacttgaaag agcccattta    30900
tacacaaaat ggaaaactag gactaaagta cgggctcct ttgcatgtaa cagacgacct     30960
aaacactttg accgtagcaa ctggtccagg tgtgactatt aataatactt ccttgcaaac    31020
taaagttact ggagccttgg gttttgattc acaaggcaat atgcaactta atgtagcagg    31080
aggactaagg attgattctc aaaacagacg ccttatactt gatgttagtt atccgtttga    31140
tgctcaaaac caactaaatc taagactagg acagggccct cttttttataa actcagccca    31200
caacttggat attaactaca acaaaggcct ttacttgttt acagcttcaa acaattccaa    31260
aaagcttgag gttaacctaa gcactgccaa ggggttgatg tttgacgcta cagccatagc    31320
```

```
cattaatgca ggagatgggc ttgaatttgg ttcacctaat gcaccaaaca caaatcccct   31380
caaaacaaaa attggccatg gcctagaatt tgattcaaac aaggctatgg ttcctaaact   31440
aggaactggc cttagttttg acagcacagg tgccattaca gtaggaaaca aaataatga   31500 taagctaact ttgtggacca caccagctcc atctcctaac tgtagactaa atgcagagaa   31560
agatgctaaa ctcactttgg tcttaacaaa atgtggcagt caaatacttg ctacagtttc   31620
agttttggct gttaaaggca gtttggctcc aatatctgga acagttcaaa gtgctcatct   31680
tattataaga tttgacgaaa atggagtgct actaaacaat tccttcctgg acccagaata   31740
ttggaacttt agaatggag atcttactga aggcacagcc tatacaaacg ctgttggatt    31800
tatgcctaac ctatcagctt atccaaaatc tcacggtaaa actgccaaaa gtaacattgt   31860
cagtcaagtt tacttaaacg gagacaaaac taaacctgta acactaacca ttacactaaa   31920
cggtacacag gaaacaggag acacaactcc aagtgcatac tctatgtcat tttcatggga   31980
ctggtctggc cacaactaca ttaatgaaat atttgccaca tcctcttaca ctttttcata   32040
cattgcccaa gaataaagaa tcgtttgtgt tatgtttcaa cgtgtttatt tttcaattgc   32100
agaaaatttc aagtcatttt tcattcagta gtatagcccc accaccacat agcttataca   32160
gatcaccgta ccttaatcaa actcacagaa ccctagtatt caacctgcca cctccctccc   32220
aacacacaga gtacacagtc ctttctcccc ggctggcctt aaaaagcatc atatcatggg   32280
taacagacat attcttaggt gttatattcc acacggtttc ctgtcgagcc aaacgctcat   32340
cagtgatatt aataaactcc ccgggcagct cacttaagtt catgtcgctg tccagctgct   32400
gagccacagg ctgctgtcca acttgcggtt gcttaacggg cggcgaagga gaagtccacg   32460
cctacatggg ggtagagtca taatcgtgca tcaggatagg gcggtggtgc tgcagcagcg   32520
cgcgaataaa ctgctgccgc cgccgctccg tcctgcagga atacaacatg gcagtggtct   32580
cctcagcgat gattcgcacc gcccgcagca taaggcgcct tgtcctccgg gcacagcagc   32640
gcaccctgat ctcacttaaa tcagcacagt aactgcagca cagcaccaca atattgttca   32700
aaatcccaca gtgcaaggcg ctgtatccaa agctcatggc ggggaccaca gaacccacgt   32760
ggccatcata ccacaagcgc aggtagatta agtggcgacc cctcataaac acgctggaca   32820
taaacattac ctcttttggc atgttgtaat tcaccacctc ccggtaccat ataaacctct   32880
gattaaacat ggcgccatcc accaccatcc taaaccagct ggccaaaacc tgcccgccgg   32940
ctatacactg cagggaaccg ggactggaac aatgacagtg gagagcccag gactcgtaac   33000
catggatcat catgctcgtc atgatatcaa tgttggcaca acacaggcac acgtgcatac   33060
acttcctcag gattacaagc tcctcccgcg ttagaaccat atcccaggga acaacccatt   33120
cctgaatcag cgtaaatccc acactgcagg gaagacctcg cacgtaactc acgttgtgca   33180
ttgtcaaagt gttacattcg ggcagcagcg gatgatcctc cagtatggta gcgcgggttt   33240
ctgtctcaaa aggaggtaga cgatccctac tgtacggagt gcgccgagac aaccgagatc   33300
gtgttggtcg tagtgtcatg ccaaatggaa cgccggacgt agtcatattt cctgaagcaa   33360
aaccaggtgc gggcgtgaca aacagatctg cgtctccggt ctcgccgctt agatcgctct   33420
gtgtagtagt tgtagtatat ccactctctc aaagcatcca ggcgcccct ggcttcgggt    33480 tctatgtaaa ctccttcatg cgccgctgcc ctgataacat ccaccaccgc agaataagcc   33540
acacccagcc aacctacaca ttcgttctgc gagtcacaca cgggaggagc gggaagagct   33600
ggaagaacca tgtttttttt tttattccaa aagattatcc aaaacctcaa atgaagatc    33660 tattaagtga acgcgctccc ctccggtggc gtggtcaaac tctacagcca aagaacagat   33720
```

```
aatggcattt gtaagatgtt gcacaatggc ttccaaaagg caaacggccc tcacgtccaa    33780
gtggacgtaa aggctaaacc cttcagggtg aatctcctct ataaacattc cagcaccttc    33840
aaccatgccc aaataattct catctcgcca ccttctcaat atatctctaa gcaaatcccg    33900
aatattaagt ccggccattg taaaaatctg ctccagagcg ccctccacct tcagcctcaa    33960
gcagcgaatc atgattgcaa aaattcaggt tcctcacaga cctgtataag attcaaaagc    34020
ggaacattaa caaaaatacc gcgatcccgt aggtcccttc gcagggccag ctgaacataa    34080
tcgtgcaggt ctgcacggac cagcgcggcc acttccccgc caggaaccat gacaaaagaa    34140
cccacactga ttatgacacg catactcgga gctatgctaa ccagcgtagc cccgatgtaa    34200
gcttgttgca tgggcggcga tataaaatgc aaggtgctgc tcaaaaaatc aggcaaagcc    34260
tcgcgcaaaa aagaaagcac atcgtagtca tgctcatgca gataaaggca ggtaagctcc    34320
ggaaccacca cagaaaaaga caccattttt ctctcaaaca tgtctgcggg tttctgcata    34380
aacacaaaat aaaataacaa aaaaacattt aaacattaga agcctgtctt acaacaggaa    34440
aaacaaccct tataagcata agacggacta cggccatgcc ggcgtgaccg taaaaaaact    34500
ggtcaccgtg attaaaaagc accaccgaca gctcctcggt catgtccgga gtcataatgt    34560
aagactcggt aaacacatca ggttgattca catcggtcag tgctaaaaag cgaccgaaat    34620
agcccggggg aatacatacc cgcaggcgta gagacaacat tacagccccc ataggaggta    34680
taacaaaatt aataggagag aaaaacacat aaacacctga aaaccctcc tgcctaggca    34740
aaatagcacc ctcccgctcc agaacaacat acagcgcttc cacagcggca gccataacag    34800
tcagccttac cagtaaaaaa gaaaacctat taaaaaaaca ccactcgaca cggcaccagc    34860
tcaatcagtc acagtgtaaa aagggccaa gtgcagagcg agtatatata ggactaaaaa    34920
atgacgtaac ggttaaagtc cacaaaaaac acccagaaaa ccgcacgcga acctacgccc    34980
agaaacgaaa gccaaaaaac ccacaacttc ctcaaatcgt cacttccgtt ttcccacgtt    35040
acgtcacttc ccatttttaag aaaactacaa ttcccaacac atacaagtta ctccgcccta    35100
aaacctacgt cacccgcccc gttcccacgc cccgcgccac gtcacaaact ccaccccctc    35160
attatcatat tggcttcaat ccaaaataag gtatattatt gatgatg                 35207
```

<210> SEQ ID NO 20
<211> LENGTH: 35203
<212> TYPE: DNA
<213> ORGANISM: Artificial Sequence
<220> FEATURE:
<223> OTHER INFORMATION: Construct containing two mismatches with no duplication

<400> SEQUENCE: 20

```
catcatcaat aatataccttt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagtacgta cgtgtacttc tgatcggcga     480
tactagggag ataaggatgt acctgacaaa accacattgt tgttgttatc attattattt     540
```

```
agttttcctt ccttgctaac tcctgacgga atctttctca cctcaaatgc gaagtacttt    600
agtttagaaa agacttggtg aaggggtgg tggtggaaaa gtagggtgat cttccaaact    660
aatctggttc cccgcccgcc ccagtagctg ggattcaaga gcgaagagtg gggatcgtcc    720
ccttgtttga tcagaaagac ataaaaggaa atcaagtga acaatgatca gccccacctc    780
caccccaccc ccctgcgcgc gcacaataca atctatttaa ttgtacttca tacttttcat    840
tccaatgggg tgactttgct tctggagaaa ctcttgattc ttgaactctg gggctggcag    900
ctagcctcca gaagcaaagt caccccattg gaatgaaaag tatgaagtac aatgaaagt    960 atgaagtact ggctccagaa gcaaagtcac cctccagaag caaagtcacc ccattggaat   1020
gaaaagtatg aagtacgcta gcaaaggggg aagcgggctg ctgctctctg caggttctgc   1080
agcggtctct gtctagtggg tgttttcttt ttcttagccc tgcccctgga ttgtcagacg   1140
gcgggcgtct gcctctgaag ttagccgtga tttcctctag agccgggtct tatctctggc   1200
tgcacgttgc ctgtgggtga ctaatcacac aataacattg tttagggctg gaataaagtc   1260
agagctgttt accccccactc tatagggggtt caatataaaa aggcggcgga gaactgtccg   1320
agtcagaagc gttcctgcac cggcgctgag agcctgaccc ggtctgctcc gctgtccttg   1380
cgcgctgcct cccggctgcc cgcgacgctt tcgccccagt ggaagggcca cttgctgcgg   1440
ccgctaattc tgcagatcgg gatccggcat gggcctctcc accgtgcctg acctgctgct   1500
gccgctggtg ctcctggagc tgttggtggg aatataccc tcagggggtta ttggactggt   1560 ccctcaccta ggggacaggg agaagagaga tagtgtgtgt ccccaaggaa aatatatcca   1620
ccctcaaaat aattcgattt gctgtaccaa gtgccacaaa ggaacctact tgtacaatga   1680
ctgtccaggc ccggggcagg atacggactg cagggagtgt gagagcggct ccttcaccgc   1740
ttcagaaaac cacctcagac actgcctcag ctgctccaaa tgccgaaagg aaatgggtca   1800
ggtggagatc tcttcttgca cagtggaccg ggacaccgtg tgtggctgca ggaagaacca   1860
gtaccggcat tattggagtg aaaaccttt ccagtgcttc aattgcagcc tctgcctcaa   1920
tgggaccgtg cacctctcct gccaggagaa acagaacacc gtgtgcacct gccatgcagg   1980
tttctttcta agagaaaacg agtgtgtctc ctgtagtaac tgtaagaaaa gcctggagtg   2040
cacgaagttg tgcctaccaa gcttaggatc cagatctaac ttggggtggc tttgtcttct   2100
tcttttgcca attccactaa ttgtttgggt gaagagaaag gaagtacaga aaacatgcag   2160
aaagcacaga aaggaaaacc aaggttctca tgaatctcca accttaaatc ctgaaacagt   2220
ggcaataaat ttatctgatg ttgacttgag taaatatatc accactattg ctggagtcat   2280
gacactaagt caagttaaag gctttgttcg aaagaatggt gtcaatgaag ccaaaataga   2340
tgagatcaag aatgacaatg tccaagacac agcagaacag aaagttcaac tgcttcgtaa   2400
ttggcatcaa cttcatggaa agaaagaagc gtatgacaca ttgattaaag atctcaaaaa   2460
agccaatctt tgtactcttg cagagaaaat tcagactatc atcctcaagg acattactag   2520
tgactcagaa aattcaaact tcagaaatga atccaaagc ttggtctagc tcgagcatgc   2580
atctaggcgg ccgcatggca gaaattcgcg aattcgctag cgttaacgga tcctctagac   2640
gagatccgaa cttgttttatt gcagcttata atggttacaa ataaagcaat agcatcacaa   2700
atttcacaaa taaagcattt ttttcactgc attctagttg tggtttgtcc aaactcatca   2760
atgtatctta tcatgtctag atctgtactg aaatgtgtgg gcgtggctta agggtgggaa   2820
agaatatata aggtgggggt cttatgtagt tttgtatctg ttttgcagca gccgccgccg   2880
```

```
ccatgagcac caactcgttt gatggaagca ttgtgagctc atatttgaca acgcgcatgc    2940
ccccatgggc cggggtgcgt cagaatgtga tgggctccag cattgatggt cgccccgtcc    3000
tgcccgcaaa ctctactacc ttgacctacg agaccgtgtc tggaacgccg ttggagactg    3060
cagcctccgc cgccgcttca gccgctgcag ccaccgcccg cgggattgtg actgactttg    3120
cttttcctgag cccgcttgca agcagtgcag cttcccgttc atccgcccgc gatgacaagt    3180
tgacggctct tttggcacaa ttggattctt tgacccggga acttaatgtc gtttctcagc    3240
agctgttgga tctgcgccag caggtttctg ccctgaaggc ttcctcccct cccaatgcgg    3300
tttaaaacat aaataaaaaa ccagactctg tttggatttg atcaagcaa gtgtcttgct    3360
gtctttattt aggggttttg cgcgcgcggt aggcccggga ccagcggtct cggtcgttga    3420
gggtcctgtg tattttttcc aggacgtggt aaaggtgact ctggatgttc agatacatgg    3480
gcataagccc gtctctgggg tggaggtagc accactgcag agcttcatgc tgcggggtgg    3540
tgttgtagat gatccagtcg tagcaggagc gctgggcgtg gtgcctaaaa atgtctttca    3600
gtagcaagct gattgccagg ggcaggccct tggtgtaagt gtttacaaag cggttaagct    3660
gggatgggtg catacgtggg gatatgagat gcatcttgga ctgtattttt aggttggcta    3720
tgttcccagc catatccctc cggggattca tgttgtgcag aaccaccagc acagtgtatc    3780
cggtgcactt gggaaatttg tcatgtagct tagaaggaaa tgcgtggaag aacttggaga    3840
cgcccttgtg acctccaaga ttttccatgc attcgtccat aatgatgcca atgggcccac    3900
gggcggcggc ctgggcgaag atatttctgg gatcactaac gtcatagttg tgttccagga    3960
tgagatcgtc ataggccatt tttacaaagc gcggcggag ggtgccagac tgcggtataa    4020
tggttccatc cggcccaggg gcgtagttac cctcacagat ttgcatttcc cacgctttga    4080
gttcagatgg ggggatcatg tctacctgcg gggcgatgaa gaaaacggtt ccgggggtag    4140
gggagatcag ctgggaagaa agcaggttcc tgagcagctg cgacttaccg cagccggtgg    4200
gcccgtaaat cacacctatt accggctgca actggtagtt aagagagctg cagctgccgt    4260
catccctgag caggggggcc acttcgttaa gcatgtccct gactcgcatg ttttccctga    4320
ccaaatccgc cagaaggcgc tcgccgccca gcgatagcag ttcttgcaag gaagcaaagt    4380
ttttcaacgg tttgagaccg tccgccgtag gcatgctttt gagcgtttga ccaagcagtt    4440
ccaggcggtc ccacagctcg gtcacctgct ctacggcatc tcgatccagc atatctcctc    4500
gtttcgcggg ttggggcggc tttcgctgta cggcagtagt cggtgctcgt ccagacgggc    4560
cagggtcatg tctttccacg ggcgcagggt cctcgtcagc gtagtctggg tcacggtgaa    4620
ggggtgcgct ccgggctgcg cgctggccag ggtgcgcttg aggctggtcc tgctggtgct    4680
gaagcgctgc cggtcttcgc cctgcgcgtc ggccaggtag catttgacca tggtgtcata    4740
gtccagcccc tccgcggcgt ggcccttggc gcgcagcttg cccttggagg aggcgccgca    4800
cgaggggcag tgcagacttt tgagggcgta gagcttgggc gcgagaaata ccgattccgg    4860
ggagtaggca tccgcgccgc aggcccccgca gacggtctcg cattccacga gccaggtgag    4920
ctctggccgt tcggggtcaa aaaccaggtt tcccccatgc tttttgatgc gtttcttacc    4980
tctggtttcc atgagccggt gtccacgctc ggtgacgaaa aggctgtccg tgtcccgta    5040
tacagacttg agaggcctgt cctcgagcgg tgttccgcgg tcctcctcgt atagaaactc    5100
ggaccactct gagacaaagg ctcgcgtcca ggccagcacg aaggaggcta agtgggaggg    5160
gtagcggtcg ttgtccacta gggggtccac tcgctccagg gtgtgaagac acatgtcgcc    5220
ctcttcggca tcaaggaagg tgattggttt gtaggtgtag gccacgtgac cgggtgttcc    5280
```

```
tgaaggggggg ctataaaagg gggtgggggc gcgttcgtcc tcactctctt ccgcatcgct   5340
gtctgcgagg gccagctgtt ggggtgagta ctccctctga aaagcgggca tgacttctgc   5400
gctaagattg tcagtttcca aaaacgagga ggatttgata ttcacctggc ccgcggtgat   5460
gcctttgagg gtggccgcat ccatctggtc agaaaagaca atcttttgt tgtcaagctt    5520 ggtggcaaac gacccgtaga gggcgttgga cagcaacttg gcgatggagc gcagggtttg   5580 gttttttgtcg cgatcggcgc gctccttggc cgcgatgttt agctgcacgt attcgcgcgc  5640
aacgcaccgc cattcgggaa agacggtggt gcgctcgtcg ggcaccaggt gcacgcgcca   5700
accgcggttg tgcagggtga caaggtcaac gctggtggct acctctccgc gtaggcgctc   5760
gttggtccag cagaggcggc cgcccttgcg cgagcagaat ggcggtaggg ggtctagctg   5820
cgtctcgtcc gggggggtctg cgtccacggt aaagaccccg ggcagcaggc gcgcgtcgaa  5880
gtagtctatc ttgcatcctt gcaagtctag cgcctgctgc catgcgcggg cggcaagcgc   5940
gcgctcgtat gggttgagtg ggggaccccca tggcatgggg tgggtgagcg cggaggcgta  6000
catgccgcaa atgtcgtaaa cgtagagggg ctctctgagt attccaagat atgtagggta   6060
gcatcttcca ccgcggatgc tggcgcgcac gtaatcgtat agttcgtgcg agggagcgag   6120
gaggtcggga ccgaggttgc tacgggcggg ctgctctgct cggaagacta tctgcctgaa   6180
gatggcatgt gagttggatg atatggttgg acgctgaaag acgttgaagc tggcgtctgt   6240
gagacctacc gcgtcacgca cgaaggaggc gtaggagtcg cgcagcttgt tgaccagctc   6300
ggcggtgacc tgcacgtcta gggcgcagta gtccagggtt tccttgatga tgtcatactt   6360
atcctgtccc ttttttttcc acagctcgcg gttgaggaca aactcttcgc ggtctttcca   6420
gtactcttgg atcggaaacc cgtcggcctc cgaacggtaa gagcctagca tgtagaactg   6480
gttgacggcc tggtaggcgc agcatccctt ttctacgggt agcgcgtatg cctgcgcggc   6540
cttccggagc gaggtgtggg tgagcgcaaa ggtgtccctg accatgactt tgaggtactg   6600
gtatttgaag tcagtgtcgt cgcatccgcc ctgctcccag agcaaaaagt ccgtgcgctt   6660
tttggaacgc ggatttggca gggcgaaggt gacatcgttg aagagtatct ttcccgcgcg   6720
aggcataaag ttgcgtgtga tgcggaaggg tcccggcacc tcggaacggt tgttaattac   6780
ctgggcggcg agcacgatct cgtcaaagcc gttgatgttg tggcccacaa tgtaaagttc   6840
caagaagcgc gggatgccct tgatggaagg caattttttta agttcctcgt aggtgagctc   6900
ttcaggggag ctgagcccgt gctctgaaag ggcccagtct gcaagatgag ggttggaagc   6960
gacgaatgag ctccacaggt cacgggccat tagcatttgc aggtggtcgc gaaaggtcct   7020
aaactggcga cctatggcca ttttttctgg ggtgatgcag tagaaggtaa gcgggtcttg   7080
ttcccagcgg tcccatccaa ggttcgcggc taggtctcgc gcggcagtca ctagaggctc   7140
atctccgccg aacttcatga ccagcatgaa gggcacgagc tgcttcccaa aggcccccat   7200
ccaagtatag gtctctacat cgtaggtgac aaagagacgc tcggtgcgag gatgcgagcc   7260
gatcgggaag aactggatct cccgccacca attggaggag tggctattga tgtggtgaaa   7320
gtagaagtcc ctgcgacggg ccgaacactc gtgctggctt ttgtaaaaac gtgcgcagta   7380
ctggcagcgg tgcacgggct gtacatcctg cacgaggttg acctgacgac cgcgcacaag   7440
gaagcagagt gggaatttga gccctcgcc tggcgggttt ggctggtggt cttctacttc    7500
ggctgcttgt ccttgaccgt ctggctgctc gagggagtt acgtggatc ggaccaccac     7560 gccgcgcgag cccaaagtcc agatgtccgc gcgcggcggt cggagcttga tgacaacatc   7620
```

-continued

```
gcgcagatgg gagctgtcca tggtctggag ctcccgcggc gtcaggtcag gcgggagctc    7680
ctgcaggttt acctcgcata gacgggtcag ggcgcgggct agatccaggt gatacctaat    7740 ttccagggc tggttggtgg cggcgtcgat ggcttgcaag aggccgcatc cccgcggcgc     7800
gactacggta ccgcgcggcg ggcggtgggc gcgggggtg tccttggatg atgcatctaa     7860
aagcggtgac gcgggcgagc ccccggaggt agggggggct ccggaccgc cgggagaggg     7920 ggcaggggca cgtcggcgcc gcgcgcgggc aggagctggt gctgcgcgcg taggttgctg    7980
gcgaacgcga cgacgcggcg gttgatctcc tgaatctggc gcctctgcgt gaagacgacg    8040
ggcccggtga gcttgaacct gaaagagagt tcgacagaat caatttcggt gtcgttgacg    8100
gcggcctggc gcaaaatctc ctgcacgtct cctgagttgt cttgataggc gatctcggcc    8160
atgaactgct cgatctcttc ctcctggaga tctccgcgtc cggctcgctc cacggtggcg    8220
gcgaggtcgt tggaaatgcg ggccatgagc tgcgagaagg cgttgaggcc tccctcgttc    8280
cagacgcggc tgtagaccac gccccttcg gcatcgcggg cgcgcatgac cacctgcgcg     8340
agattgagct ccacgtgccg ggcgaagacg gcgtagtttc gcaggcgctg aaagaggtag    8400
ttgagggtgg tggcggtgtg ttctgccacg aagaagtaca taacccagcg tcgcaacgtg    8460
gattcgttga tatcccccaa ggcctcaagg cgctccatgg cctcgtagaa gtccacggcg    8520
aagttgaaaa actgggagtt gcgcgccgac acggttaact cctcctccag aagacggatg    8580
agctcggcga cagtgtcgcg cacctcgcgc tcaaaggcta caggggcctc ttcttcttct    8640
tcaatctcct cttccataag ggcctccct tcttcttctt ctggcggcgg tgggggaggg     8700
gggacacggc ggcgacgacg gcgcaccggg aggcggtcga caaagcgctc gatcatctcc    8760
ccgcggcgac ggcgcatggt ctcggtgacg gcgcggccgt tctcgcgggg gcgcagttgg    8820
aagacgccgc ccgtcatgtc ccggttatgg gttggcgggg ggctgccatg cggcagggat    8880
acggcgctaa cgatgcatct caacaattgt tgtgtaggta ctccgccgcc gagggacctg    8940
agcgagtccg catcgaccgg atcggaaaac ctctcgagaa aggcgtctaa ccagtcacag    9000
tcgcaaggta ggctgagcac cgtggcgggc ggcagcgggc ggcggtcggg gttgtttctg    9060
gcggaggtgc tgctgatgat gtaattaaag taggcggtct tgagacgcg gatggtcgac     9120 agaagcacca tgtccttggg tccggcctgc tgaatgcgca ggcggtcggc catgcccag     9180 gcttcgtttt gacatcggcg caggtctttg tagtagtctt gcatgagcct ttctaccggc    9240
acttcttctt ctccttcctc ttgtcctgca tctcttgcat ctatcgctgc ggcggcggcg    9300
gagtttggcc gtaggtggcg ccctcttcct cccatgcgtg tgaccccgaa gcccctcatc    9360
ggctgaagca gggctaggtc ggcgacaacg cgctcggcta atatggcctg ctgcacctgc    9420
gtgagggtag actggaagtc atccatgtcc acaaagcggt ggtatgcgcc cgtgttgatg    9480
gtgtaagtgc agttggccat aacggaccag ttaacggtct ggtgacccgg ctgcgagagc    9540
tcggtgtacc tgagacgcga gtaagccctc gagtcaaata cgtagtcgtt gcaagtccgc    9600
accaggtact ggtatcccac caaaaagtgc ggcggcggct ggcggtagag gggccagcgt    9660
agggtggccg gggctccggg ggcgagatct tccaacataa ggcgatgata tccgtagatg    9720
tacctggaca tccaggtgat gccgcgcg gtggtgagg cgcgcggaaa gtcgcggacg       9780
cggttccaga tgttgcgcag cggcaaaaag tgctccatgg tcgggacgct ctggccggtc    9840
aggcgcgcgc aatcgttgac gctctagacc gtgcaaaagg agagcctgta agcgggcact    9900
cttccgtggt ctggtggata aattcgcaag ggtatcatgg cggacgaccg gggttcgagc    9960
cccgtatccg gccgtccgcc gtgatccatg cggttaccgc ccgcgtgtcg aacccaggtg   10020
```

```
tgcgacgtca gacaacgggg gagtgctcct tttggcttcc ttccaggcgc ggcggctgct   10080
gcgctagctt ttttggccac tggccgcgcg cagcgtaagc ggttaggctg gaaagcgaaa   10140
gcattaagtg gctcgctccc tgtagccgga gggttatttt ccaagggttg agtcgcggga   10200
cccccggttc gagtctcgga ccggccggac tgcggcgaac gggggtttgc ctccccgtca   10260
tgcaagaccc cgcttgcaaa ttcctccgga aacagggacg agcccctttt ttgcttttcc   10320
cagatgcatc cggtgctgcg gcagatgcgc ccccctcctc agcagcggca agagcaagag   10380
cagcggcaga catgcagggc accctcccct cctcctaccg cgtcaggagg ggcgacatcc   10440
gcggttgacg cggcagcaga tggtgattac gaaccccgc ggcgccgggc ccggcactac    10500
ctggacttgg aggagggcga gggcctggcg cggctaggag cgccctctcc tgagcggcac   10560
ccaagggtgc agctgaagcg tgatacgcgt gaggcgtacg tgccgcggca gaacctgttt   10620
cgcgaccgcg agggagagga gcccgaggag atgcgggatc gaaagttcca cgcagggcgc   10680
gagctgcggc atggcctgaa tcgcgagcgg ttgctgcgcg aggaggactt tgagcccgac   10740
gcgcgaaccg ggattagtcc cgcgcgcgca cacgtggcgg ccgccgacct ggtaaccgca   10800
tacgagcaga cggtgaacca ggagattaac tttcaaaaaa gctttaacaa ccacgtgcgt   10860
acgcttgtgg cgcgcgagga ggtggctata ggactgatgc atctgtggga ctttgtaagc   10920
gcgctggagc aaaacccaaa tagcaagccg ctcatggcgc agctgttcct tatagtgcag   10980
cacagcaggg acaacgaggc attcagggat gcgctgctaa acatagtaga gcccgagggc   11040
cgctggctgc tcgatttgat aaacatcctg cagagcatag tggtgcagga gcgcagcttg   11100
agcctggctg acaaggtggc cgccatcaac tattccatgc ttagcctggg caagttttac   11160
gcccgcaaga tataccatac cccttacgtt cccatagaca aggaggtaaa gatcgagggg   11220
ttctacatgc gcatggcgct gaaggtgctt accttgagcg acgacctggg cgtttatcgc   11280
aacgagcgca tccacaaggc cgtgagcgtg agccggcggc gcgagctcag cgaccgcgag   11340
ctgatgcaca gcctgcaaag ggccctggct ggcacgggca gcggcgatag agaggccgag   11400
tcctactttg acgcgggcgc tgacctgcgc tgggccccaa gccgacgcgc cctggaggca   11460
gctggggccg gacctgggct ggcggtggca cccgcgcgcg ctggcaacgt cggcggcgtg   11520
gaggaatatg acgaggacga tgagtacgag ccagaggacg gcgagtacta agcggtgatg   11580
tttctgatca gatgatgcaa gacgcaacgg acccggcggt gcggcggcg ctgcagagcc    11640
agccgtccgg ccttaactcc acggacgact ggcgccaggt catggaccgc atcatgtcgc   11700
tgactgcgcg caatcctgac gcgttccggc agcagccgac ggccaaccgg ctctccgcaa   11760
ttctggaagc ggtggtcccg gcgcgcgcaa accccacgca cgagaaggtg ctggcgatcg   11820
taaacgcgct ggccgaaaac agggccatcc ggcccgacga ggccggcctg gtctacgacg   11880
cgctgcttca gcgcgtggct cgttacaaca gcggcaacgt gcagaccaac ctggaccggc   11940
tggtggggga tgtgcgcgag gccgtggcgc agcgtgagcg cgcgcagcag cagggcaacc   12000
tgggctccat ggttgcacta aacgccttcc tgagtacaca gcccgccaac gtgccgcggg   12060
gacaggagga ctacaccaac tttgtgagcg cactgcggct aatggtgact gagacaccgc   12120
aaagtgaggt gtaccagtct gggccagact atttttttcca gaccagtaga caaggcctgc   12180
agaccgtaaa cctgagccag gctttcaaaa acttgcaggg gctgtggggg gtgcgggctc   12240
ccacaggcga ccgcgcgacc gtgtctagct tgctgacgcc caactcgcgc ctgttgctgc   12300
tgctaatagc gcccttcacg gacagtggca gcgtgtcccg ggacacatac ctaggtcact   12360
```

```
tgctgacact gtaccgcgag gccataggtc aggcgcatgt ggacgagcat actttccagg    12420
agattacaag tgtcagccgc gcgctggggc aggaggacac gggcagcctg gaggcaaccc    12480
taaactacct gctgaccaac cggcggcaga agatcccctc gttgcacagt ttaaacagcg    12540
aggaggagcg cattttgcgc tacgtgcagc agagcgtgag ccttaacctg atgcgcgacg    12600
gggtaacgcc cagcgtggcg ctggacatga ccgcgcgcaa catggaaccg ggcatgtatg    12660
cctcaaaccg gccgtttatc aaccgcctaa tggactactt gcatcgcgcg gccgccgtga    12720
accccgagta tttcaccaat gccatcttga acccgcactg gctaccgccc cctggtttct    12780 acaccgggggg attcgaggtg cccgagggta acgatggatt cctctgggac gacatagacg    12840
acagcgtgtt ttccccgcaa ccgcagaccc tgctagagtt gcaacagcgc gagcaggcag    12900
aggcggcgct gcgaaaggaa agcttccgca ggccaagcag cttgtccgat ctaggcgctg    12960
cggccccgcg gtcagatgct agtagcccat ttccaagctt gatagggtct cttaccagca    13020
ctcgcaccac ccgcccgcgc ctgctgggcg aggaggagta cctaaacaac tcgctgctgc    13080
agccgcagcg cgaaaaaaac ctgcctccgg catttcccaa caacgggata gagagcctag    13140
tggacaagat gagtagatgg aagacgtacg cgcaggagca cagggacgtg ccaggcccgc    13200
gcccgcccac ccgtcgtcaa aggcacgacc gtcagcgggg tctggtgtgg gaggacgatg    13260
actcggcaga cgacagcagc gtcctggatt tgggagggag tggcaacccg tttgcgcacc    13320
ttcgccccag gctggggaga atgtttttaaa aaaaaaaaa gcatgatgca aataaaaaa    13380 ctcaccaagg ccatggcacc gagcgttggt tttcttgtat tccccttagt atgcggcgcg    13440
cggcgatgta tgaggaaggt cctcctccct cctacgagag tgtggtgagc gcggcgccag    13500
tggcggcggc gctgggttct cccttcgatg ctccctgga cccgccgttt gtgcctccgc    13560
ggtacctgcg gcctaccggg gggagaaaca gcatccgtta ctctgagttg gcacccctat    13620
tcgacaccac ccgtgtgtac ctggtggaca acaagtcaac ggatgtggca tccctgaact    13680
accagaacga ccacagcaac tttctgacca cggtcattca aaacaatgac tacagcccgg    13740
gggaggcaag cacacagacc atcaatcttg acgaccggtc gcactggggc ggcgacctga    13800
aaaccatcct gcataccaac atgccaaatg tgaacgagtt catgtttacc aataagtta    13860 aggcgcgggt gatggtgtcg cgcttgccta ctaaggacaa tcaggtggag ctgaaatacg    13920
agtgggtgga gttcacgctg cccgagggca actactccga gaccatgacc atagaccta    13980 tgaacaacgc gatcgtggag cactacttga aagtgggcag acagaacggg gttctggaaa    14040
gcgacatcgg ggtaaagttt gacacccgca acttcagact ggggtttgac cccgtcactg    14100
gtcttgtcat gcctggggta tatacaaacg aagccttcca tccagacatc attttgctgc    14160
caggatgcgg ggtggacttc acccacagcc gcctgagcaa cttgttgggc atccgcaagc    14220 ggcaacctt ccaggagggc tttaggatca cctacgatga tctggagggt ggtaacattc    14280
ccgcactgtt ggatgtggac gcctaccagg cgagcttgaa agatgacacc gaacagggcg    14340 gggtgcgc aggcggcagc aacagcagtg gcagcggcgc ggaagagaac tccaacgcgg    14400
cagccgcggc aatgcagccg gtggaggaca tgaacgatca tgccattcgc ggcgacacct    14460
ttgccacacg ggctgaggag aagcgcgctg aggccgaagc agcggccgaa gctgccgccc    14520
ccgctgcgca acccgaggtc gagaagcctc agaagaaacc ggtgatcaaa ccccctgacag    14580 aggacagcaa gaaacgcagt tacaacctaa taagcaatga cagcaccttc acccagtacc    14640
gcagctggta ccttgcatac aactacgcg accctcagac cggaatccgc tcatggaccc    14700
tgctttgcac tcctgacgta acctgcggct cggagcaggt ctactggtcg ttgccagaca    14760
```

```
tgatgcaaga ccccgtgacc ttccgctcca cgcgccagat cagcaacttt ccggtggtgg   14820
gcgccgagct gttgcccgtg cactccaaga gcttctacaa cgaccaggcc gtctactccc   14880
aactcatccg ccagtttacc tctctgaccc acgtgttcaa tcgctttccc gagaaccaga   14940
ttttggcgcg cccgccagcc cccaccatca ccaccgtcag tgaaaacgtt cctgctctca   15000
cagatcacgg gacgctaccg ctgcgcaaca gcatcggagg agtccagcga gtgaccatta   15060
ctgacgccag acgccgcacc tgcccctacg tttacaaggc cctgggcata gtctcgccgc   15120
gcgtcctatc gagccgcact ttttgagcaa gcatgtccat ccttatatcg cccagcaata   15180
acacaggctg gggcctgcgc ttcccaagca agatgtttgg cggggccaag aagcgctccg   15240
accaacaccc agtgcgcgtg cgcgggcact accgcgcgcc ctgggcgcg cacaaacgcg    15300 gccgcactgg gcgcaccacc gtcgatgacg ccatcgacgc ggtggtggag gaggcgcgca   15360
actacacgcc cacgccgcca ccagtgtcca cagtggacgc ggccattcag accgtggtgc   15420
gcggagcccg gcgctatgct aaaatgaaga gacggcggag gcgcgtagca cgtcgccacc   15480
gccgccgacc cggcactgcc gcccaacgcg cggcggcggc cctgcttaac cgcgcacgtc   15540
gcaccggccg acgggcggcc atgcgggccg ctcgaaggct ggccgcgggt attgtcactg   15600 tgcccccag gtccaggcga cgagcggccg ccgcagcagc cgcggccatt agtgctatga    15660
ctcagggtcg caggggcaac gtgtattggg tgcgcgactc ggttagcggc ctgcgcgtgc   15720
ccgtgcgcac ccgcccccg cgcaactaga ttgcaagaaa aaactactta gactcgtact    15780
gttgtatgta tccagcggcg gcggcgcgca acgaagctat gtccaagcgc aaaatcaaag   15840
aagagatgct ccaggtcatc gcgccggaga tctatggccc ccgaagaag gaagagcagg    15900 attacaagcc ccgaaagcta aagcgggtca aaagaaaaa gaaagatgat gatgatgaac    15960
ttgacgacga ggtggaactg ctgcacgcta ccgcgcccag gcgacgggta cagtggaaag   16020
gtcgacgcgt aaaacgtgtt ttgcgacccg gcaccaccgt agtctttacg cccggtgagc   16080
gctccacccg cacctacaag cgcgtgtatg atgaggtgta cggcgacgag gacctgcttg   16140
agcaggccaa cgagcgcctc ggggagtttg cctacgaaaa gcggcataag gacatgctgg   16200
cgttgccgct ggacgagggc aacccaacac ctagcctaaa gcccgtaaca ctgcagcagg   16260
tgctgcccgc gcttgcaccg tccgaagaaa agcgcggcct aaagcgcgag tctggtgact   16320
tggcacccac cgtgcagctg atggtaccca agcgccagcg actggaagat gtcttggaaa   16380
aaatgaccgt ggaacctggg ctggagcccg aggtccgcgt gcggccaatc aagcaggtgg   16440
cgccgggact gggcgtgcag accgtggacg ttcagatacc cactaccagt agcaccagta   16500
ttgccaccgc cacagagggc atggagacac aaacgtcccc ggttgcctca gcggtggcgg   16560
atgccgcggt gcaggcggtc gctgcggccg cgtccaagac ctctacggag gtgcaaacgg   16620
acccgtggat gtttcgcgtt tcagcccccc ggcgcccgcg ccgttcgagg aagtacggcg   16680
ccgccagcgc gctactgccc gaatatgccc tacatccttc cattgcgcct accccggct    16740 atcgtggcta cacctaccgc cccagaagac gagcaactac ccgacgccga accaccactg   16800
gaacccgccg ccgccgtcgc cgtcgccagc ccgtgctggc cccgatttcc gtgcgcaggg   16860
tggctcgcga aggaggcagg accctggtgc tgccaacagc gcgctaccac cccagcatcg   16920
tttaaaagcc ggtctttgtg gttcttgcag atatggccct cacctgccgc ctccgttttcc   16980 cggtgccgga attccgagga agaatgcacc gtaggagggg catggccggc cacggcctga   17040
cgggcggcat gcgtcgtgcg caccaccggc ggcggcgcgc gtcgcaccgt cgcatgcgcg   17100
```

```
gcggtatcct gccctcctt attccactga tcgccgcggc gattggcgcc gtgcccggaa   17160
ttgcatccgt ggccttgcag gcgcagagac actgattaaa aacaagttgc atgtggaaaa   17220
atcaaaataa aaagtctgga ctctcacgct cgcttggtcc tgtaactatt ttgtagaatg   17280
gaagacatca actttgcgtc tctggccccg cgacacggct cgcgcccgtt catgggaaac   17340
tggcaagata tcggcaccag caatatgagc ggtggcgcct tcagctgggg ctcgctgtgg   17400
agcggcatta aaaatttcgg ttccaccgtt aagaactatg cagcaaggc ctggaacagc    17460 agcacaggcc agatgctgag ggataagttg aaagagcaaa atttccaaca aaggtggta    17520 gatggcctgg cctctggcat tagcggggtg gtggacctgg ccaaccaggc agtgcaaaat   17580
aagattaaca gtaagcttga tccccgccct cccgtagagg agcctccacc ggccgtggag   17640
acagtgtctc cagaggggcg tggcgaaaag cgtccgcgcc ccgacaggga agaaactctg    17700
gtgacgcaaa tagacgagcc tccctcgtac gaggaggcac taaagcaagg cctgcccacc    17760
acccgtccca tcgcgcccat ggctaccgga gtgctgggcc agcacacacc cgtaacgctg   17820
gacctgcctc ccccgccga cacccagcag aaacctgtgc tgccaggccc gaccgccgtt    17880
gttgtaaccc gtcctagccg cgcgtccctg cgccgcgccg ccagcggtcc gcgatcgttg   17940
cggcccgtag ccagtggcaa ctggcaaagc acactgaaca gcatcgtggg tctgggggtg    18000
caatccctga agcgccgacg atgcttctga tagctaacgt gtcgtatgtg tgtcatgtat    18060
gcgtccatgt cgccgccaga ggagctgctg agccgccgcg cgcccgcttt ccaagatggc   18120
taccccttcg atgatgccgc agtggtctta catgcacatc tcgggccagg acgcctcgga   18180
gtacctgagc cccgggctgg tgcagtttgc ccgcgccacc gagacgtact tcagcctgaa   18240
taacaagttt agaaaccca cggtggcgcc tacgcacgac gtgaccacag accggtccca    18300
gcgtttgacg ctgcggttca tccctgtgga ccgtgaggat actgcgtact cgtacaaggc    18360
gcggttcacc ctagctgtgg gtgataaccg tgtgctggac atggcttcca cgtactttga   18420
catccgcggc gtgctggaca ggggccctac ttttaagccc tactctggca ctgcctacaa    18480
cgccctggct cccaagggtg ccccaaatcc ttgcgaatgg gatgaagctg ctactgctct    18540
tgaaataaac ctagaagaag aggacgatga caacgaagac gaagtagacg agcaagctga   18600
gcagcaaaaa actcacgtat ttgggcaggc gccttattct ggtataaata ttacaaagga   18660
gggtattcaa ataggtgtcg aaggtcaaac acctaaatat gccgataaaa catttcaacc    18720
tgaacctcaa ataggagaat ctcagtggta cgaaacagaa attaatcatg cagctgggag   18780
agtcctaaaa aagactaccc caatgaaacc atgttacggt tcatatgcaa acccacaaa    18840 tgaaaatgga gggcaaggca ttcttgtaaa gcaacaaaat ggaaagctag aaagtcaagt   18900
ggaaatgcaa tttttctcaa ctactgaggc agccgcaggc aatggtgata acttgactcc    18960
taaagtggta ttgtacagtg aagatgtaga tatagaaacc ccagacactc atatttctta   19020
catgcccact attaaggaag gtaactcacg agaactaatg ggccaacaat ctatgcccaa    19080
caggcctaat tacattgctt ttagggacaa ttttattggt ctaatgtatt acaacagcac    19140
gggtaatatg ggtgttctgg cgggccaagc atcgcagttg aatgctgttg tagatttgca    19200
agacagaaac acagagcttt cataccagct tttgcttgat ccattggtg atagaaccag   19260 gtacttttct atgtggaatc aggctgttga cagctatgat ccagatgtta gaattattga    19320
aaatcatgga actgaagatg aacttccaaa ttactgcttt ccactgggag gtgtgattaa   19380
tacagagact cttaccaagg taaaacctaa aacaggtcag gaaaatggat gggaaaaaga    19440
tgctacagaa ttttcagata aaaatgaaat aagagttgga aataattttg ccatggaaat   19500
```

```
caatctaaat gccaacctgt ggagaaattt cctgtactcc aacatagcgc tgtatttgcc   19560
cgacaagcta aagtacagtc cttccaacgt aaaaatttct gataacccaa acacctacga   19620
ctacatgaac aagcgagtgg tggctcccgg gctagtggac tgctacatta accttggagc   19680
acgctggtcc cttgactata tggacaacgt caacccattt aaccaccacc gcaatgctgg   19740
cctgcgctac cgctcaatgt tgctgggcaa tggtcgctat gtgcccttcc acatccaggt   19800
gcctcagaag ttcttttgcca ttaaaaacct ccttctcctg ccgggctcat acacctacga   19860
gtggaacttc aggaaggatg ttaacatggt tctgcagagc tccctaggaa atgacctaag   19920
ggttgacgga gccagcatta agtttgatag catttgcctt tacgccacct tcttccccat   19980
ggcccacaac accgcctcca cgcttgaggc catgcttaga aacgacacca acgaccagtc   20040
ctttaacgac tatctctccg ccgccaacat gctctaccct atacccgcca acgctaccaa   20100
cgtgcccata tccatcccct cccgcaactg gcggctttc cgcggctggg ccttcacgcg   20160
ccttaagact aaggaaaccc catcactggg ctcgggctac gaccccttatt acacctactc   20220
tggctctata ccctacctag atggaacctt ttacctcaac cacaccttta agaaggtggc   20280
cattaccttt gactcttctg tcagctggcc tggcaatgac cgcctgctta cccccaacga   20340
gtttgaaatt aagcgctcag ttgacgggga gggttacaac gttgcccagt gtaacatgac   20400
caaagactgg ttcctggtac aaatgctagc taactataac attggctacc agggcttcta   20460
tatcccagag agctacaagg accgcatgta ctccttcttt agaaacttcc agcccatgag   20520
ccgtcaggtg gtggatgata ctaaatacaa ggactaccaa caggtgggca tcctacacca   20580
acacaacaac tctggatttg ttggctacct tgcccccacc atgcgcgaag acaggccta   20640
ccctgctaac ttcccctatc cgcttatagg caagaccgca gttgacagca ttacccagaa   20700
aaagtttctt tgcgatcgca cccttttggcg catcccattc tccagtaact ttatgtccat   20760
gggcgcactc acagacctgg gccaaaacct tctctacgcc aactccgccc acgcgctaga   20820
catgactttt gaggtggatc ccatggacga gcccacccct ctttatgttt tgtttgaagt   20880
ctttgacgtg gtccgtgtgc accagccgca ccgcggcgtc atcgaaaccg tgtacctgcg   20940
cacgcccttc tcggccggca acgccacaac ataaagaagc aagcaacatc aacaacagct   21000
gccgccatgg gctccagtga gcaggaactg aaagccattg tcaaagatct tggttgtggg   21060
ccatatttt tgggcaccta tgacaagcgc tttccaggct ttgttctcc acacaagctc   21120
gcctgcgcca tagtcaatac ggccggtcgc gagactgggg gcgtacactg gatggccttt   21180
gcctggaacc cgcactcaaa acatgctac ctctttgagc cctttggctt ttctgaccag   21240
cgactcaagc aggtttacca gtttgagtac gagtcactcc tgcgccgtag cgccattgct   21300
tcttcccccg accgctgtat aacgctgaa aagtccaccc aaagcgtaca ggggcccaac   21360
tcggccgcct gtggactatt ctgctgcatg tttctccacg cctttgccaa ctggccccaa   21420
actcccatgg atcacaaccc caccatgaac cttattaccg gggtacccaa ctccatgctc   21480
aacagtcccc aggtacagcc caccctgcgt cgcaaccagg aacagctcta cagcttcctg   21540
gagcgccact cgccctactt ccgcagccac agtgcgcaga ttaggagcgc cacttctttt   21600
tgtcacttga aaaacatgta aaaataatgt actagagaca ctttcaataa aggcaaatgc   21660
ttttatttgt acactctcgg gtgattattt accccaccc ttgccgtctg cgccgtttaa   21720
aaatcaaagg ggttctgccg cgcatcgcta tgcgccactg gcagggacac gttgcgatac   21780
tggtgtttag tgctccactt aaactcaggc acaaccatcc gcggcagctc ggtgaagttt   21840
```

-continued

| | |
|---|---|
| tcactccaca ggctgcgcac catcaccaac gcgtttagca ggtcgggcgc cgatatcttg | 21900 |
| aagtcgcagt tggggcctcc gccctgcgcg cgcgagttgc gatacacagg gttgcagcac | 21960 |
| tggaacacta tcagcgccgg gtggtgcacg ctggccagca cgctcttgtc ggagatcaga | 22020 |
| tccgcgtcca ggtcctccgc gttgctcagg gcgaacggag tcaactttgg tagctgcctt | 22080 |
| cccaaaaagg gcgcgtgccc aggctttgag ttgcactcgc accgtagtgg catcaaaagg | 22140 |
| tgaccgtgcc cggtctgggc gttaggatac agcgcctgca taaaagcctt gatctgctta | 22200 |
| aaagccacct gagcctttgc gccttcagag aagaacatgc cgcaagactt gccggaaaac | 22260 |
| tgattggccg gacaggccgc gtcgtgcacg cagcaccttg cgtcggtgtt ggagatctgc | 22320 |
| accacatttc ggccccaccg gttcttcacg atcttggcct tgctagactg ctccttcagc | 22380 |
| gcgcgctgcc cgttttcgct cgtcacatcc atttcaatca cgtgctcctt atttatcata | 22440 |
| atgcttccgt gtagacactt aagctcgcct tcgatctcag cgcagcggtg cagccacaac | 22500 |
| gcgcagcccg tgggctcgtg atgcttgtag gtcacctctg caaacgactg caggtacgcc | 22560 |
| tgcaggaatc gccccatcat cgtcacaaag gtcttgttgc tggtgaaggt cagctgcaac | 22620 |
| ccgcggtgct cctcgttcag ccaggtcttg catacggccg ccagagcttc cacttggtca | 22680 |
| ggcagtagtt tgaagttcgc cttagatcg ttatccacgt ggtacttgtc catcagcgcg | 22740 |
| cgcgcagcct ccatgccctt ctcccacgca gacacgatcg gcacactcag cgggttcatc | 22800 |
| accgtaattt cactttccgc ttcgctgggc tcttcctctt cctcttgcgt ccgcatacca | 22860 |
| cgcgccactg ggtcgtcttc attcagccgc cgcactgtgc gcttacctcc tttgccatgc | 22920 |
| ttgattagca ccggtgggtt gctgaaaccc accatttgta cgccacatc ttctctttct | 22980 |
| tcctcgctgt ccacgattac ctctggtgat ggcgggcgct cgggcttggg agaagggcgc | 23040 |
| ttcttttttct tcttgggcgc aatggccaaa tccgccgccg aggtcgatgg ccgcgggctg | 23100 |
| ggtgtgcgcg gcaccagcgc gtcttgtgat gagtcttcct cgtcctcgga ctcgatacgc | 23160 |
| cgcctcatcc gctttttggg gggcgccggg ggaggcggcg gcgacgggga cggggacgac | 23220 |
| acgtcctcca tggttgggg acgtcgcgcc gcaccgcgtc cgcgctcggg ggtggtttcg | 23280 |
| cgctgctcct cttcccgact ggccatttcc ttctcctata ggcagaaaaa gatcatggag | 23340 |
| tcagtcgaga agaaggacag cctaaccgcc ccctctgagt tcgccaccac cgcctccacc | 23400 |
| gatgccgcca acgcgcctac caccttcccc gtcgaggcac ccccgcttga ggaggaggaa | 23460 |
| gtgattatcg agcaggaccc aggttttgta agcgaagacg acgaggaccg ctcagtacca | 23520 |
| acagaggata aaagcaagaa ccaggacaac gcagaggcaa acgaggaaca agtcgggcgg | 23580 |
| ggggacgaaa ggcatggcga ctacctagat gtgggagacg acgtgctgtt gaagcatctg | 23640 |
| cagcgccagt gcgccattat ctgcgacgcg ttgcaagagc gcagcgatgt gcccctcgcc | 23700 |
| atagcggatg tcagccttgc ctacgaacgc caccttattct caccgcgcgt accccccaaa | 23760 |
| cgccaagaaa acggcacatg cgagcccaac ccgcgcctca acttctaccc cgtatttgcc | 23820 |
| gtgccagagg tgcttgccac ctatcacatc tttttccaaa actgcaagat accctatcc | 23880 |
| tgccgtgcca accgcagccg agcggacaag cagctggcct gcggcagggg cgctgtcata | 23940 |
| cctgatatcg cctcgctcaa cgaagtgcca aaaatctttg agggtcttgg acgcgacgag | 24000 |
| aagcgcgcgg caaacgctct gcaacaggaa aacagcgaaa atgaaagtca ctctggagtg | 24060 |
| ttggtggaac tcgagggtga caacgcgcgc ctagccgtac taaaacgcag catcgaggtc | 24120 |
| acccactttg cctacccggc acttaaccta cccccccaagg tcatgagcac agtcatgagt | 24180 |
| gagctgatcg tgcgccgtgc gcagcccctg gagagggatg caaatttgca agaacaaaca | 24240 |

```
gaggagggcc tacccgcagt tggcgacgag cagctagcgc gctggcttca aacgcgcgag    24300
cctgccgact tggaggagcg acgcaaacta atgatggccg cagtgctcgt taccgtggag    24360
cttgagtgca tgcagcggtt ctttgctgac ccggagatgc agcgcaagct agaggaaaca    24420
ttgcactaca cctttcgaca gggctacgta cgccaggcct gcaagatctc caacgtggag    24480
ctctgcaacc tggtctccta ccttggaatt ttgcacgaaa accgccttgg caaaacgtg     24540 cttcattcca cgctcaaggg cgaggcgcgc cgcgactacg tccgcgactg cgtttactta    24600
tttctatgct acacctggca gacggccatg ggcgtttggc agcagtgctt ggaggagtgc    24660
aacctcaagg agctgcagaa actgctaaag caaaacttga aggacctatg acggccttc     24720 aacgagcgct ccgtggccgc gcacctggcg acatcatttt tccccgaacg cctgcttaaa    24780
accctgcaac agggtctgcc agacttcacc agtcaaagca tgttgcagaa ctttaggaac    24840
tttatcctag agcgctcagg aatcttgccc gccacctgct gtgcacttcc tagcgacttt    24900
gtgcccatta gtaccgcga atgccctccg ccgctttggg gccactgcta ccttctgcag     24960
ctagccaact accttgccta ccactctgac ataatggaag acgtgagcgg tgacggtcta    25020
ctggagtgtc actgtcgctg caacctatgc accccgcacc gctccctggt ttgcaattcg    25080
cagctgctta acgaaagtca aattatcggt accttttgagc tgcagggtcc ctcgcctgac   25140
gaaaagtccg cggctccggg gttgaaactc actccggggc tgtggacgtc ggcttacctt    25200
cgcaaatttg tacctgagga ctaccacgcc cacgagatta ggttctacga agaccaatcc    25260
cgcccgccta atgcggagct taccgcctgc gtcattaccc agggccacat tcttggccaa    25320
ttgcaagcca tcaacaaagc ccgccaagag tttctgctac gaaagggacg ggggggttac    25380
ttggaccccc agtccggcga ggagctcaac ccaatccccc cgccgccgca gccctatcag    25440
cagcagccgc gggcccttgc ttcccaggat ggcacccaaa aagaagctgc agctgccgcc    25500
gccacccacg gacgaggagg aatactggga cagtcaggca gaggaggttt tggacgagga    25560
ggaggaggac atgatggaag actgggagag cctagacgag gaagcttccg aggtcgaaga    25620
ggtgtcagac gaaacaccgt caccctcggt cgcattcccc tcgccggcgc cccagaaatc    25680
ggcaaccggt tccagcatgg ctacaacctc cgctcctcag gcgccgccgg cactgcccgt    25740
tcgccgaccc aaccgtagat gggacaccac tggaaccagg gccggtaagt ccaagcagcc    25800
gccgccgtta gcccaagagc aacaacgcg ccaaggctac cgctcatggc gcgggcacaa     25860
gaacgccata gttgcttgct tgcaagactg tgggggcaac atctccttcg cccgccgctt    25920
tcttctctac catcacggcg tggccttccc ccgtaacatc ctgcattact accgtcatct    25980
ctacagccca tactgcaccg gcggcagcgg cagcaacagc agcggccaca cagaagcaaa    26040
ggcgaccgga tagcaagact ctgacaaagc ccaagaaatc cacagcggcg gcagcagcag    26100
gaggaggagc gctgcgtctg gcgcccaacg aacccgtatc gacccgcgag cttagaaaca    26160
ggatttttcc cactctgtat gctatatttc aacagagcag gggccaagaa caagagctga    26220
aaataaaaaa caggtctctg cgatccctca cccgcagctg cctgtatcac aaaagcgaag    26280
atcagcttcg gcgcacgctg gaagacgcgg aggctctctt cagtaaatac tgcgcgctga    26340
ctcttaagga ctagtttcgc gccctttctc aaatttaagc gcgaaaacta cgtcatctcc    26400
agcggccaca cccggcgcca gcacctgttg tcagcgccat tatgagcaag gaaattccca    26460
cgccctacat gtggagttac cagccacaaa tgggacttgc ggctgagct gcccaagact    26520 actcaacccg aataaactac atgagcgcgg gaccccacat gatatcccgg gtcaacggaa    26580
```

```
tacgcgccca ccgaaaccga attctcctgg aacaggcggc tattaccacc acacctcgta    26640
ataaccttaa tccccgtagt tggcccgctg ccctggtgta ccaggaaagt cccgctccca    26700
ccactgtggt acttcccaga gacgcccagg ccgaagttca gatgactaac tcagggcgc     26760 agcttgcggg cggctttcgt cacagggtgc ggtcgcccgg gcagggtata actcacctga    26820
caatcagagg gcgaggtatt cagctcaacg acgagtcggt gagctcctcg cttggtctcc    26880
gtccggacgg gacatttcag atcggcggcg ccggccgctc ttcattcacg cctcgtcagg    26940
caatcctaac tctgcagacc tcgtcctctg agccgcgctc tggaggcatt ggaactctgc    27000
aatttattga ggagtttgtg ccatcggtct actttaaccc cttctcggga cctcccggcc    27060
actatccgga tcaatttatt cctaactttg acgcggtaaa ggactcggcg gacggctacg    27120
actgaatgtt aagtggagag gcagagcaac tgcgcctgaa acacctggtc cactgtcgcc    27180
gccacaagtg ctttgcccgc gactccggtg agttttgcta ctttgaattg cccgaggatc    27240
atatcgaggg cccggcgcac ggcgtccggc ttaccgccca gggagagctt gcccgtagcc    27300
tgattcggga gtttacccag cgcccctgc tagttgagcg ggacagggga ccctgtgttc    27360
tcactgtgat ttgcaactgt cctaaccctg gattacatca agatctttgt tgccatctct    27420
gtgctgagta taataaatac agaaattaaa atatactggg gctcctatcg ccatcctgta    27480
aacgccaccg tcttcacccg cccaagcaaa ccaaggcgaa ccttacctgg tactttaac    27540 atctctccct ctgtgattta caacagtttc aacccagacg gagtgagtct acgagagaac    27600
ctctccgagc tcagctactc catcagaaaa aacaccaccc tccttacctg ccgggaacgt    27660
acgagtgcgt caccggccgc tgcaccacac ctaccgcctg accgtaaacc agactttttc    27720
cggacagacc tcaataactc tgtttaccag aacaggaggt gagcttagaa aaccccttagg   27780 gtattaggcc aaaggcgcag ctactgtggg gtttatgaac aattcaagca actctacggg    27840
ctattctaat tcaggtttct ctagaatcgg ggttggggtt attctctgtc ttgtgattct    27900
ctttattctt atactaacgc ttctctgcct aaggctcgcc gcctgctgtg tgcacatttg    27960
catttattgt cagcttttta aacgctgggg tcgccaccca agatgattag gtacataatc    28020
ctaggtttac tcacccttgc gtcagcccac ggtaccaccc aaaaggtgga ttttaaggag    28080
ccagcctgta atgttacatt cgcagctgaa gctaatgagt gcaccactct tataaaatgc    28140
accacagaac atgaaaagct gcttattcgc cacaaaaaca aaattggcaa gtatgctgtt    28200 tatgctatt ggcagccagg tgacactaca gagtataatg ttacagttt ccagggtaaa      28260 agtcataaaa cttttatgta tacttttcca ttttatgaaa tgtgcgacat taccatgtac    28320
atgagcaaac agtataagtt gtggccccca caaaattgtg tggaaaacac tggcacttc     28380 tgctgcactg ctatgctaat tacagtgctc gctttggtct gtaccctact ctatattaaa    28440
tacaaaagca gacgcagctt tattgaggaa aagaaaatgc cttaatttac taagttacaa    28500
agctaatgtc accactaact gctttactcg ctgcttgcaa aacaaattca aaaagttagc    28560
attataatta gaataggatt taaaccccccc ggtcatttcc tgctcaatac cattcccctg    28620
aacaattgac tctatgtggg atatgctcca gcgctacaac cttgaagtca ggcttcctgg    28680
atgtcagcat ctgactttgg ccagcacctg tcccgcggat ttgttccagt ccaactacag    28740
cgacccaccc taacagagat gaccaacaca accaacgcgg ccgccgctac cggacttaca    28800
tctaccacaa atacacccca agtttctgcc tttgtcaata actgggataa cttgggcatg    28860
tggtggttct ccatagcgct tatgtttgta tgccttatta ttatgtggct catctgctgc    28920
ctaaagcgca aacgcgcccg accacccatc tatagtccca tcattgtgct acacccaaac    28980
```

```
aatgatggaa tccatagatt ggacggactg aaacacatgt tcttttctct tacagtatga   29040
ttaaatgaga catgattcct cgagtttta tattactgac ccttgttgcg cttttttgt      29100 gcgtgctcca cattggctgc ggtttctcac atcgaagtag actgcattcc agccttcaca   29160
gtctatttgc tttacggatt tgtcaccctc acgctcatct gcagcctcat cactgtggtc   29220
atcgccttta tccagtgcat tgactgggtc tgtgtgcgct ttgcatatct cagacaccat   29280
ccccagtaca gggacaggac tatagctgag cttcttagaa ttctttaatt atgaaattta   29340
ctgtgacttt tctgctgatt atttgcaccc tatctgcgtt ttgttccccg acctccaagc   29400
ctcaaagaca tatatcatgc agattcactc gtatatggaa tattccaagt tgctacaatg   29460
aaaaaagcga tctttccgaa gcctggttat atgcaatcat ctctgttatg gtgttctgca   29520
gtaccatctt agccctagct atatatccct accttgacat tggctggaac gcaatagatg   29580
ccatgaacca cccaactttc cccgcgcccg ctatgcttcc actgcaacaa gttgttgccg   29640
gcggctttgt cccagccaat cagcctcgcc caccttctcc cacccccact gaaatcagct   29700
actttaatct aacaggagga gatgactgac accctagatc tagaaatgga cggaattatt   29760
acagagcagc gcctgctaga aagacgcagg gcagcggccg agcaacagcg catgaatcaa   29820
gagctccaag acatggttaa cttgcaccag tgcaaaaggg gtatcttttg tctggtaaag   29880
caggccaaag tcacctacga cagtaatacc accggacacc gccttagcta caagttgcca   29940
accaagcgtc agaaattggt ggtcatggtg ggagaaaagc ccattaccat aactcagcac   30000
tcggtagaaa ccgaaggctg cattcactca ccttgtcaag gacctgagga tctctgcacc   30060
cttattaaga ccctgtgcgg tctcaaagat cttattccct ttaactaata aaaaaaaata   30120
ataaagcatc acttacttaa aatcagttag caaatttctg tccagtttat tcagcagcac   30180
ctccttgccc tcctcccagc tctggtattg cagcttcctc ctggctgcaa actttctcca   30240
caatctaaat ggaatgtcag tttcctcctg ttcctgtcca tccgcaccca ctatcttcat   30300
gttgttgcag atgaagcgcg caagaccgtc tgaagatacc ttcaaccccg tgtatccata   30360
tgacacggaa accggtcctc caactgtgcc ttttcttact cctcccttg tatcccccaa     30420 tgggtttcaa gagagtcccc ctggggtact ctctttgcgc ctatccgaac ctctagttac   30480
ctccaatggc atgcttgcgc tcaaaatggg caacggcctc tctctggacg aggccggcaa   30540
ccttacctcc caaaatgtaa ccactgtgag cccacctctc aaaaaaacca agtcaaacat   30600
aaacctggaa atatctgcac ccctcacagt tacctcagaa gccctaactg tggctgccgc   30660
cgcacctcta atggtcgcgg gcaacacact caccatgcaa tcacaggccc cgctaaccgt   30720
gcacgactcc aaacttagca ttgccaccca aggacccctc acagtgtcag aaggaaagct   30780
agccctgcaa acatcaggcc ccctcaccac caccgatagc agtaccctta ctatcactgc   30840
ctcaccccct ctaactactg ccactggtag cttgggcatt gacttgaaag agcccattta   30900
tacacaaaat ggaaaactag gactaaagta cgggctcct ttgcatgtaa cagacgacct    30960
aaacactttg accgtagcaa ctggtccagg tgtgactatt aataatactt ccttgcaaac   31020
taaagttact ggagccttgg gttttgattc acaaggcaat atgcaactta atgtagcagg   31080
aggactaagg attgattctc aaaacagacg cctttatactt gatgttagtt atccgtttga   31140
tgctcaaaac caactaaatc taagactagg acagggccct cttttttataa actcagccca   31200 caacttggat attaactaca acaaaggcct ttacttgttt acagcttcaa acaattccaa   31260
aaagcttgag gttaacctaa gcactgccaa ggggttgatg tttgacgcta cagccatagc   31320
```

```
cattaatgca ggagatgggc ttgaatttgg ttcacctaat gcaccaaaca caaatcccct   31380
caaaacaaaa attggccatg gcctagaatt tgattcaaac aaggctatgg ttcctaaact   31440
aggaactggc cttagttttg acagcacagg tgccattaca gtaggaaaca aaataatga    31500
taagctaact tgtgtggacca caccagctcc atctcctaac tgtagactaa atgcagagaa  31560
agatgctaaa ctcactttgg tcttaacaaa atgtggcagt caaatacttg ctacagtttc   31620
agttttggct gttaaaggca gtttggctcc aatatctgga acagttcaaa gtgctcatct   31680
tattataaga tttgacgaaa atggagtgct actaaacaat tccttcctgg acccagaata   31740
ttggaacttt agaatggag atcttactga aggcacagcc tatacaaacg ctgttggatt    31800
tatgcctaac ctatcagctt atccaaaatc tcacggtaaa actgccaaaa gtaacattgt   31860
cagtcaagtt tacttaaacg agacaaaac taaacctgta acactaacca ttacactaaa    31920
cggtacacag gaaacaggag acacaactcc aagtgcatac tctatgtcat tttcatggga   31980
ctggtctggc cacaactaca ttaatgaaat atttgccaca tcctcttaca cttttttcata  32040
cattgcccaa gaataaagaa tcgtttgtgt tatgtttcaa cgtgtttatt tttcaattgc   32100
agaaaatttc aagtcatttt tcattcagta gtatagcccc accaccacat agcttataca   32160
gatcaccgta ccttaatcaa actcacagaa ccctagtatt caacctgcca cctccctccc   32220
aacacacaga gtacagtc cttttctcccc ggctggcctt aaaaagcatc atatcatggg    32280
taacagacat attcttaggt gttatattcc acacggtttc ctgtcgagcc aaacgctcat   32340
cagtgatatt aataaactcc ccgggcagct cacttaagtt catgtcgctg tccagctgct   32400
gagccacagg ctgctgtcca acttgcggtt gcttaacggg cggcgaagga gaagtccacg   32460
cctacatggg ggtagagtca taatcgtgca tcaggatagg gcggtggtgc tgcagcagcg   32520
cgcgaataaa ctgctgccgc cgccgctccg tcctgcagga atacaacatg gcagtggtct   32580
cctcagcgat gattcgcacc gcccgcagca taaggcgcct tgtcctccgg gcacagcagc   32640
gcaccctgat ctcacttaaa tcagcacagt aactgcagca cagcaccaca atattgttca   32700
aaatcccaca gtgcaaggcg ctgtatccaa agctcatggc ggggaccaca gaacccacgt   32760
ggccatcata ccacaagcgc aggtagatta agtggcgacc cctcataaac acgctggaca   32820
taaacattac ctcttttggc atgttgtaat tcaccacctc ccggtaccat ataaacctct   32880
gattaaacat ggcgccatcc accaccatcc taaaccagct ggccaaaacc tgcccgccgg   32940
ctatacactg cagggaaccg ggactggaac aatgacagtg gagagcccag gactcgtaac   33000
catggatcat catgctcgtc atgatatcaa tgttggcaca acacaggcac acgtgcatac   33060
acttcctcag gattacaagc tcctcccgcg ttagaaccat atcccaggga acaacccatt   33120
cctgaatcag cgtaaatccc acactgcagg gaagacctcg cacgtaactc acgttgtgca   33180
ttgtcaaagt gttacattcg ggcagcagcg gatgatcctc cagtatggta gcgcgggttt   33240
ctgtctcaaa aggaggtaga cgatccctac tgtacggagt gcgccgagac aaccgagatc   33300
gtgttggtcg tagtgtcatg ccaaatggaa cgccggacgt agtcatattt cctgaagcaa   33360
aaccaggtgc gggcgtgaca aacagatctg cgtctccggt ctcgccgctt agatcgctct   33420
gtgtagtagt tgtagtatat ccactctctc aaagcatcca ggcgcccct ggcttcgggt    33480
tctatgtaaa ctccttcatg cgccgctgcc ctgataacat ccaccaccgc agaataagcc   33540
acacccagcc aacctacaca ttcgttctgc gagtcacaca cgggaggagc gggaagagct   33600
ggaagaacca tgtttttttt tttattccaa aagattatcc aaaacctcaa aatgaagatc   33660
tattaagtga acgcgctccc ctccggtggc gtggtcaaac tctacagcca aagaacagat   33720
```

```
aatggcattt gtaagatgtt gcacaatggc ttccaaaagg caaacggccc tcacgtccaa    33780
gtggacgtaa aggctaaacc cttcaggtg aatctcctct ataaacattc cagcaccttc    33840
aaccatgccc aaataattct catctcgcca ccttctcaat atatctctaa gcaaatcccg    33900
aatattaagt ccggccattg taaaaatctg ctccagagcg ccctccacct tcagcctcaa    33960
gcagcgaatc atgattgcaa aaattcaggt tcctcacaga cctgtataag attcaaaagc    34020
ggaacattaa caaaatacc gcgatcccgt aggtcccttc gcagggccag ctgaacataa    34080
tcgtgcaggt ctgcacggac cagcgcggcc acttccccgc caggaaccat gacaaaagaa    34140
cccacactga ttatgacacg catactcgga gctatgctaa ccagcgtagc cccgatgtaa    34200
gcttgttgca tgggcggcga tataaaatgc aaggtgctgc tcaaaaaatc aggcaaagcc    34260
tcgcgcaaaa aagaaagcac atcgtagtca tgctcatgca gataaaggca ggtaagctcc    34320
ggaaccacca cagaaaaaga caccattttt ctctcaaaca tgtctgcggg tttctgcata    34380
aacacaaaat aaaataacaa aaaacattt aaacattaga agcctgtctt acaacaggaa    34440
aaacaaccct tataagcata agacggacta cggccatgcc ggcgtgaccg taaaaaaact    34500
ggtcaccgtg attaaaaagc accaccgaca gctcctcggt catgtccgga gtcataatgt    34560
aagactcggt aaacacatca ggttgattca catcggtcag tgctaaaaag cgaccgaaat    34620
agcccggggg aatacatacc cgcaggcgta gagacaacat tacagccccc ataggaggta    34680
taacaaaatt aataggagag aaaaacacat aaacacctga aaaccctcc tgcctaggca    34740 aaatagcacc ctcccgctcc agaacaacat acagcgcttc cacagcggca gccataacag    34800
tcagccttac cagtaaaaaa gaaaacctat taaaaaaaca ccactcgaca cggcaccagc    34860
tcaatcagtc acagtgtaaa aagggccaa gtgcagagcg agtatatata ggactaaaaa    34920
atgacgtaac ggttaaagtc cacaaaaaac acccagaaaa ccgcacgcga acctacgccc    34980
agaaacgaaa gccaaaaaac ccacaacttc ctcaaatcgt cacttccgtt ttcccacgtt    35040
acgtcacttc ccatttttaag aaaactacaa ttcccaacac atacaagtta ctccgcccta    35100
aaacctacgt cacccgcccc gttcccacgc cccgcgccac gtcacaaact ccaccccctc    35160
attatcatat tggcttcaat ccaaaataag gtatattatt gat                     35203
```

<210> SEQ ID NO 21
<211> LENGTH: 36460
<212> TYPE: DNA
<213> ORGANISM: Artificial Sequence
<220> FEATURE:
<223> OTHER INFORMATION: Contruct containing two mismatches with
      duplication

<400> SEQUENCE: 21

```
catcatcaat aatataccct attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttg    180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagtacgta cgtgtacttc tgatcggcga    480
tactagggag ataaggatgt acctgacaaa accacattgt tgttgttatc attattattt    540
```

```
agttttcctt ccttgctaac tcctgacgga atctttctca cctcaaatgc gaagtacttt    600
agtttagaaa agacttggtg aaggggtgg tggtggaaaa gtagggtgat cttccaaact    660
aatctggttc cccgcccgcc ccagtagctg ggattcaaga gcgaagagtg gggatcgtcc    720
ccttgtttga tcagaaagac ataaaaggaa atcaagtga acaatgatca gccccacctc    780
caccccaccc ccctgcgcgc gcacaataca atctatttaa ttgtacttca tacttttcat    840
tccaatgggg tgactttgct tctggagaaa ctcttgattc ttgaactctg gggctggcag    900
ctagcctcca gaagcaaagt caccccattg gaatgaaaag tatgaagtac aatgaaaagt    960
atgaagtact ggctccagaa gcaaagtcac cctccagaag caaagtcacc ccattggaat   1020
gaaaagtatg aagtacgcta gcaaaggggg aagcgggctg ctgctctctg caggttctgc   1080
agcggtctct gtctagtggg tgttttcttt tccttagccc tgcccctgga ttgtcagacg   1140
gcgggcgtct gcctctgaag ttagccgtga tttcctctag agccgggtct tatctctggc   1200
tgcacgttgc ctgtgggtga ctaatcacac aataacattg tttagggctg aataaagtc    1260 agagctgttt accccactc tatagggggtt caatataaaa aggcggcgga gaactgtccg   1320
agtcagaagc gttcctgcac cggcgctgag agcctgaccc ggtctgctcc gctgtccttg   1380
cgcgctgcct cccggctgcc cgcgacgctt tcgccccagt ggaagggcca cttgctgcgg   1440
ccgctaattc tgcagatcgg gatccggcat gggcctctcc accgtgcctg acctgctgct   1500
gccgctggtg ctcctggagc tgttggtggg aatataccccc tcagggggtta ttggactggt   1560 ccctcaccta ggggacaggg agaagagaga tagtgtgtgt ccccaaggaa aatatatcca   1620
ccctcaaaat aattcgattt gctgtaccaa gtgccacaaa ggaacctact tgtacaatga   1680
ctgtccaggc ccggggcagg atacggactg cagggagtgt gagagcggct ccttcaccgc   1740
ttcagaaaac cacctcagac actgcctcag ctgctccaaa tgccgaaagg aaatgggtca   1800
ggtggagatc tcttcttgca cagtggaccg ggacaccgtg tgtggctgca ggaagaacca   1860
gtaccggcat tattggagtg aaaaccttttt ccagtgcttc aattgcagcc tctgcctcaa   1920
tgggaccgtg cacctctcct gccaggagaa acagaacacc gtgtgcacct gccatgcagg   1980
tttctttcta agagaaaacg agtgtgtctc ctgtagtaac tgtaagaaaa gcctggagtg   2040
cacgaagttg tgcctaccaa gcttaggatc cagatctaac ttggggtggc tttgtcttct   2100
tcttttgcca attccactaa ttgtttgggt gaagagaaag gaagtacaga aaacatgcag   2160
aaagcacaga aaggaaaacc aaggttctca tgaatctcca accttaaatc ctgaaacagt   2220
ggcaataaat ttatctgatg ttgacttgag taaatatatc accactattg ctggagtcat   2280
gacactaagt caagttaaag gctttgttcg aaagaatggt gtcaatgaag ccaaaataga   2340
tgagatcaag aatgacaatg tccaagacac agcagaacag aaagttcaac tgcttcgtaa   2400
ttggcatcaa cttcatggaa agaaagaagc gtatgacaca ttgattaaag atctcaaaaa   2460
agccaatctt tgtactcttg cagagaaaat tcagactatc atcctcaagg acattactag   2520
tgactcagaa aattcaaact tcagaaatga aatccaaagc ttggtctagc tcgagcatgc   2580
atctaggcgg ccgcatggca gaaattcgcg aattcgctag cgttaacgga tcctctagac   2640
gagatccgaa cttgtttatt gcagcttata atggttacaa ataaagcaat agcatcacaa   2700
atttcacaaa taaagcattt ttttcactgc attctagttg tggtttgtcc aaactcatca   2760
atgtatctta tcatgtctag atctgtactg aaatgtgtgg gcgtggctta agggtgggaa   2820
agaatatata aggtgggggt cttatgtagt tttgtatctg ttttgcagca gccgccgccg   2880
```

```
ccatgagcac caactcgttt gatggaagca ttgtgagctc atatttgaca acgcgcatgc   2940
ccccatgggc cggggtgcgt cagaatgtga tgggctccag cattgatggt cgccccgtcc   3000
tgcccgcaaa ctctactacc ttgacctacg agaccgtgtc tggaacgccg ttggagactg   3060
cagcctccgc cgccgcttca gccgctgcag ccaccgcccg cgggattgtg actgactttg   3120 cttttcctgag cccgcttgca agcagtgcag cttcccgttc atccgcccgc gatgacaagt   3180
tgacggctct tttggcacaa ttggattctt tgacccggga acttaatgtc gtttctcagc   3240
agctgttgga tctgcgccag caggtttctg ccctgaaggc ttcctcccct cccaatgcgg   3300
tttaaaacat aaataaaaaa ccagactctg tttggatttg atcaagcaa gtgtcttgct   3360 gtctttattt aggggttttg cgcgcgcggt aggcccggga ccagcggtct cggtcgttga   3420
gggtcctgtg tattttttcc aggacgtggt aaaggtgact ctggatgttc agatacatgg   3480
gcataagccc gtctctgggg tggaggtagc accactgcag agcttcatgc tgcgggtgg    3540 tgttgtagat gatccagtcg tagcaggagc gctgggcgtg gtgcctaaaa atgtctttca   3600
gtagcaagct gattgccagg ggcaggcccct tggtgtaagt gtttacaaag cggttaagct   3660
gggatgggtg catacgtggg gatatgagat gcatcttgga ctgtattttt aggttggcta   3720
tgttcccagc catatccctc cggggattca tgttgtgcag aaccaccagc acagtgtatc   3780
cggtgcactt gggaaatttg tcatgtagct tagaaggaaa tgcgtggaag aacttggaga   3840
cgcccttgtg acctccaaga ttttccatgc attcgtccat aatgatgcaa tgggcccac    3900 gggcggcggc ctgggcgaag atatttctgg gatcactaac gtcatagttg tgttccagga   3960
tgagatcgtc ataggccatt tttacaaagc gcggcggag ggtgccagac tgcggtataa    4020
tggttccatc cggcccaggg gcgtagttac cctcacagat ttaagggtgg gaaagaatat   4080
ataaggtggg ggtctctatgt agttttgtat ctgttttgca gcagccgccg ccgccatgag   4140
caccaactcg tttgatggaa gcattgtgag ctcatatttg acaacgcgca tgcccccatg   4200
ggccggggtc cgtcagaatg tgatgggctc cagcattgat ggtcgccccg tcctgcccgc   4260
aaactctact accttgacct acgagaccgt gtctggaacg ccgttggaga ctgcagcctc   4320
cgccgccgct tcagccgctg cagccaccgc ccgcgggatt gtgactgact ttgctttcct   4380
gagcccgctt gcaagcagtg cagcttcccg ttcatccgcc cgcgatgaca agttgacggc   4440
tcttttggca caattggatt ctttgacccg ggaacttaat gtcgtttctc agcagctgtt   4500
ggatctgcgc cagcaggttt ctgccctgaa ggcttcctcc cctcccaatg cggtttaaaa   4560
cataaataaa aaaccagact ctgtttggat ttggatcaag caagtgtctt gctgtctttat   4620 tttagggggtt ttgcgcgcgc ggtaggcccg ggaccagcgg tctcggtcgt tgagggtcct   4680
gtgtattttt tccaggacgt ggtaaaggtg actctggatg ttcagataca tgggcataag   4740
cccgtctctg gggtggaggt agcaccactg cagagcttca tgctgcgggg tggtgttgta   4800
gatgatccag tcgtagcagg agcgctgggc gtggtgccta aaaatgtctt tcagtagcaa   4860
gctgattgcc aggggcaggc ccttggtgta agtgtttaca aagcggttaa gctgggatgg   4920
gtgcatacgt ggggatatga gatgcatctt ggactgtatt tttaggttgg ctatgttccc   4980
agccatatcc ctccggggat tcatgttgtg cagaaccacc agcacagtgt atccggtgca   5040
cttgggaaat ttgtcatgta gcttagaagg aaatgcgtgg aagaacttgg agacgccctt   5100
gtgacctcca agattttcca tgcattcgtc cataatgatg gcaatgggcc cacgggcggc   5160
ggcctgggcg aagatatttc tgggatcact aacgtcatag ttgtgttcca ggatgagatc   5220
gtcataggcc attttacaa agcgcgggcg gagggtgcca gactgcggta atggttcc      5280
```

```
atccggccca ggggcgtagt taccctcaca gatttgcatt tcccacgctt tgagttcaga   5340
tgggggatc atgtctacct gcggggcgat gaagaaaacg gtttccgggg taggggagat    5400
cagctgggaa gaaagcaggt tcctgagcag ctgcgactta ccgcagccgg tgggcccgta   5460
aatcacacct attaccggct gcaactggta gttaagagag ctgcagctgc cgtcatccct   5520
gagcagggg gccacttcgt taagcatgtc cctgactcgc atgttttccc tgaccaaatc    5580
cgccagaagg cgctcgccgc ccagcgatag cagttcttgc aaggaagcaa agttttcaa    5640
cggtttgaga ccgtccgccg taggcatgct tttgagcgtt tgaccaagca gttccaggcg   5700
gtcccacagc tcggtcacct gctctacggc atctcgatcc agcatatctc ctcgtttcgc   5760
gggttgggc ggctttcgct gtacggcagt agtcggtgct cgtccagacg ggccagggtc    5820
atgtctttcc acgggcgcag ggtcctcgtc agcgtagtct gggtcacggt gaaggggtgc   5880
gctccgggct gcgcgctggc cagggtgcgc ttgaggctgg tcctgctggt gctgaagcgc   5940
tgccggtctt cgccctgcgc gtcggccagg tagcatttga ccatggtgtc atagtccagc   6000
ccctccgcgg cgtggcccct ggcgcgcagc ttgcccttgg aggaggcgcc gcacgagggg   6060
cagtgcagac ttttgagggc gtagagcttg gcgcgagaa ataccgattc cggggagtag    6120
gcatccgcgc cgcaggcccc gcagacggtc tcgcattcca cgagccaggt gagctctggc   6180
cgttcggggt caaaaaccag gtttcccca tgctttttga tgcgtttctt acctctggtt    6240
tccatgagcc ggtgtccacg ctcggtgacg aaaaggctgt ccgtgtcccc gtatacagac   6300
ttgagaggcc tgtcctcgag cggtgttccg cggtcctcct cgtatagaaa ctcggaccac   6360
tctgagacaa aggctcgcgt ccaggccagc acgaaggagg ctaagtggga ggggtagcgg   6420
tcgttgtcca ctaggggtc cactcgctcc agggtgtgaa gacacatgtc gccctcttcg    6480
gcatcaagga aggtgattgg tttgtaggtg taggccacgt gaccgggtgt tcctgaaggg   6540
gggctataaa aggggtggg ggcgcgttcg tcctcactct cttccgcatc gctgtctgcg    6600
agggccagct gttggggtga gtactccctc tgaaaagcgg gcatgacttc tgcgctaaga   6660
ttgtcagttt ccaaaaacga ggaggatttg atattcacct ggcccgcggt gatgcctttg   6720
agggtggccg catccatctg gtcagaaaag acaatctttt tgttgtcaag cttggtggca   6780
aacgacccgt agagggcgtt ggacagcaac ttggcgatgg agcgcagggt ttggttttg    6840
tcgcgatcgg cgcgctcctt ggccgcgatg tttagctgca cgtattcgcg cgcaacgcac   6900
cgccattcgg gaaagacggt ggtgcgctcg tcgggcacca ggtgcacgcg ccaaccgcgg   6960
ttgtgcaggg tgacaaggtc aacgctggtg gctacctctc cgcgtaggcg ctcgttggtc   7020
cagcagaggc ggccgcccctt gcgcgagcag aatggcggta gggggtctag ctgcgtctcg   7080
tccgggggt ctgcgtccac ggtaaagacc ccgggcagca ggcgcgcgtc gaagtagtct    7140
atcttgcatc cttgcaagtc tagcgcctgc tgccatgcgc gggcggcaag cgcgcgctcg   7200
tatgggttga gtgggggacc ccatggcatg ggtgggtga gcgcggaggc gtacatgccg    7260
caaatgtcgt aaacgtagag gggctctctg agtattccaa gatatgtagg gtagcatctt   7320
ccaccgcgga tgctggcgcg cacgtaatcg tatagttcgt gcgagggagc gaggaggtcg   7380
ggaccgaggt tgctacgggc gggctgctct gctcggaaga ctatctgcct gaagatggca   7440
tgtgagttgg atgatatggt tggacgctgg aagacgttga agctggcgtc tgtgagacct   7500
accgcgtcac gcacgaagga ggcgtaggag tcgcgcagct tgttgaccag ctcggcggtg   7560
acctgcacgt ctagggcgca gtagtccagg gtttccttga tgatgtcata cttatcctgt   7620
```

```
cccttttttt tccacagctc gcggttgagg acaaactctt cgcggtctttc ccagtactct    7680
tggatcggaa acccgtcggc ctccgaacgg taagagccta gcatgtagaa ctggttgacg    7740
gcctggtagg cgcagcatcc cttttctacg ggtagcgcgt atgcctgcgc ggccttccgg    7800
agcgaggtgt gggtgagcgc aaaggtgtcc ctgaccatga ctttgaggta ctggtatttg    7860
aagtcagtgt cgtcgcatcc gccctgctcc cagagcaaaa agtccgtgcg cttttttggaa   7920
cgcggatttg gcagggcgaa ggtgacatcg ttgaagagta tctttcccgc gcgaggcata    7980
aagttgcgtg tgatgcggaa gggtcccggc acctcggaac ggttgttaat tacctgggcg    8040
gcgagcacga tctcgtcaaa gccgttgatg ttgtggccca caatgtaaag ttccaagaag    8100
cgcgggatgc ccttgatgga aggcaatttt ttaagttcct cgtaggtgag ctcttcaggg    8160
gagctgagcc cgtgctctga aagggcccag tctgcaagat gagggttgga agcgacgaat    8220
gagctccaca ggtcacgggc cattagcatt tgcaggtggt cgcgaaaggt cctaaactgg    8280
cgacctatgg ccattttttc tggggtgatg cagtagaagg taagcgggtc ttgttcccag    8340
cggtcccatc caaggttcgc ggctaggtct cgcgcggcag tcactagagg ctcatctccg    8400
ccgaacttca tgaccagcat gaagggcacg agctgcttcc caaaggcccc catccaagta    8460
taggtctcta catcgtaggt gacaaagaga cgctcggtgc gaggatgcga gccgatcggg    8520
aagaactgga tctcccgcca ccaattggag gagtggctat tgatgtggtg aaagtagaag    8580
tccctgcgac gggccgaaca ctcgtgctgg cttttgtaaa aacgtgcgca gtactggcag    8640
cggtgcacgg gctgtacatc ctgcacgagg ttgacctgac gaccgcgcac aaggaagcag    8700
agtgggaatt tgagcccctc gcctggcggg tttggctggt ggtcttctac ttcggctgct    8760
tgtccttgac cgtctggctg ctcgagggga gttacggtgg atcggaccac cacgccgcgc    8820
gagcccaaag tccagatgtc cgcgcgcggc ggtcggagct tgatgacaac atcgcgcaga    8880
tgggagctgt ccatggtctg gagctcccgc ggcgtcaggt caggcgggag ctcctgcagg    8940
tttacctcgc atagacgggt cagggcgcgg gctagatcca ggtgatacct aatttccagg    9000
ggctggttgg tggcggcgtc gatggcttgc aagaggccgc atccccgcgg cgcgactacg    9060
gtaccgcgcg gcgggcggtg ggccgcgggg gtgtccttgg atgatgcatc taaaagcggt    9120
gacgcgggcg agcccccgga ggtagggggg gctccggacc cgccgggaga ggggcaggg    9180
gcacgtcggc gccgcgcgcg ggcaggagct ggtgctgcgc gcgtaggttg ctggcgaacg    9240
cgacgacgcg gcggttgatc tcctgaatct ggcgcctctg cgtgaagacg acgggcccgg    9300
tgagcttgaa cctgaaagag agttcgacag aatcaatttc ggtgtcgttg acggcggcct    9360
ggcgcaaaat ctcctgcacg tctcctgagt tgtcttgata ggcgatctcg gccatgaact    9420
gctcgatctc ttcctcctgg agatctccgc gtccggctcg ctccacggtg gcggcgaggt    9480
cgttggaaat gcgggccatg agctgcgaga aggcgttgag gcctccctcg ttccagacgc    9540
ggctgtagac cacgcccct tcggcatcgc gggcgcgcat gaccacctgc gcagagattga   9600
gctccacgtg ccgggcgaag acggcgtagt ttcgcaggcg ctgaaagagg tagttgaggg    9660
tggtggcggt gtgttctgcc acgaagaagt acataaccca gcgtcgcaac gtggattcgt    9720
tgatatcccc caaggcctca aggcgctcca tggcctcgta gaagtccacg gcgaagttga    9780
aaaactggga gttgcgcgcc gacacggtta actcctcctc cagaagacgg atgagctcgg    9840
cgacagtgtc gcgcacctcg cgctcaaagg ctacagggc ctcttcttct tcttcaatct    9900
cctcttccat aagggcctcc ccttcttctt cttctggcgg cggtggggga ggggggacac    9960
ggcggcgacg acggcgcacc gggaggcggt cgacaaagcg ctcgatcatc tccccgcggc   10020
```

```
gacggcgcat ggtctcggtg acggcgcggc cgttctcgcg ggggcgcagt tggaagacgc   10080
cgcccgtcat gtcccggtta tgggttggcg gggggctgcc atgcggcagg gatacggcgc   10140
taacgatgca tctcaacaat tgttgtgtag gtactccgcc gccgagggac ctgagcgagt   10200
ccgcatcgac cggatcggaa aacctctcga gaaaggcgtc taaccagtca cagtcgcaag   10260
gtaggctgag caccgtggcg ggcggcagcg ggcggcggtc ggggttgttt ctggcggagg   10320
tgctgctgat gatgtaatta aagtaggcgg tcttgagacg gcggatggtc gacagaagca   10380
ccatgtcctt gggtccggcc tgctgaatgc gcaggcggtc ggccatgccc caggcttcgt   10440
tttgacatcg gcgcaggtct ttgtagtagt cttgcatgag cctttctacc ggcacttctt   10500
cttctccttc ctcttgtcct gcatctcttg catctatcgc tgcggcggcg gcggagtttg   10560
gccgtaggtg gcgccctctt cctcccatgc gtgtgacccc gaagcccctc atcggctgaa   10620
gcagggctag gtcggcgaca acgcgctcgg ctaatatggc ctgctgcacc tgcgtgaggg   10680
tagactggaa gtcatccatg tccacaaagc ggtggtatgc gcccgtgttg atggtgtaag   10740
tgcagttggc cataacggac cagttaacgg tctggtgacc cggctgcgag agctcggtgt   10800
acctgagacg cgagtaagcc ctcgagtcaa atacgtagtc gttgcaagtc cgcaccaggt   10860
actggtatcc caccaaaaag tgcggcggcg gctggcggta gaggggccag cgtagggtgg   10920
ccggggctcc gggggcgaga tcttccaaca taaggcgatg atatccgtag atgtacctgg   10980
acatccaggt gatgccggcg gcggtggtgg aggcgcgcgg aaagtcgcgg acgcggttcc   11040
agatgttgcg cagcggcaaa aagtgctcca tggtcgggac gctctggccg gtcaggcgcg   11100
cgcaatcgtt gacgctctag accgtgcaaa aggagagcct gtaagcgggc actcttccgt   11160
ggtctggtgg ataaattcgc aagggtatca tggcggacga ccggggttcg agccccgtat   11220
ccggccgtcc gccgtgatcc atgcggttac cgcccgcgtg tcgaacccag gtgtgcgacg   11280
tcagacaacg ggggagtgct cctttttggct tccttccagg cgcggcggct gctgcgctag   11340
cttttttggc cactggccgc gcgcagcgta agcggttagg ctggaaagcg aaagcattaa   11400
gtggctcgct ccctgtagcc ggagggttat tttccaaggg ttgagtcgcg gaccccggg   11460 ttcgagtctc ggaccggccg gactgcggcg aacgggggtt tgcctcccg tcatgcaaga   11520 ccccgcttgc aaattcctcc ggaaacaggg acgagcccct tttttgcttt cccagatgc   11580 atccggtgct gcggcagatg cgcccccctc ctcagcagcg gcaagagcaa gagcagcggc   11640
agacatgcag ggcaccctcc cctcctccta ccgcgtcagg aggggcgaca tccgcggttg   11700
acgcggcagc agatggtgat tacgaacccc cgcggcgccg ggcccggcac tacctggact   11760
tggaggaggg cgagggcctg gcgcggctag gagcgccctc tcctgagcgg cacccaaggg   11820
tgcagctgaa gcgtgatacg cgtgaggcgt acgtgccgcg gcagaacctg tttcgcgacc   11880
gcgagggaga ggagcccgag gagatgcggg atcgaaagtt ccacgcaggg cgcgagctgc   11940
ggcatggcct gaatcgcgag cggttgctgc gcgaggagga ctttgagccc gacgcgcgaa   12000
ccgggattag tcccgcgcgc gcacacgtgg cggccgccga cctggtaacc gcatacgagc   12060
agacggtgaa ccaggagatt aactttcaaa aaagctttaa caaccacgtg cgtacgcttg   12120
tggcgcgcga ggaggtggct ataggactga tgcatctgtg ggactttgta agcgcgctgg   12180
agcaaaaccc aaatagcaag ccgctcatgg cgcagctgtt ccttatagtg cagcacagca   12240
gggacaacga ggcattcagg gatgcgctgc taaacatagt agagcccgag ggccgctggc   12300
tgctcgattt gataaacatc ctgcagagca tagtggtgca ggagcgcagc ttgagcctgg   12360
```

```
ctgacaaggt ggccgccatc aactattcca tgcttagcct gggcaagttt tacgcccgca    12420
agatatacca tacccttac gttcccatag acaaggaggt aaagatcgag gggttctaca     12480
tgcgcatggc gctgaaggtg cttaccttga gcgacgacct gggcgtttat cgcaacgagc    12540
gcatccacaa ggccgtgagc gtgagccggc ggcgcgagct cagcgaccgc gagctgatgc    12600
acagcctgca aagggccctg gctggcacgg gcagcggcga tagagaggcc gagtcctact    12660
ttgacgcggg cgctgacctg cgctgggccc aagccgacg cgccctggag gcagctgggg     12720
ccggacctgg gctggcggtg gcacccgcgc gcgctggcaa cgtcggcggc gtggaggaat    12780
atgacgagga cgatgagtac gagccagagg acggcgagta ctaagcggtg atgtttctga    12840
tcagatgatg caagacgcaa cggacccggc ggtgcgggcg gcgctgcaga gccagccgtc    12900
cggccttaac tccacggacg actgcgcca ggtcatggac cgcatcatgt cgctgactgc     12960
gcgcaatcct gacgcgttcc ggcagcagcc gcaggccaac cggctctccg caattctgga    13020
agcggtggtc ccggcgcgcg caaaccccac gcacgagaag gtgctggcga tcgtaaacgc    13080
gctggccgaa acagggcca tccggcccga cgaggccggc ctggtctacg acgcgctgct     13140
tcagcgcgtg gctcgttaca acagcggcaa cgtgcagacc aacctggacc ggctggtggg    13200
ggatgtgcgc gaggccgtgg cgcagcgtga gcgcgcgcag cagcagggca acctgggctc    13260
catggttgca ctaaacgcct tcctgagtac acagcccgcc aacgtgccgc ggggacagga    13320
ggactacacc aactttgtga gcgcactgcg gctaatggtg actgagacac cgcaaagtga    13380
ggtgtaccag tctgggccag actatttttt ccagaccagt agacaaggcc tgcagaccgt    13440
aaacctgagc caggctttca aaaacttgca ggggctgtgg ggggtgcggg ctcccacagg    13500
cgaccgcgcg accgtgtcta gcttgctgac gcccaactcg cgcctgttgc tgctgctaat    13560
agcgcccttc acgacagtg gcagcgtgtc ccgggacaca tacctaggtc acttgctgac    13620
actgtaccgc gaggccatag gtcaggcgca tgtggacgag catactttcc aggagattac    13680
aagtgtcagc cgcgcgctgg ggcaggagga cacgggcagc ctggaggcaa ccctaaaacta   13740 cctgctgacc aaccggcggc agaagatccc ctcgttgcac agtttaaaca gcgaggagga    13800
gcgcattttg cgctacgtgc agcagagcgt gagccttaac ctgatgcgcg acggggtaac    13860
gcccagcgtg gcgctggaca tgaccgcgcg caacatggaa ccgggcatgt atgcctcaaa    13920
ccggccgttt atcaaccgcc taatggacta cttgcatcgc gcggccgccg tgaaccccga    13980
gtatttcacc aatgccatct tgaacccgca ctggctaccg ccccctggtt tctacaccgg    14040
gggattcgag gtgcccgagg gtaacgatgg attcctctgg gacgacatag acgacagcgt    14100 gtttttccccg caaccgcaga ccctgctaga gttgcaacag cgcgagcagg cagaggcggc    14160
gctgcgaaag gaaagcttcc gcaggccaag cagcttgtcc gatctaggcg ctgcggcccc    14220
gcggtcagat gctagtagcc catttccaag cttgataggg tctcttacca gcactcgcac    14280
cacccgcccg cgcctgctgg gcgaggagga gtacctaaac aactcgctgc tgcagccgca    14340
gcgcgaaaaa aacctgcctc cggcatttcc caacaacggg atagagagcc tagtggacaa    14400
gatgagtaga tggaagacgt acgcgcagga gcacagggac gtgccaggcc cgcgcccgcc    14460
cacccgtcgt caaaggcacg accgtcagcg gggtctggtg tggaggacg atgactcggc     14520 agacgacagc agcgtcctgg atttgggagg gagtggcaac ccgtttgcgc accttcgccc    14580
caggctgggg agaatgtttt aaaaaaaaaa aaagcatgat gcaaaataaa aaactcacca    14640
aggccatggc accgagcgtt ggttttcttg tattccccctt agtatgcggc gcgcggcgat    14700
gtatgaggaa ggtcctcctc cctcctacga gagtgtggtg agcgcggcgc cagtggcggc    14760
```

```
ggcgctgggt tctcccttcg atgctcccct ggacccgccg tttgtgcctc cgcggtacct    14820
gcggcctacc gggggagaa acagcatccg ttactctgag ttggcacccc tattcgacac     14880
cacccgtgtg tacctggtgg acaacaagtc aacggatgtg gcatccctga actaccagaa    14940
cgaccacagc aactttctga ccacggtcat tcaaaacaat gactacagcc cggggaggc     15000 aagcacacag accatcaatc ttgacgaccg gtcgcactgg ggcggcgacc tgaaaaccat    15060
cctgcatacc aacatgccaa atgtgaacga gttcatgttt accaataagt ttaaggcgcg    15120
ggtgatggtg tcgcgcttgc ctactaagga caatcaggtg gagctgaaat acgagtgggt    15180
ggagttcacg ctgcccgagg gcaactactc cgagaccatg accatagacc ttatgaacaa    15240
cgcgatcgtg gagcactact tgaaagtggg cagacagaac ggggttctgg aaagcgacat    15300
cggggtaaag tttgacaccc gcaacttcag actggggttt gacccccgtca ctggtcttgt    15360 catgcctggg gtatatacaa acgaagcctt ccatccagac atcattttgc tgccaggatg    15420
cggggtggac ttcacccaca gccgcctgag caacttgttg ggcatccgca agcggcaacc    15480
cttccaggag ggctttagga tcacctacga tgatctggag ggtggtaaca ttcccgcact    15540
gttggatgtg gacgcctacc aggcgagctt gaaagatgac accgaacagg gcggggtgg    15600 cgcaggcggc agcaacagca gtggcagcgg cgcggaagag aactccaacg cggcagccgc    15660
ggcaatgcag ccggtggagg acatgaacga tcatgccatt cgcggcgaca cctttgccac    15720
acgggctgag gagaagcgcg ctgaggccga agcagcggcc gaagctgccg cccccgctgc    15780
gcaacccgag gtcgagaagc ctcagaagaa accggtgatc aaaccccctga cagaggacag    15840 caagaaacgc agttacaacc taataagcaa tgacagcacc ttcacccagt accgcagctg    15900
gtaccttgca tacaactacg gcgaccctca gaccggaatc cgctcatgga ccctgctttg    15960
cactcctgac gtaacctgcg gctcggagca ggtctactgg tcgttgccag acatgatgca    16020
agaccccgtg accttccgct ccacgcgcca gatcagcaac tttccggtgg tgggcgccga    16080
gctgttgccc gtgcactcca agagcttcta caacgaccag gccgtctact cccaactcat    16140
ccgccagttt acctctctga cccacgtgtt caatcgcttt cccgagaacc agattttggc    16200
gcgcccgcca gcccccacca tcaccaccgt cagtgaaaac gttcctgctc tcacagatca    16260
cgggacgcta ccgctgcgca acagcatcgg aggagtccag cgagtgacca ttactgacgc    16320
cagacgccgc acctgcccct acgtttacaa ggccctgggc atagtctcgc gcgcgtcct    16380 atcgagccgc acttttgag caagcatgtc catccttata tcgcccagca ataacacagg    16440
ctggggcctg cgcttcccaa gcaagatgtt tggcggggcc aagaagcgct ccgaccaaca    16500
cccagtgcgc gtgcgcgggc actaccgcgc gccctgggc gcgcacaaac gcggccgcac    16560
tgggcgcacc accgtcgatg acgccatcga cgcggtggtg gaggaggcgc gcaactacac    16620
gcccacgccg ccaccagtgt ccacagtgga cgcggccatt cagaccgtgg tgcgcggagc    16680
ccggcgctat gctaaaatga agagacgcg gaggcgcgta gcacgtcgcc accgccgccg    16740
acccggcact gccgcccaac gcgcggcggc ggccctgctt aaccgcgcac gtcgcaccgg    16800
ccgacgggcg gccatgcggg ccgctcgaag gctggccgcg ggtattgtca ctgtgccccc    16860
caggtccagg cgacgagcgg ccgccgcagc agccgcggcc attagtgcta tgactcaggg    16920 tcgcagggc aacgtgtatt gggtgcgcga ctcggttagc ggcctgcgcg tgcccgtgcg    16980
cacccgcccc ccgcgcaact agattgcaag aaaaaactac ttagactcgt actgttgtat    17040
gtatccagcg gcggcggcgc gcaacgaagc tatgtccaag cgcaaaatca agaagagat     17100
```

```
gctccaggtc atcgcgccgg agatctatgg cccccgaag aaggaagagc aggattacaa   17160
gccccgaaag ctaaagcggg tcaaaagaa aaagaaagat gatgatgatg aacttgacga   17220
cgaggtggaa ctgctgcacg ctaccgcgcc caggcgacgg gtacagtgga aggtcgacg   17280
cgtaaaacgt gttttgcgac ccggcaccac cgtagtcttt acgcccggtg agcgctccac   17340
ccgcacctac aagcgcgtgt atgatgaggt gtacggcgac gaggacctgc ttgagcaggc   17400
caacgagcgc ctcggggagt ttgcctacgg aaagcggcat aaggacatgc tggcgttgcc   17460
gctggacgag ggcaacccaa cacctagcct aaagcccgta acactgcagc aggtgctgcc   17520
cgcgcttgca ccgtccgaag aaaagcgcgg cctaaagcgc gagtctggtg acttggcacc   17580
caccgtgcag ctgatggtac ccaagcgcca gcgactggaa gatgtcttgg aaaaaatgac   17640
cgtggaacct gggctggagc ccgaggtccg cgtgcggcca atcaagcagg tggcgccggg   17700
actgggcgtg cagaccgtgg acgttcagat acccactacc agtagcacca gtattgccac   17760
cgccacagag ggcatggaga cacaaacgtc cccggttgcc tcagcggtgg cggatgccgc   17820
ggtgcaggcg gtcgctgcgg ccgcgtccaa gacctctacg gaggtgcaaa cggacccgtg   17880
gatgtttcgc gtttcagccc ccggcgcgcc gcgccgttcg aggaagtacg gcgccgccag   17940
cgcgctactg cccgaatatg ccctacatcc ttccattgcg cctaccccg gctatcgtgg   18000
ctacacctac cgccccagaa gacgagcaac tacccgacgc cgaaccacca ctggaacccg   18060
ccgccgccgt cgccgtcgcc agcccgtgct ggccccgatt ccgtgcgca gggtggctcg   18120
cgaaggaggc aggaccctgg tgctgccaac agcgcgctac caccccagca tcgtttaaaa   18180
gccggtcttt gtggttcttg cagatatggc cctcacctgc cgcctccgtt tcccggtgcc   18240
gggattccga ggaagaatgc accgtaggag gggcatggcc ggccacggcc tgacgggcgg   18300
catgcgtcgt gcgcaccacc ggcggcggcg cgcgtcgcac cgtcgcatgc gcggcggtat   18360
cctgcccctc cttattccac tgatcgccgc ggcgattggc gccgtgcccg gaattgcatc   18420
cgtggccttg caggcgcaga gacactgatt aaaaacaagt tgcatgtgga aaaatcaaaa   18480
taaaaagtct ggactctcac gctcgcttgg tcctgtaact attttgtaga atggaagaca   18540
tcaactttgc gtctctggcc ccgcgacacg gctcgcgccc gttcatggga aactggcaag   18600
atatcggcac cagcaatatg agcggtggcg ccttcagctg gggctcgctg tggagcggca   18660
ttaaaaattt cggttccacc gttaagaact atggcagcaa ggcctggaac agcagcacag   18720
gccagatgct gagggataag ttgaaagagc aaaatttcca acaaaaggtg gtagatggcc   18780
tggcctctgg cattagcggg gtggtggacc tggccaacca ggcagtgcaa aataagatta   18840
acagtaagct tgatccccgc cctcccgtag aggagcctcc accggccgtg gagacagtgt   18900
ctccagaggg gcgtggcgaa aagcgtccgc gccccgacag ggaagaaact ctggtgacgc   18960
aaatagacga gcctccctcg tacgaggagg cactaaagca aggcctgccc accacccgtc   19020
ccatcgcgcc catggctacc ggagtgctgg ccagcacac acccgtaacg ctggacctgc   19080
ctcccccgc cgacacccag cagaaacctg tgctgccagg cccgaccgcc gttgttgtaa   19140
cccgtcctag ccgcgcgtcc ctgcgccgcg ccgccagcgg tccgcgatcg ttgcggcccg   19200
tagccagtgg caactggcaa agcacactga acagcatcgt gggtctgggg gtgcaatccc   19260
tgaagcgccg acgatgcttc tgatagctaa cgtgtcgtat gtgtgtcatg tatgcgtcca   19320
tgtcgccgcc agaggagctg ctgagccgcc gcgcgcccgc tttccaagat ggctacccct   19380
tcgatgatgc cgcagtggtc ttacatgcac atctcgggcc aggacgcctc ggagtacctg   19440
agccccgggc tggtgcagtt tgcccgcgcc accgagacgt acttcagcct gaataacaag   19500
```

```
tttagaaacc ccacggtggc gcctacgcac gacgtgacca cagaccggtc ccagcgtttg   19560
acgctgcggt tcatccctgt ggaccgtgag gatactgcgt actcgtacaa ggcgcggttc   19620
accctagctg tgggtgataa ccgtgtgctg gacatggctt ccacgtactt tgacatccgc   19680
ggcgtgctgg acaggggccc tacttttaag ccctactctg gcactgccta caacgccctg   19740
gctcccaagg gtgccccaaa tccttgcgaa tgggatgaag ctgctactgc tcttgaaata   19800
aacctagaag aagaggacga tgacaacgaa gacgaagtag acgagcaagc tgagcagcaa   19860
aaaactcacg tatttgggca ggcgccttat tctggtataa atattacaaa ggagggtatt   19920
caaataggtg tcgaaggtca aacacctaaa tatgccgata aaacatttca acctgaacct   19980
caaataggag aatctcagtg gtacgaaaca gaaattaatc atgcagctgg gagagtccta   20040
aaaaagacta ccccaatgaa accatgttac ggttcatatg caaacccac aaatgaaaat    20100 ggagggcaag gcattcttgt aaagcaacaa aatggaaagc tagaaagtca agtggaaatg   20160
caatttttct caactactga ggcagccgca ggcaatggtg ataacttgac tcctaaagtg   20220
gtattgtaca gtgaagatgt agatatagaa accccagaca ctcatatttc ttacatgccc   20280
actattaagg aaggtaactc acgagaacta atgggccaac aatctatgcc caacaggcct   20340
aattacattg cttttaggga caattttatt ggtctaatgt attacaacag cacgggtaat   20400
atgggtgttc tggcgggcca agcatcgcag ttgaatgctg ttgtagattt gcaagacaga   20460
aacacagagc tttcatacca gcttttgctt gattccattg gtgatagaac caggtacttt   20520
tctatgtgga atcaggctgt tgacagctat gatccagatg ttagaattat tgaaaatcat   20580
ggaactgaag atgaacttcc aaattactgc tttccactgg gaggtgtgat taatacagag   20640
actcttacca aggtaaaacc taaaacaggt caggaaaatg gatgggaaaa agatgctaca   20700
gaattttcag ataaaaatga aataagagtt ggaaataatt ttgccatgga aatcaatcta   20760
aatgccaacc tgtggagaaa tttcctgtac tccaacatag cgctgtattt gcccgacaag   20820
ctaaagtaca gtccttccaa cgtaaaaatt tctgataacc caaacaccta cgactacatg   20880
aacaagcgag tggtggctcc cgggctagtg gactgctaca ttaaccttgg agcacgctgg   20940
tcccttgact atatggacaa cgtcaaccca tttaaccacc accgcaatgc tggcctgcgc   21000
taccgctcaa tgttgctggg caatggtcgc tatgtgccct ccacatcca ggtgcctcag    21060 aagttctttg ccattaaaaa cctccttctc ctgccgggct catacaccta cgagtggaac   21120
ttcaggaagg atgttaacat ggttctgcag agctccctag gaaatgacct aagggttgac   21180
ggagccagca ttaagtttga tagcatttgc ctttacgcca ccttcttccc catggccac    21240 aacaccgcct ccacgcttga ggccatgctt agaaacgaca ccaacgacca gtcctttaac   21300
gactatctct ccgccgccaa catgctctac cctatacccg ccaacgctac caacgtgccc   21360
atatccatcc cctcccgcaa ctgggcggct ttccgcggct gggccttcac gcgccttaag   21420
actaaggaaa cccatcact gggctcgggc tacgacccct attacccta ctctggctct     21480 atacccatcc tagatggaac ctttaacctc aaccacacct ttaagaaggt ggccattacc   21540
tttgactctt ctgtcagctg gcctggcaat gaccgcctgc ttaccccaa cgagtttgaa    21600 attaagcgct cagttgacgg ggagggttac aacgttgccc agtgtaacat gaccaaagac   21660
tggttcctgg tacaaatgct agctaactat aacattggct accagggctt ctatatccca   21720
gagagctaca aggaccgcat gtactccttc tttagaaact tccagcccat gagccgtcag   21780
gtggtggatg atactaaata caaggactac caacaggtgg gcatcctaca ccaacacaac   21840
```

```
aactctggat tgttggcta ccttgcccccc accatgcgcg aaggacaggc ctaccctgct   21900
aacttcccct atccgcttat aggcaagacc gcagttgaca gcattaccca gaaaaagttt   21960
ctttgcgatc gcacccttg gcgcatccca ttctccagta actttatgtc catgggcgca    22020
ctcacagacc tgggccaaaa ccttctctac gccaactccg cccacgcgct agacatgact   22080
tttgaggtgg atcccatgga cgagcccacc cttctttatg ttttgtttga agtctttgac   22140
gtggtccgtg tgcaccagcc gcaccgcggc gtcatcgaaa ccgtgtacct gcgcacgccc   22200
ttctcggccg gcaacgccac aacataaaga agcaagcaac atcaacaaca gctgccgcca   22260
tgggctccag tgagcaggaa ctgaaagcca ttgtcaaaga tcttggttgt gggccatatt   22320
ttttgggcac ctatgacaag cgcttccag gctttgtttc tccacacaag ctcgcctgcg    22380
ccatagtcaa tacggccggt cgcgagactg ggggcgtaca ctggatggcc tttgcctgga   22440
acccgcactc aaaaacatgc tacctctttg agcccttttgg cttttctgac cagcgactca   22500
agcaggttta ccagtttgag tacgagtcac tcctgcgccg tagcgccatt gcttcttccc   22560
ccgaccgctg tataacgctg gaaaagtcca cccaaagcgt acaggggccc aactcggccg   22620
cctgtggact attctgctgc atgtttctcc acgcctttgc caactggccc caaactccca   22680
tggatcacaa ccccaccatg aaccttatta ccggggtacc caactccatg ctcaacagtc   22740
cccaggtaca gcccacccctg cgtcgcaacc aggaacagct ctacagcttc ctggagcgcc   22800
actcgcccta cttccgcagc cacagtgcgc agattaggag cgccacttct ttttgtcact   22860
tgaaaaacat gtaaaaataa tgtactagag cactttcaa taaaggcaaa tgcttttatt     22920
tgtacactct cgggtgatta tttacccccca cccttgccgt ctgcgccgtt taaaaatcaa   22980
aggggttctg ccgcgcatcg ctatgcgcca ctggcaggga cacgttgcga tactggtgtt   23040
tagtgctcca cttaaactca ggcacaacca tccgcggcag ctcggtgaag ttttcactcc   23100
acaggctgcg caccatcacc aacgcgttta gcaggtcggg cgccgatatc ttgaagtcgc   23160
agttggggcc tccgccctgc gcgcgcgagt tgcgatacac agggttgcag cactggaaca   23220
ctatcagcgc cgggtggtgc acgctggcca gcacgctctt gtcggagatc agatccgcgt   23280
ccaggtcctc cgcgttgctc agggcgaacg gagtcaactt tggtagctgc cttcccaaaa   23340
agggcgcgtg cccaggcttt gagttgcact cgcaccgtag tggcatcaaa aggtgaccgt   23400
gcccggtctg ggcgttagga tacagcgcct gcataaaagc cttgatctgc ttaaaagcca   23460
cctgagcctt tgcgccttca gagaagaaca tgccgcaaga cttgccggaa aactgattgg   23520
ccggacaggc cgcgtcgtgc acgcagcacc ttgcgtcggt gttggagatc tgcaccacat   23580
ttcggcccca ccggttcttc acgatcttgg ccttgctaga ctgctccttc agcgcgcgct   23640
gcccgttttc gctcgtcaca tccatttcaa tcacgtgctc cttatttatc ataatgcttc   23700
cgtgtagaca cttaagctcg ccttcgatct cagcgcagcg gtgcagccac aacgcgcagc   23760
ccgtgggctc gtgatgcttg taggtcacct ctgcaaacga ctgcaggtac gcctgcagga   23820 atcgcccat catcgtcaca aaggtcttgt tgctggtgaa ggtcagctgc aacccgcggt   23880
gctcctcgtt cagccaggtc ttgcatacgg ccgccagagc ttccacttgg tcaggcagta   23940
gtttgaagtt cgcctttaga tcgttatcca cgtggtactt gtccatcagc gcgcgcgcag   24000
cctccatgcc cttctcccac gcagacacga tcggcacact cagcgggttc atcaccgtaa   24060
tttcactttc cgcttcgctg ggctcttcct cttcctcttg cgtccgcata ccacgcgcca   24120
ctgggtcgtc ttcattcagc cgccgcactg tgcgcttacc tcctttgcca tgcttgatta   24180
gcaccggtgg gttgctgaaa cccaccattt gtagcgccac atcttctctt tcttcctcgc   24240
```

```
tgtccacgat tacctctggt gatggcgggc gctcgggctt gggagaaggg cgcttcttt  24300 tcttcttggg cgcaatggcc aaatccgccg ccgaggtcga tggccgcggg ctgggtgtgc  24360
gcggcaccag cgcgtcttgt gatgagtctt cctcgtcctc ggactcgata cgccgcctca  24420 tccgctttt tgggggcgcc cggggaggcg gcggcgacgg ggacggggac gacacgtcct  24480
ccatggttgg gggacgtcgc gccgcaccgc gtccgcgctc gggggtggtt tcgcgctgct  24540
cctcttcccg actggccatt tccttctcct ataggcagaa aaagatcatg gagtcagtcg  24600
agaagaagga cagcctaacc gcccctctg agttcgccac caccgcctcc accgatgccg  24660
ccaacgcgcc taccaccttc cccgtcgagg caccccgct tgaggaggag gaagtgatta  24720
tcgagcagga cccaggtttt gtaagcgaag acgacgagga ccgctcagta ccaacagagg  24780
ataaaaagca agaccaggac aacgcagagg caaacgagga caagtcgggg cgggggacg  24840 aaaggcatgg cgactaccta gatgtgggag acgacgtgct gttgaagcat ctgcagcgcc  24900
agtgcgccat tatctgcgac gcgttgcaag agcgcagcga tgtgcccctc gccatagcgg  24960
atgtcagcct tgcctacgaa cgccacctat tctcaccgcg cgtacccccc aaacgccaag  25020
aaaacggcac atgcgagccc aacccgcgcc tcaacttcta ccccgtattt gccgtgccag  25080
aggtgcttgc cacctatcac atcttttttcc aaaactgcaa gataccccta tcctgccgtg  25140
ccaaccgcag ccgagcggac aagcagctgg ccttgcggca gggcgctgtc atacctgata  25200
tcgcctcgct caacgaagtg ccaaaaatct ttgagggtct tggacgcgac gagaagcgcg  25260
cggcaaacgc tctgcaacag gaaaacagcg aaaatgaaag tcactctgga gtgttggtgg  25320
aactcgaggg tgacaacgcg cgcctagccg tactaaaacg cagcatcgag gtcacccact  25380
ttgcctaccc ggcacttaac ctacccccca aggtcatgag cacagtcatg agtgagctga  25440
tcgtgcgccg tgcgcagccc ctggagaggg atgcaaattt gcaagaacaa acagaggagg  25500
gcctacccgc agttggcgac gagcagctag cgcgctggct tcaaacgcgc gagcctgccg  25560
acttggagga gcgacgcaaa ctaatgatgg ccgcagtgct cgttaccgtg gagcttgagt  25620
gcatgcagcg gttctttgct gacccggaga tgcagcgcaa gctagaggaa acattgcact  25680
acacctttcg acagggctac gtacgccagg cctgcaagat ctccaacgtg gagctctgca  25740
acctggtctc ctaccttgga attttgcacg aaaaccgcct tgggcaaaac gtgcttcatt  25800
ccacgctcaa gggcgaggcg cgccgcgact acgtccgcga ctgcgtttac ttatttctat  25860
gctacacctg gcagacggcc atgggcgttt ggcagcagtg cttggaggag tgcaacctca  25920
aggagctgca gaaactgcta aagcaaaact gaaggacct atggacgcc ttcaacgagc  25980 gctccgtggc cgcgcacctg gcggacatca ttttccccga acgcctgctt aaaaccctgc  26040
aacagggtct gccagacttc accagtcaaa gcatgttgca gaactttagg aactttatcc  26100
tagagcgctc aggaatcttg cccgccacct gctgtgcact tcctagcgac tttgtgccca  26160
ttaagtaccg cgaatgccct ccgccgcttt ggggccactg ctaccttctg cagctagcca  26220
actaccttgc ctaccactct gacataatgg aagacgtgag cggtgacggt ctactggagt  26280
gtcactgtcg ctgcaaccta tgcacccgc accgctccct ggtttgcaat tcgcagctgc  26340
ttaacgaaag tcaaattatc ggtaccttg agctgcaggg tccctcgcct gacgaaaagt  26400
ccgcggctcc ggggttgaaa ctcactccgg ggctgtggac gtcggcttac cttcgcaaat  26460
ttgtacctga ggactaccac gcccacgaga ttaggttcta cgaagaccaa tcccgccgc  26520 ctaatgcgga gcttaccgcc tgcgtcatta cccagggcca cattcttggc caattgcaag  26580
```

```
ccatcaacaa agcccgccaa gagtttctgc tacgaaaggg acgggggggtt tacttggacc   26640 cccagtccgg cgaggagctc aacccaatcc ccccgccgcc gcagccctat cagcagcagc   26700
cgcgggccct tgcttcccag gatggcaccc aaaaagaagc tgcagctgcc gccgccaccc   26760
acggacgagg aggaatactg ggacagtcag gcagaggagg ttttggacga ggaggaggag   26820
gacatgatgg aagactggga gagcctagac gaggaagctt ccgaggtcga agaggtgtca   26880
gacgaaacac cgtcaccctc ggtcgcattc ccctcgccgg cgcccagaa atcggcaacc    26940 ggttccagca tggctacaac ctccgctcct caggcgccgc cggcactgcc cgttcgccga   27000
cccaaccgta gatgggacac cactggaacc agggccggta agtccaagca gccgccgccg   27060
ttagcccaag agcaacaaca gcgccaaggc taccgctcat ggcgcgggca caagaacgcc   27120
atagttgctt gcttgcaaga ctgtgggggc aacatctcct tcgcccgccg ctttcttctc   27180
taccatcacg gcgtggcctt cccccgtaac atcctgcatt actaccgtca tctctacagc   27240
ccatactgca ccggcggcag cggcagcaac agcagcggcc acacagaagc aaaggcgacc   27300
ggatagcaag actctgacaa agcccaagaa atccacagcg gcggcagcag caggaggagg   27360
agcgctgcgt ctggcgccca acgaacccgt atcgacccgc gagcttagaa acaggatttt   27420
tcccactctg tatgctatat ttcaacagag caggggccaa gaacaagagc tgaaaataaa   27480
aaacaggtct ctgcgatccc tcacccgcag ctgcctgtat cacaaaagcg aagatcagct   27540
tcggcgcacg ctggaagacg cggaggctct cttcagtaaa tactgcgcgc tgactcttaa   27600
ggactagttt cgcgcccttt ctcaaattta agcgcgaaaa ctacgtcatc tccagcggcc   27660
acacccggcg ccagcacctg ttgtcagcgc cattatgagc aaggaaattc ccacgcccta   27720
catgtggagt taccagccac aaatgggact tgcggctgga gctgcccaag actactcaac   27780
ccgaataaac tacatgagcg cgggaccccca catgatatcc cgggtcaacg gaatacgcgc   27840
ccaccgaaac cgaattctcc tggaacaggc ggctattacc accacacctc gtaataacct   27900
taatccccgt agttggcccg ctgccctggt gtaccaggaa agtcccgctc ccaccactgt   27960
ggtacttccc agagacgccc aggccgaagt tcagatgact aactcagggg cgcagcttgc   28020
gggcggcttt cgtcacaggg tgcggtcgcc cgggcaggga taactcacc tgacaatcag    28080 agggcgaggt attcagctca acgacgagtc ggtgagctcc tcgcttggtc tccgtccgga   28140
cgggacattt cagatcggcg gcgcggccg ctcttcattc acgcctcgtc aggcaatcct    28200
aactctgcag acctcgtcct ctgagccgcg ctctggaggc attggaactc tgcaatttat   28260
tgaggagttt gtgccatcgg tctactttaa ccccttctcg ggacctcccg gccactatcc   28320
ggatcaattt attcctaact ttgacgcggt aaaggactcg gcggacggct acgactgaat   28380
gttaagtgga gaggcagagc aactgcgcct gaaacacctg gtccactgtc gccgccacaa   28440
gtgctttgcc cgcgactccg gtgagttttg ctactttgaa ttgcccgagg atcatatcga   28500
gggcccggcg cacggcgtcc ggcttaccgc ccagggagag cttgcccgta gcctgattcg   28560
ggagtttacc cagcgccccc tgctagttga gcggacagg ggaccctgtg ttctcactgt     28620
gatttgcaac tgtcctaacc ctggattaca tcaagatctt tgttgccatc tctgtgctga   28680
gtataataaa tacagaaatt aaaatatact ggggctccta tcgccatcct gtaaacgcca   28740
ccgtcttcac ccgcccaagc aaaccaaggc gaaccttacc tggtacttttt aacatctctc   28800 cctctgtgat ttacaacagt ttcaacccag acggagtgag tctacgagag aacctctccg   28860
agctcagcta ctccatcaga aaaaacacca ccctccttac ctgccgggaa cgtacgagtg   28920
cgtcaccggc cgctgcacca cacctaccgc ctgaccgtaa accagacttt ttccggacag   28980
```

```
acctcaataa ctctgtttac cagaacagga ggtgagctta gaaaacccct agggtattag   29040
gccaaaggcg cagctactgt ggggtttatg aacaattcaa gcaactctac gggctattct   29100
aattcaggtt tctctagaat cggggttggg gttattctct gtcttgtgat tctctttatt   29160
cttatactaa cgcttctctg cctaaggctc gccgcctgct gtgtgcacat ttgcatttat   29220
tgtcagcttt ttaaacgctg gggtcgccac ccaagatgat taggtacata atcctaggtt   29280
tactcaccct tgcgtcagcc cacggtacca cccaaaaggt ggattttaag gagccagcct   29340
gtaatgttac attcgcagct gaagctaatg agtgcaccac tcttataaaa tgcaccacag   29400
aacatgaaaa gctgcttatt cgccacaaaa acaaaattgg caagtatgct gtttatgcta   29460
tttggcagcc aggtgacact acagagtata atgttacagt tttccagggt aaaagtcata   29520
aaacttttat gtatacttttt ccattttatg aaatgtgcga cattaccatg tacatgagca   29580
aacagtataa gttgtggccc ccacaaaatt gtgtggaaaa cactggcact ttctgctgca   29640
ctgctatgct aattacagtg ctcgctttgg tctgtacccct actctatatt aaatacaaaa   29700
gcagacgcag ctttattgag gaaagaaaaa tgccttaatt tactaagtta caaagctaat   29760
gtcaccacta actgctttac tcgctgcttg caaaacaaat tcaaaaagtt agcattataa   29820
ttagaatagg atttaaaccc cccggtcatt tcctgctcaa taccattccc ctgaacaatt   29880
gactctatgt gggatatgct ccagcgctac aaccttgaag tcaggcttcc tggatgtcag   29940
catctgactt tggccagcac ctgtcccgcg gatttgttcc agtccaacta cagcgaccca   30000
ccctaacaga gatgaccaac acaaccaacg cggccgccgc taccggactt acatctacca   30060
caaatacacc ccaagtttct gcctttgtca ataactggga taacttgggc atgtggtggt   30120
tctccatagc gcttatgttt gtatgcctta ttattatgtg gctcatctgc tgcctaaagc   30180
gcaaacgcgc ccgaccaccc atctatagtc ccatcattgt gctacaccca aacaatgatg   30240
gaatccatag attggacgga ctgaaacaca tgttcttttc tcttacagta tgattaaatg   30300
agacatgatt cctcgagttt ttatattact gaccccttgtt gcgctttttt tgtgcgtgct   30360
ccacattggc tgcggtttct cacatcgaag tagactgcat tccagccttc acagtctatt   30420
tgctttacgg atttgtcacc ctcacgctca tctgcagcct catcactgtg gtcatcgcct   30480
ttatccagtg cattgactgg gtctgtgtgc gctttgcata tctcagacac catcccagt   30540
acagggacag gactatagct gagcttctta gaattcttta attatgaaat ttactgtgac   30600
ttttctgctg attatttgca ccctatctgc gttttgttcc ccgacctcca gcctcaaag   30660
acatatatca tgcagattca ctcgtatatg gaatattcca agttgctaca atgaaaaaag   30720
cgatcttttcc gaagcctggt tatatgcaat catctctgtt atggtgttct gcagtaccat   30780
cttagcccta gctatatatc cctaccttga cattggctgg aacgcaatag atgccatgaa   30840
ccacccaact ttccccgcgc ccgctatgct tccactgcaa caagttgttg ccggcggctt   30900
tgtcccagcc aatcagcctc gcccaccttc tcccaccccc actgaaatca gctactttaa   30960
tctaacagga ggagatgact gacaccctag atctagaaat ggacggaatt attacagagc   31020
agcgcctgct agaaagacgc agggcagcgg ccgagcaaca gcgcatgaat caagagctcc   31080
aagacatggt taacttgcac cagtgcaaaa gggtatcttt tgtctggta aagcaggcca   31140
aagtcaccta cgacagtaat accaccggac accgccttag ctacaagttg ccaaccaagc   31200
gtcagaaatt ggtggtcatg gtgggagaaa agcccattac cataactcag cactcggtag   31260
aaaccgaagg ctgcattcac tcaccttgtc aaggacctga ggatctctgc acccttatta   31320
```

```
agaccctgtg cggtctcaaa gatcttattc cctttaacta ataaaaaaaa ataataaagc   31380
atcacttact taaaatcagt tagcaaattt ctgtccagtt tattcagcag cacctccttg   31440
ccctcctccc agctctggta ttgcagcttc ctcctggctg caaactttct ccacaatcta   31500
aatggaatgt cagtttcctc ctgttcctgt ccatccgcac ccactatctt catgttgttg   31560
cagatgaagc gcgcaagacc gtctgaagat accttcaacc ccgtgtatcc atatgacacg   31620
gaaaccggtc ctccaactgt gccttttctt actcctccct ttgtatcccc caatgggttt   31680
caagagagtc cccctggggt actctctttg cgcctatccg aacctctagt tacctccaat   31740
ggcatgcttg cgctcaaaat gggcaacggc ctctctctgg acgaggccgg caaccttacc   31800
tcccaaaatg taaccactgt gagcccacct ctcaaaaaaa ccaagtcaaa cataaacctg   31860
gaaatatctg cacccctcac agttacctca gaagccctaa ctgtggctgc cgccgcacct   31920
ctaatggtcg cgggcaacac actcaccatg caatcacagg ccccgctaac cgtgcacgac   31980
tccaaactta gcattgccac ccaaggaccc ctcacagtgt cagaaggaaa gctagccctg   32040
caaacatcag gccccctcac caccaccgat agcagtaccc ttactatcac tgcctcaccc   32100
cctctaacta ctgccactgg tagcttgggc attgacttga agagcccat ttatacacaa    32160 aatggaaaac taggactaaa gtacgggct cctttgcatg taacagacga cctaaacact     32220
ttgaccgtag caactggtcc aggtgtgact attaataata cttccttgca aactaaagtt   32280
actggagcct gggttttga ttcacaaggc aatatgcaac ttaatgtagc aggaggacta    32340
aggattgatt ctcaaaacag acgccttata cttgatgtta gttatccgtt tgatgctcaa   32400
aaccaactaa atctaagact aggacagggc cctcttttta taaactcagc ccacaacttg   32460
gatattaact acaacaaagg cctttacttg tttacagctt caaacaattc caaaaagctt   32520
gaggttaacc taagcactgc caaggggttg atgtttgacg ctacagccat agccattaat   32580
gcaggagatg ggcttgaatt tggttcacct aatgcaccaa acacaaatcc cctcaaaaca   32640
aaaattggcc atggcctaga atttgattca acaaggcta tggttcctaa actaggaact    32700
ggccttagtt ttgacagcac aggtgccatt acagtaggaa acaaaaataa tgataagcta   32760
actttgtgga ccacaccagc tccatctcct aactgtagac taaatgcaga gaaagatgct   32820
aaactcactt tggtcttaac aaaatgtggc agtcaaatac ttgctacagt ttcagtttg    32880 gctgttaaag gcagttttggc tccaatatct ggaacagttc aaagtgctca tcttattata   32940
agatttgacg aaaatggagt gctactaaac aattccttcc tggacccaga atattggaac   33000
tttagaaatg gagatcttac tgaaggcaca gcctatacaa acgctgttgg atttatgcct   33060
aacctatcag cttatccaaa atctcacggt aaaactgcca aaagtaacat tgtcagtcaa   33120
gtttacttaa acggagacaa aactaaacct gtaacactaa ccattacact aaacggtaca   33180
caggaaacag gagacacaac tccaagtgca tactctatgt cattttcatg ggactggtct   33240
ggccacaact acattaatga aatatttgcc acatcctctt acactttttc atacattgcc   33300
caagaataaa gaatcgtttg tgttatgttt caacgtgttt attttcaat tgcagaaaat   33360 ttcaagtcat tttcattca gtagtatagc cccaccacca catagcttat acagatcacc    33420
gtaccttaat caaactcaca gaaccctagt attcaacctg ccactccct cccaacacac    33480 agagtacaca gtcctttctc cccggctggc cttaaaaagc atcatatcat gggtaacaga   33540
catattctta ggtgttatat tccacacggt ttcctgtcga gccaaacgct catcagtgat   33600
attaataaac tccccgggca gctcacttaa gttcatgtcg ctgtccagct gctgagccac   33660
aggctgctgt ccaacttgcg gttgcttaac gggcggcgaa ggagaagtcc acgcctacat   33720
```

```
gggggtagag tcataatcgt gcatcaggat agggcggtgg tgctgcagca gcgcgcgaat   33780
aaactgctgc cgccgccgct ccgtcctgca ggaatacaac atggcagtgg tctcctcagc   33840
gatgattcgc accgcccgca gcataaggcg ccttgtcctc cgggcacagc agcgcaccct   33900
gatctcactt aaatcagcac agtaactgca gcacagcacc acaatattgt tcaaaatccc   33960
acagtgcaag gcgctgtatc caaagctcat ggcggggacc acagaaccca cgtggccatc   34020
ataccacaag cgcaggtaga ttaagtggcg acccctcata aacacgctgg acataaacat   34080
tacctctttt ggcatgttgt aattccaccac ctcccggtac catataaacc tctgattaaa   34140
catggcgcca tccaccacca tcctaaacca gctggccaaa acctgcccgc cggctataca   34200
ctgcagggaa ccgggactgg aacaatgaca gtggagagcc caggactcgt aaccatggat   34260
catcatgctc gtcatgatat caatgttggc acaacacagg cacacgtgca tacacttcct   34320
caggattaca agctcctccc gcgttagaac catatcccag ggaacaaccc attcctgaat   34380
cagcgtaaat cccacactgc agggaagacc tcgcacgtaa ctcacgttgt gcattgtcaa   34440
agtgttacat tcgggcagca gcggatgatc ctccagtatg gtagcgcggg tttctgtctc   34500
aaaaggaggt agacgatccc tactgtacgg agtgcgccga gacaaccgag atcgtgttgg   34560
tcgtagtgtc atgccaaatg gaacgccgga cgtagtcata tttcctgaag caaaaccagg   34620
tgcgggcgtg acaaacagat ctgcgtctcc ggtctcgccg cttagatcgc tctgtgtagt   34680
agttgtagta tatccactct ctcaaagcat ccaggcgccc cctggcttcg ggttctatgt   34740
aaactccttc atgcgccgct gccctgataa catccaccac cgcagaataa gccacaccca   34800
gccaacctac acattcgttc tgcgagtcac acacgggagg agcgggaaga gctggaagaa   34860
ccatgttttt ttttttattc caaaagatta tccaaaacct caaaatgaag atctattaag   34920
tgaacgcgct ccccctccggt ggcgtggtca aactctacag ccaaagaaca gataatggca   34980
tttgtaagat gttgcacaat ggcttccaaa aggcaaacgg ccctcacgtc caagtggacg   35040
taaaggctaa acccttcagg gtgaatctcc tctataaaca ttccagcacc ttcaaccatg   35100
cccaaataat tctcatctcg ccaccttctc aatatatctc taagcaaatc ccgaatatta   35160
agtccggcca ttgtaaaaat ctgctccaga gcgcccctcca ccttcagcct caagcagcga   35220
atcatgattg caaaaattca ggttcctcac agacctgtat aagattcaaa agcggaacat   35280
taacaaaaat accgcgatcc cgtaggtccc ttcgcagggc cagctgaaca taatcgtgca   35340
ggtctgcacg gaccagcgcg gccacttccc cgccaggaac catgacaaaa gaacccacac   35400
tgattatgac acgcatactc ggagctatgc taaccagcgt agccccgatg taagcttgtt   35460
gcatgggcgg cgatataaaa tgcaaggtgc tgctcaaaaa atcaggcaaa gcctcgcgca   35520 aaaagaaag cacatcgtag tcatgctcat gcagataaag gcaggtaagc tccggaacca   35580
ccacagaaaa agacaccatt tttctctcaa acatgtctgc gggtttctgc ataaacacaa   35640
aataaaataa caaaaaaaca tttaaacatt agaagcctgt cttacaacag gaaaacaac   35700 ccttataagc ataagacgga ctacggccat gccggcgtga ccgtaaaaaa actggtcacc   35760
gtgattaaaa agcaccaccg acagctcctc ggtcatgtcc ggagtcataa tgtaagactc   35820
ggtaaacaca tcaggttgat tcacatcggt cagtgctaaa aagcgaccga aatagcccgg   35880
gggaatacat acccgcaggc gtagagacaa cattacagcc cccataggag gtataacaaa   35940
attaatagga gagaaaaaca cataaacacc tgaaaaaccc tcctgcctag gcaaaatagc   36000
accctcccgc tccagaacaa catacagcgc ttccacagcg gcagccataa cagtcagcct   36060
```

-continued

```
taccagtaaa aaagaaaacc tattaaaaaa acaccactcg acacggcacc agctcaatca    36120
gtcacagtgt aaaaaagggc caagtgcaga gcgagtatat ataggactaa aaaatgacgt    36180
aacggttaaa gtccacaaaa aacacccaga aaaccgcacg cgaacctacg cccagaaacg    36240
aaagccaaaa aacccacaac ttcctcaaat cgtcacttcc gttttcccac gttacgtcac    36300
ttcccatttt aagaaaacta caattcccaa cacatacaag ttactccgcc ctaaaaccta    36360
cgtcacccgc cccgttccca cgccccgcgc cacgtcacaa actccacccc ctcattatca    36420
tattggcttc aatccaaaat aaggtatatt attgatgatg                          36460

<210> SEQ ID NO 22
<211> LENGTH: 19
<212> TYPE: DNA
<213> ORGANISM: Artificial Sequence
<220> FEATURE:
<223> OTHER INFORMATION: Endothelial Cell-Specific Enhancer Element

<400> SEQUENCE: 22
ggtgactttg cttctggag                                                 19

<210> SEQ ID NO 23
<211> LENGTH: 19
<212> TYPE: DNA
<213> ORGANISM: Artificial Sequence
<220> FEATURE:
<223> OTHER INFORMATION: Endothelial Cell-Specific Enhancer Element

<400> SEQUENCE: 23
ctccagaagc aaagtcacc                                                 19

<210> SEQ ID NO 24
<211> LENGTH: 19
<212> TYPE: DNA
<213> ORGANISM: Artificial Sequence
<220> FEATURE:
<223> OTHER INFORMATION: Endothelial Cell-Specific Enhancer Element

<400> SEQUENCE: 24
gtacttcata cttttcatt                                                 19

<210> SEQ ID NO 25
<211> LENGTH: 19
<212> TYPE: DNA
<213> ORGANISM: Artificial Sequence
<220> FEATURE:
<223> OTHER INFORMATION: Endothelial Cell-Specific Enhancer Element

<400> SEQUENCE: 25
aatgaaaagt atgaagtac                                                 19

<210> SEQ ID NO 26
<211> LENGTH: 6
<212> TYPE: DNA
<213> ORGANISM: Artificial Sequence
<220> FEATURE:
<223> OTHER INFORMATION: Hypoxia Response element

<400> SEQUENCE: 26 gcacgt                                                               6

<210> SEQ ID NO 27
<211> LENGTH: 40
<212> TYPE: PRT
<213> ORGANISM: Artificial Sequence
```

```
<220> FEATURE:
<223> OTHER INFORMATION: peptide linker

<400> SEQUENCE: 27

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
            35                  40
```

TREATMENT METHODS USING ADENOVIRUS

REFERENCE TO RELATED APPLICATIONS

This application is a divisional application of U.S. patent application Ser. No. 14/949,779, filed on Nov. 23, 2015, which is a continuation application of U.S. patent application Ser. No. 14/527,667, filed on Oct. 29, 2014, now U.S. Pat. No. 9,200,056, which is a continuation application of PCT Application No. PCT/IB2013/003015, filed on Oct. 17, 2013, which claims the benefit of U.S. Provisional Patent Application Nos. 61/785,287, filed on Mar. 14, 2013, and 61/715,206, filed on Oct. 17, 2012. The contents of the above applications are all incorporated herein by reference in their entireties.

REFERENCE TO SEQUENCE LISTING SUBMITTED ELECTRONICALLY

The contents of this electronically submitted sequence listing in ASCII text file (Name: 3182.0430005_ST25_SL.TXT; Size: 165,872 bytes; and Date of Creation: Jul. 23, 2018), filed herewith, is incorporated by reference in its entirety.

BACKGROUND OF THE DISCLOSURE

Field of the Disclosure

This disclosure relates to cancer biology, immunology and pharmacology. More particularly, it relates to methods of treating diseases or disorders relating to gynecological cancer by administration of a nucleic acid construct expressing a Fas-chimera transgene product or a homogeneous population of the nucleic acid construct.

Background Art

Gynecological cancers are clinically aggressive, usually develop in tissues of the female genital tract, and are associated with a poor outcome. These cancers include cancers of the ovaries, uterus, fallopian tubes, and the cervix, and also malignant mixed müllerian tumors (MMMT). In rare instances, MMMTs can also develop in the female peritoneum (lining of the abdominal wall).

Gynecological cancers can be difficult to detect and are often diagnosed when they are at an advanced stage. Ovarian cancer accounts for approximately three percent of cancers in women. While the ninth most common cancer among women, ovarian cancer is the fifth leading cause of cancer-related death among women, and is the deadliest of gynecologic cancers. 2012. Ovarian cancer is sensitive to chemotherapy with a high response rate to platinum and taxane-based therapies. However, in spite of advances in therapeutic design and delivery, cancer recurrence and chemotherapeutic resistance remain obstacles to treatment of these types of cancers. Despite aggressive primary therapy and high initial response rates, most women with advanced ovarian carcinoma will relapse and develop drug-resistant disease. In these advanced disease states, response rates to subsequent chemotherapy are substantially diminished, highlighting the crucial need to develop improved therapeutic agents and strategies.

BRIEF SUMMARY OF THE DISCLOSURE

The present invention is directed to a method of reducing or decreasing a size of a tumor or eliminating or slowing the growth of a tumor in a patient comprising administering to the patient an effective amount of a nucleic acid construct, which comprises a Fas-chimera gene operably linked to an endothelial cell specific promoter, wherein a Fas-chimera gene product encoded by the nucleic acid construct reduces or decreases the size of the tumor or eliminates the tumor in the patient and wherein the tumor is associated with a female gynecological cancer or a metastasis thereof. The invention also provides a method of inhibiting, decreasing, or reducing neo-vascularization or angiogenesis in a tumor comprising administering to a patient having the tumor an effective amount of a nucleic acid construct, which comprises a Fas-chimera gene operably linked to an endothelial cell specific promoter, wherein a Fas-chimera gene product encoded by the nucleic acid construct inhibits, reduces, or decreases the neo-vascularization or angiogenesis in the tumor and wherein the tumor is associated with a female gynecological cancer or a metastasis thereof. In addition, the invention includes a method of treating or preventing a tumor associated with or derived from Müllerian cancer, ovarian cancer, peritoneal cancer, fallopian tube cancer, or uterine papillary serous carcinoma in a patient comprising administering an effective amount of a nucleic acid construct, which comprises a Fas-chimera gene operably linked to an endothelial cell specific promoter, wherein a Fas-chimera gene product encoded by the nucleic acid construct treats or prevents a female gynecological cancer or a metastasis thereof. In one embodiment, the tumor or a metastasis thereof is decreased in size or eliminated after the administration or the growth of the tumor or. In another embodiment, tumor or a metastasis thereof is decreased such that the longest diameter (LD) of the tumor is decreased at least about 10%, 20%, 30%, 40%, 50%, 60%, 70%, 80%, 90%, or 100% compared to the LD prior to the administration. In other embodiments, the female gynecological cancer is associated with or derived from Müllerian cancer, ovarian cancer, peritoneal cancer, fallopian tube cancer, uterine papillary serous carcinoma, any combinations thereof, or a metastasis thereof.

In some embodiments, the patient has had a prior platinum based therapy. In one example, the patient has recurrent platinum-resistant cancer. In another example, the patient having the recurrent platinum-resistant cancer or the recurrent taxane-resistant cancer has a progressive tumor within six months of completing or receiving a platinum based therapy or a taxane based therapy.

In certain embodiments, the patient does not have a pre-existing antibody against adenovirus or does not develop an antibody against adenovirus.

In other embodiments, the methods of the invention further comprise administering an effective amount of one or more chemotherapeutic agents. The one or more chemotherapeutic agents can be administered prior to, concurrently with, or after the administration of the nucleic acid construct. In a specific embodiment, the chemotherapeutic agent is paclitaxel.

In certain embodiments, the nucleic acid construct for the method of the invention is an adenovirus. In one example, the adenovirus expresses a Fas-chimera gene product comprising an extracellular domain of a TNF Receptor 1 (TNFR1) polypeptide fused to a transmembrane domain and an intracellular domain of a Fas polypeptide. The polynucleotide encoding the Fas-chimera gene product is operably linked to an endothelial cell specific promoter, e.g., a PPE-1-3X promoter. In a particular embodiment, the adenovirus comprises a nucleotide sequence at least 70%, 80%, 90%, 95%, 96%, 97%, 98%, 99%, or 100% identical to SEQ ID NO: 19.

One aspect of the invention includes a nucleic acid construct comprising SEQ ID NO: 18. In another aspect, the nucleic acid construct further comprises a nucleotide sequence encoding a Fas-chimera protein. In other embodiments, the invention is a vector comprising SEQ ID NO: 19. The vector can be an adenovirus.

In still other embodiments, the invention is an adenovirus having the European Collection of Cell Cultures (ECACC) deposit designation No. 13021201. The adenovirus can be at least 60%, at least 70%, at least 80%, at least 90%, at least 95%, at least 96%, at least 97%, at least 98%, at least 99%, or 100% pure. In one example, the invention comprises a pharmaceutical composition comprising the adenovirus and a pharmaceutically acceptable carrier, wherein the composition does not contain another type of adenovirus, e.g., adenovirus comprising SEQ ID NO: 20 or SEQ ID NO: 21.

The invention also includes a method of inhibiting, decreasing, or reducing angiogenesis or neo-vascularization in a tissue of a subject in need thereof comprising administering the nucleic acid construct, the vector, the adenovirus, or the composition to the subject. In one embodiment, the tissue comprises a tumor. In another embodiment, the size of the tumor is reduced or decreased after the administration or the growth of the tumor is slowed after the administration. In other embodiments, the tumor is derived from or associated with thyroid cancer, neuroendocrine cancer, glioblastoma, a female gynecological cancer, any combinations thereof or a metastasis thereof.

BRIEF DESCRIPTION OF THE DRAWINGS/FIGURES

FIG. 1 shows the average tumor burden (y axis) among the Lewis Lung Carcinoma mice administered with vehicle, VB111 1E9 ($10^9$ Virus Particles (VPs) of VB-111), VB111 1E1 ($10^{11}$ VPs of VB-111), ComLow (20 mg/kg Carboplatin+10 mg/kg Alimta), ComHigh (50 mg/kg Carboplatin+30 mg/kg Alimta), VB111 1E9+ComLow (VB-111 $10^9$ VPs+20 mg/kg Carboplatin+10 mg/kg Alimta), VB111 1E9+ComHigh (VB-111 $10^9$ VP+50 mg/kg Carboplatin+30 mg/kg Alimta), VB111 1E11+ComLow (VB-111 $10^{11}$ VP+20 mg/kg Carboplatin+10 mg/kg Alimta), and VB111 1E11+ComHigh (VB-111 $10^{11}$ VP+50 mg/kg Carboplatin+30 mg/kg Alimta) (x axis).

Figure 2:
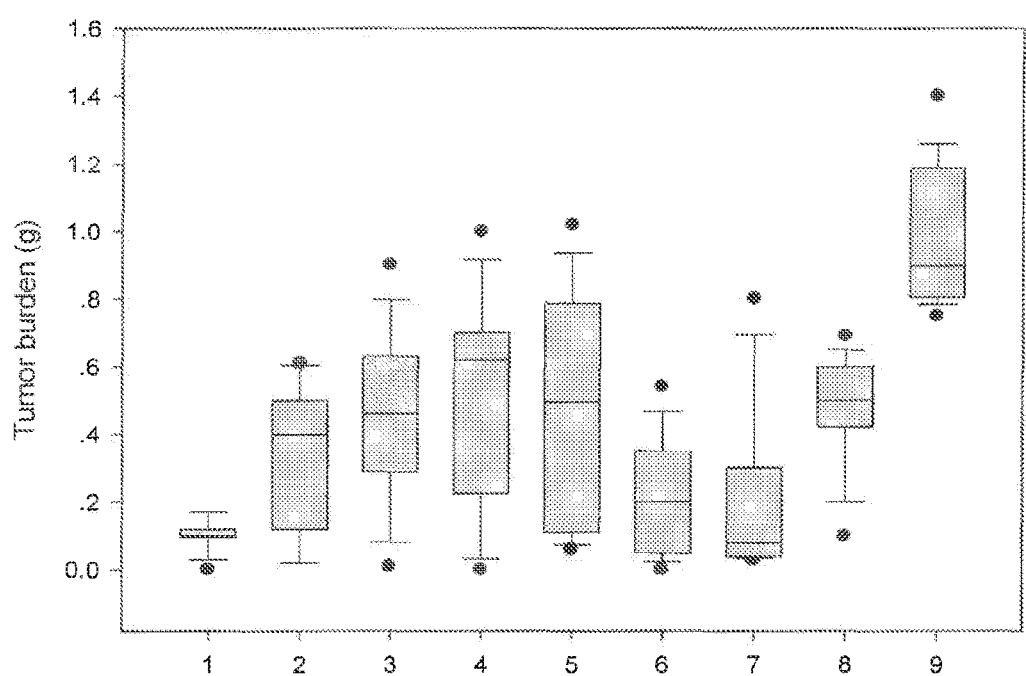

FIG. 2 shows a box plot of the average tumor burden (y axis) among the Lewis Lung Carcinoma mice administered with vehicle (1), VB111 1E9 ($10^9$ Virus Particles (VPs) of VB-111)(2), VB111 1E11 ($10^{11}$ VPs of VB-111)(3), ComLow (20 mg/kg Carboplatin+10 mg/kg Alimta)(4), ComHigh (50 mg/kg Carboplatin+30 mg/kg Alimta)(5), VB111 1E9+ComLow (VB-111 $10^9$ VPs+20 mg/kg Carboplatin+10 mg/kg Alimta)(6), VB111 1E9+ComHigh (VB-111 $10^9$ VP+50 mg/kg Carboplatin+30 mg/kg Alimta)(7), VB111 1E11+ComLow (VB-111 $10^{11}$ VP+20 mg/kg Carboplatin+10 mg/kg Alimta)(8), and VB111 1E11+ComHigh (VB-111 $10^{11}$ VP+50 mg/kg Carboplatin+30 mg/kg Alimta) (9) (x axis).

Figure 3:
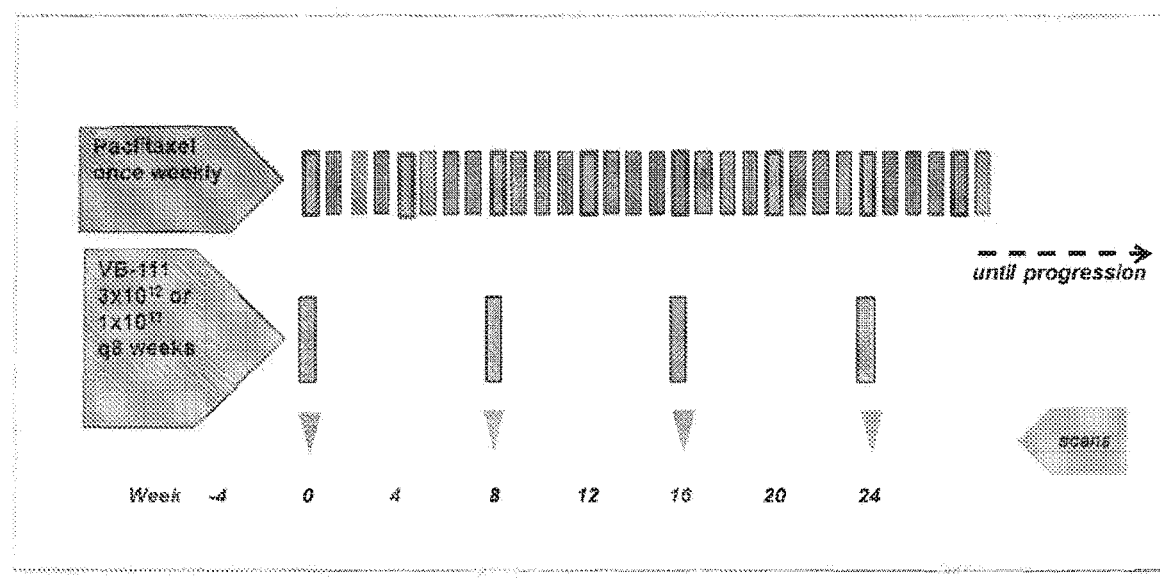

FIG. 3 shows a combination therapy regimen of an adenovirus comprising a FAS-chimera gene operably linked to an endothelial cell-specific promoter (e.g., VB-111) and paclitaxel. About $3 \times 10^{12}$ VPs or $1 \times 10^{13}$ VPs of VB-111 is administered every eight weeks, and paclitaxel is administered once weekly.

DETAILED DESCRIPTION OF THE INVENTION

I. Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

As used herein, "antibody" means an intact immunoglobulin, or an antigen-binding fragment thereof. Antibodies of this invention can be of any isotype or class (e.g., M, D, G, E and A) or any subclass (e.g., G1-4, A1-2) and can have either a kappa (κ) or lambda (λ) light chain.

The term "effective amount" as used herein refers to an amount effective, at dosages and for periods of time necessary, to achieve a desired result. A desired result can be, for example, reduction or inhibition of neo-vascularization or angiogenesis in vitro or in vivo. An effective amount need not be a complete removal of neo-vascularization or angiogenesis.

As used herein, a "therapeutically effective amount" refers to an amount effective, at dosages and for periods of time necessary, to achieve a desired therapeutic result. A therapeutic result may be, e.g., lessening of symptoms, regression or stabilization of tumor size in radiological imaging, prolonged survival, improved mobility, and the like. A therapeutic result need not be a "cure."

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)).

As used herein, a "polynucleotide," "nucleotide," "nucleic acid" can be used interchangeably and contain the nucleotide sequence of the full-length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In the present invention, a polypeptide can be composed of amino acids joined to each other by peptide bonds or modified peptide bonds, i.e., peptide isosteres, and may contain amino acids other than the 20 gene-encoded amino acids (e.g. non-naturally occurring amino acids). The polypeptides of the present invention may be modified by either natural process, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W.H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

The terms "fragment," "variant," "derivative" and "analog" when referring to any polypeptide or polynucleotide of the present invention include any polypeptides or polynucleotides which retain at least some activities, i.e., the ability to function as any naturally-occurring function of the polypeptide or polynucleotide. For example, a "fragment," "variant," "derivative" and "analog" of Tumor necrosis factor Receptor 1 (TNFR1) has some activities of the naturally occurring full-length TNFR1, e.g., the ability to bind to TNFR1 ligand, i.e., TNF-alpha or lymphotoxin. In another example, a "fragment," "variant," "derivative" and "analog" of a FAS polypeptide have some activities of a naturally-occurring full-length FAS polypeptide, e.g., the ability to induce apoptosis. In other examples, a "fragment," "variant," "derivative" and "analog" of an endothelial cell-specific promoter can induce endothelial cell-specific expression of a gene operably linked to the promoter. Additional non-limiting examples of the various fragments, variants, analogues, or derivatives of the TNFR1, FAS polypeptide, and endothelial cell-specific promoters are described below.

In the present invention, a "polypeptide fragment" or "protein fragment" refers to a short amino acid sequence of a polypeptide. Protein or polypeptide fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculated percent sequence identity may be curated either automatically or manually.

As used herein, the terms "linked," "fused," "fusion," "chimeric," and "chimera" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion or chimeric protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

The terms "heterologous" and "heterologous moiety" mean that a polynucleotide, polypeptide, or other moiety is derived from a distinct entity from that of the entity to which it is being compared. For instance, a heterologous polypeptide can be synthetic, or derived from a different species, different cell type of an individual, or the same or different type of cell of distinct individuals. In one aspect, a heterologous moiety can be a polypeptide fused to another polypeptide to produce a fusion polypeptide or protein. In another aspect, a heterologous moiety can be a non-polypeptide such as PEG conjugated to a polypeptide or protein.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

II. Nucleic Acid Constructs Comprising a Fas-Chimera Gene and an Endothelial Cell Specific Promoter The present invention is related to methods of reducing or decreasing a size of a tumor in a female gynecological cancer by inhibiting, decreasing, or reducing angiogenesis or neo-vascularization in the tumor comprising administering a nucleic acid construct expressing a FAS-chimera protein. The gene encoding the FAS-chimera protein (or gene product), in the present invention can be linked to an endothelial cell-specific promoter, which directs expression of the FAS-chimera gene product in an endothelial cell. Expression of such a cytotoxic gene product is useful in a situation where excessive neo-vascularization or blood vessel growth is not desirable, e.g., in a tumor.

The present invention also provides a homogeneous population of a nucleic acid construct comprising a FAS-chimera gene operably linked to an endothelial cell-specific promoter.

A. FAS-Chimera

A FAS-chimera protein expressed by the nucleic acid construct of the invention comprises at least two "death receptor" polypeptides, each of the polypeptides is derived from a different protein. The first polypeptide of the FAS-chimera protein comprises a ligand binding domain of Tumor Necrosis Factor Receptor 1 (TNFR1). The second polypeptide of the FAS-chimera protein comprises an effector domain of a FAS polypeptide.

The ligand binding domain of TNFR1 can be any domain that binds to a TNFR1 ligand. In one embodiment, the TNFR1 ligand is TNF-α. In another embodiment, the TNFR1 ligand is lymphotoxin-α. The ligand binding domain of TNFR1 can be an extracellular domain of TNFR1 or any fragments, variants, derivatives, or analogues thereof. Non-limiting examples of the TNFR1 ligand binding domain are described below.

The effector domain of a FAS polypeptide useful for the invention comprises any FAS domains that form death-inducing signaling complex (DISC), thereby inducing apoptosis. In one embodiment, an effector domain of a FAS polypeptide comprises an intracellular domain, a transmembrane domain, or both. Non-limiting examples of FAS polypeptide effector domains are described below.

The TNFR1 and the FAS polypeptide can be linked by a peptide bond or by a linker. The linker connecting the TNFR1 ligand binding domain with the FAS effector domain can be a polypeptide linker or a non-peptide linker. For example, a linker for the FAS-chimera protein can comprise one or more glycine, serine, leucine, or any combinations thereof. In one embodiment, a linker useful for the invention comprises Ser-Leu. In another embodiment, a linker useful for the invention comprises (GGGS)n, (Denise et al. *J. Biol. Chem.* 277:35035-35043 (2002)), wherein n can be 0, 1, 2, 3, 4, 5, 6, 7, 8, 9, or 10 or more (SEQ ID NO: 27).

1. Tumor Necrosis Factor Receptor 1

The full-length human TNFR1 polypeptide is 455 amino acids in length and is also known as TNF-R1, Tumor necrosis factor receptor type I (TNFRI), TNFR-I, TNFRSF1A, TNFAR, p55, P60, or CD120a. Naturally-occurring human TNFR1 polypeptide is known to bind to TNF-α or homotrimeric lymphotoxin-α. Binding of TNF-α to the extracellular domain leads to homotrimerization of TNFR1, which then interacts specifically with the death domain of Tumor Necrosis Factor Receptor Type 1-Associated Death Domain Protein (TRADD). Various TRADD-interacting proteins such as TNF Receptor Associated Factors (TRAFS), Receptor-Interacting Serine/Threonine-Protein Kinase 1 (RIPK1), and Fas-Associated Protein with Death Domain (FADD) are recruited to the complex by their association with TRADD. The complex activates at least two distinct signaling cascades, apoptosis and NF-kappa-B signaling.

A 455 aa polypeptide sequence reported as a human TNFR1 polypeptide sequence has the identifier number P19438-1 in the UniProtKB database. This human TNFR1 polypeptide sequence is designated herein as isoform A and SEQ ID NO: 2. SEQ ID NO: 1 is a nucleotide sequence encoding SEQ ID NO: 2. A polypeptide sequence of 108 as was reported as an isoform of the human TNFR1 polypeptide sequence and has the identifier number P19438-2 in the UniProtKB database. The 108 as polypeptide corresponds to amino acids 1 to 108 of isoform A (SEQ ID NO: 2) and is designated herein as isoform B. Another variant of the human TNFR1 polypeptide having 232 as was reported as the identifier number P19438-3 in the UniProtKB database. The 232 as polypeptide corresponds to amino acids 1 to 232 of isoform A (SEQ ID NO: 2) and is designated herein as isoform C. Additional natural variants of human TNFR1 include, but are not limited to, the TNFR1 polypeptide of isoforms A, B, and C comprising one or more mutations selected from the group consisting of H51Q, C59R, C59S, C62G, C62Y, P75L, T79M, C81F, C99S, S115G, C117R, C117Y, R121P, R121Q, P305T, and any combinations thereof. Other known TNFR1 variants include the TNFR1 polypeptide of isoforms A, B, and C comprising L13LILPQ, K255E, S286G, R394L, 412:Missing, GPAA443-446APP, or any combinations thereof.

Table 1 shows the human wild-type TNFR1 amino acid sequence and a nucleotide sequence encoding the wild-type TNFR1.

TABLE 1

TNFR1 Sequences

| SEQ ID No. | Sequences |
|---|---|
| Amino acid sequence of TNFR1 (SEQ ID NO: 2) | MGLSTVPDLLLPLVLLELLVGIYPSGVIGLVPHLGDREKRDSVCPQGKYIHPQNNSICCT KCHKGTYLYNDCPGPGQDTDCRECESGSFTASENHLRHCLSCSKCRKEMGQVEISSCTVD RDTVCGCRKNQYRHYWSENLFQCFNCSLCLNGTVHLSCQEKQNTVCTCHAGFFLRENECV SCSNCKKSLECTKLCLPQIENVKGTEDSGTTVLLPLVIFFGLCLLSLLFIGLMYRYQRWK SKLYSIVCGKSTPEKEGELEGTTTKPLAPNPSFSPTPGFTPTLGFSPVPSSTFTSSSTYT PGDCPNFAAPRREVAPPYQGADPILATALASDPIPNPLQKWEDSAHKPQSLDTDDPATLY AVVENVPPLRWKEFVRRLGLSDHEIDRLELQNGRCLREAQYSMLATWRRRTPRREATLEL LGRVLRDMDLLGCLEDIEEALCGPAALPPAPSLLR |
| Nucleotide Sequence encoding TNFR1 (SEQ ID NO: 1) | Atgggcctctccaccgtgcctgacctgctgctgccgctggtgctcctggagctgttggtg Ggaatataccctcaggggttattggactggtccctcacctaggggacagggagaagaga Gatagtgtgtgtccccaaggaaaatatatccaccctcaaaataattcgatttgctgtacc Aagtgccacaaaggaacctacttgtacaatgactgtccaggcccggggcaggatacggac Tgcagggagtgtgagagcggctccttcaccgcttcagaaaaccacctcagacactgcctc Agctgctccaaatgccgaaaggaaatgggtcaggtggagatctcttcttgcacagtggac Cgggacaccgtgtgtggctgcaggaagaaccagtaccggcattattggagtgaaaacctt Ttccagtgcttcaattgcagcctctgcctcaatgggaccgtgcacctctcctgccaggag Aaacagaacaccgtgtgcacctgccatgcaggtttctttctaagagaaaacgagtgtgtc Tcctgtagtaactgtaagaaaagcctggagtgcacgaagttgtgcctaccccagattgag Aatgttaagggcactgaggactcaggcaccacagtgctgttgcccctggtcattttcttt Ggtctttgccttttatccctcctcttcattggtttaatgtatcgctaccaacggtggaag Tccaagctctactccattgtttgtgggaaatcgacacctgaaaaagaggggagcttgaa Ggaactactactaagcccctggccccaaacccaagcttcagtcccactccaggcttcacc Cccaccctgggcttcagtcccgtgcccagttccaccttcacctccagctccacctatacc Cccggtgactgtcccaactttgcggctccccgcagagaggtggcaccaccctatcagggg Gctgaccccatccttgcgacagccctcgcctccgaccccatccccaacccccttcagaag Tgggaggacagcgcccacaagccacagagcctagacactgatgaccccgcgacgctgtac Gccgtgttggagaacgtgccccgttgcgctgaaggaattcgtgcggcgcctagggctg Agcgaccacgagatcgatcggctggagctgcagaacgggcgctgcctgcgcgaggcgcaa Tacagcatgctggcgacctggaggcggcgcacgccgcgggcgcgaggcacgctggagctg Ctgggacgcgtgctccgcgacatggacctgctgggctgcctggaggacatcgaggaggcg ctttgcggccccgccgccctcccgcccgcgcccagtcttctcaga |

TABLE 1-continued

TNFR1 Sequences

| SEQ ID No. | Sequences |
|---|---|
| Amino acid sequence of a Ligand Binding Domain of TNFR1 (SEQ ID NO: 4) | MGLSTVPDLLLPLVLLELLVGIYPSGVIGLVPHLGDREKRDSVCPQGKYIHPQNNSICCT KCHKGTYLYNDCPGPGQDTDCRECESGSFTASENHLRHCLSCSKCRKEMGQVEISSCTVD RDTVCGCRKNQYRHYWSENLFQCFNCSLCLNGTVHLSCQEKQNTVCTCHAGFFLRENECV SCSNCKKSLECTKLCLP |
| Nucleotide sequence encoding a Ligand Binding Domain of TNFR1 (SEQ ID NO: 3) | atgggcctct ccaccgtgcc tgacctgctg ctgccgctgg tgctcctgga gctgttggtg ggaatatacc cctcaggggt tattggactg gtccctcacc taggggacag ggagaagaga gatagtgtgt gtccccaagg aaaatatatc caccctcaaa ataattcgat ttgctgtacc aagtgccaca aaggaaccta cttgtacaat gactgtccag gcccggggca ggatacggac tgcagggagt gtgagagcgg ctccttcacc gcttcagaaa accacctcag acactgcctc agctgctcca aatgccgaaa ggaaatgggt caggtggaga tctcttcttg cacagtggac cgggcacccg tgtgtggctg caggaagaac cagtaccggc attattggag tgaaaacctt ttccagtgct tcaattgcag cctctgcctc aatgggaccg tgcacctctc ctgccaggag aaacagaaca ccgtgtgcac ctgccatgca ggtttctttc taagagaaaa cgagtgtgtc tcctgtagta actgtaagaa aagcctggag tgcacgaagt tgtgcctacc a |

The mouse TNFR1 polypeptide sequence and its variants are also reported. The 454 as mouse TNFR1 polypeptide has the identifier number P25118 in UniProtKB database. TNFR1 polypeptides known in other animals include, but are not limited to, rat (e.g., P22934 in the UniProtKB database), cow (e.g., O19131 in the UniProtKB database), pig (e.g., P50555 in the UniProtKB database), or horse (e.g., D1MH71 in the UniProtKB database).

The full-length TNFR1 can be cleaved into two chains, (1) TNF Receptor Superfamily Member 1A, membrane form (i.e., amino acids 22 to 455 corresponding to full-length TNFR1) and (2) TNF-binding protein 1 (TBPI) (i.e., amino acids 41 to 291 corresponding to full-length TNFR1). The full-length human TNFR1 polypeptide consists of a signal sequence (amino acids 1 to 21 of SEQ ID NO: 2), an extracellular domain (amino acids 22 to 211 of SEQ ID NO: 2), a trans-membrane domain (amino acids 212 to 234 of SEQ ID NO: 2), and a cytoplasmic domain (amino acids 235 to 455 of SEQ ID NO: 2). The TNFR1 extracellular domain comprises four cysteine repeat regions, TNFR-Cys1 (amino acids 43 to 82 corresponding to SEQ ID NO: 2), TNFR-Cys2 (amino acids 83 to 125 corresponding to SEQ ID NO: 2), TNFR-Cys3 (amino acids 126 to 166 corresponding to SEQ ID NO: 2), and TNFR-Cys4 (amino acids 167 to 196 corresponding to SEQ ID NO: 2).

As one of skill in the art will appreciate, the beginning and ending residues of the domains listed above can vary depending upon the computer modeling program used or the method used for determining the domain. As such, various functional domains of TNFR1 may vary from those defined above.

In one embodiment, a ligand binding domain of TNFR1 useful for the FAS-chimera protein comprises, consists essentially of, or consists of an extracellular domain of TNFR1, or any fragment, variant, derivative, or analogue thereof, wherein the extracellular domain of TNFR1, or any fragment, variant, derivative, or analogue thereof binds to TNF-α. In another embodiment, a ligand binding domain of TNFR1 comprises TNFR-Cys1; TNFR-Cys2; TNFR-Cys3; TNFR-Cys4; TNFR-Cys1 and TNFR-Cys2; TNFR-Cys1 and TNFR-Cys3; TNFR-Cys1 and TNFR-Cys4; TNFR-Cys2 and TNFR-Cys3; TNFR-Cys2 and TNFR-Cys4; TNFR-Cys3 and TNFR-Cys4; TNFR-Cys1, TNFR-Cys2, and TNFR-Cys3; TNFR-Cys1, TNFR-Cys2, and TNFR-Cys4; TNFR-Cys2, TNFR-Cys3, and TNFR-Cys4; or TNFR-Cys1, TNFR-Cys2, TNFR-Cys3, and TNFR-Cys4. In other embodiments, a ligand binding domain of TNFR1 in the FAS-chimera protein comprises TNF binding protein I. In yet other embodiments, a TNFR1 ligand binding domain of the FAS-chimera protein comprises, consists essentially of or consists of an amino acid sequence at least 60%, 70%, 80%, 90%, 95%, 96%, 97%, 98%, 99%, or 100% identical to amino acids 22 to 190, amino acids 22 to 191, amino acids 22 to 192, amino acids 22 to 193, amino acids 22 to 194, amino acids 22 to 195, amino acids 22 to 196, amino acids 22 to 197, amino acids 22 to 198, amino acids 22 to 199, amino acids 22 to 200, amino acids 22 to 201, amino acids 22 to 202, amino acids 22 to 203, amino acids 22 to 204, amino acids 22 to 205, amino acids 22 to 206, amino acids 22 to 207, amino acids 22 to 208, amino acids 22 to 209, amino acids 22 to 210, or amino acids 22 to 211 of SEQ ID NO: 2, wherein the ligand binding domain binds to a TNFR1 ligand, e.g., TNF-α.

In other embodiments, the ligand binding domain of TNFR1 further comprises a signal peptide. One example of the suitable signal peptides is the signal peptide of TNFR1, e.g., amino acids 1 to 21 of SEQ ID NO: 2. In yet other embodiments, a ligand binding domain of the FAS-chimera gene product comprises, consists essentially of, or consists of an amino acid sequence at least 60%, 70%, 80%, 90%, 95%, 96%, 97%, 98%, 99%, or 100% identical to amino acids 1 to 190, amino acids 1 to 191, amino acids 1 to 192, amino acids 1 to 193, amino acids 1 to 194, amino acids 1 to 195, amino acids 1 to 196, amino acids 1 to 197, amino acids 1 to 198, amino acids 1 to 199, amino acids 1 to 200, amino acids 1 to 201, amino acids 1 to 202, amino acids 1 to 203, amino acids 1 to 204, amino acids 1 to 205, amino acids 1 to 206, amino acids 1 to 207, amino acids 1 to 208, amino acids 1 to 209, amino acids 1 to 210, or amino acids 1 to 211 of SEQ ID NO: 2, wherein the ligand binding domain binds to a TNFR1 ligand, e.g., TNF-α. In a specific embodiment, a TNFR1 ligand binding domain of the FAS-chimera protein comprises, consists essentially of or consists of an amino acid sequence at least 60%, 70%, 80%, 90%, 95%, 96%, 97%, 98%, 99%, or 100% identical to SEQ ID NO: 4, wherein the ligand binding domain binds to a TNFR1 ligand, e.g., TNF-α.

In yet other embodiments, the ligand binding domain of TNFR1 is encoded by a nucleotide sequence at least 60%, 70%, 80%, 90%, 95%, 96%, 97%, 98%, 99%, or 100% identical to SEQ ID NO: 3.

In still other embodiments, a TNFR1 ligand binding domain of the FAS-chimera protein comprises, consists essentially of, or consists of an amino acid sequence at least 60%, 70%, 80%, 90%, 95%, 96%, 97%, 98%, 99%, or 100% identical to amino acids 22 to 108 of SEQ ID NO: 2 (TNFR1 isoform B), amino acids 22 to 232 of SEQ ID NO: 2 (TNFR1 isoform C), or amino acids 44 to 291 of SEQ ID NO: 2 (TBP1), wherein the ligand binding domain binds to a TNFR1 ligand, e.g., TNF-α.

2. FAS Polypeptide

The full-length human FAS polypeptide is 335 amino acids in length and is also known as Tumor Necrosis Factor Receptor Superfamily Member 6, Apo-1 antigen, Apoptosis-mediating surface antigen FAS, FASLG receptor, or CD95. Naturally occurring FAS polypeptide is a receptor for TNFSF6/FASLG. When the FAS polypeptide binds to the FAS ligand (FasL), the interaction between FAS and FasL results in the formation of the death-inducing signaling complex (DISC), which contains the FADD, caspase-8 and caspase-10. In some types of cells (type I), processed caspase-8 directly activates other members of the caspase family, and triggers the execution of apoptosis of the cell. In other types of cells (type II), the FAS-DISC starts a feedback loop that spirals into increasing release of proapoptotic factors from mitochondria and the amplified activation of caspase-8. FAS-mediated apoptosis may have a role in the induction of peripheral tolerance, in the antigen-stimulated suicide of mature cells or both.

A 335 aa polypeptide sequence reported as a human FAS polypeptide sequence has the identifier number P25445-1 in the UniProtKB database. This human FAS polypeptide sequence is designated herein as SEQ ID NO: 6. SEQ ID NO: 5 is a nucleotide sequence encoding SEQ ID NO: 6. The nucleotide sequence encoding the FAS polypeptide is also known as APT1, FAS1, or TNFRSF6. The full-length FAS polypeptide contains a signal peptide (amino acids 1 to 25 corresponding to SEQ ID NO: 6), an extracellular domain (amino acids 26 to 173 corresponding to SEQ ID NO: 6), a trans-membrane domain (amino acids 174 to 190 corresponding to SEQ ID NO: 6), and an intracellular (or cytoplasmic) domain (amino acids 191 to 335 corresponding to SEQ ID NO: 6). The intracellular domain contains a death domain (e.g., amino acids 230 to 314 corresponding to SEQ ID NO: 6).

As one of skill in the art will appreciate, the beginning and ending residues of the domains listed above may vary depending upon the computer modeling program used or the method used for determining the domain. As such, various functional domains of FAS may vary from those defined above. Table 2 shows the wild-type human FAS amino acid sequence and a nucleotide sequence encoding the FAS protein.

TABLE 2

FAS Sequences

| | Sequences |
|---|---|
| Amino acid sequence of human FAS protein (SEQ ID NO: 6) | MLGIWTLLPLVLTSVARLSSKSVNAQVTDINSKGLELRKTVTTVETQNLEGLHHDGQFCH KPCPPGERKARDCTVNGDEPDCVPCQEGKEYTDKAHFSSKCRRCRLCDEGHGLEVEINCT RTQNTKCRCKPNFFCNSTVCEHCDPCTKCEHGIIKECTLTSNTKCKEEGSRSNLGWLCLL LLPIPLIVWVKRKEVQKTCRKHRKENQGSHESPTLNPETVAINLSDVDLSKYITTIAGVM TLSQVKGFVRKNGVNEAKIDEIKNDNVQDTAEQKVQLLRNWHQLHGKKEAYDTLIKDLKK ANLCTLAEKIQTIILKDITSDSENSNFRNEIQSLV |
| Nucleotide sequence encoding human FAS sequence (SEQ ID NO: 5) | Atgctgggcatctggaccctcctacctctggttcttacgtctgttgctagattatcgtcc Aaaagtgttaatgcccaagtgactgacatcaactccaagggattggaattgaggaagact Gttactacagttgagactcagaactgaaggcctgcatcatgatggccaattctgccat Aagccctgtcctccaggtgaaaggaaagctagggactgcacagtcaatggggatgaacca Gactgcgtgccctgccaagaagggaaggagtacacagacaaagcccatttttcttccaaa Tgcagaagatgtagattgtgtgatgaaggacatggcttagaagtggaaataaactgcacc Cggacccagaataccaagtgcagatgtaaaccaaacttttttgtaactctactgtatgt Gaacactgtgacccttgcaccaaatgtgaacatggaatcatcaaggaatgcacactcacc Agcaacaccaagtgcaaagaggaaggatccagatctaacttgggggtggctttgtcttctt Cttttgccaattccactaattgtttgggtgaagagaaaggaagtacagaaaacatgcaga Aagcacagaaaggaaaaccaaggttctcatgaatctccaactttaaatcctgaaacagtg Gcaataaatttatctgatgttgacttgagtaaatatatcaccactattgctggagtcatg Acactaagtcaagttaaaggctttgttcgaaagaatggtgtcaatgaagccaaaatagat Gagatcaagaatgacaatgtccaagacacagcagaacagaaagttcaactgcttcgtaat Tggcatcaacttcatggaaagaaagaagcgtatgacacattgattaaagatctcaaaaaa Gccaatctttgtactcttgcagagaaaattcagactatcatcctcaaggacattactagt Gactcagaaaattcaaacttcagaaatgaaatccaaagcttggtctag |
| Amino acid sequence of an Effector Domain of FAS (SEQ ID NO: 8) | GSRSNLGWLCLLLLPIPLIVWVKRKEVQKTCRKHRKENQGS HESPTLNPETVAINLSDVDLSKYITTTAGVMTLSQVKGFVR KNGVNEAKIDEIKNDNVQDTAEQKVQLLRNWHQLHGKKEAY DTLIKDLKKANLOTLAEKTQTIILKDITSDSENSNFRNEIQ SLV |

TABLE 2-continued

FAS Sequences

| Sequences | |
|---|---|
| Nucleotide sequence encoding an Effector Domain of FAS (SEQ ID NO: 71) | Aggatccagatctaacttggggtggctttgtcttcttcttttgccaattccactaatt<br>Gtttgggtgaagagaaaggaagtacagaaaacatgcagaaagcacagaaaggaaaacc<br>Aaggttctcatgaatctccaaccttaaatcctgaaacagtggcaataaatttatctga<br>Tgttgacttgagtaaatatatcaccactattgctggagtcatgacactaagtcaagtt<br>Aaaggctttgttcgaaagaatggtgtcaatgaagccaaaatagatgagatcaagaatg<br>Acaatgtccaagacacagcagaacagaaagttcaactgcttcgtaattggcatcaact<br>Tcatggaaagaaagaagcgtatgacacattgattaaagatctcaaaaaagccaatctt<br>Tgtactcttgcagagaaaattcagactatcatcctcaaggacattactagtgactcag<br>aaaattcaaacttcagaaatgaaatccaaagcttggtctag |

The mouse FAS polypeptide sequence and its variants are also reported. The 327 as mouse FAS polypeptide has the identifier number P25446 in UniProtKB database. FAS polypeptides known in other animals include, but are not limited to, Old World monkey (e.g., Q9BDN4 in the UniProtKB database), Rhesus monkey (e.g., Q9BDP2 in the UniProtKB database), rat (e.g., Q63199 in the UniProtKB database), or cow (e.g., P51867 in the UniProtKB database).

Based on the sequence variation in the FAS polypeptide, a person of ordinary skill in the art can identify sequence variations in the effector domain of the FAS polypeptide. For example, natural variants of the FAS effector domains can include one or more substitutions or mutations of C178R, L180F, P183L, I184V, T198I, Y232C, T241K, T241P, V249L, R250P, R250Q, G253D, G253S, N255D, A257D, I259R, D260G, D260V, D260Y, I262S, N264K, T270I, T270K, E272G, E272K, L278F, K299N, T305I, I310S, or any combinations thereof.

In one embodiment, an effector domain of the FAS polypeptide useful for the invention comprises a death domain of the FAS polypeptide. In another embodiment, an effector domain of the FAS polypeptide comprises, consists essentially of, or consists of an amino acid sequence at least 60%, 70%, 80%, 90%, 95%, 96%, 97%, 98%, 99%, or 100% identical to amino acids 230 to 314 of SEQ ID NO: 6. In other embodiments, an effector domain of the FAS polypeptide comprises an intracellular domain of the FAS polypeptide. In yet other embodiments, an effector domain of the FAS polypeptide comprises an amino acid sequence at least 60%, 70%, 80%, 90%, 95%, 96%, 97%, 98%, 99%, or 100% identical to amino acids 185 to 335, amino acids 186 to 335, amino acids 187 to 335, amino acids 188 to 335, amino acids 189 to 335, amino acids 190 to 335, amino acids 191 to 335, amino acids 192 to 335, amino acids 193 to 335, amino acids 194 to 335, amino acids 195 to 335, amino acids 196 to 335, amino acids 197 to 335, amino acids 198 to 335, amino acids 199 to 335 of SEQ ID NO: 6.

In still other embodiments, the effector domain of the FAS polypeptide further comprises a trans-membrane domain of the FAS polypeptide. In yet other embodiments, an effector domain of the FAS polypeptide comprises an amino acid sequence at least 60%, 70%, 80%, 90%, 95%, 96%, 97%, 98%, 99%, or 100% identical to amino acids 174 to 335 of SEQ ID NO: 6. In some embodiments, an effector domain of the FAS polypeptide further comprises about ten, about nine, about eight, about seven, about six, about five, about four, about three, about two, or about one amino acid from the C-terminal portion of the FAS extracellular domain. In certain embodiments, an effector domain of the FAS polypeptide comprises an amino acid sequence at least 60%, 70%, 80%, 90%, 95%, 96%, 97%, 98%, 99%, or 100% identical to amino acids 179 to 335, amino acids 178 to 335, amino acids 177 to 335, amino acids 176 to 335, amino acids 175 to 335, amino acids 174 to 335, amino acids 173 to 335, amino acids 172 to 335, amino acids 171 to 335, amino acids 170 to 335, amino acids 169 to 335, amino acids 168 to 335, amino acids 167 to 335, amino acids 166 to 335, amino acids 165 to 335, amino acids 164 to 335, or amino acids 163 to 335 of SEQ ID NO: 6, wherein the effector domain forms a death-inducing signaling complex (DISC), activates caspase 8, or induces apoptosis.

In some embodiments, an effector domain of the FAS polypeptide comprises, consists essentially of, or consists of an amino acid sequence at least 70%, 80%, 90%, 95%, 96%, 97%, 98%, 99%, or 100% identical to SEQ ID NO: 8, wherein the effector domain forms a death-inducing signaling complex (DISC), activates caspase 8, or induces apoptosis.

In other embodiments, an effector domain of the FAS polypeptide is encoded by a nucleotide sequence at least 60%, 70%, 80%, 90%, 95%, 96%, 97%, 98%, 99%, or 100% identical to SEQ ID NO: 7.

In one embodiment, the FAS-chimera gene product for the invention comprises, consists essentially of, or consists of an amino acid sequence at least 70%, 80%, 90%, 95%, 96%, 97%, 98%, 99%, or 100% identical to SEQ ID NO: 10, wherein the FAS-chimera gene product induces apoptosis. In another embodiment, the FAS-chimera gene product is encoded by a nucleotide sequence at least 60%, 70%, 80%, 90%, 95%, 96%, 97%, 98%, 99%, or 100% identical to SEQ ID NO: 9, wherein the FAS-chimera gene product induces apoptosis.

B. Endothelial Cell-Specific Promoter

The nucleic acid construct comprising a FAS-chimera gene further comprises one or more expression control elements useful for regulating the expression of an operably linked FAS-chimera gene. The expression control elements include, but are not limited to, promoters, secretion signals, and other regulatory elements.

The nucleic acid construct useful for the present invention utilizes an endothelial cell-specific promoter to direct expression of the FAS-chimera protein in an endothelial cell, thereby inducing apoptosis of the endothelial cell.

For the purpose of the present invention, an endothelial cell-specific promoter can contain one or more cis-regulatory elements, which improve the endothelial cell-specificity of the promoters compared to the promoter without the cis-regulatory elements. In one example, the cis-regulatory element comprises an enhancer. In another aspect, the cis-regulatory element comprises a hypoxia response element. In other examples, the cis-regulatory element comprises both an enhancer and a hypoxia response element.

In one embodiment, an enhancer useful for the invention comprises a nucleotide sequence at least 60%, 70%, 80%, 90%, 95%, 96%, 97%, 98%, 99%, or 100% identical to SEQ ID NO: 11 or SEQ ID NO: 12 (the complementary sequence of SEQ ID NO: 11), wherein the enhancer improves endothelial cell specificity of a promoter compared to a promoter without the enhancer. The enhancer can further comprise an additional nucleotide sequence at least 60%, 70%, 80%, 90%, 95%, 96%, 97%, 98%, 99%, or 100% identical to SEQ ID NO: 13 or SEQ ID NO: 14 (the complementary sequence of SEQ ID NO: 13).

In another embodiment, an enhancer for the invention comprises a nucleotide sequence at least 60%, 70%, 80%, 90%, 95%, 96%, 97%, 98%, 99%, or 100% identical to SEQ ID NO: 13 or SEQ ID NO: 14 (the complementary sequence of SEQ ID NO: 13), wherein the enhancer improves endothelial cell specificity of a promoter compared to a promoter without the enhancer. The enhancer can further comprise an additional nucleotide sequence at least 60%, 70%, 80%, 90%, 95%, 96%, 97%, 98%, 99%, or 100% identical to SEQ ID NO: 11 or SEQ ID NO: 12 (the complementary sequence of SEQ ID NO: 11).

In other embodiments, an enhancer for the invention comprises a nucleotide sequence at least 60%, 70%, 80%, 90%, 95%, 96%, 97%, 98%, 99%, or 100% identical to SEQ ID NO: 15 or SEQ ID NO: 16 (the complementary sequence of SEQ ID NO: 15), wherein the enhancer improves endothelial cell specificity of a promoter compared to a promoter without the enhancer. In yet other embodiments, an enhancer for the nucleic acid construct comprises SEQ ID NO: 15 or SEQ ID NO: 16 or any fragments, variants, derivatives, or analogs thereof; wherein the fragments, variants, derivatives, or analogs improve endothelial cell specificity of a promoter compared to a promoter without the enhancer.

In some embodiments, an enhancer for the invention comprises a nucleotide sequence at least 60%, 70%, 80%, 90%, 95%, 96%, 97%, 98%, 99%, or 100% identical to SEQ ID NO: 22 or SEQ ID NO: 23, wherein the enhancer improves endothelial cell specificity of a promoter compared to a promoter without the enhancer. In yet other embodiments, an enhancer for the nucleic acid construct comprises SEQ ID NO: 22 or SEQ ID NO: 23 or any fragments, variants, derivatives, or analogs thereof, wherein the fragments, variants, derivatives, or analogs improve endothelial cell specificity of a promoter compared to a promoter without the enhancer.

In other embodiments, an enhancer for the invention comprises a nucleotide sequence at least 60%, 70%, 80%, 90%, 95%, 96%, 97%, 98%, 99%, or 100% identical to SEQ ID NO: 24 or SEQ ID NO: 25, wherein the enhancer improves endothelial cell specificity of a promoter compared to a promoter without the enhancer. In yet other embodiments, an enhancer for the nucleic acid construct comprises SEQ ID NO: 24 or SEQ ID NO: 25 or any fragments, variants, derivatives, or analogs thereof, wherein the fragments, variants, derivatives, or analogs improve endothelial cell specificity of a promoter compared to a promoter without the enhancer.

Table 3 shows various enhancer sequences useful for the invention.

TABLE 3

Endothelial Cell-Specific Enhancer Elements and Promoters

| SEQ ID NOs | Sequences |
|---|---|
| SEQ ID NO: 11 | ctggagggtg actttgcttc tggagccagt acttcatact tttcatt |
| SEQ ID NO: 12 | aatgaaaagt atgaagtact ggctccagaa gcaaagtcac cctccag |
| SEQ ID NO: 13 | gtacttcata cttttcattc caatggggtg actttgcttc tgga |
| SEQ ID NO: 14 | tccagaagca aagtcacccc attggaatga aaagtatgaa gtac |
| SEQ ID NO: 15 | 3X enhancer element<br>ctccagaagcaaagtcacccattggaatgaaaagtatgaagtacaatgaaaagtatgaagt<br>actggctccagaagcaaagtcaccctccagaagcaaagtcacccattggaatgaaaagtat<br>gaagtac |
| SEQ ID NO: 16 | 3x enhancer element (Complementary Sequence of SEQ ID NO: 15)<br>gtacttcatactttttcattccaatggggtgactttgcttctggagggtgactttgcttctgg<br>agccagtacttcatactttttcattgtacttcatactttttcattccaatggggtgactttgct<br>tctggag |
| SEQ ID NO: 17 | PPE-1 Promoter<br>gtacgtgtacttctgatcggcgatactagggagataaggatgtgcctgacaaaaccacattg<br>ttgttgttatcattattatttagttttccttccttgctaactcctgacggaatctttctcac<br>ctcaaatgcgaagtactttagtttagaaaagacttggtggaaggggtggtggtggaaaagta<br>gggtgatcttccaaactaatctggttccccgcccgccccagtagctgggattcaagagcgaa<br>gagtggggatcgtccccttgtttgatcagaaagacataaaaggaaaatcaagtgaacaatga<br>tcagcccacctccaccccaccccctgcgcgcgcacaatacaatctatttaattgtacttc<br>atactttcattccaatggggtgactttgcttctggagaaactcttgattcttgaactctgg<br>ggctggcagctagcaaaaggggaagcgggctgctgctctctgcaggttctgcagcggtctct<br>gtctagtgggtgttttcttttcttagccctgccctggattgtcagacggcgggcgtctgc<br>ctctgaagttagccgtgatttcctctagagccgggtcttatctctggctgcacgttgcctgt<br>gggtgactaatcacacaataacattgtttagggctggaatgaagtcagagctgtttaccccc |

TABLE 3-continued

Endothelial Cell-Specific Enhancer Elements and Promoters

| SEQ ID NOs | Sequences |
|---|---|
| | actctatagggggttcaatataaaaaggcggcggagaactgtccgagtcagaagcgttcctgc<br>accggcgctgagagcctgacccggtctgctccgctgtccttgcgcgctgcctcccggctgcc<br>cgcgacgctttcgccccagtggaagggccacttgctgcggccgc |
| SEQ ID NO: 18 | PPE-1-3X promoter<br>gtacgtgtacttctgatcggcgatactagggagataaggatgtgcctgacaaaaccacattg<br>ttgttgttatcattattatttagttttccttccttgctaactcctgacggaatctttctcac<br>ctcaaatgcgaagtactttagtttagaaaagacttggtggaagggtggtggtggaaaagta<br>gggtgatcttccaaactaatctggttccccgcccgccccagtagctgggattcaagagcgaa<br>gagtggggatcgtcccccttgtttgatcagaaagacataaaaggaaaatcaagtgaacaatga<br>tcagcccacctccaccccacccccctgcgcgcgcacaatacaatctatttaattgtacttc<br>atactttcattccaatgggggtgactttgcttctggagaaactcttgattcttgaactctgg<br>ggctggcagctagcctccagaagcaaagtcaccccattggaatgaaaagtatgaagtacaat<br>gaaaagtatgaagtactggctccagaagcaaagtcaccctccagaagcaaagtcaccccatt<br>ggaatgaaaagtatgaagtacgctagcaaaaggggaagcgggctgctgctctctgcaggttc<br>tgcagcggtctctgtctagtgggtgtttctttttcttagccctgccccctggattgtcagac<br>ggcgggcgtctgcctctgaagttagccgtgatttcctctagagccgggtcttatctctggct<br>gcacgttgcctgtgggtgactaatcacacaataacattgtttagggctggaatgaagtcaga<br>gctgtttaccccactctatagggggttcaatataaaaaggcggcggagaactgtccgagtca<br>gaagcgttcctgcaccggcgctgagagcctgacccggtctgctccgctgtccttgcgcgctg<br>cctcccggctgccgcgacgctttcgccccagtggaagggccacttgctgcggccgc |
| SEQ ID NO: 22 | ggtgactttg cttctggag |
| SEQ ID NO: 23 | ctccagaagcaaagtcacc |
| SEQ ID NO: 24 | gtacttcata cttttcatt |
| SEQ ID NO: 25 | aatgaaaagtatgaagtac |
| SEQ ID NO: 26 | Hypoxia Response element<br>gcacgt |

An enhancer for the present invention can be linked to a promoter upstream or downstream of the promoter or inserted between the two nucleotides in the promoter. The endothelial cell-specific promoter for the present invention can utilize any promoters known in the art. For example, suitable promoters which can be utilized for the present invention include the endothelial-specific promoters: pre-proendothelin-1 (PPE-1 promoter), US 2010/0282634, published Nov. 11, 2010; and WO 2011/083464, published Jul. 14, 2011); the PPE-1-3X promoter (U.S. Pat. Nos. 7,579,327, 8,071,740, 8,039,261, US2010/0282634, US 2007/0286845, WO 2011/083464, and WO2011/083466); the TIE-1 (S79347, S79346) and the TIE-2 (U53603) promoters [Sato T N, Proc Natl Acad Sci USA 1993 Oct. 15; 90(20): 9355-8], the Endoglin promoter [Y11653; Rius C, Blood 1998 Dec. 15; 92(12):4677-90], the von Willerbrand factor [AF152417; Collins C J Proc Natl Acad Sci USA 1987 July; 84(13):4393-7], the KDR/flk-1 promoter [X89777, X89776; Ronicke V, Circ Res 1996 August; 79(2):277-85], The FLT-1 promoter [D64016 AJ224863; Morishita K, J Biol Chem 1995 Nov. 17; 270(46):27948-53], the Egr-1 promoter [AJ245926; Sukhatme V P, Oncogene Res 1987 September-October; 1(4):343-55], the E-selectin promoter [Y12462; Collins T J Biol Chem 1991 Feb. 5; 266(4):2466-73], The endothelial adhesion molecules promoters: ICAM-1 [X84737; Horley K J EMBO J 1989 October; 8(10):2889-96], VCAM-1 [M92431; Iademarco M F, J Biol Chem 1992 Aug. 15; 267(23): 16323-9], PECAM-1 [AJ313330 X96849; CD31, Newman P J, Science 1990 Mar. 9; 247 (4947): 1219-22], the vascular smooth-muscle-specific elements: CArG box X53154 and aortic carboxypeptidase-like protein (ACLP) promoter [AF332596; Layne M D, Circ Res. 2002; 90: 728-736] and Aortic Preferentially Expressed Gene-1 [Yen-Hsu Chen J. Biol. Chem, Vol. 276, Issue 50, 47658-47663, Dec. 14, 2001], all of which are incorporated herein by reference in their entireties.

In one embodiment, a promoter linked to the endothelial cell-specific enhancer comprises a nucleotide sequence at least 60%, 70%, 80%, 90%, 95%, 96%, 97%, 98%, 99%, or 100% of SEQ ID NO: 17, wherein the promoter linked to the enhancer induces endothelial cell-specificity to the gene operably linked to the promoter. In another embodiment, a promoter linked to the endothelial cell-specific enhancer comprises a fragment, a variant, a derivative, or an analog of a wild-type PPE-1 promoter, wherein said fragment, variant, derivative, or analog thereof induces endothelial cell-specificity to the gene operably linked to the promoter. In one example, the endothelial cell-specific enhancer can be inserted between nucleotide residues 442 and 449 corresponding to SEQ ID NO: 17.

In further embodiments, an endothelial cell-specific promoter comprises a hypoxia responsive element. A hypoxia responsive element (HRE) is located on the antisense strand of the endothelin-1 promoter. This element is a hypoxia-inducible factor-1 binding site that is required for positive regulation of the endothelin-1 promoter (of the human, rat and murine gene) by hypoxia. Hypoxia is a potent signal, inducing the expression of several genes including erythropoietin (Epo), VEGF, and various glycolytic enzymes. The core sequence (8 base pairs) is conserved in all genes that respond to hypoxic conditions and the flanking regions are different from other genes. The ET-I hypoxia responsive element is located between the GAT A-2 and the AP-1 binding sites. In one example, a hypoxia response element comprises SEQ ID NO: 26, a fragment, a variant, a derivative, or an analog thereof.

In other embodiments, an endothelial cell-specific promoter useful for the invention comprises, consists essentially of; or consists of a nucleotide sequence at least 60%, 70%, 80%, 90%, 95%, 96%, 97%, 98%, 99%, or 100% of SEQ ID NO: 18, wherein the promoter linked to the enhancer induces endothelial cell-specificity to the gene operably linked to the promoter. In another embodiment, an endothelial cell-specific promoter comprises a fragment, a variant, a derivative, or an analog of SEQ ID NO: 18, wherein said fragment, variant, derivative, or analog thereof induces endothelial cell-specificity to the gene operably linked to the promoter.

Additional variations of the endothelial cell-specific promoters can be found at WO2011/083464, WO2011/083466, and WO2012/052423, which are incorporated herein by reference in their entireties.

The present invention also provides a novel promoter sequence comprising a nucleotide sequence SEQ ID NO: 17. In one example, the promoter further comprises an endothelial cell-specific enhancer. In one example, the endothelian cell-specific enhancer comprises SEQ ID NO: 11, SEQ ID NO: 12, SEQ ID NO: 13, SEQ ID NO: 14, SEQ ID NO: 15, SEQ ID NO: 16, SEQ ID NO: 22, SEQ ID NO: 23, SEQ ID NO: 24, SEQ ID NO: 25, SEQ ID NO: 26 or any fragments, derivatives, variants, or analogs thereof; wherein the fragments, derivatives, variants, or analogs thereof improve endothelial cell-specificity of the promoter compared to a promoter without the enhancer. In another example, the promoter comprises a nucleotide sequence of SEQ ID NO: 18. The invention includes a nucleic acid construct comprising the novel promoter and a heterologous nucleotide sequence. In one embodiment, the heterologous nucleic acid sequence comprises a nucleotide sequence encoding a FAS-chimera protein described herein. In another embodiment, the heterologous nucleotide sequence comprises an adenovirus sequence.

C. Vector

The invention also provides a vector comprising the nucleic acid construct, which comprises a FAS-chimera gene operably linked to an endothelial cell-specific promoter. For the purposes of this invention, numerous vector systems may be employed. For example, various viral gene delivery systems that can be used in the practice of this aspect of the invention include, but are not limited to, an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, an adeno-associated viral vector and a herpes simplex viral vector.

In another embodiment, a vector comprising a FAS-chimera gene operably linked to an endothelial cell-specific promoter is an adenovirus. For example, the adenovirus can be any one or more of human adenovirus species A (serotypes 12, 18, and 31), B (serotypes 3, 7, 11, 14, 16, 21, 34, 35, 50, and 55), C (serotypes 1, 2, 5, 6, and 57), D (8, 9, 10, 13, 15, 17, 19, 20, 22-30, 32, 33, 36-39, 42-49, 51, 53, 54, and 56), E (serotype 4), F (serotype 40 and 41), or G (serotype 52). In a particular embodiment, the adenovirus for the invention is human adenovirus serotype 5. In some embodiments, the adenovirus useful for gene therapy is a recombinant non-replicating adenovirus, which does not contain an E1 region and an E3 region. In certain embodiments, the adenovirus for the invention is a conditionally replicating adenovirus, which does not contain an E3 region, but contains an E1 region.

D. Biological Deposits

Biological deposits were made with the European Collection of Cell Cultures (ECACC) located at Health Protection Agency Culture Collections, Health Protection Agency, Microbiology Services, Porton Down, Salisbury, SP4 0JG, UK, pursuant to the Budapest Treaty and pursuant to 37 C.F.R. § 1.808. Samples of the deposited materials will become available to the public upon grant of a patent. The invention described and claimed herein is not to be limited by the scope of the strain deposited, since the deposited embodiment is intended only as an illustration of the invention.

| Strain | ECACC Accession No. | Date Deposited |
| --- | --- | --- |
| VB-111 | 13021201 | Feb. 12, 2013 |

III. Treatment Methods Using Adenovirus Expressing Fas-Chimera Protein

One embodiment of the present invention provides methods for using a nucleic acid construct expressing a FAS chimera protein or an adenovirus comprising the nucleic acid construct. In one aspect, a nucleic acid construct expressing a FAS-chimera protein or an adenovirus comprising the nucleic acid construct is useful for reducing or decreasing a size of a tumor or eliminating a tumor in a subject, wherein the FAS-chimera protein encoded by the nucleic acid construct reduces or decreases the size of the tumor or slows the rate of tumor growth or prevents appearance of new tumor metastatic lesions or eliminates the tumor in the subject and wherein the tumor is associated with or derived from a female gynecological cancer or a metastasis thereof. These effects may be assessed based on radiological diagnostic tests (such as CT scan) and/or tumor markers (such as blood level of CA-125). In another aspect, a nucleic acid construct expressing a FAS-chimera protein or an adenovirus comprising the nucleic acid construct is useful for inhibiting, decreasing, or reducing neo-vascularization or angiogenesis in a tumor, wherein a FAS-chimera protein encoded by the nucleic acid construct inhibits, reduces, or decreases the neo-vascularization or angiogenesis in the tumor and wherein the tumor is associated with or derived from a female gynecological cancer or a metastasis thereof. In other aspects, a nucleic acid construct expressing a FAS-chimera protein or an adenovirus comprising the nucleic acid construct is capable of treating or preventing a tumor associated with or derived from a female gynecological cancer or a metastasis thereof in a subject, wherein the FAS-chimera protein encoded by the nucleic acid construct treats or prevents the female gynecological cancer or a metastasis thereof in the subject.

Therefore, in one aspect, the invention provides a method of reducing or decreasing a size of a tumor or a metastasis thereof, eliminating a tumor or a metastasis thereof, or slowing the growth of a tumor or a metastasis thereof in a subject comprising administering to the patient an effective amount of a nucleic acid construct, which comprises a Fas-chimera gene operably linked to an endothelial cell specific promoter, or an adenovirus comprising the nucleic acid construct, wherein a Fas-chimera gene product encoded by the nucleic acid construct reduces or decreases the size of the tumor or a metastasis thereof or eliminates the tumor or a metastasis thereof in the subject and wherein the tumor or a metastasis thereof is associated with or derived from a female gynecological cancer. In another aspect, the invention provides a method of inhibiting, decreasing, or reducing neo-vascularization or angiogenesis in a tumor or a metastasis thereof comprising administering to a subject having the tumor or a metastasis thereof an effective amount of a nucleic acid construct, or an adenovirus comprising the nucleic acid construct, which comprises a FAS-chimera gene operably linked to an endothelial cell specific promoter, wherein a FAS-chimera gene product encoded by the nucleic acid construct inhibits, reduces, or decreases the neo-vascularization or angiogenesis in the tumor or a metastasis thereof and wherein the tumor or a metastasis thereof is associated with or derived from a female gynecological cancer. In other aspects, the invention provides a method of treating or preventing a tumor or a metastasis thereof associated with or derived from a female gynecological cancer in a subject comprising administering an effective amount of a nucleic acid construct, which comprises a Fas-chimera gene operably linked to an endothelial cell specific promoter, wherein a Fas-chimera gene product encoded by the nucleic acid construct treats or prevents the female gynecological cancer in the patient. In still other embodiments, the tumor of the female gynecological cancer or a metastasis thereof is decreased in size or eliminated after the administration. In certain embodiments, the size of the tumor or a metastasis thereof is decreased such that the longest diameter (LD) of the tumor is decreased at least about 10%, 20%, 30%, 40%, 50%, 60%, 70%, 80%, 90%, or 100% compared to the LD prior to the administration. In some embodiments, the invention includes a method of stabilizing a disease or disorder associated with a female gynecological cancer. For example, the invention includes a method of preventing or slowing further growth of a tumor associated with a female gynecological cancer. In further embodiments, the present invention reduces the volume of malignant peritoneal fluid, e.g., ascites, reduces pain to the subject, prolongs survival of the subject, or any combinations thereof. In other embodiments, the adenovirus of the invention when administered to the subject prolongs the overall survival of the subject. In further embodiments, the adenovirus of the invention when administered to the subject prolongs progression-free survival of the subject.

In one embodiment, the female gynecological cancer can be Müllerian cancer, ovarian cancer, peritoneal cancer, fallopian tube cancer, uterine papillary serous carcinoma, a metastasis thereof, or any combinations thereof. In another embodiment, the female gynecological cancer can be cervical cancer, endometrial cancer, gestational trophoblastic disease, uterine cancer, vulvar cancer, a metastasis thereof or any combinations thereof. In other embodiments, the female gynecological cancer includes any cancerous growth arising from a gynecological tissue, e.g., uterus, ovary, fallopian tube, cervix, egg cells, the supporting cells, or any combinations thereof. In certain embodiments, the tumor associated with or derived from a female gynecological cancer can be selected from the group consisting of surface epithelial-stromal tumor (adenocarcinoma), papillary serous cystadenocarcinoma, endometrioid tumor, serous cystadenocarcinoma, papillary tumor, mucinous cystadenocarcinoma, clear-cell ovarian tumor, mucinous adenocarcinoma, cystadenocarcinoma, carcinoma, sex cord-stromal tumour, germ cell tumor, teratoma, dysgerminoma, epidermoid (Squamous cell carcinoma), Brenner tumor, a metastasis thereof or any combinations thereof.

Müllerian cancer for the purpose of the present invention includes a malignant mixed Müllerian tumor, also known as malignant mixed mesodermal tumor, MMMT and carcinosarcoma. MMMT is a malignant neoplasm found in the uterus, the ovaries, the fallopian tubes and other parts of the body that contains both carcinomatous (epithelial tissue) and sarcomatous (connective tissue) components. It is divided into two types, homologous (in which the sarcomatous component is made of tissues found in the uterus such as endometrial, fibrous and/or smooth muscle tissues) and a heterologous type (made up of tissues not found in the uterus, such as cartilage, skeletal muscle and/or bone). MMMT account for between two and five percent of all tumors derived from the body of the uterus, and are found predominantly in postmenopausal women with an average age of 66 years.

Ovarian cancer comprises any cancerous growth arising from the ovary. Most (more than 90%) ovarian cancers are classified as "epithelial" and are believed to arise from the surface (epithelium) of the ovary. However, fallopian tubes could also be the source of some ovarian cancers. Since the ovaries and tubes are closely related to each other, it is thought that these fallopian cancer cells can mimic ovarian cancer. Other types may arise from the egg cells (germ cell tumor) or supporting cells. In some embodiments, ovarian cancer is a secondary cancer, the result of metastasis from a primary cancer elsewhere in the body. About 7% of ovarian cancers are due to metastases while the rest are primary cancers. Common primary cancers are breast cancer and gastrointestinal cancer.

Peritoneal cancer or carcinoma is also known as: serous surface papillary carcinoma, primary peritoneal carcinoma, extra-ovarian serous carcinoma, primary serous papillary carcinoma, or psammomacarcinoma. It was historically classified under "carcinoma of unknown primary" (CUP). Primary peritoneal cancer (PPC, or PPCa) is a cancer of the cells lining the peritoneum, or abdominal cavity. Histomorphological and molecular biological characteristics suggest that serous carcinomas, which include ovarian serous carcinoma, uterine serous carcinoma, fallopian tube serous carcinoma, cervical serous carcinoma, and primary peritoneal serous carcinoma really represent one entity.

Primary fallopian tube cancer (PFTC), often just tubal cancer, is a malignant neoplasm that originates from the fallopian tube. Tubal cancer is thought to be a relatively rare primary cancer among women accounting for 1 to 2 percent of all gynecologic cancers.

Uterine serous carcinoma (USC), also known as uterine papillary serous carcinoma (UPSC) and uterine serous adenocarcinoma, is an uncommon form of endometrial cancer that typically arises in postmenopausal women. It is typically diagnosed on endometrial biopsy, prompted by post-menopausal bleeding. Unlike the more common low-grade endometrioid endometrial adenocarcinoma, USC does not develop from endometrial hyperplasia and is not hormone-sensitive. It arises in the setting of endometrial atrophy and is classified as a type II endometrial cancer.

The term "subject" or "individual" or "animal" or "patient" or "mammal," is meant any subject, particularly a mammalian subject, having or being expected to develop at least one tumor associated with or derived from peritoneal cancer or female gynecological cancer. In one embodiment, the subject is a human. In another embodiment, the subject is a cancer patient.

In one embodiment of the invention, the subject is a subject who has had a prior platinum based therapy. Such a prior platinum based therapy includes, but is not limited to, cisplatin, carboplatin, oxaliplatin, nedaplatin, satraplatin, picoplatin, triplatin tetranitrate, or aroplatin. Platinum-based antineoplastic agents cause cross-linking of DNA as monadduct, interstrand crosslinks, intrastrand crosslinks or DNA protein crosslinks. Mostly they act on the adjacent N-7 position of guanine, forming 1, 2 intrastrand crosslink. The resultant crosslinking inhibit DNA repair and/or DNA synthesis in cancer cells. Platinum-based antineoplastic agents are sometimes described as "alkylating-like" due to similar effects as alkylating antineoplastic agents, although they do not have an alkyl group. In certain embodiments, the prior platinum-based therapy is a therapy using cisplatin, also known as cisplatinum or cis-diamminedichloroplatinum(II) (CDDP) (trade name Cisplatin, brand name Platin marketed by Cadila Healthcare according to FDA Orange Book). Cisplatin is administered intravenously as short-term infusion in normal saline for treatment of solid malignancies. It is used to treat various types of cancers, including sarcomas, some carcinomas (e.g. small cell lung cancer, and ovarian cancer), lymphomas, and germ cell tumors.

In other embodiments, the subject has had a prior taxane-based therapy. Taxanes are diterpenes produced by the plants of the genus *Taxus* (yews), and are widely used as chemotherapy agents. Taxane can now be synthesized artificially. Taxane agents include, but are not limited to, paclitaxel (TAXOL®) and docetaxel (TAXOTERE®).

In one aspect, taxane can be fused to or bound to a heterologous moiety. Such a heterologous moiety can improve solubility of taxane formulation or reduce toxicity of taxane. For example, taxane can be fused to or bound to albumin: albumin-bound paclitaxel (ABRAXANE®, also called nab-paclitaxel) is an alternative formulation where paclitaxel is bound to albumin nano-particles.

Synthetic approaches to paclitaxel production led to the development of docetaxel. Docetaxel has a similar set of clinical uses to paclitaxel and is marketed under the name of TAXOTERE®.

In another aspect, taxane useful for the present invention includes, but is not limited to, paclitaxel, 10-deacetylbaccatin III, baccatin III, paclitaxel C, and 7-epipaclitaxel in the shells and leaves of hazel plants.

In other embodiments, the subject has had up to three, up to two, or up to one previous line of chemotherapy. The previous line of chemotherapy can be a platinum-based therapy or a taxane-based therapy. In yet other embodiments, the subject has not had more than 3 prior lines of chemotherapy for recurrent cancer.

In certain embodiments, the subject is a patient who has recurrent platinum-resistant cancer or platinum refractory disease. In some embodiments, the subject is a patient who has recurrent taxane resistant cancer. In one aspect, the recurrent platinum-resistant cancer or the recurrent taxane-resistant cancer has a progressive tumor during the platinum or taxane treatment, within about one months, within about two months, within about three months, about four months, about five months, about six months, about seven months, about eight months, about nine months, about ten months, about 11 months, or about 12 months of completing or receiving a platinum based therapy or a taxane based therapy. In a particular embodiment, the recurrent platinum-resistant cancer or the recurrent taxane-resistant cancer has a progressive tumor within about six months of completing or receiving a platinum based therapy or a taxane based therapy. The recurrent platinum-resistant cancer or the recurrent taxane-resistant cancer can be determined by Response Evaluation Criteria In Solid Tumors (RECIST), measurement of one or more tumor markers, e.g., CA-125, physical examination, reassessment or second-look laparotomy, and/or one or more imaging studies (e.g., X-ray, CT or MRI).

RECIST is a set of published rules that define when cancer patients improve ("respond"), stay the same ("stable") or worsen ("progression") during treatments. The original criteria were published in February 2000 by an international collaboration including the European Organization for Research and Treatment of Cancer (EORTC), National Cancer Institute (NCI) of the United States and the National Cancer Institute of Canada Clinical Trials Group. RECIST 1.1, published in January 2009, is an update to the original criteria. The majority of clinical trials evaluating cancer treatments for objective response in solid tumors are using RECIST.

In some embodiments, a subject can exhibit a tumor marker, e.g., CA-125. In one aspect, the CA-125 expression level in the subject is reduced at least about 10%, at least about 20%, at least about 30%, at least about 40%, at least about 50%, at least about 55%, at least about 60%, at least about 65%, at least about 70%, at least about 75%, at least about 80%, at least about 85%, at least about 90%, or at least about 100% after the administration compared to the CA-125 level prior to the administration.

In some embodiments, a subject has received only one platinum-based treatment for recurrent platinum sensitive disease with a subsequence platinum free interval of less than six months.

In other embodiments, a subject has an Eastern Cooperative Oncology Group (ECOG) performance status of 0-1. ECOG is scales or criteria used to assess progression of a patient's disease, effects of the disease in daily living of the patient, and determination of appropriate treatment and prognosis. TABLE 4 shows ECOG performance status:

TABLE 4

| ECOG PERFORMANCE STATUS* | |
|---|---|
| Grade | ECOG |
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities. Up and about more than 50% of waking hours |
| 3 | Capable of only limited selfcare, confined to bed or chair more than 50% of waking hours |
| 4 | Completely disabled. Cannot carry on any selfcare. Totally confined to bed or chair |
| 5 | Dead |

*As published in Am. J. Clin. Oncol.: Oken, M. M., Creech, R. H., Tormey, D. C., Horton, J., Davis, T. E., McFadden, E. T., Carbone, P. P.: *Toxicity And Response Criteria Of The Eastern Cooperative Oncology Group. Am J Clin Oncol* 5: 649-655, 1982.

In some embodiments, a subject has a bone marrow function comparable to a subject without the cancer. Bone marrow functions comparable to a subject without the cancer include, but are not limited to, its role as the major hematopoietic organ and a primary lymphoid tissue, and being responsible for the production of blood cells, e.g., erythrocytes, granulocytes, monocytes, lymphocytes and platelets. Detailed description of the bone marrow structure and function is found in Jain, C., 1986b, *Schalm's Veterinary Hematology*, The hematopoietic system (Lea and Febiger, Philadelphia, Pa.), 4, pp 350-387; Weiss and Geduldig, 1991, Blood 78:975-90; Wickramasinghe, 1992, in *Histology for Pathologists, Bone marrow*, ed Sternberg S S (Raven Press, New York), pp 1-31; Picker and Siegelman, 1999, in *Fundamental Immunology*, Lymphoid tissues and organs, ed Paul W E (Lippincott-Raven, Philadelphia, Pa.), 4, pp 479-531; Hoffman et al., 2000, *Hematology Basic Principals and Practice* (Churchill Livingstone, N.Y.), 3; Abboud and Lichtman, 2001, in *Williams' Hematology*, Structure of the marrow and the hematopoietic microenvironment, eds Bentler E, Lichtman M A, Coller B S, Kipps T J, Seligsohn U (McGraw-Hill, New York), 6, pp 29-58, each of which is incorporated herein by reference in its entirety.

In further embodiments, a subject has a hematological function comparable to a subject without the cancer, wherein the indicator of hematological function is selected from the group consisting of:

a. Absolute Neutrophil Count (ANC) is equal to or higher than 1,000/mm3;

b. Platelet (PLT) count is equal to or higher than 100,000/mm3;

c. Prothrombin time (PT) is less than 1.2× Upper Limit of Normal (ULN) seconds;

d. Thromboplastin time (PTT) is less than 1.2×ULN seconds, wherein if PTT is higher than ULN, the patient has a negative lupus anti-coagulant (LAC); and e. any combinations thereof.

In other embodiments, a subject has an organ function comparable to a subject without the cancer, wherein the organ function is analyzed using common toxicity criteria selected from the group consisting of:

a. less than or equal to grade 1 common toxicity criteria (CTC) neuropathy;

b. no more than 30% of major bone marrow containing areas (e.g., pelvis or lumbar spine) having received prior radiation;

c. less than 2.5× upper limit of normal (ULN) or less than 5×ULN of serum glutamic oxaloacetic transaminase (SGOT), serum glutamic pyruvic transaminase (SGPT), or alkaline phosphatase;

d. less than or equal to 1.5×ULN level of bilirubin;

e. less than or equal to 1.5×ULN level of creatinine;

f. less than 2+ by dip stick of proteinuria at screening or less than 1.0 ratio of urinary protein creatinine; and g. any combinations thereof.

In still other embodiments, a subject has recovered from acute toxicity from prior treatment, e.g., any chemotherapy, radiotherapy, or biologic therapy. However, the subject may need to recover from grade 1 neuropathy, any grade anemia, or alopecia.

In certain embodiments, a subject has received a prior anti-angiogenic agent. In some embodiments, the subject does not have any prior gastrointestinal (GI) perforation, GI obstruction, or involvement of the bowel on imaging studies. In yet other embodiments, the subject does not have active, untreated psychiatric disease or neurologic symptoms requiring treatment (Grade I sensory neuropathy allowed), does not have presence of untreated central nervous system or brain metastases, does not have any dementia or significantly altered mental status that would prohibit the understanding and/or giving of informed consent, does not have any known hypersensitivity to Cremophor EL, does not have evidence of uncontrolled bacterial, viral or fungal infections, or any combinations thereof. In still other embodiments, the subject is suitable for the present invention if the subject has had a prior paclitaxel reaction, but subsequently tolerated the drug at rechallenge.

A subject suitable for the invention can be identified by measurement of the plasma biomarker or cell surface biomarker for an anti-angiogenic therapy. In one embodiment, a subject suitable for the invention exhibits a plasma biomarker, which includes, but is not limited to vascular endothelial growth factor (VEGF), phosphatidylinositol-glycan biosynthesis class F protein (PIGF), soluble vascular endothelial growth factor receptor-1 (sVEGFR-1), sVEGFR-2, sVEGFR-3, basic fibroblast growth factor (bFOF), interleukin-1β (IL-1β), interleukin-6 (IL-6), interleukin-8 (IL-8), tumor necrosis factor-α (TNF-α), Von Willebrand Factor (vWF), soluble c-kit (c-kit), stromal derived factor 1α (SDF1α), alpha fetoprotein (AFP), and any combinations thereof. In another embodiment, a subject suitable for the invention exhibits a cell surface biomarker, which includes, but is not limited to, CD31, CD34, CD45, CD133, vascular endothelial growth factor receptor-1 (VEGFR-1), VEGFR-2, or any combinations thereof.

It is known that presence or formation of neutralizing antibodies may hinder efficient gene transfer upon a second administration of virus. In one embodiment, a subject does not have a pre-existing antibody response against adenovirus. In another embodiment, a subject does not develop an antibody response against adenovirus upon administration of the adenovirus.

In some aspects of the invention, a subject does not exhibit lupus anticoagulant (LAC, also known as lupus antibody, LA, or lupus inhibitors). The presence of LAC can be determined by any known methods, e.g., by measuring the LAC by an LAC test or an APLA test. LAC is an immunoglobulin that binds to phospholipids and proteins associated with the cell membrane. Joussen, J., et al., in *Documenta Ophthalmologica*, 2008, Volume 117, Number 3, Pages 263-265, Retinal Vascular Disease, S. J. Ryan (eds), Springer, 2007, 780 p, 1040, ISBN: 978-3-540-29541-9. LAC is a prothrombotic agent; that is, presence of LAC antibodies precipitates the formation of thrombi in vivo. Presence of these antibodies in laboratory tests causes an increase in aPTT. It is speculated that the presence of the antibodies interferes with phospholipids utilized to induce in vitro coagulation. It is thought to interact with platelet membrane phospholipids in vivo, increasing adhesion and aggregation of platelets; thus its in vivo prothrombotic characteristics. Therefore, LAC acts as a coagulation agent in vivo.

IV. Homogeneous Population of Adenovirus Expressing Fas-Chimera

The present invention also provides a homogeneous population of an adenovirus comprising SEQ ID NO: 19 or of an adenovirus having ECACC deposit designation No. 13021201. The term "homogeneous" as used herein refers to a single population of an adenovirus without contamination of heterologous adenoviruses having different sequences. Examples of the heterologous adenovirus include, but are not limited to, the adenovirus comprising a nucleotide sequence which comprises SEQ ID NO: 20 or SEQ ID NO: 21.

The adenovirus comprising a nucleotide sequence which comprises SEQ ID NO: 20 and the adenovirus comprising a nucleotide sequence which comprises SEQ ID NO: 21 were previously disclosed in International Application Nos. PCT/IL2011/00007 and PCT/IL2011/00009, published on Jul. 14, 2011 as WO2011/083464 and WO2011/083466, respectively, which are incorporated herein by reference in their entireties.

The present invention provides an adenovirus comprising SEQ ID NO: 19 (35,208 bps), which includes two nucleotide residues different from SEQ ID NO: 20 (35203 bps) and SEQ ID NO: 21. The two mismatches (i.e., Gly→Ala) in SEQ ID NO: 20 and SEQ ID NO: 21 are at nucleotide residues 501 and 1255. In addition, SEQ ID NO: 19 contains an extra thymidine at nucleotide residue 33624 and four extra base pairs at the 3' end. Moreover, SEQ ID NO: 21 contains an amino acid encoding an extra E1 region.

SEQ ID NO: 19 comprises a nucleotide sequence of an endothelial cell-specific promoter (i.e., PPE-1-3x promoter) at nucleotide residues 458 to 1444 corresponding to SEQ ID NO: 18, and a nucleotide sequence encoding a FAS-chimera protein at nucleotide residues 1469 to 2569 corresponding to SEQ ID NO: 9.

In one embodiment, the present invention is a composition comprising an adenovirus comprising a FAS-chimera gene operably linked to an endothelial cell-specific promoter, wherein the adenovirus does not contain SEQ ID NO: 20 and does not contain SEQ ID NO: 21. In another embodiment, the present invention is a composition comprising an adenovirus comprising SEQ ID NO: 19 or an adenovirus having ECACC deposit designation No. 13021201, wherein the composition does not contain an adenovirus comprising SEQ ID NO: 20 and does not contain an adenovirus comprising SEQ ID NO: 21.

In another embodiment, a composition comprises an adenovirus comprising nucleotide residues 458 to 2569 of SEQ ID NO: 19, wherein the composition does not comprise an adenovirus comprising nucleotide residues 458 to 2569 of SEQ ID NO: 20 or SEQ ID NO: 21.

In other embodiments, a composition of the present invention comprises an adenovirus comprising a nucleic acid sequence at least 80%, 85%, 90%, 95%, 96%, 97%, 98%, 99%, or 100% identical to SEQ ID NO: 19, wherein the nucleic acid sequence is not SEQ ID NO: 20 and is not SEQ ID NO: 21 and wherein the composition does not contain an adenovirus comprising SEQ ID NO: 20 and does not contain an adenovirus comprising SEQ ID NO: 21.

In still other embodiments, a composition of the present invention comprising an adenovirus comprising SEQ ID NO: 19 or an adenovirus having ECACC deposit designation No. 13021201, wherein the adenovirus is at least about 51% pure, at least 55% pure, at least about 60% pure, at least about 70% pure, at least about 80% pure, at least about 90% pure, at least about 95% pure, at least about 96% pure, at least about 97% pure, at least about 98% pure, at least about 99% pure, or about 100% pure. The term "pure" as used herein means a degree of homogeneity, i.e., without heterologous adenoviruses. For example, about 51% pure composition comprising an adenovirus comprising SEQ ID NO: 19 contains about 51% of the adenovirus comprising SEQ ID NO: 19 and about 49% of an adenovirus comprising a heterologous sequence, e.g., SEQ ID NO: 20 or SEQ ID NO: 21. The composition for the invention can contain other ingredients including, but not limited to, a pharmaceutically acceptable carrier, excipient, tonicity modifying agent, or any necessary ingredients for formulation.

In some embodiments, the invention includes a method of isolating or purifying a homogeneous population of the nucleic acid construct. In other embodiments, the invention provides a method of removing heterologous populations of adenovirus, e.g., SEQ ID NO: 20, SEQ ID NO: 21, or both, from a composition comprising an adenovirus comprising SEQ ID NO: 19 or a nucleic acid construct having ECACC deposit designation No. 13021201

Also provided is a method of reducing or decreasing a size of a tumor or slowing the rate of tumor growth eliminating a tumor in a subject comprising administering to the subject an effective amount of a homogeneous population of the adenovirus or a composition comprising the homogeneous population of the adenovirus. The invention also includes a method of inhibiting, decreasing, or reducing neo-vascularization or angiogenesis in a tumor comprising administering to a subject having the tumor an effective amount of a homogeneous population of the adenovirus or a composition comprising the homogeneous population of the adenovirus. Moreover, the invention includes a method of treating or preventing a tumor associated with or derived from cancer in a subject comprising administering an effective amount of the homogeneous population of the adenovirus or a composition comprising the homogeneous population of the adenovirus.

The invention also includes a method of reducing or decreasing a size of a tumor or slowing the rate of tumor growth eliminating a tumor in a subject comprising administering to the subject an effective amount of a homogeneous population of the adenovirus or a composition comprising the homogeneous population of the adenovirus repeatedly without administering a heterogeneous population of an adenovirus comprising SEQ ID NO: 20 or SEQ ID NO: 21 or a composition comprising the heterogeneous population of the adenovirus. Also included is a method of inhibiting, decreasing, or reducing neo-vascularization or angiogenesis in a tumor comprising administering to a subject having the tumor an effective amount of a homogeneous population of the adenovirus or a composition comprising the homogeneous population of the adenovirus repeatedly without administering a heterogeneous population of the adenovirus comprising SEQ ID NO: 20 or SEQ ID NO: 21 or a composition comprising the heterogeneous population of the adenovirus. In addition, the invention includes a method of treating or preventing a tumor associated with or derived from cancer in a subject comprising administering an effective amount of the homogeneous population of the adenovirus or a composition comprising the homogeneous population of the adenovirus repeatedly without administering a heterogeneous population of the adenovirus comprising SEQ ID NO: 20 or SEQ ID NO: 21 or a composition comprising the heterogeneous population of the adenovirus.

The tumor that can be reduced, inhibited, or treated with the homogeneous population of the adenovirus or the composition can be a solid tumor, a primary tumor, or a metastatic tumor. The term "metastatic" or "metastasis" refers to tumor cells that are able to establish secondary tumor lesions in another parts or organ.

In other embodiments, the homogeneous population of the invention when administered to a subject in need thereof prolongs the overall survival of the subject. In further embodiments, the homogeneous population of the invention when administered to a subject in need thereof prolongs progression-free survival of the subject.

A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acra-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

Additional cancers that may be inhibited or treated include, for example, Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Müllerian cancer, ovarian cancer, peritoneal cancer, fallopian tube cancer, or uterine papillary serous carcinoma.

V. Pharmaceutical Compositions

Also provided in the invention is a pharmaceutical composition comprising a nucleic acid construct expressing a FAS-chimera protein used in the methods of the invention, an adenovirus comprising the nucleic acid construct, or a homogeneous population of the adenovirus. The pharmaceutical composition can be formulated for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In one embodiment, the composition is formulated by adding saline.

The compositions of the present invention may be administered by any suitable method, e.g., parenterally (e.g., includes subcutaneous, intravenous, intramuscular, intra-articular, intra-synovial, intrasternal, intrathecal, intrahepatic, intralesional and intracranial injection or infusion techniques), intraventricularly, orally, by inhalation spray, topically, rectally, nasally, buccally, vaginally or via an implanted reservoir. As described previously, the composition comprising a nucleic acid construct which comprises a FAS-chimera gene or the homogeneous population of the adenovirus expresses the FAS-chimera gene product in an endothelial cell and thereby induces apoptosis of the endothelial cell. Accordingly, the composition can inhibit, reduce, or decrease the size of a tumor or a metastasis thereof by inhibiting neo-vascularization and/or angiogenesis of the tumor endothelial cells. Therefore, in one embodiment, the composition is delivered systemically or locally. For systemic or local delivery, the pharmaceutical formulation containing the nucleic acid construct, the adenovirus, or the homogeneous population of the adenovirus can utilize a mechanical device such as a needle, cannula or surgical instruments.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of a nucleic acid construct expressing a FAS-chimera protein, an adenovirus comprising the nucleic acid construct, or a homogeneous population of the adenovirus that may be combined with the carrier materials to produce a single dosage form will vary depending upon the host treated, the type of polypeptide used and the particular mode of administration. The composition may be administered as a single dose, multiple doses or over an established period of time in an infusion. Dosage regimens also may be adjusted to provide the optimum desired response (e.g., a therapeutic or prophylactic response).

In one embodiment, a composition comprising a nucleic acid construct expressing a FAS-chimera protein, an adenovirus, or a homogeneous population of the adenovirus is infused on day 1 (i.e., the first dose) and followed by one or more subsequence doses, e.g., every one week cycle, every two week cycle, every three week cycle, every four week cycle, every five week cycle, every six week cycle, every seven week cycle, every eight week cycle, every nine week cycle, every ten week cycle, every 11 week cycle, or every 12 week cycle. In another embodiment, a composition comprising a nucleic acid construct expressing a FAS-chimera protein, an adenovirus, or a homogeneous population of the adenovirus is infused on day 1 (i.e., the first dose) and followed by one or more subsequence doses, e.g., every two weeks cycle, every monthly cycle, every two months cycle, every three months cycle, every four months cycle, every five months cycle or every six months cycle.

The methods of the invention use an "effective amount" or a "therapeutically effective amount" of a composition comprising a nucleic acid construct expressing a FAS-chimera protein, an adenovirus comprising the nucleic acid construct, or a homogeneous population of the adenovirus. Such an effective amount or a therapeutically effective amount may vary according to factors such as the disease state, age, sex, and weight of the individual. An effective amount or a therapeutically effective amount is also one in which any toxic or detrimental effects are outweighed by the therapeutically beneficial effects.

A specific dosage and treatment regimen for any particular patient will depend upon a variety of factors, including the particular composition used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

An effective amount of an adenovirus comprising the nucleic acid construct encoding a FAS-chimera or a homogeneous population of an adenovirus comprising the nucleic acid construct encoding a FAS-chimera protein can be any suitable doses. In one embodiment, an effective amount of the adenovirus or the homogeneous population of the adenovirus is at least about $10^9$ VPs, at least about $10^{10}$ VPs, at least about $10^{11}$ VPs, at least about $10^{12}$ VPs, or at least about $10^{13}$ VPs per subject. In another embodiment, an effective amount of the adenovirus or the homogeneous population of the adenovirus is at least about $1 \times 10^{12}$ VPs, at least about $2 \times 10^{12}$ VPs, at least about $3 \times 10^{12}$ VPs, at least about $4 \times 10^{12}$ VPs, at least about $5 \times 10^{12}$ VPs, at least about $6 \times 10^{12}$ VPs, at least about $7 \times 10^{12}$ VPs, at least about $8 \times 10^{12}$ VPs, at least about $9 \times 10^{12}$ VPs, or at least about $1 \times 10^{13}$ VPs per subject. In other embodiments, an effective amount of the adenovirus or the homogeneous population of the adenovirus is about $10^9$ to about $10^{15}$ VPs, about $10^{10}$ to about $10^{14}$ VPs, about $10^{11}$ to about $10^{13}$ VPs, or about $10^{12}$ to about $10^{13}$ VPs, or about $3 \times 10^{12}$ to about $10^{13}$ VPs per subject.

In other aspects, an effective amount of an adenovirus expressing a FAS-chimera protein or a homogeneous population of the adenovirus is escalated if the first dose does not induce any toxicity. For example, the first dose of the adenovirus expressing a FAS-chimera protein or a homogeneous population of the adenovirus can be at least about $1 \times 10^9$, about $1 \times 10^{10}$ VPs, at least about $1 \times 10^{11}$ VPs, at least about $1 \times 10^{12}$ VPs, at least about $2 \times 10^{12}$ VPs, at least about $3 \times 10^{12}$ VPs, at least about $4 \times 10^{12}$ VPs, at least about $5 \times 10^{12}$ VPs, at least about $6 \times 10^{12}$ VPs, at least about $7 \times 10^{12}$ VPs, at least about $8 \times 10^{12}$ VPs, or at least about $9 \times 10^{12}$ VPs per subject, and the second dose or the subsequence doses of the adenovirus expressing a FAS-chimera protein can be at least about $5 \times 10^{12}$ VPs, at least about $6 \times 10^{12}$ VPs, at least about $7 \times 10^{12}$ VPs, at least about $8 \times 10^{12}$ VPs, or at least about $9 \times 10^{12}$ VPs, at least about $1 \times 10^{13}$ VPs, at least about $2 \times 10^{13}$ VPs, at least about $3 \times 10^{13}$ VPs, at least about $4 \times 10^{13}$ VPs, at least about $5 \times 10^{13}$ VPs, at least about $6 \times 10^{13}$ VPs, at least about $7 \times 10^{13}$ VPs, at least about $8 \times 10^{13}$ VPs, at least about $9 \times 10^{13}$ VPs, at least about $1 \times 10^{14}$ VPs per subject. In a specific example, the first dose of the adenovirus expressing a FAS-chimera protein or a homogeneous population of the adenovirus is about $3 \times 10^{12}$ VPs per subject, and the second dose of the adenovirus construct expressing FAS-chimera is about $1 \times 10^{13}$ VPs per subject. However, an effective amount of the adenovirus expressing a FAS-chimera protein or a homogeneous population of the adenovirus can be reduced if a particular dose induces dose limiting toxicity.

A composition comprising the adenovirus or the homogeneous population of the adenovirus can be infused to the subject for about 10 minutes, about 20 minutes, about 30 minutes, about 40 minutes, about 50 minutes, about 60 minutes, about 70 minutes, about 80 minutes, about 90 minutes, about 100 minutes, about 110 minutes, or about 120 minutes. In one embodiment, the nucleic acid construct of the invention is infused intravenously for not more than 60 minutes. In another embodiment, a composition comprising the adenovirus or the homogeneous population of the adenovirus is infused at a rate of 1 mL/minute for doses equal to or less than $3\times10^{12}$ VPs per subject. If the dose is more than $3\times10^{12}$ VPs per subject, the composition comprising the adenovirus or the homogeneous population of the adenovirus is infused at a rate of 1 mL/minute for the first 10 mL and then at a rate of 3 mL/minute for the remainder.

Supplementary active compounds also can be incorporated into the compositions used in the methods of the invention. For example, a nucleic acid construct encoding a FAS-chimera gene product or a homogeneous population of the nucleic acid construct may be coformulated with and/or coadministered with one or more additional therapeutic agents.

The invention encompasses any suitable delivery method for a nucleic acid construct encoding FAS-chimera gene product or a homogeneous population of the nucleic acid construct to a selected target tissue, including bolus injection of an aqueous solution or implantation of a controlled-release system. Use of a controlled-release implant reduces the need for repeat injections.

A nucleic acid construct encoding FAS-chimera gene product, an adenovirus comprising the nucleic acid construct, or a homogeneous population of the adenovirus may be directly infused into the tumor. Various implants for direct tumor infusion of compounds are known and are effective in the delivery of therapeutic compounds to human patients suffering from female gynecological cancer.

The compositions may also comprise a nucleic acid construct encoding FAS-chimera gene product, an adenovirus comprising the nucleic acid construct, or a homogeneous population of the adenovirus dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

According to the methods of the present invention, administration of the nucleic acid construct, the adenovirus, or the homogeneous population of the adenovirus can be combined with administration of one or more chemotherapeutic agents. The chemotherapeutic agent can be administered prior to, concurrently with, or after administration of the adenovirus expressing a FAS-chimera protein or a homogeneous population of the adenovirus.

One or more chemotherapeutic agent that can be co-administered with the adenovirus of the invention include, but are not limited to Acivicin; Aclarubicin; Acodazole Hydrochloride; Acronine; Adriamycin; Adozelesin; Aldesleukin; Alimta; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bevacizumab, Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper, Mitotane; Mitoxantrone Hydrochloride; Mycophenolic Acid; Nocodazole; Nogalamycin; Ormaplatin; Oxisuran; pazotinib; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sorafinib; Sparfosate Sodium; Sparsomycin; Spirogermanium Hydrochloride; Spiromustine; Spiroplatin; Streptonigrin; Streptozocin; Sulofenur; Sunitinib; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; or Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc.

In some embodiments, a subject administered with an adenovirus expressing a FAS-chimera protein or a homogeneous population of the adenovirus is concurrently treated with radiotherapy. In other embodiments, a subject administered with an adenovirus expressing a FAS-chimera protein or a homogeneous population of the adenovirus is concurrently treated with two or more chemotherapeutic agents. In certain embodiments, a subject administered with an adenovirus expressing a FAS-chimera protein or a homogeneous population of the adenovirus is concurrently treated with a chemotherapeutic agent and radiotherapy.

In the combination therapy aspect of the invention, the chemotherapeutic agent can be paclitaxel. In one aspect, an adenovirus expressing a FAS-chimera protein or a homogeneous population of the adenovirus can be administered concurrently with paclitaxel. In another aspect, an adenovirus expressing a FAS-chimera protein or a homogeneous population of the adenovirus is administered before or after administration of paclitaxel. In other embodiments, paclitaxel is administered at least 30 minutes, at least about one hour, at least about two hours, at least about three hours, at least about four hours, at least about five hours, at least about six hours, at least about seven hours, at least about eight hours, at least about nine hours, at least about ten hours, at least about 11 hours, at least about 12 hours, at least about 13 hours, at least about 14 hours, at least about 19 hours, at least about 20 hours, at least about 21 hours, at least about 22 hours, at least about 23 hours, at least about 24 hours, at least about one day, at least about 36 hours, at least about 2 days, at least about 60 hours, or at least about 3 days prior to the administration of an adenovirus expressing a FAS-chimera protein or a homogeneous population of the adenovirus.

The chemotherapeutic agent can also be administered by any suitable methods, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional, intraperitoneal, intracranial injection or infusion techniques.

An effective amount of the chemotherapeutic agent is available in the art. In one aspect, for example, an effective amount of paclitaxel can be at least about 10 mg/m$^2$, at least about 20 mg/m$^2$, at least about 30 mg/m$^2$, at least about 40 mg/m$^2$, at least about 50 mg/m$^2$, at least about 60 mg/m$^2$, at least about 70 mg/m$^2$, at least about 80 mg/m$^2$, at least about 90 mg/m$^2$, at least about 100 mg/m$^2$, or at least about 110 mg/m$^2$. In another aspect, an effective amount of paclitaxel is from about 10 mg/m$^2$ to about 200 mg/m$^2$, from about 20 mg/m$^2$ to about 150 mg/m$^2$, from about 30 mg/m$^2$ to about 100 mg/m$^2$, or from 40 mg/m$^2$ to about 80 mg/m$^2$. In other aspects, an effective amount of paclitaxel is about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, or about 100 mg/m$^2$.

In certain aspects for the paclitaxel administration, paclitaxel is infused for at least 10 minutes, at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, at least 120 minutes, at least 150 minutes, at least 180 minutes, at least 210 minutes, at least 240 minutes, at least 270 minutes, or at least 300 minutes. In a specific example, paclitaxel is infused for at least one hour. The infusion methods for paclitaxel can be used any methods known in the art. For example, paclitaxel can be administered through an in-line filter with a microporous membrane not greater than 0.22 microns over three hours.

In some aspects, paclitaxel is infused on day 1 (the same day that the adenovirus expressing a FAS-chimera protein or a homogeneous population of the adenovirus is administered) (i.e., the first dose) and followed by one or more subsequence doses, e.g., every three days, every four days, every five days, every six days, every seven days, every eight days, every nine days, every ten days, every 11 days, every 12 days, every 13 days, or every 14 days infusion. In a specific example, paclitaxel is administered on day 1 (i.e., the first dose) and followed by 8 day (i.e., the second dose), 15 day (i.e., the third dose) and 22 day (i.e., the fourth dose) schedule every 28 days.

In yet other aspects, an effective amount of a chemotherapeutic agent to be coadministered together with the adenovirus expressing a FAS-chimera protein or a homogeneous population of the adenovirus is escalated if the first dose does not induce any toxicity. For example, the first dose of paclitaxel can be about 10 to about 70 mg/m$^2$, about 20 to about 60 mg/m$^2$, about 30 to about 50 mg/m$^2$, or about 40 mg/m$^2$, and the second dose or any subsequent doses can be escalated by about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, or about 80 mg/m$^2$. In one embodiment, the first dose of paclitaxel is about 40 mg/m$^2$, and the second dose of paclitaxel is about 80 mg/m$^2$. In another embodiment, the first dose of paclitaxel is about 40 mg/m$^2$, the second dose of paclitaxel is about 80 mg/m$^2$, and the third dose of paclitaxel is about 80 mg/m$^2$. In other embodiments, the first dose of paclitaxel is about 40 mg/m$^2$, the second dose of paclitaxel is about 80 mg/m$^2$, the second dose of paclitaxel is about 80 mg/m$^2$, and the fourth dose of paclitaxel is about 80 mg/m$^2$.

However, an effective amount of paclitaxel can be reduced if the first dose induces a dose limiting toxicity to the subject. The dose limiting toxicity can be determined by any known methods: for example, (1) absolute neutrophil count (ANC) of $<0.5 \times 10^9$/L lasting for $\geq 4$ days or an absolute neutrophil count $<0.5 \times 10^9$/L with sepsis, or grade 3-4 fever ($>100.2°$ F.) which is not readily controlled with anti-pyretic medication; (2) platelet count $<10 \times 10^9$/L for any duration; (3) any other drug-related non hepatic and non-hematologic grade $\geq 3$ toxicity, or any combinations thereof. This does not include grade $\geq 3$ nausea or vomiting that can be controlled medically (if nausea and/or vomiting cannot be controlled medically and occurs during the first cycle, it will be considered a DLT) or grade $\geq 3$ hypokalemia, hyponatremia, hypophosphatemia, hypomagnesemia, and hypocalcemia if they can be easily corrected, are clinically asymptomatic, and not accompanied by medically significant complications (e.g., ECG changes).

In one embodiment, the first dose of paclitaxel in day 1 is 40 mg/m$^2$, and if the subject exhibits no dose limiting toxicity, the second dose at day 8 and the subsequent doses at day 15, day 22, and day 28 are escalated to 80 mg/m$^2$. In another embodiment, if ANC/drug in a subject is $\geq 1,000$/mm$^3$, the subject is administered with a full dose of paclitaxel, e.g., 80 mg/m$^2$. If ANC/drug in the subject is $<1,000$/mm$^3$, the paclitaxel administration is stopped. If there is a further incidence of ANC $<1,000$/mm$^3$, the paclitaxel dose can be reduced to 60 mg/m$^2$. In other embodiments, if a subject has the platelets/drug of $\geq 100,000$/mm$^3$ or has the first incidence of $<100,000$/mm$^3$ and $>75,000$/mm3, the subject is administered with a full dose of paclitaxel, e.g., 80 mg/m$^2$. If a subject shows the platelets/drug of $<75,000$/mm$^3$, the paclitaxel administration is stopped. If the subject shows a repeat incidence of platelets/drug of $<100,000$/mm$^3$ and $>75,000$/mm$^3$, the paclitaxel dose is reduced to 69 mg/m$^2$. In some embodiments, if a subject shows the first incidence of neuropathy grade $>2$, the paclitaxel dose is reduced from the full dose, e.g., about 80 mg/m$^2$, to about 60 mg/m$^2$. If the subject exhibits the second incidence (or shows persistence despite the dose reduction) of neuropathy grade >2, the paclitaxel dose is reduced to 40 mg/m². If the subject exhibits the third incidence (or persistence despite dose reduction), the paclitaxel administration is discontinued.

Paclitaxel is not known to cause hepatic toxicity; however, its elimination is delayed in patients with severe hepatic dysfunction. Therefore, the dose of paclitaxel in subject with hepatic dysfunction can be modified according to the following table.

TABLE 5

Paclitaxel Dose Modification for Subjects with Hepatic Dysfunction.

| Serum AST, or ALT | Paclitaxel |
|---|---|
| <3x ULN | 80 mg/m2 |
| ≥3x ULN | 60 mg/m2 |
| ≥5x ULN | Hold drug |

Subjects with elevated bilirubin >1.5 mg/dl may not receive paclitaxel until the abnormal laboratory values improve to ≤grade 1. Treatment can be resumed after recovery with paclitaxel at one dose level lower, per the above table. The subjects exhibiting paclitaxel toxicity that lasts more than 2 weeks can discontinue the drug.

In certain embodiments, a subject is administered with an immunosuppressant agent prior to, concomitantly with, or after administration of one or more chemotherapeutic agent, e.g., paclitaxel. In one embodiment, the immunosuppressant agent useful for administering to the subject is selected from the group consisting of $H_2$-receptor antagonists, cimetidine, ranitidine, famotidine, corticosteroids, dexamethasone, cyclosporine, diphenhydramine, and any combinations thereof.

In further embodiments, methods of the invention further comprise administering one or more anti-angiogenetic agents prior to, concurrently with, or after the administration of a nucleic acid construct expressing a FAS chimera protein.

In some embodiments, a subject for the invention is administered with an anti-emetic agent. Examples of suitable anti-emetic agents include, but are not limited to, 5-HT3 receptor antagonists (e.g., dolasetron, granisetron, ondansetro, tropisetron, palonosetron, or mirtazapine), dopamine antagonists (e.g., domperidone, olanzapine, droperidol, haloperidol, chlorpromazine, promethazine, prochlorperazine, metoclopramide, alizapride, or prochlorperazine, compazine, stemzine, buccastem, stemetil, or phenotil), NK1 receptor antagonist (e.g., aprepitant or casopitant), antihistamines (H1 histamine receptor antagonists) (e.g, cyclizine, diphenhydramine, dimenhydrinate, doxylamine, meclozine, promethazine, or hydroxyzine), cannabinoids (e.g., cannabis, dronabinol, nabilone, the JWH series, or Sativex), benzodiazepines (e.g., midazolam or lorazepam), anticholinergics (e.g., hyoscine), steroids (e.g., dexamethasone), trimethobenzamide, ginger, emetrol, propofol, peppermint, muscimol, or ajwain), or any combinations thereof. In other embodiments, the suitable anti-emetic agents are dexamethasone, PRN Ativan, kytril, compazine, perphenazine, zofran, perphenazine, or any combinations thereof.

In other embodiments, antipyretic agents is administered prior to, concurrently with, or after the administration of the nucleic acid construct encoding a FAS-chimera protein. Examples of the antipyretic agents include, but are not limited to NSAIDs (e.g., ibuprofen, naproxen, ketoprofen, and nimesulide), aspirin, acetaminophen, metamizole, nabumetone, phenazone, quinine, or any combinations thereof.

The methods of the present invention further comprise determining disease progression in the subject before or after receiving the nucleic acid construct expressing a FAS-chimera protein or the chemotherapeutic agent. In one embodiment, disease progression is determined by measuring size of the tumor. In another embodiment, disease progression is determined by measuring expression of a tumor antigen, e.g., CA-125. In order to determine the disease progression, the subject's blood and urine are collected prior to the infusion, at the end of the infusion, about three hours after the infusion, and/or about six hours after the infusion of the nucleic acid construct expressing a FAS-chimera gene product. In other embodiments, vital signs for the subject are recorded at 0 minutes-15 minutes (just prior to dosing), 30 minutes±15 minutes after start of dosing, 60 minutes±15 minutes after start of dosing, four hours±15 minutes post start of dosing, six hours±15 minutes post start of dosing, and/or on the occasion of any adverse events. The vital signs to be measured include, but are not limited to systolic and diastolic blood pressure, peripheral heart rate, body temperature, respiration rate, or any combinations thereof. In still other embodiments, the subject is measured for hematology (e.g., complete blood count with differential, INR and activated PTT); coagulation (e.g., PTT level); biodistribution of the nucleic acid construct expressing FAS-chimera; expression of angiogenic and inflammatory biomarkers (e.g., VEGF, PlGF, sVEGFR1, bFGF, IL-1β, IL-6, IL-8, TNF-α, sVEGFR2, SDF1α, CD31, CD34, VEGFR2, vWF, any combinations thereof); expression of tumor marker, e.g., CA-125, or any combinations thereof.

The subjects suitable for the methods of the invention are managed in the usual fashion for fever and neutropenia. The subjects need to recover from fever and active infectious issues prior to resuming therapy. In some embodiments, the subjects who are not on growth factors have Neupogen or Neulasta added to their next cycle. The subjects on Neupogen 5 ug/kg/day can have their dose escalated to 10 ug/kg on the same schedule.

EXAMPLES

Example 1

Construction and Cloning of the Viral Vector

The vector was constructed using a backbone containing most of the genome of adenovirus type 5, as well as partial homology to an adaptor plasmid, which enables recombination.

The E1 early transcriptional unit was deleted from the backbone plasmid, and further modified by deleting the pWE25 and the Amp resistance selection marker site.

The adaptor plasmid, containing sequences of the Ad5, CMV promoter, MCS, and SV40 polyA was modified to delete deleting the CMV promoter, and the PPE-1 promoter and Fas-c fragment were inserted by restriction digestion. The modified PPE-1 promoter (PPE-1-3X, SEQ ID NO: 18) and the Fas-chimera transgene (Fas-c, SEQ ID NO: 9) were utilized for construction of the adenoviral vector. The PPE-1-(3X)-Fas-c element (2115 bp) was constructed from the PPE-1-(3X)-luc element. This element contains the 1.4 kb of the murine preproendothelin PPE-1-(3X) promoter, the Luciferase gene, the SV40 polyA site and the first intron of the murine ET-1 gene, originated from the pEL8 plasmid (8848 bp) used by Harats et al (Harats D. et al., JCI, 1995). The PPE-3-Luc cassette was extracted from the pEL8 plasmid using the BamHI restriction enzyme. The Luciferase gene was substituted by the Fas-c gene [composed of the extra cellular and intra membranal domains of the human TNF-R1 (Tumor Necrosis Factor Receptor 1, SEQ ID NO: 4) and of the Fas (p55) intracellular domain (SEQ ID NO: 8) (Boldin et al, JBC, 1995)] to obtain the PPE-1-3x-Fas-c cassette.

PPE-1 (3x)-Fas-c Plasmid—The cassette was further introduced into the backbone plasmid by restriction digestion, resulting with the PPE-1 (3x)-Fas-c plasmid.

Adaptor-PPE-1(3x)-Fas-c Plasmid—The PPE-1-3x-Fas-c element was extracted from the first generation construct PPE-1-3x-Fas-c plasmid, and was amplified with designated PCR primers introducing SnaB1 and EcoR1 restriction sites at the 5'-and-3'-end respectively. These sites were used to clone the PPE-Fas-c fragment into the adaptor plasmid digested with SnaB1 and EcoR1, resulting in the adaptor-PPE-1-3x-Fas-c used for transfection of the host cells (for example, PER.C6 cells).

Example 2

Efficacy and Safety of VB-111 in Mice with Metastatic Lewis Lung Carcinoma (LLC)

Summary

In this study, LLC model mice were treated with VB-111 ($10^9$ or $10^{11}$ virus particles (VPs)), Carboplatin (20 or 50 mg/kg) and Alimta (10 or 30 mg/kg) or with a combinations of these small molecules and the adenovector.

VB-111 treatment with both doses resulted in 100% survival. Administration of low dosage of chemotherapy resulted in a mildly lowered survival rate (94.1%) which was similar to that seen with vehicle administration (93.8%). However, administration of high dosage of chemotherapy resulted in the lowest percentage of survival (50%). Combination treatments decreased survival compared to administration of VB-111 alone (64%-93%).

Organ weights (heart, kidneys and brain) were mostly similar among the different groups. Some differences between groups were seen in liver, spleen and testes weights, mainly higher weights for the single VB-111 higher dose, or any of the combinations with this dose.

No significant differences were observed in liver function compared to vehicle treatment. Generally, combination therapy did not result in higher toxicities than the single therapies from which they are assembled.

The combination of VB-111 $10^9$+high chemo is significantly more effective than high chemo treatment alone. Furthermore, the combined treatment improves the average and median tumor burden of VB-111 $10^9$ treatment alone (1.5 and 5 fold for average and median, respectively) although not statistically significant. This effect may exhibit statistical significance when applying the treatment on larger groups.

The combination of VB-111 $10^9$+high chemo resembles the high tumor burden reduction obtained with VB-111 $10^{11}$, as there is no significant difference between these two groups. This significant resemblance to VB-111 $10^{11}$ is not obtained with treatment with VB-111 $10^9$ alone.

The combination of VB111 $10^9$+high chemo therapy may enable reducing VB-111 dose while preserving its high efficacy and improving the low efficacy of Carboplatin and Alimta chemotherapy alone.

Introduction

Lewis Lung Carcinoma (LLC) is a widely-used mouse model for metastasis (Varda-Bloom et al., 2001). This study is to identify the potential synergism of combined treatments of VB-111 with established chemotherapies (e.g. Carboplatin and Alimta): To assess the efficacy of single dose VB-111 ($10^9$ or $10^{11}$ VPs/mouse) as sole treatment or in combination with repeat intra peritoneal treatments of Carboplatin (20 or 50 mg/kg) and Alimta (10 or 30 mg/kg) and to assess and characterize the safety and tolerability of VB-111 as single treatment and in combination with the mentioned above chemotherapy.

The study design is shown in TABLE 6.

TABLE 6

Study Design

STUDY GROUPS and 9 groups of treatment are planned as below:
BASIC TIMELINE

|  | Treatment | Dose (vp/mice) | Number of Animals |
|---|---|---|---|
| Group 1 | VB-111 | $10^{11}$ | 15 |
| Group 2 | VB-111 | $10^9$ | 15 |
| Group 3 | VB-111<br>Carboplatin +<br>Alimta | $10^{11}$<br>20 mg/kg +<br>10 mg/kg | 15 |
| Group 4 | VB-111<br>Carboplatin +<br>Alimta | $10^9$<br>20 mg/kg +<br>10 mg/kg | 13 |
| Group 5 | Carboplatin +<br>Alimta | 20 mg/kg +<br>10 mg/kg | 16 |
| Group 6 | VB-111<br>Carboplatin +<br>Alimta | $10^{11}$<br>50 mg/kg +<br>30 mg/kg | 15 |
| Group 7 | VB-111<br>Carboplatin +<br>Alimta | $10^9$<br>50 mg/kg +<br>30 mg/kg | 14 |
| Group 8 | Carboplatin +<br>Alimta | 50 mg/kg +<br>30 mg/kg | 14 |
| Group 9 | Vehicle | — | 16 |

TABLE 6-continued

Study Design

| | |
|---|---|
| | Each animal received a single injection of either VB-111 dose or vehicle in a randomized fashion on day 0 ± 1, 5 days after primary tumor amputation. 2 doses of Carboplatin treatment were given on days 5-6, 10 doses of Alimta treatment were given from day 5. The animals were evaluated for safety and efficacy throughout the study and until sacrifice day, which took place on the same day on which the 5th control animal (Group 9) died. |
| STUDY DURATION | Approximately 1 month from time 0 |
| ANIMALS | 133 male C57B16 mice (11-13 weeks old), which were expected to have developed metastases in the lung, following injection of D122 Lewis Lung Carcinoma cells to the left footpad and resection of the primary tumor (amputation of the distal segment of the limb). |
| TEST DRUG AND FORMULATION | VB-111: Adenovirus 5, E1 deleted, partial E3 deleted, with the PPE-1(3x) promoter, containing the transgene fas-chimera, formulated in the vehicle (see below).<br>Vehicle: PBS 10% glycerol.<br>ALIMTA: Pemetrexed, 500 mg powder.<br>Carboplatin: "EBEWE" 10 mg/ml. |
| DOSAGE | VB-111 treatment was administered by injection to the mouse tail vein, in a total volume of 100 µl, 20 or 50 mg/kg/Carboplatin was administered in two doses on days 5-6, 0.1 ml IP, and 10 doses of 10 or 30 mg/kg/Alimta were administered from day 5, 0.1 ml IP. |
| SAFETY EVALUATIONS | The general health of all animals was followed on a daily basis throughout the study. Weight of the animals and clinical signs were recorded prior to the beginning of the study, after resection of the primary tumor, on day 0 (day of dosing), and then on a weekly basis until the end of the study. Laboratory assessment included blood chemistry (for liver function) of samples taken from 5 mice/group at the end of the study. Major organs (liver, spleen, heart, kidney, lung, gonads and brain) were evaluated upon animal sacrifice (5 mice/group). |
| EFFICACY EVALUATIONS | The effect of treatment was evaluated upon the death of each animal, by lung weight and tumor burden. |
| STATISTICS | Treatment groups were compared using one way ANOVA for comparison of Organ weights, Tumor burden and Liver function parameters.<br>To isolate the group or groups that differ from the others, Dunn's multiple comparison procedure followed (GPT day 16 GOT day 16 & tumor burden).<br>Body weights of each group on day 0 were compared with those on sacrifice day (Paired t-test).<br>For Efficacy, groups were analyzed using one way ANOVA. In cases where normality test failed, Dunn's method was applied. Additionally, Mann-Whitney test was performed for individual comparisons between two groups. |

Materials and Methods
 Test and Reference Materials
Name: VB-111 (PPE-fas).
Chemical Name: Not specified
Active components: Adenovirus 5, E1 deleted, E3 partially deleted, with the PPE-1(3x) promoter, containing the fas-chimera transgene
Vehicle: PBS and glycerol
Supplied by: VBL
Physical state: Liquid
Storage conditions: ≤−65° C., in cryogenic vials
Item preparation: Vial is to be thawed on day of treatment and mixed by inversions
Name: Carboplatia
Chemical Name: Ebewe
Vehicle: Water for Injection
Supplied by: Ebewe
Physical state: Liquid (450 mg/45 ml)
Storage conditions: RT
Name: Alimta
Chemical Name: Pemetrexed
Vehicle: Water for Injection
Supplied by: Lilly
Physical state: powder
Storage conditions: RT
 Control Item:
Name: PBS 10% glycerol
Supplied by: VBL
Physical state: Liquid
Storage conditions: ≤−65° C., in cryogenic vial.
Item preparation: Vial is to be thawed on day of treatment and kept on ice for not more than 30 minutes.

D122 Lewis Lung Carcinoma cells were thawed. On day one of cell injection, cells were collected and suspended to a final concentration of $5\times10^5/50$ µl and injected to the left foot pad. Tumor diameter was measured using a caliper five days after injection. It was subsequently measured weekly until it reached 5 mm, and then daily until amputation at 7 mm (defined as day −5). Following sacrifice, brain, heart, liver, spleen, kidneys and testes were collected, weighed and evaluated according to the following parameters: colour and texture of the intact organ, existence of lesions or any evidence of metastasis in the organ internally (after slicing). Laboratory analyses of liver functions (GOT and GPT levels in blood) included samples taken from 5 mice/group on day 5±1 and at the end of the study (day 16).

All animal procedures were approved by the "Animal Care and Use Committee" of Sheba Medical Center, Tel-Hashomer. The study was a placebo-controlled, blinded study. C57Bl6 mice received Lewis Lung Carcinoma cells (D122) by a subcutaneous injection to the left foot pad. When the tumor tissue reached a diameter of 7 mm (approximately 3 weeks after injection of cells), the foot-pad with the primary tumor was resected under anesthesia. This day was defined as day −5. Day 0 is the day of first dosing, 5 days after primary tumor resection. The mice were randomized to the various treatment groups on day 0, as described in the table below. The tested adenoviral vector or the control substance, were injected to the tail vein in a total volume of 100 μl per mouse. Carboplatin and Alimta were administrated IP in a total volume of 100 μl per mouse per daily dose.

The animals were followed for safety and efficacy (as listed in the schedule of evaluations below) throughout the study and until sacrifice time. The death of each animal during the study was recorded and an attempt was made to identify the cause of death. The day of sacrifice for each mouse was set as follows: when the 5th of the control mice (PBS 10% glycerol—Group 9) dies of metastasis, the number of days that passed from day 0 (the first IV administration of vehicle to that mouse) was determined. That day number was set as the day of sacrifice for all surviving mice (i.e., if the 5th control mouse died on its day 16, every mouse was sacrificed when it reaches its own day 16).

The evaluation of the effects was scheduled as shown in TABLE 7.

Results

In mice groups treated with $10^9$ and $10^{11}$ VPs VB-111 alone, all animals survived to day 16. Combination treatment revealed decrease in survival, while the lowest percentage of survival was seen in mice treated with high dose of chemotherapy as shown in TABLE 8.

TABLE 8

Mortality by Day 16.

| Group | Total (n) | Survived (n) | Survival (%) |
|---|---|---|---|
| Vehicle | 16 | 15 | 93.8% |
| VB-111 $10^9$ VP | 15 | 15 | 100% |
| VB-111 $10^{11}$ VP | 15 | 15 | 100% |
| 20 mg/kg Carboplatin + 10 mg/kg Alimta | 17 | 16 | 94.1% |
| 50 mg/kg Carboplatin + 30 mg/kg Alimta | 14 | 7 | 50% |
| VB-111 $10^9$ VP + 20 mg/kg Carboplatin + 10 mg/kg Alimta | 13 | 11 | 84.6% |
| VB-111 $10^9$ VP + 50 mg/kg Carboplatin + 30 mg/kg Alimta | 14 | 9 | 64.3% |
| VB-111 $10^{11}$ VP + 20 mg/kg Carboplatin + 10 mg/kg Alimta | 15 | 12 | 80% |
| VB-111 $10^{11}$ VP + 50 mg/kg Carboplatin + 30 mg/kg Alimta | 15 | 14 | 93.3% |

For evaluation of efficacy, lungs were weighed on the day of sacrifice. The mass of normal lungs is ~0.2 g. Tumor burden is defined as lungs mass minus 0.2 g, The average and median tumor burden is shown in TABLE 9.

TABLE 7

Schedule of Evaluation

| Parameter | Method | <−5 | −5 Primary tumor resection | 0 | 5 ± 1 | Weekly thereafter ±1 | End |
|---|---|---|---|---|---|---|---|
| Primary tumor width | Caliper | Starting 5 days after D122 injection once every 5 days until reaches 5 mm, then daily | | | | | |
| Body weight | — | | ✓ After resection baseline weight w/o foot | ✓ | | ✓ | ✓ |
| Clinical signs | See below* | ✓ | ✓ | ✓ | ✓ | ✓ | ✓ |
| Blood chemistry (liver functions)** | SM 30-20-06 | | | | ✓ | | ✓ |
| General health | SOP 10-25-01 | ✓ | ✓ | ✓ | ✓ | ✓ | ✓ |
| Lung weight | Weight | | | | | | ✓ |
| Major organs Assesment** | Visual & Staining of abnormal tissues | | | | | | ✓ |

*Skin, Fur, Eyes, Mucous membranes, Breathing, Neural control, Tremors, Salivation, Diarrhea, Somatomotor activity, Lethargy, Convulsions, Abnormal behavior patterns, Sleep, Coma.
**From 5 mice per group

TABLE 9

Average and Median Tumor Burden

| Group number | treatment | Average Tumor burden (g) ± SD | Median (g) |
|---|---|---|---|
| 1 | VB111 $10^{11}$ | 0.10 ± 0.04 | 0.10 |
| 2 | VB111 $10^9$ | 0.34 ± 0.21 | 0.40 |
| 8 | high chemo | 0.48 ± 0.15 | 0.50 |
| 5 | low chemo | 0.49 ± 0.34 | 0.50 |
| 6 | VB111 $10^{11}$ + high chemo | 0.22 ± 0.16 | 0.20 |
| 7 | VB111 $10^9$ + high chemo | 0.20 ± 0.24 | 0.08 |
| 3 | VB111 $10^{11}$ + low chemo | 0.47 ± 0.26 | 0.46 |
| 4 | VB111 $10^9$ + low chem | 0.53 ± 030 | 0.62 |
| 9 | Vehicle | 1.00 ± 0.20 | 0.90 |

All treatments resulted with lower tumor burden compared to vehicle treatment as shown in FIG. 1. FIG. 1 shows that treatment with E11, E9+high chemo and E11+high chemo all showed lower average tumor burden than other treatment groups.

Several statistical comparisons for efficacy were performed. When one way ANOVA method was used, there is a statistically significant higher tumor burden for the Vehicle treatment (p=<0.001) than for all other treatments except for the combination of VB E9+low chemo. Tumor burden was significantly lower for VB-111 E11 treatment compared to both chemo treatments and to both combination treatments with low chemo. When Mann-Whitney with individual comparisons between two groups was used, tumor burden in VB-111 E11 is significantly lower than in all groups except for E9+high chemo. E9+high chemo is significantly lower than all groups except for E11, E9 and E11+high chemo. FIG. 2 shows the box plot of the data.

Conclusion

VB-111 treatment in both doses resulted in 100% survival. Administration of low dosage of chemotherapy resulted in a mildly lowered survival rate (94.1%) which was similar to that seen with vehicle administration (93.8%). However, administration of high dosage of chemotherapy resulted in the lowest percentage of survival (50%). Combination treatments decreased survival compared to administration of VB-111 alone (64%-93%).

Organ weights (heart, kidneys and brain) were mostly not different among the different groups. Some differences between groups were seen in liver, spleen and testes weights, mainly higher weights for the single VB-111 higher dose, or combination with this dose.

No significant differences in liver function compared to vehicle treatment were observed. Generally, combination therapy did not result in higher toxicities than for the single therapies from which they are assembled.

The combination of VB111 $10^9$+high chemo treatment significantly improves the effect compared to high chemo treatment alone. Furthermore, it improves the average and median tumor burden compared to VB111 $10^9$ treatment alone (1.5 and 5 fold for average and median, respectively) although not statistically significant. This effect may exhibit statistical significance when applying the treatment on larger groups.

The combination of VB111 $10^9$+high chemo resembles the tumor burden reduction effect obtained with E11, as there is no significant difference between these two groups (can be seen in the box plot and the Mann-Whitney statistical comparison). This significant resemblance to VB111 $10^{11}$ is not obtained by treatment with VB111 $10^9$ alone.

The combination of VB111 $10^9$+high chemo therapy may enable reducing VB-111 dose while preserving its high efficacy and improving the low efficacy of Carboplatin and Alimta chemotherapy alone.

Both urvival rate and weight loss in the VB111 $10^9$+high chemo treatment group were better than for the high chemotherapy single treatment: survival rate—64% and 50%, respectively, weight loss—9.7% and 11.6%, respectively. No differences between these two groups were seen for any of the organ weights tested.

Example 3

Administration of Ad5PPE-1-3X-Fas Chimera in Combination with Paclitaxel

This will be a prospective, open label, dose escalating, multi-center (2 centers), Phase I/II study to determine the safety and efficacy of administration of AD5PPE-1-3X-Fas-chimera (VB-111) in the clinical setting, outcomes such as toxicity, adverse effects, antibody titer, biodistribution, disease progression and disease recurrence and survival will be monitored in subjects with solid primary and metastatic tumors (such as recurrent epithelial ovarian cancer, fallopian, primary peritoneal, MMMT and papillary serous müllerian tumors) receiving intravenous infusion of a range of doses of the Ad5PPE-1-3X-Fas chimera adenovirus vector in combination with paclitaxel.

The effect of VB-111 on the development of antibodies to the adenoviral vector, tumor response, and angiogenic biomarkers will also be evaluated.

Materials and Experimental Methods

Study Objectives

The research hypothesis is that VB-111 plus weekly paclitaxel will be associated with acceptable toxicity and response rate or clinical benefit sufficient to warrant future evaluation.

Primary Objectives

1. Define toxicities of a limited number of doses of combination VB-111 and weekly paclitaxel spanning anticipated effective doses.

2. Explore efficacy (RECIST response, CA-125 response and progression-free survival (PFS)) in an expanded cohort of the optimally tolerated dose of combination VB-111 and weekly paclitaxel.

Secondary Objective

Explore predictive markers of toxicity and response.

Overview of Study Design and Evaluation

This open-label, single center, Phase I/II trial combines VB-111 infused on day 1 every 2nd 28-day cycle with weekly paclitaxel 40-80 mg/m$^2$ infused over 1 hour on a 1, 8, 15 and 22 day schedule every 28 days in order to ascertain whether or not this combination can improve response rates compared to historical controls in this pretreated population. Patients may continue therapy with benefit and change to have scheduled breaks in paclitaxel dosing to avoid excess neuropathy but no interruption of VB-111 infusions. The trial is designed in a 2-stage Simon's design, based on ≥2 responses in 10 patients, further enrollment will proceed.

Subject Population:

Subjects with recurrent epithelial ovarian cancer, fallopian cancer, primary peritoneal, MMMT, and papillary serous müllerian tumors will be enrolled.

Number of Patients Planned to be Enrolled

Based on the study design it is estimated that 2 to 42 patients with advanced cancer are needed (max. 6 per cohort during dose escalation (=18 patients), and up to 29 patients on the MTD dose level to allow evaluation of the correlative/special studies as well as to confirm safety.

Selection of Patients

Phase I/II design to evaluate the response rates defined by RECIST criteria and CA-125 (Gynecological Cancer Intergroup (GCIG) criteria) and to describe the safety profile and characterize adverse events and toxicities. The Phase I study will enroll in a 3+3 design to 3 dose levels. The Phase II study will recruit up to 10 patients in the first stage, including participants in Dose Levels 2 and 3 who get full dose chemotherapy. If there are at least two responses, enrollment will continue with an additional 19 patients in an expansion cohort to a maximum of 29 participants. The efficacy analysis will be to estimate the response rate. Ongoing safety review will be conducted and if there are 2 or more Grade ≥3 GI perforations in the first stage, or 3 at any time the study will be closed.

Criteria for Subjects Inclusion in the Treatment Group are:
1. Patients aged >18.
2. Histologically confirmed epithelial ovarian, peritoneal, or fallopian tube cancer, and uterine papillary serous carcinomas (UPSC), and gynecologic MMMTs.
3. Up to 3 previous lines of chemotherapy for metastatic disease are allowed.
4. Patients must have had prior platinum or platinum based therapy.
5. Eastern Cooperative Oncology Group (ECOG) status 0-1.
6. Platinum resistant or refractory disease defined as progressive disease by imaging or CA-125 within 6 months of completing or while receiving a platinum and taxane containing regimen (Primary OR secondary—i.e., patients can have received only one platinum based treatment for recurrent platinum sensitive disease with a subsequent platinum free interval <6 months).
7. Measurable or evaluable disease is required using RECIST or CA-125 (to standardized eligibility if some patients are eligible by both RECIST and CA-125, evaluation by RECIST takes precedent).
8. Adequate bone marrow function.
9. Adequate hematological functions:
   i. ANC ≥1000/mm$^3$
   ii. PLT ≥100,000/mm$^3$
   iii. PT and PTT (seconds)<1.2×ULN (subjects with PTT>ULN must have a negative LAC)
10. Adequate organ function:
   a. CTC neuropathy less than or equal to grade 1.
   b. Prior radiation must not have included ≥30% of major bone marrow containing areas (pelvis, lumbar spine)
   c. SGOT/SGPT/Alkaline Phosphatase ≤2.5×ULN or <5×ULN for documented liver metastases
   d. Bilirubin ≤1.5×ULN
   e. Creatinine ≤1.5×ULN
   f. Proteinuria <2+ by dip stick at screening or UPC (Urinary protein creatinine ratio <1.0).
11. Must have recovered from acute toxicity from prior treatment including radiation therapy, chemotherapy, biologic therapy with the exception of grade 1 neuropathy or any grade anemia and alopecia.
12. Prior treatment with an anti-angiogenic agent is NOT an exclusion criterion.
13. No prior GI perforation, or GI obstruction or involvement of the bowel on imaging
14. No active, untreated psychiatric disease or neurologic symptoms requiring treatment (Grade I sensory neuropathy allowed). No presence of untreated central nervous system or brain metastases. No dementia or significantly altered mental status that would prohibit the understanding and/or giving of informed consent.
15. No patients with known hypersensitivity to Cremophor® EL. However, participants are eligible if they have had a prior paclitaxel reaction, but subsequently tolerated the drug at rechallenge.
16. No evidence of uncontrolled bacterial, viral or fungal infections.
17. No patients receiving other investigational therapy for the past 30 days before dosing.
18. Must be competent to give informed consent.

Criteria for Subject's Exclusion from the Treatment Group Will Be:
1. More than 3 prior lines of chemotherapy for recurrent cancer.
2. No active malignancy, other than superficial basal cell and superficial squamous cell, or carcinoma in situ of the cervix within last 2 years. Patient diagnosed with a concurrent müllerian tumor (typically endometrial cancer) are NOT excluded. Patients with a low risk (localized, non-inflammatory) breast cancer diagnosed within 2 years and treated with curative intent are NOT excluded.
3. Inability to comply with study and/or follow-up procedures.
4. Life expectancy of less than 3 months.
5. Common Toxicity Criteria (CTC) Grade 1 or greater neuropathy (motor or sensory) from comorbidity other than prior taxane exposure, such as diabetes.
6. Although rarely applicable, sexually active women of childbearing potential must use an effective method of birth control during the course of the study, in a manner such that risk of failure is minimized. Prior to study enrollment, women of childbearing potential must be advised of the importance of avoiding pregnancy during trial participation and the potential risk factors for an unintentional pregnancy. All women of childbearing potential MUST have a negative pregnancy test within 14 days prior to first receiving investigational product. If the pregnancy test is positive, the patient must not receive investigational product and must not be enrolled in the study.
7. Inadequately controlled hypertension.
8. Prior history of hypertensive crisis or hypertensive encephalopathy.
9. New York Heart Association (NYHA) Grade II or greater congestive heart failure.
10. History of myocardial infarction or unstable angina within 6 months prior to study Day 1.
11. History of stroke or transient ischemic attack within 6 months prior to Day 1.
12. Known CNS disease, except for treated brain metastasis: Treated brain metastases are defined as having no evidence of progression or hemorrhage after treatment and no ongoing requirement for dexamethasone, as ascertained by clinical examination and brain imaging (MRI or CT) during the screening period. Anticonvulsants (stable dose) are allowed. Treatment for brain metastases may include whole brain radiotherapy (WBRT), radiosurgery (RS; Gamma Knife, LINAC, or equivalent) or a combination as deemed appropriate by the treating physician. Patients with CNS metastases treated by neurosurgical resection or brain biopsy performed within 3 months prior to Day 1 will be excluded.
13. Significant vascular disease (e.g., aortic aneurysm, requiring surgical repair or recent peripheral arterial thrombosis) within 6 months prior to Day 1.
14. History of hemoptysis (>½ teaspoon of bright red blood per episode) within 1 month prior to Day 1.

15. Evidence of bleeding diathesis or significant coagulopathy (in the absence of therapeutic anticoagulation).

16. Major surgical procedure, open biopsy, or significant traumatic injury within 28 days prior to Day 1 or anticipation of need for major surgical procedure during the course of the study.

17. Core biopsy or other minor surgical procedure, excluding placement of a vascular access device, within 7 days prior to Day 1.

18. History of abdominal fistula or gastrointestinal perforation within 6 months prior to Day 1.

19. Current signs and symptoms of bowel obstruction.

20. Current dependency on IV hydration or total parenteral nutrition (TPN).

21. Serious, non-healing wound, active ulcer, or untreated bone fracture.

22. Patients who received anti-angiogenic therapy within the previous 4 weeks for a TKI or 6 weeks for antibody or peptibody based therapy.

23. Patients with an ongoing requirement for an immunosuppressive treatment, including the use of cyclosporine, or with a history of chronic use of any such medication within the last 4 weeks before enrollment. A stable dose (e.g. started at least 2 weeks prior to dosing) of corticosteroids is allowed.

Composition: Ad5-PPE-L-3X-Fas-Chimera

Ad5-PPE-1-3X-fas-chimera (SEQ ID NO: 19) is a vascular disruptive gene therapeutic, consisting of a non-replicating adenovirus vector (Ad5, E1 deleted) which contains a modified murine pre-proendothelin promoter (PPE-1-3x, SEQ ID NO:18) and a fas-chimera transgene [Fas and human tumor necrosis factor (TNF) receptor] (SEQ ID NO: 9). It is formulated as a sterile vector solution and supplied frozen (below −65° C.), in single use vials. Each vial contains 1.1 mL of vector solution at a specific viral titer.

Efficacy and Pharmacodynamics Objectives:

Treatment Plan

Patients will be treated with Ad5-PPE-1-3X-fas-chimera in combination with once-weekly paclitaxel. The cycle length will be 28 days. Patients will receive paclitaxel as a 60-minute IV infusion weekly (Days 1, 8, 15, and 22). Ad5-PPE-1-3X-fas-chimera will be administered as an IV infusion on Day 1 of odd cycles starting with Cycle 1 and occurring every 2 cycles thereafter. The treatment plan is shown in FIG. 3. Dose levels for Phase I are shown below in TABLE 10.

TABLE 10

Dose Levels For Phase I[1] component:

| Dose Level | n | VB-111 × Q2 cycles[2] | Paclitaxel IV Q7d |
|---|---|---|---|
| 1[3] | 3-6 | $3 \times 10^{12}$ VPs | 40 mg/m$^2$ |
| 2 | 3-6[4] | $3 \times 10^{12}$ VPs | 80 mg/m$^2$ |
| 3 | 3-6 | $1 \times 10^{13}$ VPs | 80 mg/m$^2$ |
| Expansion cohort | 29 | MTD | MTD |

Footnotes:
[1]The crossover to Phase II will occur after the maximum tolerated dose (MTD) has been defined or Dose Level 3 has been completed.
[2]Please note that total VB-111 viral particle dose for each Dose Level is different than shown for subjects who are <50 kg.
[3]Within subject dose escalation is planned for Dose Level 1. For participants enrolled to Dose Level 1 at Cycle 2 Day 1 the dose of paclitaxel may be escalated to 80 mg/m$^2$ given that this is the standard dose used clinically. If 2 participants experience dose limiting toxicities (DLTs) at Dose Level 1, the study will close without identifying an MTD.
[4]These numbers may reflect the inclusion of: (a) participants directly enrolled to Dose Level 2 and (b) Dose Level 1 participants who have been dose-escalated to Dose Level 2 at Cycle 2 Day 1 for evaluation of DLTs during Cycle 3.

Participants in the Phase I cohort will therefore be enrolled using a modified 3+3 design as shown in TABLE 11 and as described below.

Dose Escalation from Dose Level 1 to Dose Level 2: If 2 participants experience DLTs at Dose Level 1, the study will close without identifying an MTD. In Dose Level 1 there is a planned within-subject participant dose escalation to 80 mg/m2 paclitaxel at Cycle 2 Day 1, and these participants can then be counted towards the evaluation of participants enrolled to Dose Level 2, even though the concurrent VB-111 and paclitaxel dosing occurred at Cycle 3 in Dose Level 1 (i.e. both participants enrolling at Dose Level 2 and participants receiving Cycle 3 on Dose Level 1 with a paclitaxel dose escalation to 80 mg/m$^2$ will be evaluated such that at Dose Level 2 there may be 2 to 12 enrollees with up to 6 of them initially enrolled to Dose Level 1 and then dose escalated). If there is no DLT at Dose Level 2 after 3 participants have been evaluated (either as new enrollees to Dose Level 2 or as dose-escalating paclitaxel in Dose Level 1) the study will enroll to Dose Level 3. This plan only applies to the within subject dose escalation for paclitaxel (to minimize the number of participants getting a 40 mg/m$^2$ dose) and there is no within subject dose escalation of VB-111.

Dose Escalation from Dose Level 2 to Dose Level 3: Once 3 participants have been enrolled at Dose Level 2 and observed for 14 days following initial administration with VB-111 without DLT, subjects may be enrolled into Dose Level 3 ($1 \times 10^{13}$ VPs), as at least 6 participants will have been dosed at $3 \times 10^{12}$ VPs in Dose Levels 1 and 2. The 2nd dose of VB-111 on Dose Level 3 may only be given after at least 2 patients have received a dose of $3 \times 10^{12}$ VPs without DLT. Additionally, DLT monitoring will be performed simultaneously in parallel VB-111 Phase I/II studies. Safety findings from these studies will be shared with this team. If any DLT occurs at Dose Level 3, participants may continue on study and will receive further dosing with Dose Level 2 VB-111 ($3 \times 10^{12}$ VPs).

TABLE 11

Dose Escalation Decision Rules

| Number of Patients with DLT at a given Dose Level | Escalation Decision Rule |
|---|---|
| 0 out of 3** | Proceed to next dose level: **Within subject dose escalation is not permitted unless it is anticipated that 3 participants will have been fully evaluated for DLTs over 28 days on Dose Level 1. If three participants enroll within 4 weeks of initial dosing on the study and do not experience DLTs, Dose Level 2 will open and enroll 3 participants concurrent to the three participants dose-escalating to Dose Level 2 at Week 5 (Cycle 2 Day 1) on study. So, it is therefore possible, if accrual is slow, that participants in Dose Level 1 will not be allowed to dose escalate at Week 5 (Cycle 2 Day 1) until the evaluation of DLTs on Dose Level 1 has been complete, and that this will be further delayed if DLTs are experienced in this cohort. |
| 1 out of 3 | Enter 3 additional patients: If 0 of these 3 additional participants experiences a DLT, proceed to the next dose level. If 1 or more of these participants experiences a DLT, then dose escalation is stopped and the dose below |

TABLE 11-continued

Dose Escalation Decision Rules

| Number of Patients with DLT at a given Dose Level | Escalation Decision Rule |
|---|---|
| | this dose is the MTD. If the extra participants were entered at Dose Level 1 the study will close without identifying an MTD. |
| ≥2 | Dose escalation will be stopped and the dose below this dose is the MTD. If 2 participants experience DLTs at Dose Level 1, the study will close without identifying an MTD. |
| ≤1 out of 6 at highest administered dose | This is the MTD and recommended Phase II dose in this population. |

Given the novel nature of the agent, new participants will be enrolled sequentially with at least 2 days between each new person starting on study. Multiple new study participants may not be dosed on the same day. A completion of one 28-day cycle of treatment will be the basis for determining the MTD and DLT's on each of the dosing cohorts. Toxicity grade will be assessed according to the Common Terminology Criteria for Adverse Events (CTCAE) version 4 (available as a downloadable file on the internet: http://ctep.info.nih.gov).

Definition of Dose Limiting Toxicity (DLT)

Assessment of potential DLTs will occur during the first cycle (Cycle 1) and also during the third cycle for DL1 participants.

Toxicities will be assessed by the CTCAE, version 4.0. Dose-limiting toxicity is defined as follows:

1. Absolute neutrophil count of <0.5×10$^9$/L lasting for ≥4 days or an absolute neutrophil count <0.5×10$^9$/L with sepsis, or grade 3-4 fever (>100.2° F.) which is not readily controlled with anti-pyretic medication.

2. Platelet count <10×10$^9$/L for any duration.

3. Any other drug-related non hepatic and non-hematologic grade ≥3 toxicity. This does not include grade ≥3 nausea or vomiting that can be controlled medically (if nausea and/or vomiting cannot be controlled medically and occurs during the first cycle, it will be considered a DLT) or grade ≥3 hypokalemia, hyponatremia, hypophosphatemia, hypomagnesemia, and hypocalcemia if they can be easily corrected, are clinically asymptomatic, and not accompanied by medically significant complications (e.g., ECG changes).

Events of Grade 3-4 fever that occur within 24 hours post-dosing with VB-111 shall not be considered DLT if they respond to symptomatic therapy. Patients with either unacceptable toxicities and/or progression at any time point will be removed from the study.

Study Procedures

Pre-Treatment Evaluation:

A Clinician (MD or NP) will evaluate patients meeting the eligibility criteria. A history, physical examination and recording of the weight and vital signs and ECG recording will be performed within 14 days before commencing the first cycle of treatment. Investigations to establish baseline measurements, where applicable, should be done within 28 days before commencing the first cycle of treatment.

Prior to any study-dosing, on each cycle's Day 1, the eligibility of the subjects must be reconfirmed.

The following evaluations should be done within 3 days of D1 (Except for cycle 1, when blood tests can be checked within 14 days of day 1):

1. Clinical evaluation: Medical History, Physical exam, Vital Signs (VS) and check for risk of bleeding. At other times VS evaluation can be performed per institutional standard of care.

2. Hematology: complete blood count with differential, INR and activated PTT.

3. Coagulation: In case of partial thromboplastin time (PTT) prolongation above upper limit of normal (ULN), blood should be drawn for lupus anticoagulant (LAC). Patients with prolonged aPTT should not receive VB-111 until aPTT normalization. In patients who tested positive for lupus anticoagulant (LAC), a negative test is required prior to repeat dose of VB-111. For a persistent positive LAC or antiphospholipid antibodies (APLA) test, the test must be repeated within 12 weeks from the initial positive test.

4. Comprehensive metabolic panel: including electrolytes, liver function tests (LFTS), blood urea nitrogen (BUN)/creatinine (Cr), calcium, and magnesium.

5. Urine: collected for routine analysis.

6. VB-111 specific labs: Blood will be drawn for:
　(i) Biodistribution: VB-111 Adenovirus DNA levels and transgene expression determination.
　(ii) Biomarkers: Biomarkers for anti-angiogenic therapy will be tested in peripheral blood samples obtained from all patients enrolled in this study. Plasma analysis will be carried out for circulating angiogenic and inflammatory biomarkers VEGF, PlGF, sVEGFR1, bFGF, IL-1β, IL-6, IL-8, and TNF-α (using multiplex ELISA plates from Meso-Scale Discovery) and sVEGFR2 and SDF1α (using R&D Systems kits). Blood-circulating cells will be enumerated in fresh samples using a standard flow cytometry protocol. Archival tissue will be evaluated for CD31, CD34, VEGFR2, and vWF.
　(iii) Tumor marker: CA-125
　(iv) Antibodies: Levels of antibodies to AD-5 virus (including neutralizing antibodies).

Study Treatment Infusion:

ANC must be ≥1,000/mm$^3$ and Platelet count ≥100,000/mm$^3$ prior to study treatment infusion (paclitaxel or VB-111).

Paclitaxel Infusion:

Anti-emetic therapy: Anti-emetic therapy may include Dexamethasone 10 mg i.v. prn, Ativan 0.5-2.0 mg i.v., and/or Compazine 10 mg p.o., or Perphenazine 4 mg p.o., as per institutional standards.

The administration sequence will be paclitaxel followed by VB-111.

Paclitaxel will be administered weekly at an initial dose of 40-80 mg/m$^2$ through an in-line filter with a microporous membrane not greater than 0.22 microns over 60 minutes.

All patients must receive premedication before the administration of paclitaxel in order to prevent severe hypersensitivity reactions. Patients will take oral dexamethasone 20 mg the night before treatment and 20 mg the morning of treatment for the first dose, and then if paclitaxel is well tolerated, for week 2 no oral, and only IV premedication, and the dose may be weaned off and no longer used after week 3. A typical premedication regimen consists of the following given 30-60 minutes prior to paclitaxel: 10-20 mg intravenous (IV) dexamethasone, 50 mg IV diphenhydramine (or its equivalent), and 300 mg cimetidine or 50 mg IV ranitidine. Famotidine 20 mg IV can be substituted as an alternative per local formulary. The dexamethasone dose may be increased at the investigator's discretion if a patient experiences a hypersensitivity reaction when given paclitaxel.

Day 1 of Odd Cycles:

In addition to the above mentioned procedures, on D1 of odd cycles, the following procedures will be performed.

Tumor Measurements:

Prior to D1 of cycle 1 (up to 1 month prior is allowed) and then in every odd cycle (e.g. e.g. cycles 1, 3, 5 etc=every 8 weeks) until disease progression, tumor measures with CT will be performed on the chest, abdomen, and pelvis. The assessment will be performed prior to drug administration, up to 3 days before dosing.

Study Treatment Infusion: VB-111

VB-111 will be administered on Day 1 of each odd cycle until disease progression.

VB-111 should be administered after paclitaxel. This is based on the paradigm that the investigative agent should be given last as a safety precaution. There is no anticipation that there will be sequence dependent alteration in pharmacology of the two agents. Although this is anticipated to be immediately (within 1 hour) after paclitaxel it may be administered later (within 24 hours) if clinically indicated.

Patients with prolonged aPTT should not receive VB-111 until aPTT normalization. In patients who tested positive for LAC and/or APLA, a negative test is required prior to repeat dose of VB-111. While test remains positive, further VB-111 should not be administered. For a persistent positive LAC or APLA test, the test must be repeated within 12 weeks from the initial positive test.

Antipyretic Treatment: 1000 mg of acetaminophen shall be administered prior to VB-111 dosing and PRN acetaminophen post-dosing. In patients who develop a grade 3 fever, or at investigator's discretion, i.v. dexamethasone 10 mg may be administered 10 minutes prior to dosing in subsequent VB-111 doses.

VB-111 preparation and infusion: Upon completing the infusion of paclitaxel, VB-111 will be administered as a single dose of $3 \times 10^{12}$ VPs (Dose Levels 1-2) or $1 \times 10^{13}$ VPs (Dose Level 3) to patients who are fasting or have had only a lighter blander meal. Please note: fasting is suggested to avoid vomiting if the patient has significant chills rather than the usual low-grade and self-limiting fever. It is not an absolute requirement. The final solution for administration should be administered not more than 60 minutes after preparation. A regular meal will be allowed 0.5 hour after dosing. A single intravenous infusion of diluted VB-111 should be administered at the following rates:

1. For dose $3 \times 10^{12}$ VPs: 1 mL/minute
2. For dose $1 \times 10^{13}$ VPs: 1 mL/minute for the first 10 mL, and then 3 mL/minute for the remainder of the infusion.

Observation Post-VB-111 Administration

Study participants should be observed in the clinic or infusion area for the first 8 hours after the first administration of study drug, and subsequently as clinically indicated.

VB-111 Distribution Labs

Blood and urine samples will be collected for VB-111 adenovirus DNA levels expression determinations at the following time points:

Blood.
1. 0 (Prior to dosing)
2. At the end of infusion
3. 3±0.5 hours
4. 6±0.5 hours Vital Signs:

Vital signs (systolic and diastolic blood pressure, peripheral heart rate, body temperature, respiration rate) will be recorded:
1. 0 minutes (just prior to dosing) (−15 minute range)
2. 30 minutes after start of dosing (+/−15 minute range)
3. 60 minutes after start of dosing (+/−15 minute range)
4. 4 hours post start of dosing (+/−15 minute range)
5. 6 hours post start of dosing (+/−15 minute range)
6. On the occasion of any adverse event Days 8, 15, and 22 of Each Cycle Each patient will be required to return to the clinic at a fasting state, for the following evaluations:
1. Vital signs: supine systolic and diastolic blood pressure, peripheral heart rate, body temperature, respiration rate.
2. Hematology: complete blood count with differential, INR and activated PTT.
3. Coagulation: if necessary to follow up on abnormal PTT levels.
4. Urine: collected for routine analysis Blood labs will be drawn on day 8 of cycles 1-6. Blood will be drawn for:
1. Biodistribution: VB-111 Adenovirus DNA levels and transgene expression determination (every 2nd cycle following VB-111 infusion)
2. Biomarkers: Plasma analysis will be carried out for circulating angiogenic and inflammatory biomarkers VEGF, PlGF, sVEGFR1, bFGF, IL-1β, IL-6, IL-8, and TNF-α (using multiplex ELISA plates from Meso-Scale Discovery) and sVEGFR2 and SDF1α (using R&D Systems kits). Blood-circulating cells will be enumerated in fresh samples using a standard flow cytometry protocol. Archival tissue will be evaluated for CD31, CD34, VEGFR2, and vWF.
3. Tumor marker: CA-125
4. Antibodies: Levels of antibodies to the virus (including neutralizing antibodies)

NOTE: Comprehensive metabolic panel including electrolytes, LFTS, BUN/Cr, calcium, and magnesium is only required on D1, with only LFTs on Days 1, 8, 15, 22.

Paclitaxel will be administered as detailed above. ANC must be (>1,000/mm$^3$ and platelet count >100,000/mm$^3$ Anti-emetic therapy: Anti-emetic therapy may include Kytril 750 µg i.v. or 1 mg p.o., or Zofran 10 mg i.v. or 8 mg p.o., with Dexamethasone 10 mg i.v. as well as prn Ativan 0.5-2.0 mg i.v., and/or Compazine 10 mg p.o., or Perphenazine 4 mg p.o. as per institutional standards.

Study Completion Visit

Subjects will be dosed with the combination therapy (paclitaxel and VB-111) according to the cycle schedule described above until disease progression.

Following the final dose with VB-111, each patient will be required to return to the clinic for a final follow up visit, with the same clinical evaluation and laboratory samples drawn routinely and in response to a clinically significant event which will be documented as unscheduled laboratory evaluations. Adverse event and concomitant medications should be recorded in the same fashion as earlier in the study. The subject will undergo Physical Examination that will be carried out by the treating clinician (MD or NP). An ECG will be performed.

Patients who discontinued the study or experience disease progression will be followed up by clinic or telephone contact to evaluate for survival. However, following disease progression, data describing the CA125 and RECIST will be maintained in the clinical research files.

Additional Procedures

Adverse Events

Full supportive measures should be employed for all patients with any adverse event. All adverse events occurring following drug administration will be documented in the case report forms (CRFs), together with the intensity, the therapeutic measures applied, the outcome and an evaluation of the relationship to the investigational drug. Related adverse events will be followed through resolution. Unrelated adverse events will be followed through resolution or end of study.

Common side effects include nausea, vomiting, and loss of appetite. The patient may also experience constipation, loose stools or diarrhea. It is important to increase fluid intake if diarrhea occurs. If this becomes severe, the patient may have to be hospitalized and receive intravenous fluids. The administration of any investigational product involves a general risk of side effects. Since VB-111 is an investigational product, not all of the potential side effects in humans are known. VB-111 may cause all, some, or none of the side effects listed below. Side effects are undesirable medical conditions or a worsening of a pre-existing medical condition that may occur while you are in a study. In addition to the possible adverse effects listed below unexpected or uncommon side effects, which could be serious or life threatening, may occur when VB-111 is given alone or when it is combined with other medications. One of the purposes of this study is to investigate the possible side effects of VB-111. The study doctor will monitor the patient closely during this study and discuss with the patient any questions regarding risks, discomforts, and adverse effects.

Risks Associated with VB-111

Likely (More than a 50% chance that this will happen)

Flu-like symptoms such as fever, muscle aches, fatigue, chills,

Nausea

Vomiting

Occasional (Between a 1-10% chance that this will happen)

Constipation

Abnormally high levels of enzymes produced by the liver meaning that your liver is not functioning properly and can cause fatigue and jaundice (yellowing of the skin and eyes). Although this is usually mild and reversible, this can be serious or life threatening Increase in the size of the spleen usually doesn't cause any symptoms but may cause stomach pain if the spleen ruptures, and could be life threatening.

Increase in the making of new blood cells in the bone marrow that may result in increased blood cell counts but without an increased risk of leukemia An allergic reaction at the site where an injection (shot) was given, which may cause some redness and swelling Bleeding Abnormally prolonged coagulation tests (PTT) and development of certain types of antibodies (antiphospholipid antibodies) that may interfere with the normal blood clotting. This may result in thrombosis (blood clots) or bleeding, which may require treatment and may be serious or life threatening.

The ability for your wounds to heal might be affected. This can lead to infections and may require hospitalization.

High blood pressure

Excess protein in the urine. This is usually an asymptomatic lab finding but, if excessive, may cause fluid retention, such as swelling of the legs.

Headache

Loss of appetite and weight loss (anorexia)

Decreased levels of sodium in the blood, which can cause confusion, seizures, fatigue and low levels of consciousness.

Excess sugar in the blood, if severe may require hospitalization and urgent treatment.

Increased sweating (hyperhidrosis)

Rare (Less than a 1% chance that this will happen)

Low number of red blood cells that can causes tiredness and shortness of breath. This may require a blood transfusion.

Low number of platelets, which may cause bleeding and bruising. Bleeding may be serious or life threatening and may required a blood transfusion.

Mild increase in white blood cells (may increase the risk of infection)

Severe bleeding

The function of the kidneys may deteriorate (Acute Renal Failure) which may require treatment and may be serious or life threatening.

Cerebral Edema may develop in patients with tumor involving the brain (for example, brain metastasis)

Diarrhea

Cardiac (heart) and blood vessel complications: heart attack, angina (chest pain), or blood clots (thrombosis) that could occlude blood supply to vital organs and result in stroke or damage to other organs.

Congestive Cardiac Failure—The heart is not able to pump blood properly, which can cause weakness and tiredness, fluid retention, and fluid build-up in the lungs, which can cause shortness of breath. This may be serious or life threatening Risks Associated with Paclitaxel Likely (Chance of more than 50% that this will happen)

Mild to severe allergic reaction which may be life-threatening

Numbness and pain of the hands and feet that sometimes worsens with additional treatment and may not disappear after the drug is stopped Hair loss Muscle and joint aches Fatigue Frequent (Chance of 10-50% that this Will Happen)

Nausea and/or vomiting

Diarrhea

Sores in the mouth or throat

Lightheadedness

Headaches

Liver damage

Skin irritation and swelling if the drug leaks from the vein into which it is being injected into the surrounding skin Taste changes Irritation of the skin at a site of previous radiation Rash Occasional (Chance of 1-10% that this Will Happen)

Inflammation of the colon which may cause a change in your bowel movements

Inflammation of the pancreas which may cause abdominal pain that only lasts for a short time A sensation of flashing lights or spots Kidney damage Increased blood level of a form of fat called triglyceride (hypertriglyceridemia)

A slowing of the heart rate

Irregular heartbeats

Rare (Chance of Less than 1% that this Will Happen)

Liver failure

Seizures

Confusion; mood changes

Risks Associated with Biopsies:

Biopsies are normally performed under the guidance of an imaging technique. Each procedure requires a separate consent prior to the biopsy. The risks may include:

Pain and discomfort. The amount of pain and discomfort will vary, depending on the location of the biopsy site. These risks can be discussed with the study doctor.

Minor bleeding at the biopsy site.

Tenderness at the biopsy site.

Scarring at the biopsy site.

Rarely, an infection at the biopsy site.

Uncommonly, complications from biopsies can be life threatening. As with any interventional procedure, other potentially serious complications from bleeding or organ damage may occur. These might require additional surgical intervention.

Risks Associated with Radiological Scans and X-Rays:

While the patient is in the research study, CT scans may be used to evaluate the disease. The frequency of these exams is standard care. In the long term, over many years, there is a very low risk of developing a new cancer as a result of the radiological evaluation and treatment for the cancer. Certain types of drugs or combinations of these drugs with radiation may further slightly increase the risk of developing a new cancer.

There is a small risk with using the contrast agent that is injected into a vein during the scan. It may worsen kidney function in people who already have decreased kidney function. Therefore, kidney function will be closely monitored during participation in this study. If there is any change in the patient's kidney function, the patient may have to be removed from the study.

Uncommonly, some people have allergic reactions (such as hives and itching) to the contrast agent. Serious reactions (for example, drop in blood pressure, difficulty breathing or severe allergic reaction and death) are rare.

Reproductive Risks:

The drugs used in this research study may affect a fetus. While participating in this research study, the patient should not become pregnant, and should not nurse a baby. The patient should let the doctor know immediately if she becomes pregnant. Counseling about preventing pregnancy for either male or female study participants will be provided.

Concomitant Medications

There is no restriction on concomitant medication, besides the drugs listed in the exclusion criteria. However, VB-111 should not be mixed with other drugs. All concomitant medication administered during the study will be documented from baseline until a 1 month follow-up visit following the final dose. Routine drugs will be recorded with product name, indication, dosage, units, frequency, start and stop dates. Any continuing concomitant medication will be recorded as such, and does not need to reappear unless a stop date is noted prior to study end.

Antiemetic Regimens

It is anticipated that nausea should be a mild side effect. The following representative antiemetic regimens are suggested: Dexamethasone 4-8 mg PO, or Lorazepam 0.5-1.0 mg, or Prochlorperazine 10 mg PO, or Metoclopramide 10-20 mg, 30 minutes prior to administration of chemotherapy.

Aspirin

Low-dose aspirin (≤325 mg/d) may be commenced or continued in subjects at higher risk for arterial thromboembolic disease. Subjects developing signs of arterial ischemia or bleeding on study should be evaluated for drug discontinuation.

Anti-Pyretic Treatment

VB-111 administration is associated with self-limited fever usually lasting 24 hours post dosing, in some cases a low grade fever may extend for up to 2-3 days post dosing. 1000 mg of acetaminophen shall be administered 1-2 hours prior to VB-111 dosing and PRN acetaminophen post-dosing. In patients who develop a grade 3 fever, or at investigator's discretion, IV Dexamethasone 10 mg may be administered 10 minutes prior to dosing in subsequent VB-111 doses.

Other Laboratory Analyses

Laboratory samples drawn in response to a clinically significant event will be documented as unscheduled laboratory evaluations. In the event of clinically relevant abnormal laboratory values, the tests will be followed-up until the values have returned to within normal range and/or an adequate explanation of the abnormality is found. All such laboratory investigations will be performed at the study site, except for distribution assessments, which will be sent to an Independent Central Laboratory. Should any of these results require confirmation, re-testing will be performed in the same hospital laboratory where possible. Laboratory accreditation certificates and normal reference ranges must be provided for each hospital laboratory. If safety labs are drawn at local laboratories, all efforts should be made to obtain lab accreditation certificates and normal reference ranges for these labs.

ECG will be performed at screening visit and every 6 months or at early withdrawal visit.

Study Duration

Each patient will be administered with paclitaxel weekly and VB-111 every second cycle. Patients will participate in this study until disease progression and then only their files will be made available for collection of CA125 and RECIST details.

Patients can decide to withdraw from study at any time. Patients who withdraw should still be contacted and questioned about adverse effects (AEs). All AEs, irrespective of relatedness to drug or disease will be documented in the patient's record and CRF. Based on the toxicity profile from preclinical studies completed so far, as well as the specificity of expression of the transgene, one year is considered adequate time to identify any longer term toxicities that may emerge after treatment. Patients who have withdrawn or experience disease progression should be contacted approximately every 2 months for survival data.

Dose Limiting Toxicity (Cycle #1, 2 and 3 Only)

Dose limiting toxicities (DLTs) will be defined in the first cycle of the protocol and all patients triggering the DLT definitions during these cycles will be removed from protocol. No dose reductions will be allowed during cycle 1. DLT is defined as >4 days of grade IV neutropenia (ANC <500/mm$^3$), fever and neutropenia (defined as a temperature >100.2° F. and ANC <500/mm$^3$), grade IV thrombocytopenia (platelets <25,000/mm$^3$) and grade III non-hematological toxicity, excluding nausea and grade III vomiting.

Events of Grade 3-4 fever that occur within 24 hours post-dosing with VB-111 shall not be considered DLT if they respond to symptomatic therapy.

Given that paclitaxel 80 mg/m$^2$ is the clinically accepted dose for the weekly schedule, there is no plan to escalate above this dose.

Dose Modifications—Paclitaxel

No dose modification may be made during the first cycle of the dose escalation phase of the study.

In patients with symptomatic neuropathy a 'break week' is allowed after discussion with the study PI. This is anticipated to allow a dosing schedule of 3 out of 4 weeks, or 7 out of 8 weeks if on alternate cycles. If dose density cannot be maintained at one of these schedules the patient should be removed from study. If a dose modification is made to the Paclitaxel Schedule, the VB-111 dosing will therefore not need to be modified to follow the Paclitaxel cycles.

Participants may stay on study with interruptions in dosing for up to 3 weeks to allow recovery of toxicity, or social commitments.

Note: After day 28, once a patient is dose reduced, dose escalation is not permitted and the patient should continue on this dose for all subsequent cycles.

Dose adjustments should be made according to the system showing the greatest toxicity graded by the Common Terminology Criteria for Adverse Events (CTCAE-4).

In general dose modifications for hematologic toxicity will be based on blood counts obtained within 72 hours of the time of retreatment unless specifically stated otherwise. Dosing of paclitaxel will be determined based on ANC (Table 12), platelet count (Table 13), and neuropathy (Table 14).

TABLE 12

| Neutropenia Pre-Weekly Dose | |
| --- | --- |
| ANC/Drug | Paclitaxel |
| ≥1000/mm$^3$ | Full dose |
| <1000/mm$^3$ | Hold drug |
| Further incidence if ANC < 1000/mm$^3$ | Dose reduce to 60 mg/m$^2$ |

TABLE 13

| Thrombocytopenia Pre-Weekly Dose | |
| --- | --- |
| Platelets/Drug | Paclitaxel |
| ≥100,000/mm$^3$ or first incidence of <100,000/mm$^3$ and >75,000/mm$^3$ | Full dose |
| <75,000/mm$^3$ | Hold drug |
| Repeat incidence of platelets <100,000/mm$^3$ and >75,000/mm$^3$ | Dose reduce to 60 g/m$^2$ |

TABLE 14

| Sensory Neuropathy Dose Reduction Schema | |
| --- | --- |
| Neuropathy Grade > 2 | |
| First incidence | 1$^{st}$ dose reduction - Paclitaxel 60 mg/m$^2$ |
| Second incidence (or persistence despite dose reduction) | 2$^{nd}$ dose reduction - Paclitaxel 40 mg/m$^2$ |
| Third incidence (or persistence despite dose reduction) | Off study |

Once paclitaxel dose is reduced, it should not be re-escalated.

Management of Prolonged Myelosuppression

If platelets or neutrophils have failed to recover by day 28, an additional 7 days will be allowed for hematologic recovery. Patients with incomplete recovery (ANC <1,000/mm$^3$ or Platelets <100,000/mm$^3$) at 35 days will be removed from protocol.

Management of Fever and Neutropenia

Patients will be managed in the usual fashion for fever and neutropenia. Patients will need to recover from fever and active infectious issues prior to resuming therapy. Patients who are not on growth factors will have Neupogen or Neulasta added to their next cycle. Patients on Neupogen 5 ug/kg/day will have their dose escalated to 10 ug/kg on the same schedule.

Additional Toxicities and Dose Adjustments

Other toxicities are not anticipated but are possible on this trial. Patients developing drug associated grade III or IV non-hematological or non-mucosal toxicities that do not resolve or improve to grade I within 7 days of the next cycle will be removed from protocol. Patients developing serious grade III or IV non-hematological/non mucosal toxicities that resolve or improve to grade I by within one week of the start of the next cycle may continue on trial if the patient is responding to therapy and the patient toxicities have been reviewed with the principal investigator.

Dose Reductions for Abnormal Liver Function Tests are as Follows:

Paclitaxel is not known to cause hepatic toxicity, however, its elimination is delayed in patients with severe hepatic dysfunction. Therefore, the dose of paclitaxel in patients with hepatic dysfunction should be modified according to Table 15.

TABLE 15

| Paclitaxel Dosing Based on Serum Aspartate Aminotransferase (AST) and Alanine Aminotransferase (ALT) Levels | |
| --- | --- |
| Serum AST, or ALT | Paclitaxel |
| <3x ULN | 80 mg/m$^2$ |
| ≥3x ULN | 60 mg/m$^2$ |
| ≥5x ULN | Hold drug |

Patients with elevated bilirubin >1.5 mg/dl should not receive paclitaxel until the abnormal laboratory values improve to <grade 1. Treatment should be resumed after recovery with paclitaxel at one dose level lower, per the above table, and toxicity that lasts more than 2 weeks, will removed from study. Once a patient is dose reduced, dose escalation is not permitted and the patient should continue on this dose for all subsequent cycles.

Patients with prolonged aPTT should not receive VB-111 until aPTT normalization. In patients who tested positive for lupus anticoagulant (LAC) and/or antiphospholipid antibodies (APLA), a negative test is required prior to repeat dose of VB-111. While test remains positive, further VB-111 should not be administered. For a persistent positive LAC or APLA test, the test must be repeated within 12 weeks from the initial positive test.

Patients developing serious toxicities thought secondary to their ovarian carcinoma (i.e. bowel obstruction) will also be removed from protocol. In the unusual circumstance where a reversible grade 3-4 toxicity is secondary to carcinoma and the patient is felt to be benefiting from chemotherapy the treating physician should review with the study P.I. for potential continuation on the protocol once the toxicity has resolved.

The next cycle of treatment can only commence if all non-hematological toxicity has resolved to grade I or better.

Up to two dose delays, each of a week are allowed. If there is persistent toxicity the patient will be taken off study.

Participant Safety

A number of measures will be taken to ensure the safety of patients participating in this trial. These measures will be addressed through exclusion criteria and routine monitoring as follows.

Patients enrolled in this study will be evaluated clinically and with standard laboratory tests before and at regular intervals during their participation in this study. Safety evaluations will consist of medical interviews, recording of adverse events, physical examinations, blood pressure, and laboratory measurements (performed by local laboratories). Patients will be evaluated for adverse events (all grades), serious adverse events, and adverse events requiring study drug interruption or discontinuation at each study visit for the duration of their participation in the study. Patients discontinued from the treatment phase of the study for any reason will be evaluated ~30 days (28-42 days) after the decision to discontinue treatment.

If patients on treatment require elective major surgery, it is recommended that therapy be held for 2-4 weeks prior to the surgical procedure.

Re-Treatment Criteria

Dose adjustments at the start of a cycle should be based on nonhematologic toxicity or blood counts at that time. Patients should not begin a new cycle of treatment unless the absolute neutrophil count is >1,000 cells/mm$^3$, the platelet count is >100,000 cells/mm$^3$, and nonhematologic toxicities have improved to grade 1 (mild) or resolved.

Patients may be delayed for up to three weeks before re-treatment. If toxicity recovery takes more than three weeks they should be removed from study.

Treatment can continue in the setting of grade 2 fatigue, diarrhea, alopecia and nausea, if the toxicity: benefit trade-off is felt to be beneficial to participant and clinician.

Paclitaxel Formulation, Supply, Storage and Stability
Paclitaxel (NSC #673089)

Paclitaxel 40-80 mg/m2 will be infused IV over 1 hour day 1, 8, 15 and 22 with a cycle being 28 days. Drug will be dosed to a maximum body surface area (BSA) of 2.0 m$^2$, and BSA will be calculated from that day's weight Formulation Paclitaxel is supplied as a 6 mg/mL non-aqueous solution in multi dose vials containing 30 mg/5 mL, 100 mg/16.7 mL, or 300 mg/50 mL of paclitaxel. In addition to 6 mg of paclitaxel, each mL of sterile non-pyrogenic solution contains 527 mg of purified Cremophor® EL (polyoxyethylated castor oil) and 49.7% (v/v) dehydrated alcohol, USP.

Storage

Unopened vials of paclitaxel are stable to the date indicated on the package when stored between 20 to 25° C. (68 to 77° F.). Protect from light.

Preparation

Paclitaxel will be diluted prior to infusion. Paclitaxel will be diluted in 0.9% Sodium Chloride for Injection, USP; 5% Dextrose Injection, USP; 5% Dextrose and 0.9% Sodium Chloride Injection, USP; or 5% Dextrose in Ringer's Injection to a final concentration of 0.3 to 1.2 mg/mL. The solutions are physically and chemically stable for up to 27 hours at ambient temperature (approximately 25° C./77° F.) and room lighting conditions. In order to minimize patient exposure to the plasticizer DEHP, which may be leached from PVC infusion bags or sets, diluted paclitaxel solutions should be stored in bottles (glass, polypropylene) or plastic (polypropylene, polyolefin) bags and administered through polyethylene-lined administration sets.

Administration

Paclitaxel will be administered through an inline filter with a microporous membrane not greater than 0.22 microns. Use of filter devices such as IVEX-2® or IVEX-HP®, which incorporate short inlet and outlet PVC-coated tubing, has not resulted in significant leaching of DEHP.

Premedication

All patients will be premedicated with corticosteroids, diphenhydramine, and H2 antagonists prior to the first paclitaxel administration in order to prevent severe hypersensitivity reactions. Patients who experience severe hypersensitivity reactions to drug may need to repeat the premedication and to be rechallenged with a dilute solution and slow infusion. For severe hypersensitivity reactions to paclitaxel do not have to proceed with a re challenge. When the drug is well tolerated, or tolerance to cemophor is established, the oral dexamethasone may be progressively withdrawn. Docetaxel may not be substituted.

Adverse Effects: Consult the package insert for the most current and complete information.

Supplier: Commercially available both from Bristol-Myers Squibb Oncology as well as generic manufacturers. Consult the American Hospital Formulary Service Drug Information guide, Facts and Comparisons, or the package insert for additional information.

VB-111

Description

Study drug vials will be supplied for each subject dose in labeled 1.8 ml cryovials (polypropylene). Each cryovial contains a volume of 1.1 ml ($10^{12}$ vp/ml).

Formulation

VB-111 is a formulated as a sterile vector solution. The solution is supplied frozen (below 65° C.), in single use, plastic screw vials. Each vial contains 1.1 mL of vector at a viral titer of $10^{12}$ vp/ml and vehicle (10% glycerol in Phosphate Buffered Saline). The vector solution should be thawed and maintained at 2-8° C. during dilution and handling.

Stability and Storage

Stability studies of VB-111 are ongoing and to date support a shelf-life of 30 months below 65° C. Open and/or diluted vials SHOULD NOT BE RE-USED. VB-111 vials should be stored in closed vials frozen (below 65° C.), protected from light.

Preparation

VB-111 will be prepared as shown in Table 16.

TABLE 16

| | | | | | | | | | Volume | Volume |
|---|---|---|---|---|---|---|---|---|---|---|
| | | | | Take | | | | | to | to |
| | Concentration | Volume | | this | | | | | inject | inject |
| | in | of VB- | # Vials | volume | Syringe | Volume | Syringe | Total | Subject | Subject |
| | vial | 111 in | of VB- | of VB- | type for | of | type for | volume | Weight | Weight |
| Dose | (VP/ml) | tube | 111 | 111 (ml) | VB-111 | saline | saline | prepared | ≥50 Kg | <50 Kg |
| $3 \times 10^{12}$ VPs Dose Levels 1 + 2 | $10^{12}$ | 1.1 ml | 3 | 3 ml 3 × 1 ml | 3 ml | 12 ml (2 × 6 ml) | 2 × 10 ml | 15 ml | Entire volume (15 ml) | 10.5 ml |

TABLE 16-continued

VB-111 Preparation

| Dose | Concentration in vial (VP/ml) | Volume of VB-111 in tube | # Vials of VB-111 | Take this volume of VB-111 (ml) | Syringe type for VB-111 | Volume of saline | Syringe type for saline | Total volume prepared | Volume to inject Subject Weight ≥50 Kg | Volume to inject Subject Weight <50 Kg |
|---|---|---|---|---|---|---|---|---|---|---|
| 1 × 10$^{13}$ VPs Dose Level 3 | 10$^{12}$ | 1.1 ml | 10 | 10 × 1 ml | 10 ml | 40 ml | * | 50 ml | Entire volume (50 ml) | 35 ml |

* The pharmacy can either use a sterile empty bag and individually add 40 ml NS + 10 ml VB-111 to the bag, or the pharmacy can use a 50 ml bag of NS and remove the excess volume then add the VB-111. Either way is an acceptable pharmacy practice.

The entire process of drug preparation shall be carried out at room temperature in the BSC type II room. After thawing, the drug may be maintained up to 3 hours in ice water during preparations.

The drug is diluted in room temperature saline.

The preparation of the drug and drug injection shall be completed in the shortest time possible, not to exceed 1 hour.

The pharmacist preparing the drug shall verify that the information on the container is appropriate for the study and for the subject: product name, concentration, batch number.

Place volume needed of saline (brought to room temperature) in a sterile plastic tube. Thaw the vials of VB-111 solution by rubbing between the gloved hands. Immediately, pull 1 ml of VB-111 from each of the cryo vial intended for the specific subject. Use a new syringe for each 1 ml of VB-111. Add VB-11 to the plastic tube containing the saline solution prepared in advance. Mix the diluted drug by swirling the contents by hand. Determine the volume to be applied according to the patient's weight and draw the required volume for injection into the syringe for administration (see Table 16). After completing the preparation, perform a reconciliation process: check that the correct number of source vials was used and that the volume left in the tubes is approximately as expected and complete the drug accountability log. After preparation of the drug solution, clean the drug formulation area in the pharmacy according to the pharmacy procedures.

Infusion

1. A single intravenous infusion of the diluted VB-111 should be administered via a syringe pump according to the instructions below:
    a. Dose Levels 1-2: 3×10$^{12}$ VPs (15 or 10.5 ml depending on the subject's weight) should be administered at a rate of 1 ml/minute
    b. Dose Level 3: 1×10$^{13}$ VPs (50 or 35 ml depending on the subject's weight)
        i. Infusion should be administered at the following rate:
            1. 1 ml/minute for the first 10 minutes
            2. 3 ml/minute for the remaining volume of infusion A regular meal may be provided to the subject 30 minutes after completion of dosing.

Subject Discontinuation

Subjects who meet the following criteria should be discontinued from study treatment:
1. Grade 3 neuropathy lasing >7 days
2. Grade 4 hypertension or Grade 3 hypertension not controlled with medication
3. Nephrotic syndrome
4. Grade ≥2 pulmonary or CNS hemorrhage; any Grade 4 hemorrhage
5. Any grade arterial thromboembolic event
6. Grade 4 congestive heart failure
7. Gastrointestinal perforation
8. Any grade fistula
9. Any grade bowel obstruction.
10. Wound dehiscence requiring medical or surgical intervention
11. Unwillingness or inability of subject to comply with study requirements
12. Determination by the investigator that it is no longer safe for the subject to continue therapy
13. All Grade 4 events thought to be related to study treatment by the investigator Contraindications Study medication is contraindicated in patients who have a known, prior, severe (NCI CTC Grade 3/Grade 4) history of hypersensitivity reaction to a drug formulated in Cremophor®EL (polyoxyethylated castor oil).

Clinical Tests and Procedures

A series of clinical tests and procedures will be performed at specified intervals throughout the study according to Table 17.

TABLE 17

Clinical Tests and Procedures

| Assessment | Screening | Treatment | | Follow-Up Study |
|---|---|---|---|---|
| | Baseline [a] | D 1 of each cycle | Days 8, 15, 22 | Completion [i] |
| Inc./exclusion criteria | X | | | |
| Informed Consent | X | | | |
| Medical history; vital signs (incl. BP, HR, weight)[#] | X | X | X | X |

TABLE 17-continued

Clinical Tests and Procedures

| Assessment | Screening Baseline [a] | Treatment D 1 of each cycle | Treatment Days 8, 15, 22 | Follow-Up Study Completion [i] |
|---|---|---|---|---|
| Toxicity | | X | X | X |
| Physical examination | X | X | | X |
| Performance status | X | X | | X |
| CBC dif. [b] | X | X | X | X |
| Comprehensive metabolic panel [b] | X | X | Just LFTs | X |
| Urinalysis [d] | X | X | X | X |
| Coagulation [e] | X | X | | X |
| EKG | X | | | X |
| Biodistribution | | X* (Odd cycles only) | X* | X |
| Tumor response [f] | X | q2 cycles [c] | | |
| Ad-5 Antibodies | | X* (Odd cycles only) | X | X |
| Correlative Science/Biomarkers [g] | X | Cycle 1, 2, and then odd cycles only | Cycle 1 Day 8 for Cycles 2-6 | |
| Optional tumor biopsy [h] | | | | X [h] |
| CA-125 | X | X | | X |
| Paclitaxel dose | | X | X | |
| VB-111 dose | | Odd cycles only | | |

*Samples to be collected on VB-111 dosing days (every other cycle) prior to dosing, end of infusion, 6 hours post dosing and on Day 8 of that cycle (Odd cycles).
Samples to be collected prior to dosing
[#]Vital signs will be monitored on VB-111 dosing days prior to dosing, and 30 minutes, 60 minutes, 4 hours and 6 hours post dosing
[a] All physical examinations, blood tests, and urinalysis must be performed within 14 days prior to registration. Radiological assessment of tumors should be performed within 4 weeks prior to registration.
[b] Bloods can be drawn within 3 days of D 1, 8, 15, 22 of all subsequent cycles. CBC dif.: CBC with differential and platelets; Comprehensive metabolic panel including electrolytes, LFTs, BUN/Cr, calcium, and magnesium. Only LFTs and a CBC dif are required days 8, 15, 22.
[c] It is anticipated that tumor response will be evaluated 2 cycles.
[d] If there is new, or increased proteinuria, a 24 hr urine may be required. +2 dipstick requires a 24-hour collection but +3 dipstick requires holding study drug and a 24-hour collection. Urinalysis will be obtained on D 1, D 8, D 15, D 22, and as clinically indicated, as proteinuria has not been a feature of dosing with VB-111.
[e] Bloods can be drawn within 3 days of D 1 of each cycle for PT, PTT. In case of PTT prolongation above ULN, blood should be drawn for lupus anticoagulant (LAC) and for anti-phospholipid antibody (IgG and IgM for beta-2-GP-1 and anticardiolipin).
[f] Tumor assessment can be by institutional standards such as tumor response assessments: CT, MRI, etc.
NOTE:
The tumor assessment is scheduled to occur at regular intervals (every 8 weeks), which will be typically coinciding with every 2 cycles, but at a fixed interval which will allow cleaner evaluation of PFS, the primary end point.
[g] Specific biomarkers will be collected prior to dosing on Cycle 1 day 1 and on days 8, 15, 22 of Cycle 1, Cycle 2 day 1, Cycle 3 day 1 prior to dosing and every 2 cycles thereafter until disease progression.
[h] Tissue acquisition is not a mandated part of the study, but optional with a budget to cover non-clinically indicated biopsy or paracentesis to procure samples. There is no specified time for this to be done. See TISSUE COLLECTION section below.
[i] Study Completion data should be completed within one week of 30 days from last dose of study medication. Survival data may then be collected by phone.

Efficacy and Safety Assessments

Recist Criteria

Tumor response will be assessed using RECIST 1.1 criteria at baseline and every other cycle thereafter i.e. after cycles 2, 4, 6, etc. If patients continue with paclitaxel formal evaluation will continue. Independent evaluation of imaging will be performed by TumorMetrics.

Tumor Measurement

Measurable disease: the presence of at least one measurable lesion. If the measurable disease is restricted to a solitary lesion, its neoplastic nature should be confirmed by cytology/histology.

Measurable Lesions

Lesions that can be accurately measured in at least one dimension with the longest diameter >2.0 cm. With a spiral CT scan, the lesion must be >1.0 cm in at least one dimension, and for lymphnodes, the shortest diameter must be >1.5 cm.

Non-Measurable Lesions

All other lesions, including small lesions (longest diameter <2.0 cm with conventional techniques or <1.0 cm with spiral CT scans) and other non-measurable lesions. These include: bone lesions; leptomeningeal disease; ascites; pleural/pericardial effusion; inflammatory breast disease; lymphangitis cutis/pulmonis; abdominal masses that are not confirmed and followed by imaging techniques; and cystic lesions.

All measurements should be recorded in metric notation, using a ruler or calipers. All baseline evaluations should be performed as close as possible to the treatment start and never more than 4 weeks before the beginning of the treatment.

The same method of assessment and the same technique should be used to characterize each identified and reported lesion at baseline and during follow-up.

Clinical lesions will only be considered measurable when they are superficial (e.g., skin nodules, palpable lymph nodes). For the case of skin lesions, documentation by color photography including a ruler to estimate the size of the lesions is recommended.

Baseline Documentation of Target and Non-Target Lesions

All measurable lesions up to a maximum of 5 lesions representative of each involved organ should be identified as target lesions and will be recorded and measured at baseline.

Target lesions should be selected on the basis of their size (lesions with the longer diameter) and their suitability for accurate repetitive measurements (either by imaging techniques or clinically).

A sum of the longest diameter (LD) for all target lesions will be calculated and reported as the baseline sum LD. The baseline sum LD will be used as reference to further characterize the objective tumor response of the measurable dimension of the disease.

All other lesions (or sites of disease) should be identified as non-target lesions and should also be recorded at baseline. Measurements are not required and these lesions should be followed as "present" or "absent."

Response Criteria

Evaluation of target lesions:

Complete response (CR)—disappearance of all target lesions.

Partial response (PR)—at least a 30% decrease in the sum of the LD of the target lesions taking as reference the baseline sum LD.

Progression (PD)—at least a 20% increase in the sum of the LD of the target lesions taking as reference the smallest sum LD recorded since the treatment started or the appearance of one or more new lesions.

Stable disease (SD)—neither sufficient shrinkage to qualify for PR nor sufficient increase to qualify for PD taking as references the smallest sum LD since the treatment started.

Evaluation of non-target lesions:

Complete response (CR)—disappearance of all non-target lesions and normalization of tumor marker level.

Non-complete response (non-CR)/non-progression (non-PD)—persistence of one or more non-target lesion(s) or/and maintenance of tumor marker level above the normal limits.

Progressive disease (PD)—appearance of one or more new lesions. Unequivocal progression of existing non-target lesions. Although a clear progression of non-target lesions only is exceptional, in such circumstances, the opinion of the treating physician should prevail and the progression status should be confirmed later on by a review panel (or study chair/primary investigator).

Evaluation of Best Overall Response

The best overall response is the best response recorded from the start of the treatment until disease progression/recurrence (taking as reference for progressive disease the smallest measurements recorded since the treatment started). In general, the patient's best response assignment will depend on the achievement of both measurement and confirmation criteria as shown in Table 18.

TABLE 18

Overall Patient Responses Based on Measurement of Target, Non-Target, and New Lesions

| Target lesions | Non-target lesions | New lesions | Overall response |
|---|---|---|---|
| CR | CR | No | CR |
| CR | Non-CR/Non-PD | No | PR |
| PR | Non-PD | No | PR |
| SD | Non-PD | No | SD |
| PD | Any | Yes or No | PD |
| Any | PD | Yes or No | PD |
| Any | Any | Yes | PD |

Patients with a global deterioration of health status requiring discontinuation of treatment without objective evidence of disease progression at that time will be reported as "clinical deterioration." Every effort will be made to document the objective progression even after discontinuation of treatment.

In some circumstances, it may be difficult to distinguish residual disease from normal tissue. When the evaluation of complete response depends upon this determination, it is recommended that the residual lesion be investigated (fine needle aspirate/biopsy) before confirming the complete response status.

Confirmation: To be assigned a status of partial response (PR) or complete response (CR), changes in tumor measurements must be confirmed by repeat studies that should be performed no less than 4 weeks after the criteria for response are first met. In the case of SD, follow-up measurements must have met the SD criteria at least once after study entry at a minimum interval of 6-8 weeks.

Rustin criteria: If only CA125 is evaluable (Elevated over 35 U/ml), response will be defined per the GCIG rather than the Rustin criteria.

GCIG CA125 response definition: A response according to CA125 has occurred if there is at least a 50% reduction in CA125 levels from a pretreatment sample. The response must be confirmed and maintained for at least 28 days. Patients can be evaluated according to CA 125 only if they have a pretreatment sample that is at least twice the upper limit of normal and within 2 weeks prior to starting treatment.

Progression according to CA125 has occurred if there is a confirmed (documented on two occasions) rise in CA125 or a previously normal CA125 rises to ≥2×ULN documented on two occasions.

Expected Adverse Events

VB-111 caused minimal toxicity in preclinical toxicology studies in mice. Mild anemia, mild thrombocytopenia, mild leukocytosis, splenomegaly, and bone marrow hyperplasia were observed. Transient liver enzyme elevations with no correlation with clinical pathology were also observed. The administration of adenovirus vectors systemically has been well tolerated. Flu-like symptoms (fever, fatigue, rigors, nausea, and/or vomiting) are the most common adverse events. Asymptomatic prolongation of aPTT and positive LAC were observed in several patients participating in Phase I/II trials. Additionally, a single case of severe diarrhea was reported in a Phase II patient. The majority of intravenously injected adeno VPs are sequestered by the liver, which in turn causes an inflammatory response characterized by acute transaminitis and vascular damage. The major adverse effects of antiangiogenic agents have been wound healing disorders, bleeding, thromboembolic, and cardiovascular events, hypertension and proteinuria.

Correlative Studies

Distribution

For distribution assessment, blood samples will be collected from all patients according to Appendix I. Testing of these samples for Adenovirus and VB-111 transgene level determination will be conducted at the maximal tolerated dose group or the highest dose cohort. Distribution will be assessed by determination of levels of viral DNA and transgene by Q-PCR and Q-RT-PCR respectively in the blood, at predetermined time points following dosing. Samples will be collected for all patients at all pre-defined time points. Testing will be conducted in samples from patients starting at the highest does and will continue to the lower doses. Samples found with non-detectable levels of viral DNA following dosing will not be tested for levels of the transgene and will not be evaluated for later time points.

Antibodies

Serum samples will be collected for analysis of levels of antibodies (total IgG and neutralizing antibodies) to the adenovirus.

Angiogenic Biomarkers

There are no biomarkers to date for antiangiogenic therapy, but several biomarker candidates have been identified [Jain 2009]. These will be tested in peripheral blood samples obtained from all patients enrolled in this study. Plasma analysis will be carried out for circulating angiogenic and inflammatory biomarkers VEGF, PlGF, sVEGFR1, bFGF, IL-1β, IL-6, IL-8, and TNF-α (using multiplex ELISA plates from Meso-Scale Discovery) and sVEGFR2 and SDF1α (using R&D Systems kits), with samples run in duplicate, using established protocols [Horowitz Clinical Ovarian Cancer 2011 in press]. Blood-circulating cells will be enumerated in fresh samples using a standard flow cytometry protocol. The quantitative analysis endpoint was the change in the fraction of circulating CD34brightCD45dim CPCs or VEGFR2+CD45+ monocytic cells among blood mononuclear cells after treatment, as previously described [Horowitz Clinical Ovarian Cancer 2011 in press]. Archival tissue will be evaluated for CD31, CD34, VEGFR2, and vWF.

Tissue Collection

Tissue acquisition is not a mandated part of the study, but optional with a budget to cover non-clinically indicated biopsy or paracentesis to procure samples. There is no specified time for this to be done. The optimal time is considered to be one to two months after first dose of VB-111. It is anticipated that 20-50% of participants may have suitable areas for safe biopsy or ascites amenable to paracentesis.

Description of Statistical Methods

The MTD of VB-111 will be determined using a standard "3+3" design. That is, 3 patients will initially be treated at a particular dose level. If more than one patient experiences DLT accrual will stop and the next lower dose level will be accepted as the MTD. If no DLT occurs, accrual to the next higher dose level will begin. If one DLT occurs, 3 additional patients will be entered at that dose level. VB-111 will be escalated to the next higher level if none of these 3 patients experiences DLT, however, if one or more patients experience such an event, accrual will stop and the MTD will be defined to be the next lower dose level. With this escalation scheme, Table 19 gives the probability of escalation to the next higher dose level for a variety of hypothesized underlying toxicity rates.

TABLE 19

Probability of Escalation of VB-111 Dose Based on DLT

| | True Rate of DLT | | | | | | |
|---|---|---|---|---|---|---|---|
| | 10% | 20% | 30% | 40% | 50% | 60% | 70% |
| Probability of Escalation | 0.91 | 0.71 | 0.49 | 0.31 | 0.17 | 0.08 | 0.03 |

As can be seen from TABLE 19, there is a >71% chance of escalating the combination if the underlying risk of DLT is <20% and a >91% chance of escalation if the underlying risk is <10%. In contrast, there is at most a 17% chance of escalation if the underlying DLT risk is >50% and <8% chance if the risk is >60%.

The assessment of objective response will primarily be descriptive. In general, the overall response rate and corresponding 95% confidence interval will be calculated.

Phase II aspect of the design will evaluate the response rates defined by RECIST criteria or CA125 (GCIG not Rustin criteria) and to describe the safety profile and characterize adverse events and toxicities. Thirty percent will be chosen as the target response rate based on reported responses of combination chemo-antiangiogenic agents in patients with recurrent ovarian cancer, typically in the 20-25% range.

The design will be two-stage optimal design in that an initial 10 patients will be enrolled during Stage 1. This will include participants who commence at a paclitaxel dose of 80 mg/m2 on the Phase I (i.e., participants in Dose Levels 2 and 3). With a range of two to six patients enrolled from DL-2 and 3 cohorts of the Phase I part of the study, a further eight to four participants will be enrolled to the Phase II first stage before an interim analysis of efficacy. If one or no response is observed, then the trial will stop recruitment. Otherwise, if there are two or more responses, then 19 additional participants will be enrolled (i.e. possible maximum total=29) to the Phase II (Total for the whole study will then be 2-18 for Phase I overlapping with 0-29 for the Phase II). If there are five or fewer responses, then no further investigation of this therapy is warranted.

If the true RR≤10%, the chance of ending the trial during Stage 1 is at least 74%. If the true RR is ≥30%, the chance that the trial will be stopped in Stage 1 is ≤15%. The power of final analysis is 80% to reject H0: RR≤10% in favor of H1: RR≥30% at a target type-1 error rate of 5%.

The trial will be terminated if more than 2 Grade IV GI perforations are observed during Stage I. If there are 3 GI perforations at any time, then this trial will be terminated. Assuming a true GI perforations rate of 4% the probability of observing more than 2 events during Stage I is 6.2%, and the probability to observe more than 3 events from the entire trial is 2.7%.

The quantitative and semi-quantitative data such as IHC data will be considered preliminary pilot data, using descriptive statistics and non-parametric analyses, attempting to explore correlations, acknowledging that these sample sizes lack sufficient power to draw definitive conclusions, but the advantage of using the same set of analyses in multiple studies will enable us to evaluate the potentially most useful predictors of efficacy and toxicity.

Biomarkers

Primarily non-parametric methods (e.g. Wilcoxon signed-rank or rank sum test) will be used to assess the impact of VB-111 on CECs, and correlative/predictive measures, all tests of statistical significance will be two-sided and no adjustment will be made for multiple comparisons.

Level of Significance

Confidence intervals will be calculated at the (two-sided) 95% level of confidence.

Laboratory Testing

Angiogenesis Biomarkers Analyses (Local)

Plasma analysis will be carried out for circulating angiogenic and inflammatory biomarkers VEGF, PlGF, sVEGFR1, bFGF, IL-1β, IL-6, IL-8, and TNF-α (using multiplex ELISA plates from Meso-Scale Discovery) and sVEGFR2 and SDF1α (using R&D Systems kits. Blood-circulating cells will be enumerated in fresh samples using a standard flow cytometry protocol. Archival tissue will be evaluated for CD31, CD34, VEGFR2, and vWF. Tumor marker: CA-125. Ten cc total plasma for each time-point, in EDTA tubes at room temperature, will be assayed.

Samples shall be collected at the following time points:
1. At Baseline
2. At Cycle 1: on Days 1 prior to study drug dosing, and days 8, 15, and 22
3. At Cycle 2 Day 1 prior to study drug dosing
4. Every 2 cycles thereafter beginning with Cycle 3, prior to study drug dosing, until disease progression Antibody Testing Titers of antibodies to the Ad-5 virus including IgG and neutralizing antibodies shall be collected for analysis. Samples shall be collected at the following time points:
1. At Each Cycle: on Days 1, 8, 15, and 22 prior to study drug dosing;
2. At the Study Completion Visit.

Blood shall be collected and prepared in the following manner:
1. 6 ml of blood shall be collected in tubes with no anticoagulant.
2. Samples shall be left at room temperature for 1 hour, and then stored at 2-8° C. overnight to permit clot retraction.
3. Blood shall be centrifuged the next day.
4. Approximately 2 ml serum shall be extracted and split into 4 aliquot tubes (0.5 ml each, total of 2 ml each in a Nalgene 100 1.5 ml) and stored at −20° C. until shipping for analysis.

Biodistribution Testing

The following tests will be performed:
1. Blood biodistribution: Viral DNA and Transgene expression
2. Urine biodistribution: Viral DNA Whole blood sample will be collected for Biodistribution at the following time points:
1. On Day 1 & 8 of each odd cycle, prior to study drug dosing.
2. On VB-111 dosing days:
   a. Prior to infusion (Same as Day 1 sample)
   b. At end of infusion
   c. 3±0.5 hours
   d. 6±0.5 hours
   e. At the Study Completion Visit.

Blood samples will be prepared in the following manner:
1. Blood from each time point will be collected in 4 tubes (0.75 ml/tube) containing EDTA.
   a. 2 tubes for the analysis of viral DNA
   b. 2 tubes for the analysis of transgene expression
2. The tubes should be labeled with the subject numbers, initials, date and time of sample collection and stored in a freezer at or below −70° C.

Urine samples will be prepared in the following manner:
1. Two urine samples of 1-2 ml will be collected from the total collection volume saved
2. Urine samples and total collection volumes will be stored frozen until further analyses.

Results

VB-111 was administered to six patients, each having fallopian tube or epithelial ovarian cancer for a duration of at least 1 year prior to study entry, at a dose of $3 \times 10^{12}$ VPs in combination with paclitaxel (40 mg or 80 mg) per subject as shown in FIG. 3. The patients did not exhibit any serious adverse events that were related to VB-111. There were no dose limiting toxicities observed.

---

What is claimed is:

1. A method of inhibiting, reducing, or decreasing a size of a solid tumor in a subject in need thereof, the method comprising administering to the subject, via intravenous infusion, an effective amount of an adenovirus vector comprising the nucleotide sequence set forth in SEQ ID NO: 19, wherein the vector comprises a Fas-chimera transgene comprising the nucleotide sequence set forth in SEQ ID NO: 9, which is operably linked to a promoter comprising the nucleotide sequence set forth in SEQ ID NO: 18, wherein the solid tumor is derived from or associated with ovarian cancer, lung cancer, thyroid cancer, glioblastoma, or recurrent glioblastoma.

2. The method of claim 1, further comprising administering an effective amount of one or more chemotherapeutic agents.

3. The method of claim 2, wherein the one or more chemotherapeutic agents are selected from raltritrexed, topotecan, paclitaxel, docetaxel, cisplatin, carboplatin, oxaliplatin, liposomal doxorubicin, gemcitabine, cyclophosphamide, vinorelbine, ifosfamide, etoposide, altretamine, capecitabine, irinotecan, melphalan, pemetrexed, bevacizumab, and-albumin bound paclitaxel.

4. The method of claim 3, wherein the chemotherapeutic agent is bevacizumab.

5. The method of claim 3, wherein the chemotherapeutic agent is paclitaxel.

6. The method of claim 1, wherein the effective amount of the vector is about $10^9$ to about $10^{15}$ virus particles.

7. The method of claim 1, wherein expression of the vector inhibits, reduces, or decreases the size of the tumor.

8. A method of inhibiting, decreasing, or reducing neo-vascularization or angiogenesis in a solid tumor in a subject in need thereof, the method comprising administering to the subject, via intravenous infusion, an effective amount of an adenovirus vector comprising the nucleotide sequence set forth in SEQ ID NO: 19, wherein the vector comprises a Fas-chimera transgene comprising the nucleotide sequence set forth in SEQ ID NO: 9, which is operably linked to a promoter comprising the nucleotide sequence set forth in SEQ ID NO: 18, wherein the solid tumor is derived from or associated with ovarian cancer, lung cancer, thyroid cancer, glioblastoma, or recurrent glioblastoma.

9. The method of claim 8, wherein expression of the vector inhibits, decreases, or reduces neo-vascularization or angiogenesis of the tumor.

10. The method of claim 8, further comprising administering an effective amount of one or more chemotherapeutic agents.

11. The method of claim 10, wherein the one or more chemotherapeutic agents are selected from raltritrexed, topotecan, paclitaxel, docetaxel, cisplatin, carboplatin, oxaliplatin, liposomal doxorubicin, gemcitabine, cyclophosphamide, vinorelbine, ifosfamide, etoposide, altretamine, capecitabine, irinotecan, melphalan, pemetrexed, bevacizumab, and albumin bound paclitaxel.

* * * * *